US012442010B2

(12) United States Patent
Atwood et al.

(10) Patent No.: US 12,442,010 B2
(45) Date of Patent: Oct. 14, 2025

(54) POD SHATTER TOLERANCE IN *BRASSICA* PLANTS

(71) Applicant: PIONEER HI-BRED INTERNATIONAL, INC., Johnston, IA (US)

(72) Inventors: Sarah Atwood, Ankeny, IA (US); Norbert Brugiere, Johnston, IA (US); Igor Falak, Guelph (CA); Kevin A Fengler, Clive, IA (US); Siva S. Ammiraju Jetty, Johnston, IA (US); Jonathan Myrvold, Waukee, IL (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 245 days.

(21) Appl. No.: 17/617,724

(22) PCT Filed: Jun. 17, 2020

(86) PCT No.: PCT/US2020/038124

§ 371 (c)(1),
(2) Date: Dec. 9, 2021

(87) PCT Pub. No.: WO2020/257273

PCT Pub. Date: Dec. 24, 2020

(65) Prior Publication Data

US 2022/0298519 A1 Sep. 22, 2022

Related U.S. Application Data

(60) Provisional application No. 62/863,551, filed on Jun. 19, 2019.

(51) Int. Cl.

| | |
|---|---|
| ***C12Q 1/6895*** | (2018.01) |
| ***C07K 14/415*** | (2006.01) |
| ***C12N 9/22*** | (2006.01) |
| ***C12N 9/24*** | (2006.01) |
| ***C12N 15/11*** | (2006.01) |
| ***C12N 15/82*** | (2006.01) |

(52) U.S. Cl.

CPC ........ *C12N 15/8213* (2013.01); *C07K 14/415* (2013.01); *C12N 9/22* (2013.01); *C12N 9/24* (2013.01); *C12N 15/111* (2013.01); *C12Q 1/6895* (2013.01); *C12N 2310/20* (2017.05)

(58) Field of Classification Search

CPC .................................................. C12N 15/8213

See application file for complete search history.

(56) References Cited

U.S. PATENT DOCUMENTS

| | | | |
|---|---|---|---|
| 7,135,621 B2 | 11/2006 | Yanofsky et al. | |
| 2005/0120417 A1 | 6/2005 | Yanofsky et al. | |
| 2007/0020746 A1 | 1/2007 | Kunsch et al. | |
| 2009/0049568 A1 | 2/2009 | Aharoni et al. | |
| 2009/0077685 A1 | 3/2009 | Buehler et al. | |
| 2011/0030106 A1 | 2/2011 | Laga et al. | |
| 2011/0191877 A1 | 8/2011 | Russell et al. | |
| 2012/0149891 A1 | 6/2012 | Yanofsky et al. | |
| 2014/0351967 A1* | 11/2014 | Laga | C07K 14/415 536/23.6 |
| 2015/0067922 A1 | 3/2015 | Yang et al. | |
| 2017/0055480 A1 | 3/2017 | Laga et al. | |
| 2017/0159067 A1 | 6/2017 | Charne et al. | |
| 2018/0220607 A1 | 8/2018 | Abel et al. | |
| 2022/0298520 A1 | 9/2022 | Brugiere et al. | |

FOREIGN PATENT DOCUMENTS

| | | |
|---|---|---|
| KR | 20110032866 A | 3/2011 |
| RU | 2497350 C2 | 11/2013 |
| WO | 2010006732 A2 | 1/2010 |
| WO | 2014060519 A1 | 4/2014 |

OTHER PUBLICATIONS

Zhai et al., 2019, CRISPR/Cas9-mediated genome editing reveals differences in the contribution of INDEHISCENT homologues to pod shatter resistance in *Brassica napus* L., Theoretical and Applied Genetics 132: 2111-2123. (Year: 2019).*

Braatz et al., 2018, The effect of INDEHISCENT point mutations on silique shatter resistance in oilseed rape (*Brassica napus*), Theoretical and Applied Genetics 131: 959-971. (Year: 2018).*

PCT/US2020/038124 ISR and Written Opinion, Sep. 16, 2020.

Braatz, et al., CRISPR-Cas9 Targeted Mutagenesis Leads to Simultaneous Modification of Different Homoeologous Gene Copies in Polyploid Oilseed Rape (*Brassica napus*), Plant Physiology, (2017) 174:935-942.

Braatzet, et al., EMS-induced point mutations in ALCATRAZ homoeologs increase silique shatter resistance of pilseed rape (*Brassica napus*), Euphytica (2018) 214:29.

Braatzet, et al., The effect of INDEHISCENT point mutations on silique shatter resistance in oilseed rape (*Brassica napus*), Theoretical and Applied Genetics (2018) 131:959-971.

Liljegren, et al., Control of Fruit Patterning *Arabidopsis* by INDEHISCENT, Cell (2004) 116:843-853.

Rajani and Sundaresen, The *Arabidopsis* myc/bHLH gene ALCATRAZ enables cell separation in fruit dehiscence! Current Biology (2001) 11:1914-1922.

Stephenson, et al., The power of model-to-crop translation illustrated by reducing seed loss from pod shatter in oilseed rape, Plant Reproduction (2019) 32:331-340.

Zhai, et al., CRISPR/Cas9-mediated genome editing reveals differences in the contribution of INDEHISCENT homologues to pod shatter resistance in *Brassica napus* L., Theoritecal and Applied Genetics (2019) 132:2111-2123.

(Continued)

*Primary Examiner* — Bratislav Stankovic

(57) ABSTRACT

This disclosure provides methods and compositions for identifying *Brassica* plants that have a native deletion of the INDEHISCENT gene (BnIND-A) located on chromosome A of *B. napus*. Also provided are methods of improving one or more agronomic characteristics such as pod shatter and breeding methods for introducing a pod shatter tolerant phenotype in *Brassica* plants and/or their progeny.

14 Claims, 9 Drawing Sheets

Specification includes a Sequence Listing.

(56) References Cited

OTHER PUBLICATIONS

Braatz J., et al., "Production of Oilseed Rape with Increased Seed Shattering Resistance," Thesis to Obtain the Degree of Doctor from the Faculty of Agrarian Sciences and Nutritional Studies at the Christian-Albrechts-University of Kiel, 2017, 148 Pages, Retrieved from Internet URL: < https://macau.uni-kiel.de/servlets/MCRFileNodeServlet/diss_derivate_00000014/ Diss_Vollversion_Braatz_2>.

Cai Y., et al., "CRISPR/Cas9-mediated Deletion of Large Genomic Fragments in Soybean," International Journal of Molecular Sciences, 2018, vol. 19, No. 12, pp. 1-13.

International Preliminary Report on Patentability for International Application No. PCT/US2020/038087, mailed Dec. 30, 2021, 11 Pages.

International Preliminary Report on Patentability for International Application No. PCT/US2020/038124, mailed Dec. 30, 2021, 7 Pages.

International Search Report and Written Opinion for International Application No. PCT/US2020/038087, mailed Dec. 1, 2020, 15 Pages.

Kaur J., et al., "Genome Wide Association Mapping and Candidate Gene Analysis for Pod Shatter Resistance in *Brassica juncea* and Its Progenitor Species," Molecular Biology Reports, 2020, vol. 47, No. 4, pp. 1-12.

Qing Y., et al., "Oilseed Rape (*Brassica napus* L.) Pod Shatter Resistance and its Relationship with Whole Plant and Pod Characteristics," Industrial Crops and Products, 2021, vol. 166, No. 5, pp. 1-10.

Raman H., et al., "Genome-wide Delineation of Natural Variation for Pod Shatter Resistance in Brassica Napus, " PloS one, 2014, vol. 9, No. 7, pp. 1-13.

Sosnowska K., et al., "Chromosome Instabilities in Resynthesized Brassica Napus Revealed by FISH," Journal of Applied Genetics, 2020, vol. 61, No. 3, pp. 323-335.

* cited by examiner

| | | | | | | | |
|---|---|---|---|---|---|---|---|
| Number of assays: | 12 | 16 | 15 | 14 | 17 | 12 | 17 |
| Number of pods assayed: | 180 | 240 | 226 | 210 | 255 | 180 | 252 |

POD SHATTER TOLERANCE IN *BRASSICA* PLANTS

CROSS-REFERENCE TO RELATED APPLICATIONS

This application is a 35 U.S.C. § 371 national stage application of PCT International Application No. PCT/US2020/038124, filed on Jun. 17, 2020, which claims the benefit of U.S. Provisional Application No. 62/863,551, filed Jun. 19, 2019, the disclosures of which are incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing file named 8477WOPCT_ST25 created on Jun. 16, 2020 and having a size of 300 kilobytes, which is filed concurrently with the specification. The sequence listing comprised in this ASCII formatted document is part of the specification and is herein incorporated by reference in its entirety.

FIELD

This disclosure relates to compositions and methods, including sequences, markers, assays and the use of marker assisted selection for improving agronomic traits in plants, specifically improving pod shatter tolerance in *Brassica* plants.

BACKGROUND

*Brassica napus* (also referred to as canola or oilseed rape) is one of the most important vegetable oilseed crops in the world, especially in China, Canada, the European Union and Australia, where the oils are used extensively in the food industry and for biodiesel production. Oilseed rape is a recently domesticated plant and retains some of the traits of its wild ancestors which were useful in the wild but are not useful in commercial crop plants. One example of such a trait is fruit dehiscence, which refers to the natural opening of reproductive structures to disperse seeds. In species that disperse their fruit through dehiscense, siliques or pods are composed of two carpels that are held together by a central replum via a valve margin. Where the valve margin connects to the replum is called the dehiscence zone (DZ). When the pod is ripe, the valve margin detaches from the replum and the pod splits open, releasing the seeds inside. The DZ demarcates the precise location where the valves detach.

During crop domestication, farmers and breeders have selected for *Brassica* plants that avoid releasing their seeds early, before the crop is harvested. However, such early pod dehiscence (also known as "pod shatter", "seed shatter" or "seed shedding") has not been fully eliminated. Therefore, *B. napus* plants remain prone to seed losses due to pod shatter prior to harvest. Pod shatter poses significant problems for commercial production of canola seeds and adverse weather conditions can exacerbate the process resulting in an increase in shatter-related losses of 25% or more. This loss of seed not only has a dramatic effect on yield but can also result in the emergence of the crop as a weed in the subsequent growing season.

In addition to direct losses of income from reduced seed yield, increased input costs and reduced price paid for low oil content seeds, pod shatter also results in additional indirect costs to the grower. The shed seed results in self-sown or volunteer *B. napus* plants growing in the next year's crop, which creates further expense due to the need for increased herbicide use. Such self-sown *B. napus* plants cause losses due to competition with subsequent crop and can cause problems for farmers using reduced-tillage strategies such as no-till, zone-till, and strip tillage.

Resistance to pod shatter (indehiscent phenotype) is a key trait that has been selected during crop domestication. Plants have been also generated using Ethyl Methane Sulfonate (EMS) mutagenesis or through single guide gene editing. Rajani and Sundaresan, 2001, *Current Biology,* 11(24), 1914-1922; Liljegren et al., 2004, *Cell,* 116(6), 843-853; Braatz et al., 2017, *Plant Physiology,* 174(2), 935-942; Braatz et al., 2018, *Euphytica,* 214(2), 29; Braatz et al., 2018, *Theor. Applied Genetics,* 131(4), 959-971. However, some of these approaches have produced plants with "huge background mutations" and plants that are otherwise "unsuitable for agronomic purposes" (Zhai et al., 2019, *Theor. Applied Genetics,* 132: 2111-2123 at 2112 and 2121). Thus, there remain varieties of *B. napus* that are still dehiscent and prone to pod shatter. In view of the foregoing, there is a need for more *B. napus* lines having a pod shatter tolerance, i.e., indehiscent phenotype, and new approaches for generating such plants. There is also a need for pod-shatter phenotypes that permit plant seeds to be collected at harvest by threshing pods, e.g., using a combine harvester, with minimal damage to the seed.

SUMMARY

Provided herein are methods, assays and molecular markers based, at least in part, on the discovery of an unexpected deletion of genomic sequence affecting the INDEHISCENT gene (BnIND-A) located on chromosome A of *B. napus*. Also disclosed herein is the discovery that this deletion confers a pod shatter tolerant phenotype in *B. napus* plants and/or their progeny. Generally, a plant with pod shatter tolerance is one having increased pod shatter tolerance relative to an otherwise isogenic plant lacking the BnIND-A deletion disclosed herein. Therefore, the methods and markers disclosed herein can be used to identify (i) a plant having a pod shatter tolerant phenotype and/or (ii) a plant suitable for use as a parent plant in a breeding program to generate progeny plants having a pod shatter tolerant phenotype.

The methods, assays, and molecular markers can be used with a *Brassica* crop plant. As used herein, *Brassica* preferably refers to *Brassica napus, Brassica juncea, Brassica carinata, Brassica rapa* or *Brassica oleracea.*

In one aspect, this disclosure provides a method of identifying a *Brassica* plant, cell, or germplasm thereof comprising a BnIND-A genomic deletion that contributes to a pod shatter tolerance phenotype. The method comprises obtaining a nucleic acid sample from a *Brassica* plant cell, or germplasm; and screening the sample for genomic sequence comprising a deletion of the BnIND-A gene on chromosome N03. This BnIND-A deletion allele is missing a genomic segment that is from about 200 kb to about 310 kb in length, depending on the reference genome used for comparison. The deletion segment start breakpoint is located at about position 13,300,000 to 14,915,000 of an N03 wildtype reference genome and the deletion segment end breakpoint corresponds to a position located at about position 13,500,000 to 15,250,000 of a N03 wildtype reference genome. See Example 1 and Table 6 herein. The absence of this deleted genomic segment of BnIND-A contributes to a pod shatter tolerance phenotype in *Brassica*.

For example, the method of identifying a *Brassica* plant, cell, or germplasm thereof comprising a BnIND-A genomic deletion can include screening the sample for the absence of the deleted genomic segment at the breakpoint locus corresponding to positions 14,989,780 to 14,989,781 of *Brassica napus* line G00010BC N03 genome, e.g., the breakpoint locus corresponding to positions 10,002-10,003 of SEQ ID NO:2. Screening the sample can be done using any suitable method for detecting a genetic polymorphism, including any method disclosed herein.

When screening the plant sample for genomic sequence comprising the BnIND-A genomic deletion, the disclosed methods can include amplifying the genomic sequence to produce an amplicon. The amplicon comprises amplified genomic sequence which is generated using a nucleic acid amplification such as polymerase chain reaction (PCR). Thus, for example, the method can include amplifying genomic DNA to produce an amplicon that includes the breakpoint locus sequence corresponding to positions 14,989,780 to 14,989,781 of *Brassica napus* line G00010BC N03 genome or positions 10,002-10,003 of SEQ ID NO:2. The amplicon can be sequenced to confirm the presence of the breakpoint and/or the size of the amplicon produced is diagnostic for the BnIND-A genomic deletion.

In some examples, sequencing or amplification of a BnIND-A deletion allele can produce a sequencing product or amplicon, respectively, comprising the following start and end breakpoint locus (shown in bold and underlined) and flanking sequence corresponding to SEQ ID NO:2 (positions 9995-1011): ATTTCTCTATTTGTTTT. Such a sequencing product or amplicon comprising the breakpoint locus is diagnostic for the BnIND-A genomic deletion. Thus, in particular examples, detecting the BnIND-A deletion can include DNA sequencing or amplification of the breakpoint locus and 5 bp or more, 10 bp or more, 15 bp or more, 20 bp or more, 30 bp or more, 40 bp or more, 50 bp or more, 60 bp or more, 70 bp or more, 80 bp or more, 90 bp or more, 100 bp or more, 110 bp or more, 120 bp or more, 130 bp or more, 140 bp or more, 150 bp or more, 175 bp or more, 200 bp or more, 250 bp or more, 300 bp or more, 350 bp or more, 400 bp or more, 450 bp or more, 500 bp or more, 550 bp or more, or 600 bp or more of flanking sequence that is (i) upstream of (i.e., located 5' to) the deletion start breakpoint at position 10,002 of SEQ ID NO:2 and/or (ii) downstream of (i.e., located 3' to) the deletion end breakpoint at position 10,003 of SEQ ID NO:2. Further, in particular examples, the BnIND-A deletion disclosed herein can be detected amplifying genomic sequence to produce an amplicon comprising the BnIND-A deletion allele sequence indicated in Table 1 below. Additionally, the BnIND-A deletion disclosed herein can be detected by nucleotide sequencing to detect the presence of the genomic sequence (e.g., in amplified genomic sequence) comprising any one or more of the BnIND-A deletion allele sequences indicated in Table 1 below.

TABLE 1

| SEQ ID NO: 2 positions | SEQ ID NO: 2 positions | SEQ ID NO: 2 positions | SEQ ID NO: 2 positions |
|---|---|---|---|
| 9997 to 10008 | 9952 to 10053 | 9882 to 10123 | 9702 to 10303 |
| 9992 to 10013 | 9942 to 10063 | 9872 to 10133 | 9652 to 10353 |
| 9987 to 10018 | 9932 to 10073 | 9862 to 10143 | 9602 to 10403 |
| 9982 to 10023 | 9922 to 10083 | 9852 to 10153 | 9552 to 10453 |
| 9977 to 10028 | 9912 to 10093 | 9827 to 10178 | 9502 to 10503 |
| 9972 to 10033 | 9902 to 10103 | 9802 to 10203 | 9452 to 10553 |
| 9962 to 10043 | 9892 to 10113 | 9752 to 10253 | 9402 to 10603 |

The disclosure also provides an amplification, e.g., PCR assay method that comprises obtaining a nucleic acid sample from a *Brassica* plant, cell, or germplasm thereof, isolating genomic DNA from the sample and screening the isolated DNA for genomic sequence comprising the BnIND-A deletion disclosed herein by contacting the isolated genomic DNA with a deletion forward primer and deletion reverse primer to selectively produce an amplicon comprising the BnIND-A deletion breakpoint locus at positions 10,002-10,003 of SEQ ID NO:2. Selective amplification of the BnIND-A deletion amplicon can be achieved using a first deletion primer that anneals upstream of the deletion breakpoint BnIND-A deletion breakpoint and a second deletion primer that anneals downstream of the deletion breakpoint. The method can further, optionally, include contacting the isolated genomic DNA with a wildtype forward primer and wildtype reverse primer capable of selectively producing a second amplicon of wildtype genomic BnIND-A that includes sequence from the deleted genomic segment. Selective amplification of the wildtype amplicon can be achieved using at least one wildtype primer that anneals within the deleted genomic segment disclosed herein. The primers used in such a PCR assay can be labeled, e.g., with a radioactive or fluorescent label for detection of amplified product. If both deletion and wildtype labeled primers are used, the label on a deletion primer is preferably different from the label on a wildtype primer. Examples of forward and reverse primers for amplification of BnIND-A deletion allele sequence and wildtype genomic BnIND-A sequence, respectively, are provided in Table 2.

TABLE 2

| SEQ ID NO | Name | Description |
|---|---|---|
| SEQ ID NO: 34 | BP_F001 | Deletion Forward Primer |
| SEQ ID NO: 35 | BP_R001 | Deletion Reverse Primer |
| SEQ ID NO: 51 | BP_F002 | Deletion Forward Primer |
| SEQ ID NO: 52 | BP_R002 | Deletion Reverse Primer |
| SEQ ID NO: 53 | BP_F003 | Deletion Forward Primer |
| SEQ ID NO: 54 | BP_R003 | Deletion Reverse Primer |
| SEQ ID NO: 55 | BP_R004 | Deletion Reverse Primer |
| SEQ ID NO: 56 | BP_R005 | Deletion Reverse Primer |
| SEQ ID NO: 57 | BP_R006 | Deletion Reverse Primer |
| SEQ ID NO: 32 | IND_A_001_F001 | WT Forward Primer |
| SEQ ID NO: 33 | IND_A_001_R001 | WT Reverse Primer |
| SEQ ID NO: 58 | IND_A_001_R002 | WT Reverse Primer |

A disclosed amplification or PCR assay can include obtaining a nucleic acid sample from a *Brassica* plant, cell, or germplasm thereof, isolating genomic DNA from the sample and screening for genomic sequence comprising the BnIND-A deletion disclosed herein by contacting the isolated genomic DNA with a deletion forward primer and deletion reverse primer to produce an amplicon comprising the BnIND-A deletion breakpoint locus at positions 10,002-10,003 of SEQ ID NO:2, and then contacting a labeled probe (deletion probe) to the deletion amplicon comprising the deletion breakpoint, and thereby detecting the BnIND-A deletion amplicon. The method can further, optionally, include contacting the isolated genomic DNA with a wildtype forward primer and wildtype reverse primer capable of producing a second amplicon of wildtype genomic BnIND-A that includes sequence from the deleted genomic segment, and then adding a labeled wildtype probe which is capable of detecting the wildtype amplicon. The deletion probe and wildtype probe are preferably differently labeled to permit, which can enable the use of both probes in the same reaction mix or in a high throughput amplification assay method. Examples of forward primers, reverse primers, and probes for the detection of BnIND-A deletion allele and wildtype genomic BnIND-A, respectively, are provided in Table 3.

TABLE 3

| SEQ ID NO | Name | Description |
|---|---|---|
| SEQ ID NO: 39 | N101T10-F001 | Deletion Forward Primer |
| SEQ ID NO: 40 | N101T10-R001 | Deletion Reverse Primer |
| SEQ ID NO: 41 | N101T10-001-X001 | Deletion Probe |
| SEQ ID NO: 42 | N101T10-F002 | Deletion Forward Primer |
| SEQ ID NO: 43 | N101T10-R002 | Deletion Reverse Primer |
| SEQ ID NO: 44 | N101T10-001-X002 | Deletion Probe |
| SEQ ID NO: 46 | N101T10-R003 | Deletion Reverse Primer |
| SEQ ID NO: 47 | N101T10-001-X003 | Deletion Probe |
| SEQ ID NO: 36 | N101T11-F001 | WT Forward Primer |
| SEQ ID NO: 37 | N101T11-R001 | WT Reverse Primer |
| SEQ ID NO: 38 | N101T11-001-X001 | WT Probe |
| SEQ ID NO: 48 | N101T11-R002 | WT Reverse Primer |
| SEQ ID NO: 49 | N101T11-001-X002 | WT Probe |
| SEQ ID NO: 50 | N101T11-001-X003 | WT Probe |

Each of the methods disclosed herein for identifying a *Brassica* plant, cell, or germplasm thereof comprising the disclosed BnIND-A genomic deletion can further include selecting such a *Brassica* plant, cell, or germplasm thereof comprising the disclosed BnIND-A genomic deletion that contributes to a pod shatter tolerance phenotype. This method of selection can be used advantageously in methods of introducing the BnIND-A deletion into a *Brassica* variety and thereby generate new plant lines comprising the BnIND-A deletion.

In one aspect, provided herein is a method of introducing the native BnIND-A deletion into a new *Brassica* plant, e.g., a *B. napus* plant. The method can include crossing a first parent *Brassica* plant comprising a native deletion in the BnIND-A gene on chromosome N03 with a second parent *Brassica* plant that does not have the deletion to produce progeny plants (e.g. hybrid progeny), obtaining a nucleic acid sample from one or more of the progeny plants, and identifying one or more of the progeny plants that has the BnIND-A deletion. Progeny plants can be identified using one or more of the methods disclosed herein (which include, but are not limited to, whole genome sequencing, coupled genomic DNA amplification and sequencing, DNA amplification methods that include the use of labeled primers and/or labeled probes, marker assisted selection, primer extension etc.) to identify a *Brassica* plant, cell, or germplasm thereof comprising the disclosed BnIND-A genomic deletion. The method can further include selecting the hybrid progeny plant identified as having the BnIND-A genomic deletion. This method can thus be used to create progeny plants having the BnIND-A genomic deletion that provides the pod shatter tolerance trait disclosed herein.

In certain examples, the foregoing method steps can be repeated by crossing the one or more selected progeny plants with the first or second parent *Brassica* plant (the recurrent parent plant) to produce backcross progeny plants. Nucleic acid samples are obtained from one or more backcross progeny plants; and backcross progeny plants comprising the disclosed BnIND-A genomic deletion are identified. The method further includes selecting the one or more backcross progeny plants having the BnIND-A deletion to produce another generation of backcross progeny plants. This process can be further repeated two, three, four, five, six, or seven times, i.e., by crossing the latest generation of selected backcross progeny plants having the BnIND-A deletion with the recurrent parent plant, and each time identifying and selecting additional backcross progeny plants having the BnIND-A deletion. Repeated backcrossing to the recurrent parent plant can be used to create *Brassica* plant lines that combine the BnIND-A deletion shatter tolerance trait with the agronomic characteristics of the recurrent parent plant, when grown in the same environmental conditions.

Further provided is the use of gene editing technology to create a targeted genomic modification of the BnIND-A gene in a *Brassica* genomic locus. The modification produces a deletion of from about 200 kb to about 310 kb in length, wherein the deletion segment start breakpoint corresponds to about position 13,300,000 to 14,915,000 of an N03 wildtype reference genome and the deletion end breakpoint corresponds to about position 13,500,000 to 15,250,000 of an N03 wildtype reference genome. The resulting modified *Brassica* plant, cell, or germplasm comprises BnIND-A sequence that includes the breakpoint locus corresponding to positions 14,989,780 to 14,989,781 of *Brassica napus* line G00010BC N03 genome or positions 10,002-10,003 of SEQ ID NO:2 and sequence flanking thereof. Methods for creating such gene edited plants dropouts comprise inducing a first and second double strand break in genomic DNA using a TALE-nuclease (TALEN), a meganuclease, a zinc finger nuclease, or a CRISPR-associated nuclease. In a preferred aspect, the method comprises introducing a CRISPR-associated nuclease and guide RNAs into a *B. napus* plant cell.

The disclosure can be more fully understood from the following detailed description and the accompanying drawings and Sequence Listing, which form a part of this application.

BRIEF DESCRIPTION OF THE DRAWINGS AND SEQUENCE LISTING

FIG. 1 is a schematic illustrating a KASPar™ assay designed to detect a native BnIND-A deletion on chromosome N03 (SEQ ID NO: 2). In FIG. 1, "1" indicates a wildtype allele-specific forward primer, "2" indicates a wildtype specific common or reverse primer, "3" indicates a natural deletion allele-specific forward primer, and "4" indicates a natural deletion allele-specific common or reverse primer.

FIG. 2 is a schematic illustrating a TAQMAN™ assay designed to detect a native BnIND-A deletion on chromosome N03. In FIG. 2, star "1" indicates a wildtype specific probe; star "2" indicates a natural deletion specific probe; "3" indicates a wildtype and mutant common forward primer, "4" indicates a wildtype allele-specific reverse primer; and "5" indicates a natural deletion allele-specific reverse primer.

Figure 6:
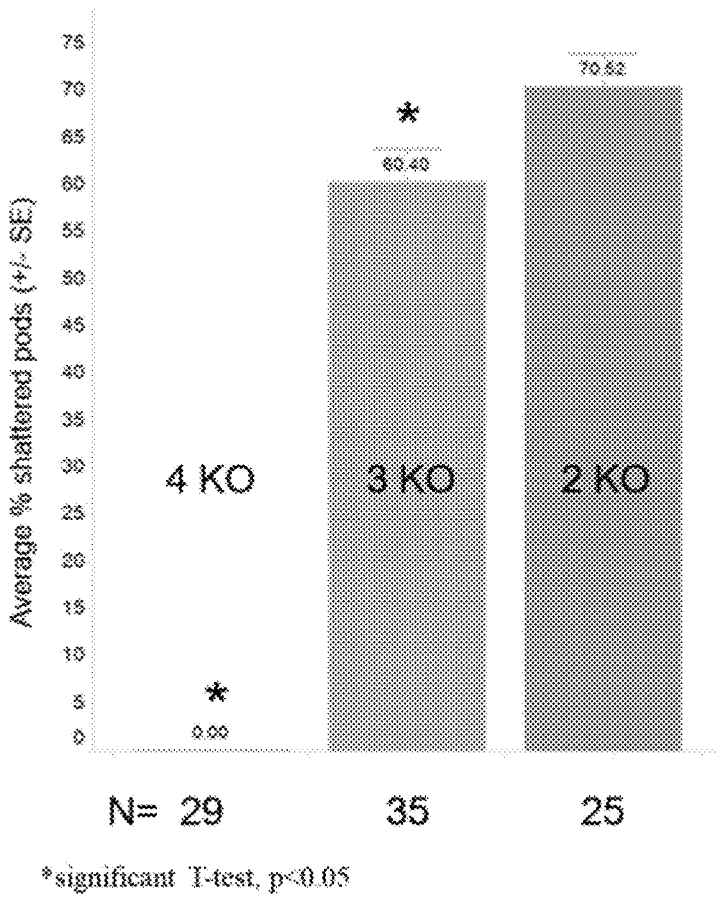

FIG. 6 is a bar graph showing the average percentage shattered pods of G00010BC plants segregating for an IND-C dropout determined using a laboratory method for phenotyping pod shatter tolerance. Asterisk indicates a significant difference (T-test, $p<0.05$) as compared to wild-type (WT) plants. N=number of 15 pods replications for each zygosity category.

Figure 7:
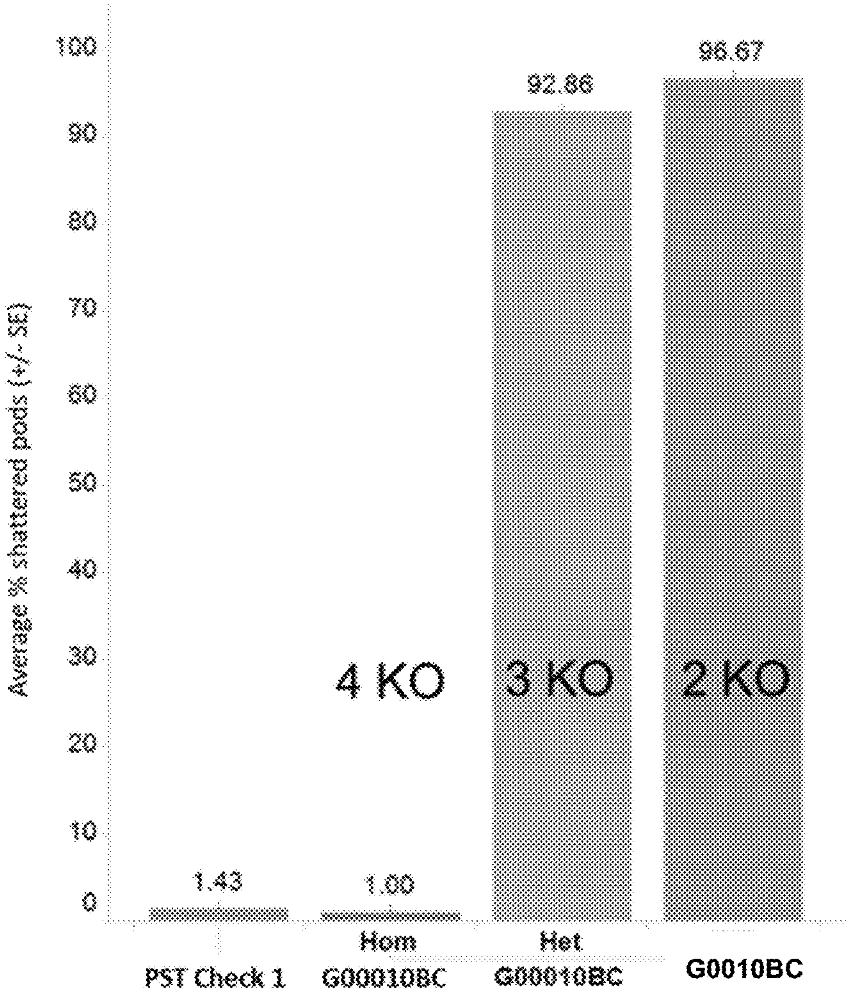

FIG. 7 is a bar graph showing the average percentage of shattered pods of a commercial pod-shatter tolerant line (PST Check 1), G00010BC plants (2 KO), and modified G00010BC plants that are either homozygous (4 KO) or heterozygous (3 KO) for gene-edited deletions of IND-C gene allele. Pod shatter tolerance was determined using a laboratory phenotyping method.

Figure 8:
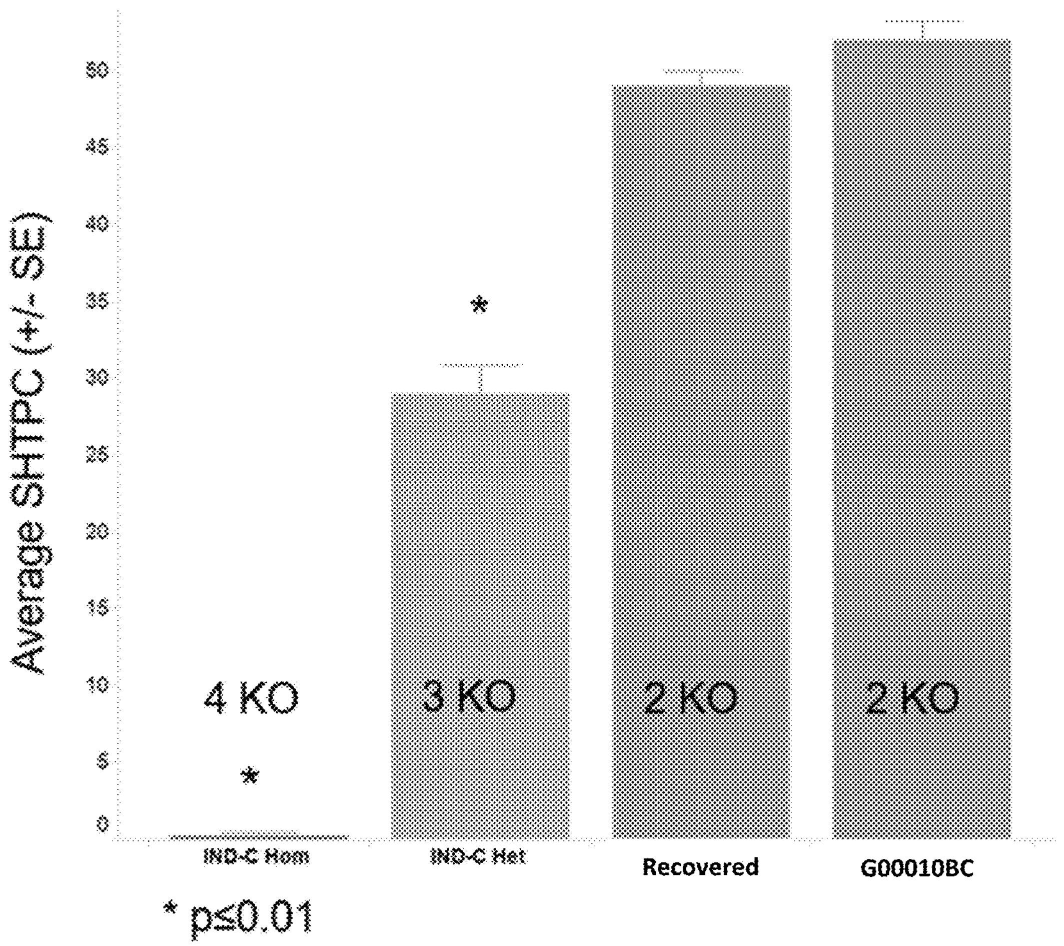

FIG. 8 is a bar graph showing the SHTPC of unmodified G00010BC plants (2 KO), Recovered segregant with homozygous BnIND-A deletion (2 KO), and G00010BC plants that are either homozygous (4 KO) or heterozygous (3 KO) for gene-edited deletions of IND-C gene allele. Pod shatter tolerance was determined using a field phenotyping method.

Figure 9:
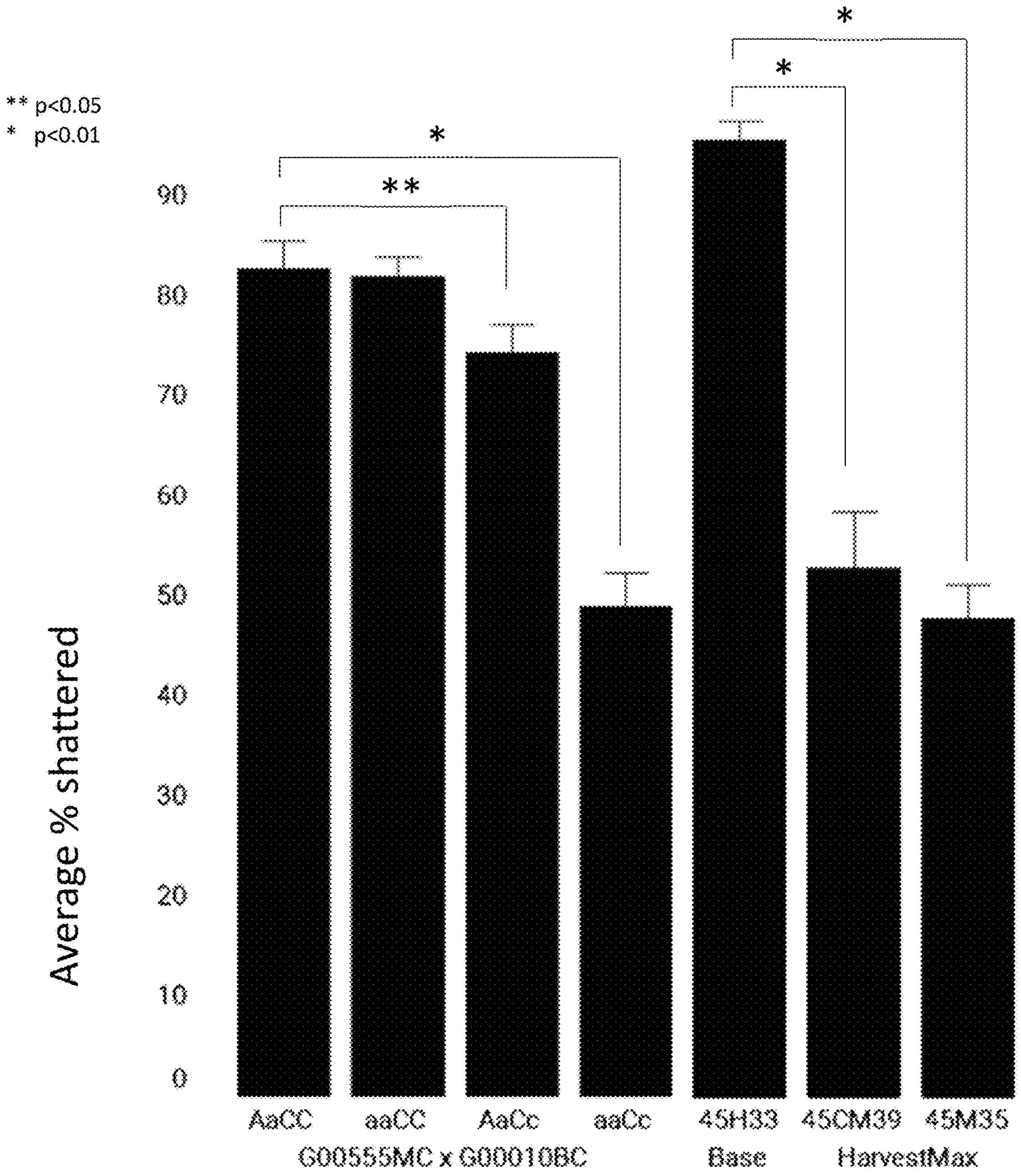

FIG. 9 is a bar graph showing the average percentage of shattered pods Shatter tolerance of G00555MC×G00010BC gene edited hybrids with indicated dropout allele combinations and hybrid checks calculated as average percent shattered pods +/−SE. Pod shatter tolerance was determined using a lab phenotyping method. A and C indicate functional IND-A and IND-C alleles, respectively and lower case a and c indicate deletions of IND-A and IND-C alleles, respectively. Single asterisk indicates a significant difference (T-test, $p<0.01$) and double asterisk indicates a significant difference (T-test, $p<0.05$).

Sequence listings are described in the following Table 4. Nucleic acid sequences listed in the accompanying sequence listing and referenced herein are shown using standard letter abbreviations for nucleotide bases. Only one strand of each nucleic acid sequence is shown, but the complementary strand is understood to be included by any reference to the displayed strand.

TABLE 4

| SEQ ID NO: | DESCRIPTION |
|---|---|
| SEQ ID NO: 1 | BnIND A genome protein |
| SEQ ID NO: 2 | G00010BC IND genomic seq A genome (Native Deletion) |
| SEQ ID NO: 3 | G00010BC BnIND genomic seq C genome |
| SEQ ID NO: 4 | G00010BC BnIND C genome dropout |
| SEQ ID NO: 5 | G00010BC BnALC genomic seq A genome |
| SEQ ID NO: 6 | G00010BC BnALC genomic seq C genome |
| SEQ ID NO: 7 | G00010BC BnPGAZ genomic seq A genome |
| SEQ ID NO: 8 | G00010BC BnPGAZ A genome dropout |
| SEQ ID NO: 9 | G00010BC BnPGAZ genomic seq C genome |
| SEQ ID NO: 10 | G00010BC BnPGAZ C genome dropout |
| SEQ ID NO: 11 | NS1822BC BnIND genomic seq A genome |
| SEQ ID NO: 12 | NS1822BC BnIND A genome dropout |
| SEQ ID NO: 13 | NS1822BC BnIND genomic seq C genome |
| SEQ ID NO: 14 | NS1822BC BnIND C genome dropout |
| SEQ ID NO: 15 | NS1822BC BnPGAZ genomic seq A genome |
| SEQ ID NO: 16 | NS1822BC BnPGAZ A genome dropout 1 |
| SEQ ID NO: 17 | NS1822BC BnPGAZ A genome dropout 2 |
| SEQ ID NO: 18 | NS1822BC BnPGAZ genomic seq C genome |
| SEQ ID NO: 19 | NS1822BC BnPGAZ C genome dropout 1 |
| SEQ ID NO: 20 | NS1822BC BnPGAZ C genome dropout 2 |
| SEQ ID NO: 21 | NS1822BC BnPGAZ C genome dropout 3 |
| SEQ ID NO: 22 | G00555MC BnIND genomic seq A genome |
| SEQ ID NO: 23 | G00555MC BnIND A genome dropout |
| SEQ ID NO: 24 | G00555MC BnIND genomic seq C genome |
| SEQ ID NO: 25 | G00555MC BnIND C genome dropout |
| SEQ ID NO: 26 | G00555MC BnALC genomic seq A genome |
| SEQ ID NO: 27 | G00555MC BnALC genomic seq C genome |
| SEQ ID NO: 28 | G00555MC BnPGAZ genomic seq A genome |
| SEQ ID NO: 29 | G00555MC BnPGAZ A genome dropout |
| SEQ ID NO: 30 | G00555MC BnPGAZ genomic seq C genome |
| SEQ ID NO: 31 | G00555MC BnPGAZ C genome dropout |
| SEQ ID NO: 32 | IND_A_001_F001 WT Forward Primer |
| SEQ ID NO: 33 | IND_A_001_R001 WT Reverse Primer |
| SEQ ID NO: 34 | BP_F003 Deletion Forward Primer |
| SEQ ID NO: 35 | BP_R003 Deletion Reverse Primer |
| SEQ ID NO: 36 | N101T11-F001 WT Forward Primer |
| SEQ ID NO: 37 | N101T11-R001 WT Reverse Primer |
| SEQ ID NO: 38 | N101T11-001-X001 WT Probe |
| SEQ ID NO: 39 | N101T10-F001 Deletion F Primer |
| SEQ ID NO: 40 | N101T10-R001 Deletion R Primer |
| SEQ ID NO: 41 | N101T10-001-X001 Deletion Probe |
| SEQ ID NO: 42 | N101T10-F002 Deletion Forward Primer |
| SEQ ID NO: 43 | N101T10-R002 Deletion Reverse Primer |
| SEQ ID NO: 44 | N101T10-001-X002 Deletion Probe |
| SEQ ID NO: 45 | Probe Sequence for BnIND-A locus SNPs (see Table 5 herein) |
| SEQ ID NO: 46 | N101T10-R003 Deletion Reverse Primer |
| SEQ ID NO: 47 | N101T10-001-X003 Deletion Probe |

TABLE 4-continued

| SEQ ID NO: | DESCRIPTION |
|---|---|
| SEQ ID NO: 48 | N101T11-R002 WT Forward Primer |
| SEQ ID NO: 49 | N101T11-001-X002 WT Probe |
| SEQ ID NO: 50 | N101T11-001-X003 WT Probe |
| SEQ ID NO: 51 | BP_F002 Deletion Forward Primer |
| SEQ ID NO: 52 | BP_R002 Deletion Reverse Primer |
| SEQ ID NO: 53 | BP_F003 Deletion Forward Primer |
| SEQ ID NO: 54 | BP_R003 Deletion Reverse Primer |
| SEQ ID NO: 55 | BP_R004 Deletion Reverse Primer |
| SEQ ID NO: 56 | BP_R005 Deletion Reverse Primer |
| SEQ ID NO: 57 | BP_R006 Deletion Reverse Primer |
| SEQ ID NO: 58 | IND_A_001_R002 WT Reverse Primer |
| SEQ ID NOs: 59-160 | Probe Sequences for BnIND-A locus SNPs (see Tables 4 and 5 herein) |

DETAILED DESCRIPTION

Terms and Definitions

"ALCATRAZ gene", "ALC gene", "ALCATRAZ allele" or "ALC allele" refers herein to a gene that can contribute to pod shatter resistance in *B. napus* and *A. thaliana*. ALC gene plays a role in cell separation during fruit dehiscence by promoting the differentiation of a cell layer that is the site of separation between the valves and the replum within the dehiscence zone. Examples of ALC gene sequences include BnALC-A (e.g. SEQ ID NO:5 or 26) and BnALC-C (SEQ ID NO:6 or 27).

An "allele" is one of several alternative forms of a gene occupying a given locus on a chromosome. When all the alleles present at a given locus on a chromosome are the same, that plant is "homozygous" at that locus. If the alleles present at a given locus on a chromosome differ, that plant is "heterozygous" at that locus. In *B. napus*, a plant can be homozygous wildtype for the IND gene in the A genome, but heterozygous mutant for the IND gene in the C genome.

An "amplicon" is amplified nucleic acid, e.g., a nucleic acid that is produced by amplifying a template nucleic acid by any available amplification method (e.g., PCR, LCR, transcription, or the like).

"Backcrossing" refers to the process whereby hybrid progeny plants are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. Backcrossing has been widely used to introduce new traits into plants. See e.g., Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the nonrecurrent parent.

"*Brassica*" refers to any one of *Brassica napus* (AACC, 2n=38), *Brassica juncea* (AABB, 2n=36), *Brassica carinata* (BBCC, 2n=34), *Brassica rapa* (syn. *B. campestris*) (AA, 2n=20), *Brassica oleracea* (CC, 2n=18) or *Brassica nigra* (BB, 2n=16).

A "Cas protein" refers to a polypeptide encoded by a Cas (CRISPR-associated) gene. A Cas protein includes but is not limited to: a Cas9 protein, a Cpf1 (Cas12) protein, a C2c1 protein, a C2c2 protein, a C2c3 protein, Cas3, Cas3-HD, Cas 5, Cas7, Cas8, Cas10, or combinations or complexes of these. A Cas protein may be a "Cas endonuclease" or "Cas effector protein", that when in complex with a suitable polynucleotide component, is capable of recognizing, binding to, and optionally nicking or cleaving all or part of a specific polynucleotide target sequence.

A "Cas endonuclease" may comprise domains that enable it to function as a double-strand-break-inducing agent. A "Cas endonuclease" may also comprise one or more modifications or mutations that abolish or reduce its ability to cleave a double-strand polynucleotide (dCas). In some aspects, the Cas endonuclease molecule may retain the ability to nick a single-strand polynucleotide (for example, a D10A mutation in a Cas9 endonuclease molecule) (nCas9). When complexed with a guide polynucleotide, the guide polynucleotide/Cas endonuclease complex", (or "guide polynucleotide/Cas endonuclease system", "guide polynucleotide/Cas complex", "guide polynucleotide/Cas system" and "guided Cas system" or "Polynucleotide-guided endonuclease", "PGEN"" are capable of directing the Cas endonuclease to a DNA target site, enabling the Cas endonuclease to recognize, bind to, and nick or cleave (introduce a single or double-strand break) the DNA target site. A guided Cas system referred to herein can comprise Cas protein(s) and suitable polynucleotide component(s) of any known CRISPR systems (Horvath and Barrangou, 2010, *Science* 327:167-170; Makarova et al. 2015, *Nature Reviews Microbiology* Vol. 13:1-15; Zetsche et al., 2015, *Cell* 163, 1-13; Shmakov et al., 2015, *Molecular Cell* 60, 1-13).

As used herein, the term "commercially useful" refers to plant lines and hybrids that have sufficient plant vigor and fertility, such that a crop of the plant line or hybrid can be produced by farmers using conventional farming equipment. In particular embodiments, plant commodity products with described components and/or qualities may be extracted from plants or plant materials of the commercially useful variety. For example, oil comprising desired oil components may be extracted from the seed of a commercially useful plant line or hybrid utilizing conventional crushing and extraction equipment. In another example, canola meal may be prepared from the crushed seed of commercially useful plant lines which are provided by the invention and which have one or more BnIND-A deletion allele disclosed herein. In certain embodiments, a commercially useful plant line is an inbred line or a hybrid line. "Agronomically elite" lines and hybrids typically have desirable agronomic characteristics; for example and without limitation: improved yield of at least one plant commodity product; maturity; disease resistance; and standability.

The term "cross" (or "crossed") refers to the fusion of gametes via pollination to produce progeny (e.g., cells, seeds, and plants). This term encompasses both sexual crosses (i.e., the pollination of one plant by another) and selfing (i.e., self-pollination, for example, using pollen and ovule from the same plant).

The terms "dropout", "gene dropout", "knockout" and "gene knockout" refer to a DNA sequence of a cell (e.g. the BnIND-C gene or BnALC gene) that has been excised from the genome by targeted deletion mediated by a Cas protein.

The term "elite line" means any line that has resulted from breeding and selection for superior agronomic performance. An elite plant is any plant from an elite line.

The term "gene" (or "genetic element") may refer to a heritable genomic DNA sequence with functional significance. A gene includes a nucleic acid fragment that expresses a functional molecule such as, but not limited to, a specific protein, including regulatory sequences preceding (5' non-coding sequences) and following (3' non-coding sequences) the coding sequence, as well as intervening intron sequences. The term "gene" may also be used to refer to, for example and without limitation, a cDNA and/or an mRNA encoded by a heritable genomic DNA sequence.

The term "genome" as it applies to a prokaryotic and eukaryotic cell or organism cells encompasses not only chromosomal DNA found within the nucleus, but organelle DNA found within subcellular components (e.g., mitochondria, or plastid) of the cell.

A "genomic sequence" or "genomic region" is a segment of a chromosome in the genome of a cell that is present on either side of the target site or, alternatively, also comprises the target site or a portion thereof. An "endogenous genomic sequence" refers to genomic sequence within a plant cell, (e.g. an endogenous genomic sequence of an IND gene present within the genome of a *Brassica* plant cell).

A "genomic locus" as used herein refers to the genetic or physical location on a chromosome of a gene. As used herein, "gene" includes a nucleic acid fragment that expresses a functional molecule such as, but not limited to, a specific protein coding sequence and regulatory elements, such as those preceding (5' non-coding sequences) and following (3' non-coding sequences) the coding sequence.

The term "genotype" refers to the physical components, i.e., the actual nucleic acid sequence at one or more loci in an individual plant.

The term "germplasm" refers to genetic material of or from an individual plant or group of plants (e.g., a plant line, variety, and family), and a clone derived from a plant or group of plants. A germplasm may be part of an organism or cell, or it may be separate (e.g., isolated) from the organism or cell. In general, germplasm provides genetic material with a specific molecular makeup that is the basis for hereditary qualities of the plant. As used herein, "germplasm" refers to cells of a specific plant; seed; tissue of the specific plant (e.g., tissue from which new plants may be grown); and non-seed parts of the specific plant (e.g., leaf, stem, pollen, and cells).

The term "germplasm" is synonymous with "genetic material," and it may be used to refer to seed (or other plant material) from which a plant may be propagated. A "germplasm bank" may refer to an organized collection of different seed or other genetic material (wherein each genotype is uniquely identified) from which a known cultivar may be cultivated, and from which a new cultivar may be generated. In embodiments, a germplasm utilized in a method or plant as described herein is from a canola line or variety. In particular examples, a germplasm is seed of the canola line or variety. In particular examples, a germplasm is a nucleic acid sample from the canola line or variety.

A "haplotype" is the genotype of an individual at a plurality of genetic loci. In some examples, the genetic loci described by a haplotype may be physically and genetically linked; i.e., the loci may be positioned on the same chromosome segment.

The terms "increased" or "improved" in connection with "pod shatter tolerance" or "pod shatter resistance" as well as "reduced seed shattering" are used herein to reference decreased seed shatter tendency and/or a delay in the timing of seed shattering, in particular until harvest, of *Brassica* plants, the fruits of which normally do not mature synchronously, but sequentially, so that some pods burst open and shatter their seeds before or during harvest.

The term "INDEHISCENT gene", "IND gene", "INDEHISCENT allele" or "IND allele" refers herein to a gene that can contribute to pod shatter resistance in *B. napus* and *A. thaliana*. IND encodes a member of an atypical class of eukaryotic bHLH proteins which are required for seed dispersal. IND genes are involved in the differentiation of all three cell types required for fruit dehiscence and acts as the key regulator in a network that controls specification of the valve margin. Examples of IND gene sequences include BnIND-A (SEQ ID NOs:2, 11, and 22) and BnIND-C (SEQ ID NOs:3, 13, and 24).

In connection with pod shatter phenotypes evaluated herein, "fully shattered pods" are those with both valves detached from the replum and all seeds dispersed. "Half shattered pods" are those with one valve fully or partially detached from the replum, seeds dispersed, though the second valve is still attached and all or some seeds remain between the attached valve and the septum. "Unshattered pods" have both valves attached to the replum and seeds are contained between both valves and the septum. The "Percent shattered pods" or "SHTPC" is used herein as a quantitative measure of seed pod integrity after a laboratory assay or field trial shatter inducing treatment. In laboratory assay results, SHTPC refers to the number of fully shattered+half shattered pods/total number of pods*100%. In field trial results, SHTPC refers to the number of fully shattered/total number of pods*100%.

As used herein, the term "introgression" refers to the transmission of an allele at a genetic locus into a genetic background. In some embodiments, introgression of a specific allele form at the locus may occur by transmitting the allele form to at least one progeny via a sexual cross between two parents of the same species, where at least one of the parents has the specific allele form in its genome. Progeny comprising the specific allele form may be repeatedly backcrossed to a line having a desired genetic background. Backcross progeny may be selected for the specific allele form, so as to produce a new variety wherein the specific allele form has been fixed in the genetic background. In some embodiments, introgression of a specific allele form may occur by recombination between two donor genomes (e.g., in a fused protoplast), where at least one of the donor genomes has the specific allele form in its genome. Introgression may involve transmission of a specific allele form that may be, for example and without limitation, a selected allele form of a marker allele, a QTL, and/or a transgene. In this disclosure, introgression may involve transmission of one or more alleles of the native BnIND-A deletion (provided by this disclosure) into a progeny plant.

As used herein an "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component. For example and without limitation, a nucleic acid may be isolated from a chromosome by breaking chemical bonds connecting the nucleic acid to the remaining DNA in the chromosome and/or the other material previously associated with the nucleic acid in its cellular milieu (e.g., the nucleus). Nucleic acid molecules and proteins that have been "isolated" include nucleic acid molecules and proteins that are enriched or purified. The term also embraces nucleic acids and proteins prepared by recombinant expression in a host cell, as well as chemically-synthesized nucleic acid molecules, proteins, and peptides.

Marker: Unlike DNA sequences that encode proteins, which are generally well-conserved within a species, other regions of DNA (e.g., non-coding DNA and introns) tend to develop and accumulate polymorphism, and therefore may be variable between individuals of the same species. The genomic variability can be of any origin, for example, the variability may be due to DNA insertions, deletions, duplications, repetitive DNA elements, point mutations, recombination events, and the presence and sequence of transposable elements. Such regions may contain useful molecular genetic markers. In general, any differentially inherited polymorphic trait (including nucleic acid polymorphisms) that segregates among progeny is a potential marker.

As used herein, the terms "marker" and "molecular marker" refer to a nucleic acid or encoded product thereof (e.g., a protein) used as a point of reference when identifying a linked locus. Thus, a marker may refer to a gene or nucleic acid that can be used to identify plants having a particular allele. A marker may be described as a variation at a given genomic locus. A genetic marker may be a short DNA sequence, such as a sequence surrounding a single base-pair change (single nucleotide polymorphism, or "SNP"), or a long one, for example, a microsatellite/simple sequence repeat ("SSR"). A "marker allele" or "marker allele form" refers to the version of the marker that is present in a particular individual. The term "marker" as used herein may refer to a cloned segment of chromosomal DNA, and may also or alternatively refer to a DNA molecule that is complementary to a cloned segment of chromosomal DNA. The term also refers to nucleic acid sequences complementary to genomic marker sequences, such as nucleic acid primers and probes.

A marker may be described, for example, as a specific polymorphic genetic element at a specific location in the genetic map of an organism. A genetic map may be a graphical representation of a genome (or a portion of a genome, such as a single chromosome) where the distances between landmarks on the chromosome are measured by the recombination frequencies between the landmarks. A genetic landmark can be any of a variety of known polymorphic markers, for example and without limitation: simple sequence repeat (SSR) markers; restriction fragment length polymorphism (RFLP) markers; and single nucleotide polymorphism (SNP) markers. As one example, SSR markers can be derived from genomic or expressed nucleic acids (e.g., expressed sequence tags (ESTs)).

Additional markers include, for example and without limitation, ESTs; amplified fragment length polymorphisms (AFLPs) (Vos et al., 1995, *Nucl. Acids Res.* 23:4407; Becker et al., 1995, *Mol. Gen. Genet.* 249:65; Meksem et al., 1995, *Mol. Gen. Genet.* 249:74); randomly amplified polymorphic DNA (RAPD); and isozyme markers. Isozyme markers may be employed as genetic markers, for example, to track isozyme markers or other types of markers that are linked to a particular first marker. Isozymes are multiple forms of enzymes that differ from one another with respect to amino acid sequence (and therefore with respect to their encoding nucleic acid sequences). Some isozymes are multimeric enzymes containing slightly different subunits. Other isozymes are either multimeric or monomeric, but have been cleaved from a pro-enzyme at different sites in the pro-enzyme amino acid sequence. Isozymes may be characterized and analyzed at the protein level or at the nucleic acid level. Thus, any of the nucleic acid based methods described herein can be used to analyze isozyme markers in particular examples.

Accordingly, genetic marker alleles that are polymorphic in a population can be detected and distinguished by one or more analytic methods such as, PCR-based sequence specific amplification methods, RFLP analysis, AFLP analysis, isozyme marker analysis, SNP analysis, SSR analysis, allele specific hybridization (ASH) analysis, detection of amplified variable sequences of the plant genome, detection of self-sustained sequence replication, detection of simple sequence repeats (SSRs), randomly amplified polymorphic DNA (RAPD) analysis. Thus, in certain examples of the invention, such known methods can be used to detect the BnIND-A deletion breakpoint and flanking sequence(s) as well as the SNP markers for detecting the presence or absence of the BnIND-A deletion allele which are disclosed herein. See, e.g., Tables 1, 4, and 5 herein.

Numerous statistical methods for determining whether markers are genetically linked to a QTL (or to another marker) are known to those of skill in the art and include, for example and without limitation, standard linear models (e.g., ANOVA or regression mapping; Haley and Knott, 1992, *Heredity* 69:315); and maximum likelihood methods (e.g., expectation-maximization algorithms; Lander and Botstein, 1989, *Genetics* 121:185-99; Jansen, 1992, *Theor. Appl. Genet.* 85:252-60; Jansen, 1993, *Biometrics* 49:227-31; Jansen, 1994, "Mapping of quantitative trait loci by using genetic markers: an overview of biometrical models," In J. W. van Ooijen and J. Jansen (eds.), Biometrics in Plant breeding: applications of molecular markers, pp. 116-24 (CPRO-DLO Netherlands); Jansen, 1996, *Genetics* 142: 305-11; and Jansen and Stam, 1994, *Genetics* 136:1447-55).

Exemplary statistical methods include single point marker analysis; interval mapping (Lander and Botstein, 1989, *Genetics* 121:185); composite interval mapping; penalized regression analysis; complex pedigree analysis; MCMC analysis; MQM analysis (Jansen, 1994, *Genetics* 138:871); HAPLO-IM+ analysis, HAPLO-MQM analysis, and HAPLO-MQM+ analysis; Bayesian MCMC; ridge regression; identity-by-descent analysis; and Haseman-Elston regression, any of which are suitable in the context of particular embodiments of the invention. Alternative statistical methods applicable to complex breeding populations that may be used to identify and localize QTLs in particular examples are described in U.S. Pat. No. 6,399,855 and PCT International Patent Publication No. W00149104 A2. All of these approaches are computationally intensive and are usually performed with the assistance of a computer-based system comprising specialized software. Appropriate statistical packages are available from a variety of public and commercial sources, and are known to those of skill in the art.

"Marker-assisted selection" (MAS) is a process by which phenotypes are selected based on marker genotypes. Marker assisted selection includes the use of marker genotypes for identifying plants for inclusion in and/or removal from a breeding program or planting.

Molecular marker technologies generally increase the efficiency of plant breeding through MAS. A molecular marker allele that demonstrates linkage disequilibrium with a desired phenotypic trait (e.g., a QTL) provides a useful tool for the selection of the desired trait in a plant population. The key components to the implementation of an MAS approach are the creation of a dense (information rich) genetic map of molecular markers in the plant germplasm; the detection of at least one QTL based on statistical associations between marker and phenotypic variability; the definition of a set of particular useful marker alleles based on the results of the QTL analysis; and the use and/or extrapolation of this information to the current set of breeding germplasm to enable marker-based selection decisions to be made.

The closer a particular marker is to a gene that encodes a polypeptide that contributes to a particular phenotype (whether measured in terms of genetic or physical distance), the more tightly-linked is the particular marker to the phenotype. In view of the foregoing, it will be appreciated that the closer (whether measured in terms of genetic or physical distance) that a marker is linked to a particular gene, the more likely the marker is to segregate with that gene (e.g., the BnIND-A deletion disclosed herein) and its associated phenotype (e.g., the contribution to pod shatter tolerance of the BnIND-A deletion disclosed herein). Thus, the extremely tightly linked genetic markers of the BnIND-A deletion disclosed herein can be used in MAS programs to identity canola varieties that have or can generate progeny that have increased pod shatter tolerance (when compared to parental varieties and/or otherwise isogenic plants lacking the BnIND-A deletion), to identify individual canola plants comprising this increased pod shatter tolerance trait, and to breed this trait into other canola varieties to improve their pod shatter tolerance.

A "marker set" or a "set" of markers or probes refers to a specific collection of markers (or data derived therefrom) that may be used to identify individuals comprising a trait of interest. In some embodiments, a set of markers linked to a BnIND-A deletion may be used to identify a *Brassica* plant comprising one or more allele of the BnIND-A deletion disclosed herein. Data corresponding to a marker set (or data derived from the use of such markers) may be stored in an electronic medium. While each marker in a marker set may possess utility with respect to trait identification, individual markers selected from the set and subsets including some, but not all, of the markers may also be effective in identifying individuals comprising the trait of interest.

A "mutated gene" or "modified gene" is a gene that has been altered through human intervention. Such a "mutated" or "modified" gene has a sequence that differs from the sequence of the corresponding non-mutated gene by at least one nucleotide addition, deletion, or substitution. In certain embodiments of the disclosure, the mutated gene comprises an excision or deletion of a sequence of nucleotides within that results from two double strands break which are specifically targeted to a genomic sequence by guide polynucleotide/Cas endonuclease system as disclosed herein. A "mutated" or "modified" plant is a plant comprising a mutated gene or deletion. As used herein, a "targeted mutation" is a mutation in a gene (referred to as the target gene), including a native gene, that was made by altering a target sequence within the target gene using any method known to one skilled in the art, including a method involving a guided Cas endonuclease system as disclosed herein.

As used herein the term "native gene" refers to a gene as found in its natural endogenous location with its own regulatory sequences. In the context of this disclosure, a "mutated" or "modified" gene is not a native gene.

As used herein, a 'nucleic acid molecule" is a polymeric form of nucleotides, which can include both sense and anti-sense strands of RNA, cDNA, genomic DNA, and synthetic forms and mixed polymers of the above. A nucleotide refers to a ribonucleotide, deoxynucleotide, or a modified form of either type of nucleotide. A "nucleic acid molecule" as used herein is synonymous with "nucleic acid", "nucleotide sequence", "nucleic acid sequence", and "polynucleotide." The term includes single- and double-stranded forms of DNA. A nucleic acid molecule can include either or both naturally occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., peptides), intercalators (e.g., acridine, psoralen, etc.), chelators, alkylators, and modified linkages (e.g., alpha anomeric nucleic acids, etc.). The term "nucleic acid molecule" also includes any topological conformation, including single-stranded, double-stranded, partially duplexed, triplexed, hairpinned, circular, and padlocked conformations. An "endogenous nucleic acid sequence" refers to a nucleic acid sequence within a plant cell, (e.g. an endogenous allele of an IND gene present within the genome of a *Brassica* plant cell).

The term "single-nucleotide polymorphism" (SNP) refers to a DNA sequence variation occurring when a single nucleotide in the genome (or other shared sequence) differs between members of a species or paired chromosomes in an individual. In some examples, markers linked to a BnIND-A deletion disclosed herein are SNP markers. Recent high-throughput genotyping technologies such as GoldenGate® and INFINIUM® assays (Illumina, San Diego, CA) may be used in accurate and quick genotyping methods by multiplexing SNPs from 384-plex to >100,000-plex assays per sample.

As used herein, "phenotype" means the detectable characteristics (e.g. pod shatter tolerance) of a cell or organism which can be influenced by genotype.

As used herein, the term "plant material" refers to any processed or unprocessed material derived, in whole or in part, from a plant. For example, and without limitation, a plant material may be a plant part, a seed, a fruit, a leaf, a root, a plant tissue, a plant tissue culture, a plant explant, or a plant cell.

As used herein, the term "plant" may refer to a whole plant, a cell or tissue culture derived from a plant, and/or any part of any of the foregoing. Thus, the term "plant" encompasses, for example and without limitation, whole plants; plant components and/or organs (e.g., leaves, stems, and roots); plant tissue; seed; and a plant cell. A plant cell may be, for example and without limitation, a cell in and/or of a plant, a cell isolated from a plant, and a cell obtained through culturing of a cell isolated from a plant. Thus, the term *Brassica* "plant" may refer to, for example and without limitation, a whole *Brassica* plant; multiple *Brassica* plants;

*Brassica* plant cell(s); *Brassica* plant protoplast; *Brassica* tissue culture (e.g., from which a canola plant can be regenerated); *Brassica* plant callus; *Brassica* plant parts (e.g., seed, flower, cotyledon, leaf, stem, bud, root, and root tip); and *Brassica* plant cells that are intact in a *Brassica* plant or in a part of a *Brassica* plant.

As used herein, a plant or *Brassica* “line” refers to a group of plants that display little genetic variation (e.g., no genetic variation) between individuals for at least one trait. Inbred lines may be created by several generations of self-pollination and selection or, alternatively, by vegetative propagation from a single parent using tissue or cell culture techniques. As used herein, the terms “cultivar,” “variety,” and “type” are synonymous, and these terms refer to a line that is used for commercial production.

Trait or phenotype: The terms “trait” and “phenotype” are used interchangeably herein. For the purposes of the present disclosure, the traits of particular interest are the pod shatter tolerance trait disclosed herein.

A “variety” or “cultivar” is a plant line that is used for commercial production which is distinct, stable and uniform in its characteristics when propagated. In the case of a hybrid variety or cultivar, the parental lines are distinct, stable, and uniform in their characteristics.

The term “POLYGALACTURONASE gene”, “POLYGALACTURONASE allele”, “PGAZ gene” or “PGAZ allele” refers herein to “polygalacturonase expressed in abscission zone” gene. PGAZ is involved in pectin degradation and subsequent loss of cell cohesion (Hadfield and Bennet 1998, *Plant physiology,* 117(2), 337-343.). PGAZ expression increases during a number of developmental processes thought to involve cell wall breakdown, including silique shattering (Jenkins et al., 1996, *Journal of Exp. Botany,* 47(1), 111-115; Jenkins et al., 1999, *Plant, Cell & Environment,* 22(2), 159-167; Ferrándiz, 2002, *Journal of Exp. Botany,* 53(377), 2031-2038). Examples of PGAZ genes include BnPGAZ-A (SEQ ID No:7, 15, or 28) and BnPGAZ-C (SEQ ID NO:9, 18, or 30).

Detection of Native Deletion in BnIND-A.

The methods and assays of the disclosure are based, at least in part, on the discovery of an unexpected deletion of genomic sequence that affects the INDEHISCENT gene on chromosome N03 (BnIND-A) of *B. napus.* The deletion was discovered by whole genome sequencing *B. napus* line G00010BC and comparing its BnIND-A sequence to that of a number of other reference genomes, which revealed a large deleted segment. As compared to reference genomes for lines NS1822BC, DH12075_v1.1, Darmor_v4.1.1, and G0055MC, the BnIND-A deletion corresponds to a deleted segment (loss of genomic sequence) ranging from about 200 kb to about 310 kb in length. See Example 1 herein.

The BnIND-A deletion disclosed herein can be detected by nucleotide sequencing and/or amplification of the genomic DNA, which will reveal the absence of the 200 kb to about 310 kb deleted genomic segment disclosed herein. For example, the BnIND-A deletion can be detected by nucleotide sequencing and/or amplification of genomic sequencing flanking and including the deletion breakpoint locus at positions 10,002-10,003 of SEQ ID NO:2. Such sequencing or amplification of a BnIND-A deletion allele will produce a sequencing product or amplicon comprising the following deletion breakpoint locus (start breakpoint and end breakpoint positions shown in bold and underlined): ATTTCTC<u>TA</u> TTTGTTTT (SEQ ID NO:2, positions 9995-1011).

In particular examples, detecting the BnIND-A deletion can include DNA sequencing, amplification, or the combined amplification and sequencing of the breakpoint locus and 5 bp or more, 10 bp or more, 15 bp or more, 20 bp or more, 30 bp or more, 40 bp or more, 50 bp or more, 60 bp or more, 70 bp or more, 80 bp or more, 90 bp or more, 100 bp or more, 110 bp or more, 120 bp or more, 130 bp or more, 140 bp or more, 150 bp or more, 175 bp or more, 200 bp or more, 250 bp or more, 300 bp or more, 350 bp or more, 400 bp or more, 450 bp or more, 500 bp or more, 550 bp or more, or 600 bp or more of flanking sequence that is (i) upstream of (i.e., located 5' to) the deletion start breakpoint at position 10,002 of SEQ ID NO:2 and/or (ii) downstream of (i.e., located 3' to) the deletion end breakpoint at position 10,003 of SEQ ID NO:2. Thus, in particular examples, the BnIND-A deletion disclosed herein can be detected by amplifying genomic sequence to produce an amplicon comprising one or more of the BnIND-A deletion allele sequences identified in Table 1 above. Additionally, the BnIND-A deletion disclosed herein can be detected by nucleotide sequencing to detect the presence of the genomic sequence (including, e.g., by first amplifying genomic sequence and sequencing the amplicon or amplified genomic sequence) comprising a BnIND-A deletion allele sequence identified in Table 1 above.

By contrast, wildtype BnIND-A sequence does not include the deletion breakpoint locus sequence corresponding to positions 10,002-10,003 of SEQ ID NO:2 because in wild type genomic DNA, the deletion start breakpoint (position 10,002 of SEQ ID NO:2) and end breakpoint (position 10,003 of SEQ ID NO:2) are separated by an intervening genomic segment (the deletion segment) that can range from about 200 kb to about 310 kb in length. Due to the presence of this intervening segment, sequencing or amplification of wildtype BnIND-A sequence will not produce a sequencing product or amplicon comprising any of the sequences disclosed in Table 1.

Detection of the BnIND-A deletion allele disclosed herein can be done using any method for detecting polymorphisms. Additionally, such methods can be used to detect a polymorphic marker that is genetically linked to the BnIND-A deletion allele. These methods include allele-specific amplification and PCR based amplification assays such as TaqMan, rhAmp-SNP, KASPar, and molecular beacons. Such an assay can include the use of one or more probes that detect the breakpoint locus of the BnIND-A deletion allele, a marker associated with the deletion, or an amplicon that is selectively amplified by amplification of genomic sequence comprising the BnIND-A deletion. Optionally, such an assay can further include an additional set of primers and/or one or more probes that detect the presence of a BnIND-A (e.g., wildtype allele) that includes the intervening ~200 kb to ~310 kb genomic segment between deletion breakpoints, as disclosed herein.

Additional methods for genotyping and detecting the BnIND-A deletion allele disclosed herein (or a linked marker) include but are not limited to, hybridization, primer extension, oligonucleotide ligation, nuclease cleavage, minisequencing and coded spheres. Such methods are reviewed in publications including Gut, 2001, *Hum. Mutat.* 17:475; Shi, 2001, *Clin. Chem.* 47:164; Kwok, 2000, *Pharmacogenomics* 1:95; Bhattramakki and Rafalski, “Discovery and application of single nucleotide polymorphism markers in plants”, in PLANT GENOTYPING: THE DNA FINGERPRINTING OF PLANTS (CABI Publishing, Wallingford 2001). A wide range of commercially available technologies utilize these and other methods to interrogate the BnIND-A deletion allele disclosed herein (or a linked marker), including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Infinium Bead Chip™ and GoldenGate™ allele-specific extension PCR-based assay (Illumina, San Diego, Calif.).

In one method, the BnIND-A deletion allele can be detected by confirming the absence of genomic sequence comprising one or more N03 genomic markers, e.g., SNPs, located within the deleted genomic segment disclosed herein. This absence can be confirmed using a commercially available substrate (e.g., Infinium Bead Chip™) having an array of probes for markers on *Brassica* chromosome N03. These are suitable for individual or high-throughput screening of N03 markers in genomic samples. For example, Table 4 below provides SNP markers and probes that bind to the markers, which are located within the deleted N03 genomic segment disclosed herein. Because genomic DNA comprising the BnIND-A deletion allele disclosed herein does not include the marker sequences that bind to the probes in Table 4 below, a sample containing genomic DNA or amplified genomic DNA sequence comprising the BnIND-A deletion will not bind to and will not generate a signal from these probes. By contrast, wildtype genomic DNA sequence retains the deleted segment and, therefore, can bind to and generate a signal from these probes. In view of the foregoing, one or more SNP marker shown in Table 4 can be used to distinguish the BnIND-A deletion genomic sequence disclosed herein from wildtype BnIND-A genomic sequence. Table 4 identifies probe sequence, commercial marker name (from Illumina), N03 SNP maker name, assay chemistry type, and genomic position (using DH12075 reference genome) of probes that detect wildtype sequence located within the deleted genomic segment disclosed herein.

TABLE 4

| Probe Sequence | Marker Name | SNP Name | Chemistry | Genomic Position |
|---|---|---|---|---|
| SEQ ID NO: 59 | N0014XD-001-I002 | N0014XD-001 | Illumina | 14,453,580 |
| SEQ ID NO: 60 | N0014XE-001-I002 | N0014XE-001 | Illumina | 14,454,264 |
| SEQ ID NO: 61 | N0014XF-001-I002 | N0014XF-001 | Illumina | 14,479,202 |
| SEQ ID NO: 62 | N0014XG-001-I002 | N0014XG-001 | Illumina | 14,479,225 |
| SEQ ID NO: 63 | N0014XH-001-I002 | N0014XH-001 | Illumina | 14,479,295 |
| SEQ ID NO: 64 | N0014XJ-001-I002 | N0014XJ-001 | Illumina | 14,483,678 |
| SEQ ID NO: 65 | N0014XK-001-I002 | N0014XK-001 | Illumina | 14,484,035 |
| SEQ ID NO: 66 | N0014XM-001-I002 | N0014XM-001 | Illumina | 14,484,391 |
| SEQ ID NO: 67 | N002C2M-001-I002 | N002C2M-001 | Illumina | 14,484,901 |
| SEQ ID NO: 68 | N0014XP-001-I003 | N0014XP-001 | IlluminaXT | 14,508,983 |
| SEQ ID NO: 69 | N0014XP-001-Q001 | N0014XP-001 | TaqMan | 14,508,983 |
| SEQ ID NO: 70 | N0014XP-001-I002 | N0014XP-001 | Illumina | 14,508,983 |
| SEQ ID NO: 71 | N0014XR-001-I002 | N0014XR-001 | Illumina | 14,509,547 |
| SEQ ID NO: 72 | N0014XT-001-I002 | N0014XT-001 | Illumina | 14,531,140 |
| SEQ ID NO: 73 | N0014XU-001-I002 | N0014XU-001 | Illumina | 14,531,428 |
| SEQ ID NO: 74 | N0014XV-001-I002 | N0014XV-001 | Illumina | 14,535,159 |
| SEQ ID NO: 75 | N0014MV-001-I003 | N0014MV-001 | IlluminaXT | 14,543,573 |
| SEQ ID NO: 76 | N0014MV-001-Q001 | N0014MV-001 | TaqMan | 14,543,573 |
| SEQ ID NO: 77 | N0014MV-001-I002 | N0014MV-001 | Illumina | 14,543,573 |
| SEQ ID NO: 78 | N0014XX-001-I002 | N0014XX-001 | Illumina | 14,544,098 |
| SEQ ID NO: 79 | N0014XY-001-I002 | N0014XY-001 | Illumina | 14,584,738 |
| SEQ ID NO: 80 | N0014Y0-001-I002 | N0014Y0-001 | Illumina | 14,599,964 |
| SEQ ID NO: 81 | N0014Y1-001-I002 | N0014Y1-001 | Illumina | 14,600,153 |
| SEQ ID NO: 82 | N0014Y2-001-I002 | N0014Y2-001 | Illumina | 14,609,027 |
| SEQ ID NO: 83 | N0014Y3-001-I002 | N0014Y3-001 | Illumina | 14,611,514 |
| SEQ ID NO: 84 | N0014Y4-001-I002 | N0014Y4-001 | Illumina | 14,617,650 |
| SEQ ID NO: 85 | N0014Y5-001-I002 | N0014Y5-001 | Illumina | 14,622,130 |
| SEQ ID NO: 86 | N0014Y6-001-I003 | N0014Y6-001 | IlluminaXT | 14,626,122 |
| SEQ ID NO: 87 | N0014Y6-001-Q001 | N0014Y6-001 | TaqMan | 14,626,122 |
| SEQ ID NO: 88 | N0014Y6-001-I002 | N0014Y6-001 | Illumina | 14,626,122 |
| SEQ ID NO: 89 | N0014Y7-001-I002 | N0014Y7-001 | Illumina | 14,627,320 |
| SEQ ID NO: 90 | N0014Y8-001-I002 | N0014Y8-001 | Illumina | 14,630,481 |
| SEQ ID NO: 91 | N0014Y9-001-I002 | N0014Y9-001 | Illumina | 14,630,797 |
| SEQ ID NO: 92 | N0014YA-001-I002 | N0014YA-001 | Illumina | 14,641,501 |

In another method, the BnIND-A deletion allele can be detected by confirming the presence of genomic sequence comprising one or more N03 genomic marker (e.g., SNP) alleles which are located on sequencing flanking the deletion breakpoint disclosed herein and which are genetically linked to the BnIND-A deletion allele (but are not genetically linked to the presence of the deleted genomic segment disclosed herein). For example, Table 5 identifies probe sequence, commercial marker name (from Illumina), N03 SNP maker name, assay chemistry type, and genomic position (using DH12075 reference genome) of probes for markers that are flanking the deletion breakpoint of the disclosed BnIND-A deletion.

TABLE 5

| SEQ ID NO | Marker Name | SNP Name | Chemistry | Genomic Position |
|---|---|---|---|---|
| SEQ ID NO: 93 | N0014ME-001-I002 | N0014ME-001 | Illumina | 14,236,228 |
| SEQ ID NO: 94 | N0014MF-001-I002 | N0014MF-001 | Illumina | 14,247,234 |
| SEQ ID NO: 95 | N0014MG-001-I002 | N0014MG-001 | Illumina | 14,247,416 |
| SEQ ID NO: 96 | N0014MH-001-I002 | N0014MH-001 | Illumina | 14,253,184 |
| SEQ ID NO: 97 | N0014MJ-001-I002 | N0014MJ-001 | Illumina | 14,273,849 |
| SEQ ID NO: 98 | N002W9W-001-I002 | N002W9W-001 | Illumina | 14,294,755 |
| SEQ ID NO: 99 | N0014MK-001-I002 | N0014MK-001 | Illumina | 14,303,293 |
| SEQ ID NO: 100 | N0014MM-001-I002 | N0014MM-001 | Illumina | 14,304,481 |
| SEQ ID NO: 101 | N0014MN-001-I002 | N0014MN-001 | Illumina | 14,304,515 |
| SEQ ID NO: 102 | N0014MP-001-I003 | N0014MP-001 | IlluminaXT | 14,309,064 |
| SEQ ID NO: 103 | N0014MP-001-Q001 | N0014MP-001 | TaqMan | 14,309,064 |
| SEQ ID NO: 104 | N0014MP-001-I002 | N0014MP-001 | Illumina | 14,309,064 |
| SEQ ID NO: 105 | N0014MR-001-I002 | N0014MR-001 | Illumina | 14,310,286 |
| SEQ ID NO: 106 | N0014WT-001-I002 | N0014WT-001 | Illumina | 14,311,970 |
| SEQ ID NO: 107 | N0014WV-001-I002 | N0014WV-001 | Illumina | 14,323,705 |
| SEQ ID NO: 108 | N0014WW-001-I002 | N0014WW-001 | Illumina | 14,331,357 |
| SEQ ID NO: 109 | N0014WX-001-I002 | N0014WX-001 | Illumina | 14,338,096 |
| SEQ ID NO: 110 | N0014WY-001-I002 | N0014WY-001 | Illumina | 14,341,517 |
| SEQ ID NO: 111 | N0014X0-001-I002 | N0014X0-001 | Illumina | 14,348,717 |
| SEQ ID NO: 112 | N0014X1-001-I002 | N0014X1-001 | Illumina | 14,350,104 |
| SEQ ID NO: 113 | N0014X2-001-I002 | N0014X2-001 | Illumina | 14,352,324 |
| SEQ ID NO: 114 | N0014X3-001-I002 | N0014X3-001 | Illumina | 14,356,474 |
| SEQ ID NO: 115 | N0014X4-001-I002 | N0014X4-001 | Illumina | 14,362,485 |
| SEQ ID NO: 116 | N0014X5-001-I002 | N0014X5-001 | Illumina | 14,366,149 |
| SEQ ID NO: 117 | N0014X6-001-I002 | N0014X6-001 | Illumina | 14,370,593 |
| SEQ ID NO: 118 | N0014X7-001-I002 | N0014X7-001 | Illumina | 14,371,157 |
| SEQ ID NO: 119 | N0014X8-001-I002 | N0014X8-001 | Illumina | 14,418,412 |
| SEQ ID NO: 120 | N0014X9-001-I002 | N0014X9-001 | Illumina | 14,422,444 |
| SEQ ID NO: 121 | N0014XA-001-I002 | N0014XA-001 | Illumina | 14,438,774 |
| SEQ ID NO: 122 | N0014XB-001-I002 | N0014XB-001 | Illumina | 14,439,353 |
| SEQ ID NO: 123 | N0014XC-001-I002 | N0014XC-001 | Illumina | 14,447,394 |
| — | — | — | — | — |
| SEQ ID NO: 124 | N0014YK-001-I002 | N0014YK-001 | Illumina | 14,693,565 |
| SEQ ID NO: 125 | N0014YM-001-I002 | N0014YM-001 | Illumina | 14,711,636 |
| SEQ ID NO: 126 | N0014YN-001-I002 | N0014YN-001 | Illumina | 14,713,821 |
| SEQ ID NO: 127 | N0014YP-001-I002 | N0014YP-001 | Illumina | 14,728,197 |
| SEQ ID NO: 128 | N0014YR-001-I002 | N0014YR-001 | Illumina | 14,729,444 |
| SEQ ID NO: 129 | N0014YT-001-I002 | N0014YT-001 | Illumina | 14,729,492 |
| SEQ ID NO: 130 | N0014YU-001-I002 | N0014YU-001 | Illumina | 14,732,311 |
| SEQ ID NO: 131 | N0014YV-001-I002 | N0014YV-001 | Illumina | 14,738,917 |
| SEQ ID NO: 132 | N002C1P-001-I002 | N002C1P-001 | Illumina | 14,747,648 |
| SEQ ID NO: 133 | N0014YY-001-I003 | N0014YY-001 | IlluminaXT | 14,752,111 |
| SEQ ID NO: 134 | N0014YY-001-Q001 | N0014YY-001 | TaqMan | 14,752,111 |
| SEQ ID NO: 135 | N0014YY-001-I002 | N0014YY-001 | Illumina | 14,752,111 |
| SEQ ID NO: 136 | N001500-001-I002 | N001500-001 | Illumina | 14,764,950 |
| SEQ ID NO: 137 | N001501-001-I003 | N001501-001 | IlluminaXT | 14,777,622 |
| SEQ ID NO: 138 | N001501-001-Q001 | N001501-001 | TaqMan | 14,777,622 |
| SEQ ID NO: 139 | N001501-001-I002 | N001501-001 | Illumina | 14,777,622 |
| SEQ ID NO: 140 | N001502-001-I002 | N001502-001 | Illumina | 14,791,402 |
| SEQ ID NO: 141 | N001573-001-I002 | N001573-001 | Illumina | 14,792,796 |
| SEQ ID NO: 142 | N001574-001-Q001 | N001574-001 | TaqMan | 14,793,905 |
| SEQ ID NO: 143 | N001574-001-I002 | N001574-001 | Illumina | 14,793,905 |
| SEQ ID NO: 144 | N001574-001-I003 | N001574-001 | IlluminaXT | 14,793,905 |
| SEQ ID NO: 145 | N001575-001-I002 | N001575-001 | Illumina | 14,794,327 |
| SEQ ID NO: 146 | N001576-001-I002 | N001576-001 | Illumina | 14,804,413 |
| SEQ ID NO: 147 | N001577-001-I002 | N001577-001 | Illumina | 14,805,191 |
| SEQ ID NO: 148 | N001578-001-I002 | N001578-001 | Illumina | 14,805,303 |
| SEQ ID NO: 149 | N001579-001-I003 | N001579-001 | IlluminaXT | 14,806,463 |
| SEQ ID NO: 150 | N001579-001-Q003 | N001579-001 | TaqMan | 14,806,463 |
| SEQ ID NO: 151 | N001579-001-I002 | N001579-001 | Illumina | 14,806,463 |
| SEQ ID NO: 152 | N00157A-001-I002 | N00157A-001 | Illumina | 14,845,698 |
| SEQ ID NO: 153 | N00157B-001-I002 | N00157B-001 | Illumina | 14,890,862 |
| SEQ ID NO: 154 | N00157C-001-I002 | N00157C-001 | Illumina | 14,896,577 |
| SEQ ID NO: 155 | N00157D-001-I002 | N00157D-001 | Illumina | 14,922,691 |
| SEQ ID NO: 156 | N00157E-001-I002 | N00157E-001 | Illumina | 14,927,519 |
| SEQ ID NO: 157 | N00157F-001-I002 | N00157F-001 | Illumina | 14,930,339 |

TABLE 5-continued

| SEQ ID NO | Marker Name | SNP Name | Chemistry | Genomic Position |
|---|---|---|---|---|
| SEQ ID NO: 158 | N00157G-001-I002 | N00157G-001 | Illumina | 14,931,181 |
| SEQ ID NO: 159 | N00157H-001-I002 | N00157H-001 | Illumina | 14,940,380 |
| SEQ ID NO: 160 | N00157J-001-I002 | N00157J-001 | Illumina | 14,954,238 |

Other methods of detecting the BnIND-A deletion allele disclosed herein, or a linked marker, includes single base extension (SBE) methods, which involve the extension of a nucleotide primer that is adjacent to a polymorphism to incorporate a detectable nucleotide residue upon extension of the primer through the polymorphism, e.g., extension through the BnIND-A deletion breakpoint disclosed herein (or a linked marker).

Methods of detecting the BnIND-A deletion allele disclosed herein (or a linked marker) also include LCR; and transcription-based amplification methods (e.g., SNP detection, SSR detection, RFLP analysis, and others). Useful techniques include hybridization of a probe nucleic acid to a nucleic acid corresponding to the BnIND-A deletion allele disclosed herein, or a linked marker (e.g., an amplified nucleic acid produced using a genomic canola DNA molecule as a template). Hybridization formats including, for example and without limitation, solution phase; solid phase; mixed phase; and in situ hybridization assays may be useful for allele detection in particular embodiments. An extensive guide to hybridization of nucleic acids is discussed in Tij ssen, Laboratory Techniques in Biochemistry and Molecular Biology—Hybridization with Nucleic Acid Probes (Elsevier, N.Y. 1993).

Markers corresponding to genetic polymorphisms between members of a population may be detected by any of numerous methods including, for example and without limitation, nucleic acid amplification-based methods; and nucleotide sequencing of a polymorphic marker region. Many detection methods (including amplification-based and sequencing-based methods) may be readily adapted to high throughput analysis in some examples, for example, by using available high throughput sequencing methods, such as sequencing by hybridization.

The detecting of a BnIND-A deletion or a SNP allele associated with that BnIND-A deletion can be performed by any of a number or techniques, including, but not limited to, the use of nucleotide sequencing products, amplicons, or probes comprising detectable labels. Detectable labels suitable for use include any composition detectable by spectroscopic, radioisotopic, photochemical, biochemical, immunochemical, electrical, optical, or chemical means. Thus, a particular allele of a SNP may be detected using, for example, autoradiography, fluorography, or other similar detection techniques, depending on the particular label to be detected. Useful labels include biotin (for staining with labeled streptavidin conjugate), magnetic beads, fluorescent dyes, radiolabels, enzymes, and colorimetric labels. Other labels include ligands that bind to antibodies or specific binding targets labeled with fluorophores, chemiluminescent agents, and enzymes. In some embodiments of the present invention, detection techniques include the use of fluorescent dyes.

The BnIND-A deletion allele disclosed herein is associated with a pod shatter tolerance trait. Therefore, any of the methods of detecting the BnIND-A deletion can be used to detect the presence of a pod shatter tolerance trait which is heritable and therefore useful in a breeding program, for example to create progeny *Brassica* plants comprising the BnIND-A deletion and one or more other desirable agronomic or end use qualities. Accordingly, in some aspects, the invention provides a method of selecting, detecting and/or identifying a *Brassica* plant, cell, or germplasm thereof (e.g., a seed) having the pod shatter tolerance trait. The method comprises detecting in said *Brassica* plant, cell, or germplasm thereof, the presence of the BnIND-A deletion or a marker associated with the BnIND-A deletion and thereby identifying a *Brassica* plant having the pod shatter tolerance trait.

Introgression of the Native BnIND-A Deletion in *Brassica*

As set forth herein, identification of *Brassica*, e.g., *B. napus, B. juncea, B. carinata, B. rapa* or *B. oleracea* plants or germplasm comprising the BnIND-A deletion allele responsible for the pod shatter tolerance trait disclosed herein, provides a basis for performing marker assisted selection of *Brassica*. For example, at least one *Brassica* plant that comprises the BnIND-A deletion allele is selected for and plants that do not include the deletion allele may be selected against.

This disclosure thus provides methods for selecting a canola plant exhibiting pod shatter tolerant trait comprising detecting in the plant the BnIND-A deletion allele (or one or more genetic markers associated with the BnIND-A deletion allele). This can be used in a method for selecting such a plant, the method comprises providing a sample of genomic DNA from a *Brassica* plant; and (b) using any method disclosed herein for detecting in the sample of genomic DNA the BnIND-A deletion allele or at least one genetic marker associated with the with the deletion allele.

This disclosure also provides a method comprising the transfer by introgression of the BnIND-A deletion allele from one plant into a recipient plant by crossing the plants. This transfer can be accomplished using, e.g., traditional breeding techniques to improve the pod shatter tolerance of the recipient plant and/or the progeny of the recipient plant. In one aspect, the BnIND-A deletion is introgressed into one or more commercial or elite Brassica varieties using marker-assisted selection (MAS) or marker-assisted breeding (MAB). MAS and MAB involve the use of one or more molecular markers that indicate the presence or co-segregation with BnIND-A deletion, and used for the identification and selection of those offspring plants that contain BnIND-A deletion. As disclosed herein, the molecular markers for the BnIND-A deletion include the deletion breakpoint sequence disclosed herein and any genomic sequence or amplicon disclosed herein which distinguish the BnIND-A deletion allele from a BnIND-A (e.g., wildtype) allele that includes the intervening from about 200 kb to about 310 kb genomic segment between deletion breakpoints.

When a population is segregating for multiple loci affecting one or multiple traits, e.g., multiple loci involved in resistance to a single disease, or multiple loci each involved in resistance to different diseases, the efficiency of MAS compared to phenotypic screening becomes even greater because all the loci can be processed in the lab together from a single sample of DNA. Thus, MAS is particularly suitable for introgressing BnIND-A deletion allele into a plant line that includes one or more additional desirable traits. Additional desirable traits can include another pod shatter tolerance trait, disease resistance trait, or an end use trait such as oil quality or meal quality.

Another use of MAS in plant breeding is to assist the recovery of the recurrent parent genotype by backcross breeding. Backcross breeding is the process of crossing a progeny back to one of its parents. Backcrossing is usually done for the purpose of introgressing one or a few loci from a donor parent, i.e., the BnIND-A deletion, into an otherwise desirable genetic background from the recurrent parent. The more cycles of backcrossing that are done, the greater the genetic contribution of the recurrent parent to the resulting variety. This is desirable when the recurrent parent is an elite variety and/or has more desirable qualities than the donor plant, even though the recurrent parent may need improved pod shatter tolerance. For example, backcrossing can be desirable when a recurrent plant provides better yield, fecundity, oil and/or meal qualities and the like, as compared to the donor BnIND-A deletion plant.

MAB can also be used to develop near-isogenic lines (NIL) harboring the BnIND-A deletion disclosed herein, allowing a more detailed study of an effect of such allele. MAB is also an effective method for development of backcross inbred line (BIL) populations. *Brassica* plants developed according to these embodiments can derive a majority of their traits from the recipient plant and derive the pod shatter tolerance from the donor BnIND-A deletion plant. MAB/MAS techniques increase the efficiency of backcrossing and introgressing genes using marker-assisted selection (MAS) or marker-assisted breeding (MAB).

Thus, traditional breeding techniques can be used to introgress a nucleic acid sequence associated with native BnIND-A deletion into a recipient *Brassica* plant. For example, inbred BnIND-A deletion *Brassica* plant lines can be developed using the techniques of recurrent selection and backcrossing, selfing, and/or dihaploids, or any other technique used to make parental lines. In a method of recurrent selection and backcrossing, the BnIND-A deletion can be introgressed into a target recipient plant (the recurrent parent) by crossing the recurrent parent with a first donor plant, which differs from the recurrent parent and is referred to herein as the "non-recurrent parent." The recurrent parent is a plant, in some cases, comprises commercially desirable characteristics, such as, but not limited to disease and/or insect resistance, valuable nutritional characteristics, valuable abiotic stress tolerance (including, but not limited to, drought tolerance, salt tolerance), and the like. The non-recurrent parent can be any plant variety or inbred line that is cross-fertile with the recurrent parent.

The resulting progeny plant population is then screened for the desired characteristics, including the BnIND-A deletion, which screening can occur in a number of different ways. For instance, the progeny population can be screened using phenotypic pathology screens or quantitative bioassays as are known in the art. Alternatively, instead of using bioassays, MAS or MAB can be performed using one or more of molecular markers described herein to identify progeny plants or germplasm that comprise a BnIND-A deletion allele. Also, MAS or MAB can be used to confirm the results obtained from the quantitative bioassays. The markers, primers, and probes described herein can be used to select progeny plants by genotypic screening.

Following screening, the F1 progeny (e.g., hybrid) plants having the BnIND-A deletion allele can be selected and backcrossed to the recurrent parent for one or more generations in order to allow for the canola plant to become increasingly inbred. This process can be repeated for one, two, three, four, five, six, seven, eight, or more generations. In some examples, the recurrent parent plant or germplasm used in this method is of an elite variety of the *Brassica* species. Thus, this crossing and introgression method can be used to produce a progeny *Brassica* plant or germplasm having the BnIND-A deletion allele introgressed into a genome that is at least about 50%, 55%, 60%, 65%, 70%, 75%, 80%, 85%, 90%, 95%, 97%, 99% identical to that of the elite variety of the *Brassica* species.

Also provided is a method of producing a plant, cell, or germplasm (e.g., seed thereof) that comprises crossing a first *Brassica* plant or germplasm with a second *Brassica* plant or germplasm, wherein said first *Brassica* plant or germplasm comprises within its genome a the BnIND-A deletion allele disclosed herein, collecting seed from the cross and growing a progeny *Brassica* plant from the seed, wherein said progeny *Brassica* plant comprises in its genome said BnIND-A deletion allele, thereby producing a progeny plant that carries the deletion associated with the pod shatter tolerance trait disclosed herein.

In addition to the methods described above, a *Brassica* plant, cell, or germplasm having the BnIND-A deletion may be produced by any method whereby the BnIND-A deletion is introduced into the canola plant or germplasm by such methods that include, but are not limited to, transformation (including, but not limited to, bacterial-mediated nucleic acid delivery (e.g., via Agrobacteria)), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, or any combination thereof, protoplast transformation or fusion, a double haploid technique, embryo rescue, or by any other nucleic acid transfer system.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced, these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell.

The following are examples of specific embodiments of some aspects of the invention. The examples are offered for illustrative purposes only and are not intended to limit the scope of the invention in any way.

EXAMPLES

Example 1

Discovery of a Native Deletion in BnIND-A

A native deletion located in *B. napus* INDEHISCENT gene on chromosome 3A (IndA) was unexpectedly discovered in a project that used CRISPR-Cas9 gene editing for the targeted genomic deletion ("dropout") of the IndA gene. Although, the project successfully generated the expected IndA dropout in various *B. napus* lines, the same IndA dropout could not be generated in *B. napus* line G00010BC.

In the process of investigating why no BnIND-A dropouts had been identified in G00010BC, whole genome sequence was performed. The two main homoeologous copies of INDEHISCENT genes from chromosomes N03 (BnIND-A; BnaA03g27180D) and N13 (BnIND-C; BnaC03g32180D) were compared to five references genomes using the Basic Local Alignment Search Tool (BLAST™) algorithm available from the National Center for Biotechnology Information (NCBI). See Altschul et al., 1990, *J. Mol. Biol.* 215: 403-10. The five reference genomes were DH12075 (public spring canola), Darmor (public winter canola), and three high quality third generation proprietary spring canola lines (NS1822BC, G00010BC, and G00055MC). Orthologous matches for both genes were found in all genomes, except for BnIND-A in G00010BC. Comparative global sequence alignment of an extended genomic region surrounding BnIND-A revealed a large segmental deletion in the G00010BC genome. The deletion is from 229 kb to 307 kb in length, depending on reference genome used for alignment. The physical starting and ending position of the BnIND-A deletion segment, as determined by alignment to each reference genome, is shown in Table 6.

TABLE 6

| Genome | Start Position | End Position | Length (bp) |
|---|---|---|---|
| NS1822BC | 14,710,075 | 14,958,191 | 248,116 |
| DH12075_v1.1 | 14,449,859 | 14,690,232 | 240,373 |
| Darmor_v4.1.1 | 13,306,888 | 13,535,922 | 229,034 |
| G00555MC | 14,915,907 | 15,223,431 | 307,524 |
| G00010BC | 14,989,780 | 14,989,781 | (deletion breakpoint) |

Example 2

Molecular Assays to Detect the Native BnIND-A Deletion

The G00010BC and wildtype reference N3 sequences were used to develop molecular assays to detect the presence or absence of native BnIND-A deleted segment as well as sequences flanking the breakpoint site of the deletion.

Figure 1:
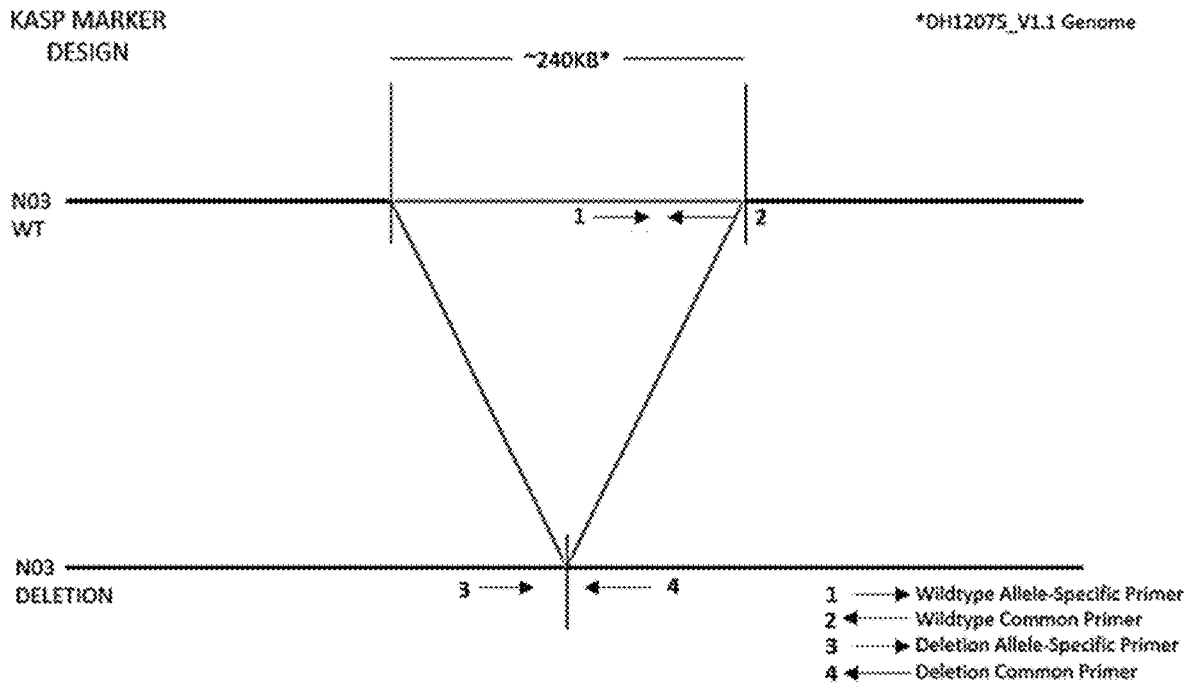

KASPar™ assay comprised of four primers was developed using an assay design algorithm available as Kraken™ (LGC Genomics, Hoddesdon, Hertfordshire, UK). Initially, BnIND-A gene sequence on N03 was compared to the homoeologous BnIND-C gene on N13 to identify unique polymorphisms. Potential primer sequence targets were then identified to detect the wildtype and native deletion states of BnIND-A. To detect the native deletion, allele-specific, fluorescently tagged (FAM) forward primer and a reverse primer flanking the breakpoint were designed as shown in FIG. 1 (N03 Deletion). To detect the wildtype state, a different fluorescently tagged (VIC) forward primer and reverse primer were designed to hybridize within the native deletion segment sequence as shown in FIG. 1 (N03 WT). The primer sequences shown in Table 7 were used in a four primer, co-dominant composite marker KASPar™ assay to detect the presence or absence of BnIND-A deletion segment.

TABLE 7

| SEQ ID NO | Oligo Name | Description |
|---|---|---|
| SEQ ID NO: 32 | IND_A_001_F001 | WT Forward Primer |
| SEQ ID NO: 33 | IND_A_001_R001 | WT Reverse Primer |
| SEQ ID NO: 34 | BP_F003 | Mutant Forward Primer |
| SEQ ID NO: 35 | BP_R003 | Mutant Reverse Primer |

The KASPar™ assay mixture was composed of 12 µl of 100 mM of each forward primer and 30 µl of 100 mM of each reverse primer. 13.6 µl of this mixture was combined with 1000 µl of KASP™ Master Mix™ (LGC Genomics, Hoddesdon, Hertfordshire, UK). A Meridian™ (LGC Genomics) liquid handler dispensed 1.3 µl of the mix onto a 1536 plate containing ~6 ng of dried DNA. The plate was sealed with a Phusion™ laser sealer (LGC Genomics) and thermocycled using a Hydrocycler (LGC Genomics) under the following conditions: 95° C. for 15 minutes (min), 10 cycles of 95° C. for 20 seconds (sec), 61° C. stepped down to 55° C. for 1 min, 29 cycles of 95° C. for 20 sec, and 55° C. for 1 min. The excitation at wavelengths 485 (FAM) and 520 (VIC) was measured with a Pherastar™ plate reader (BMG Labtech, Offenburg, Germany). Values were normalized against the passive reference dye ROX (5-(and 6)-Carboxy-X-rhodamine, succinimidyl ester), plotted and scored on scatterplots utilizing the Kraken™ software (LGC Genomics).

Figure 2:
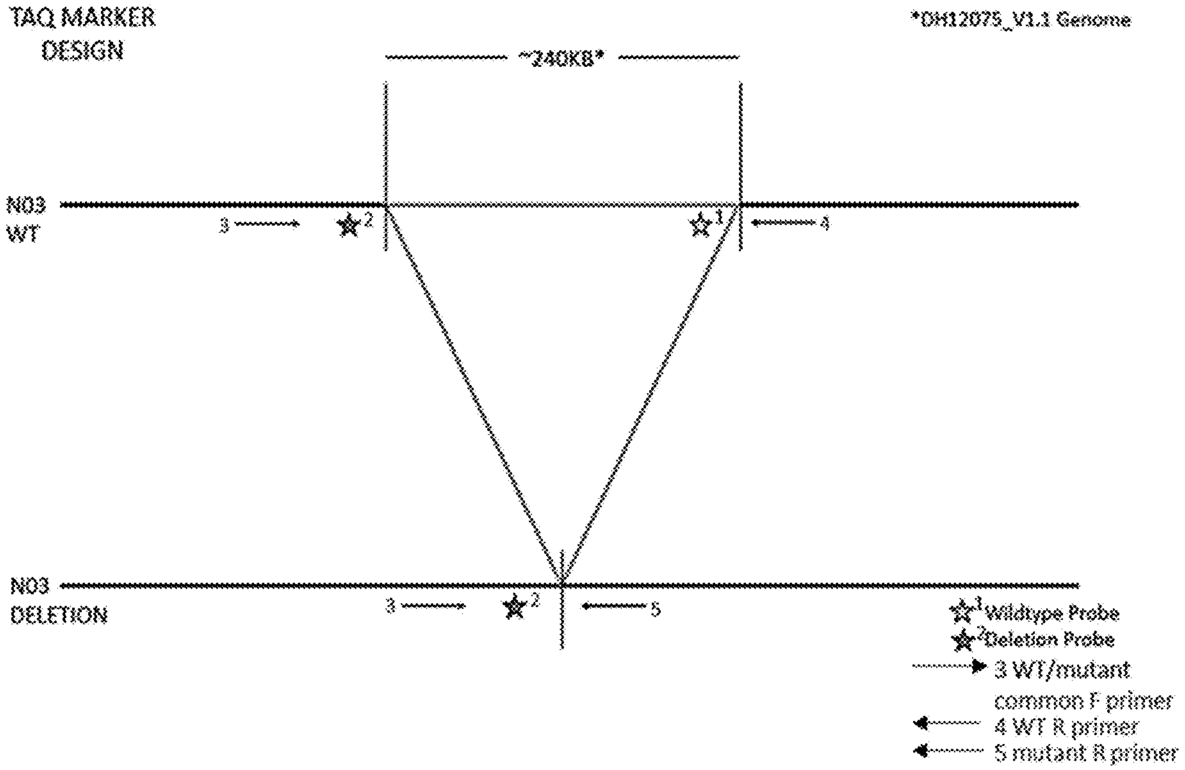

A variation on conventional TAQMAN™ end-point genotyping system was developed. Conventional TAQMAN™ assays use a forward and reverse primer and two fluorescent labeled probes. The TAQMAN™ variation developed to detect the presence or absence of the BnIND-A deletion segment is a compound assay that comprises two independent amplification reactions. The first reaction amplifies and detects wildtype gene sequence using forward and reverse primers capable of hybridizing to sequences that flank the 3' breakpoint of the BnIND-A deletion segment in wildtype N03 chromosome as shown in upper portion of FIG. 2 (N03 WT). Because the deletion segment is present in wild type N03 chromosome, the wildtype primers amplify sequence upstream the 3' breakpoint and the amplified sequence is detected using a wild type probe. The second assay reaction detects the presence of BnIND-A deletion using a deletion forward primer that hybridizes upstream of the 5' breakpoint and a deletion reverse primer that hybridizes downstream of the 3' breakpoint of the deletion as shown in lower portion of FIG. 2 (N03 Deletion). When the deletion segment is missing, the second assay amplifies sequence containing both the joined 5' breakpoint and 3' breakpoint. By contrast the second assay will not amplify N03 genomic sequence that includes the deletion segment because the 5' and 3' breakpoints are too far apart to be amplified effectively under assay conditions. The primers and probes for both wildtype and deletion reactions (4 primers and two probes shown in Table 8) were combined and the reactions were run simultaneously.

TABLE 8

| SEQ ID NO | Name | Description |
|---|---|---|
| SEQ ID NO: 36 | N101T11-F001 | WT F Primer/ Common F primer |
| SEQ ID NO: 37 | N101T11-R001 | WT R Primer |
| SEQ ID NO: 38 | N101T11-001-X001 | WT Probe |
| SEQ ID NO: 39 | N101T10-F001 | Deletion F Primer |

TABLE 8-continued

| SEQ ID NO | Name | Description |
|---|---|---|
| SEQ ID NO: 40 | N101T10-R001 | Deletion R Primer |
| SEQ ID NO: 41 | N101T10-001-X001 | Deletion Probe |

Figure 3:
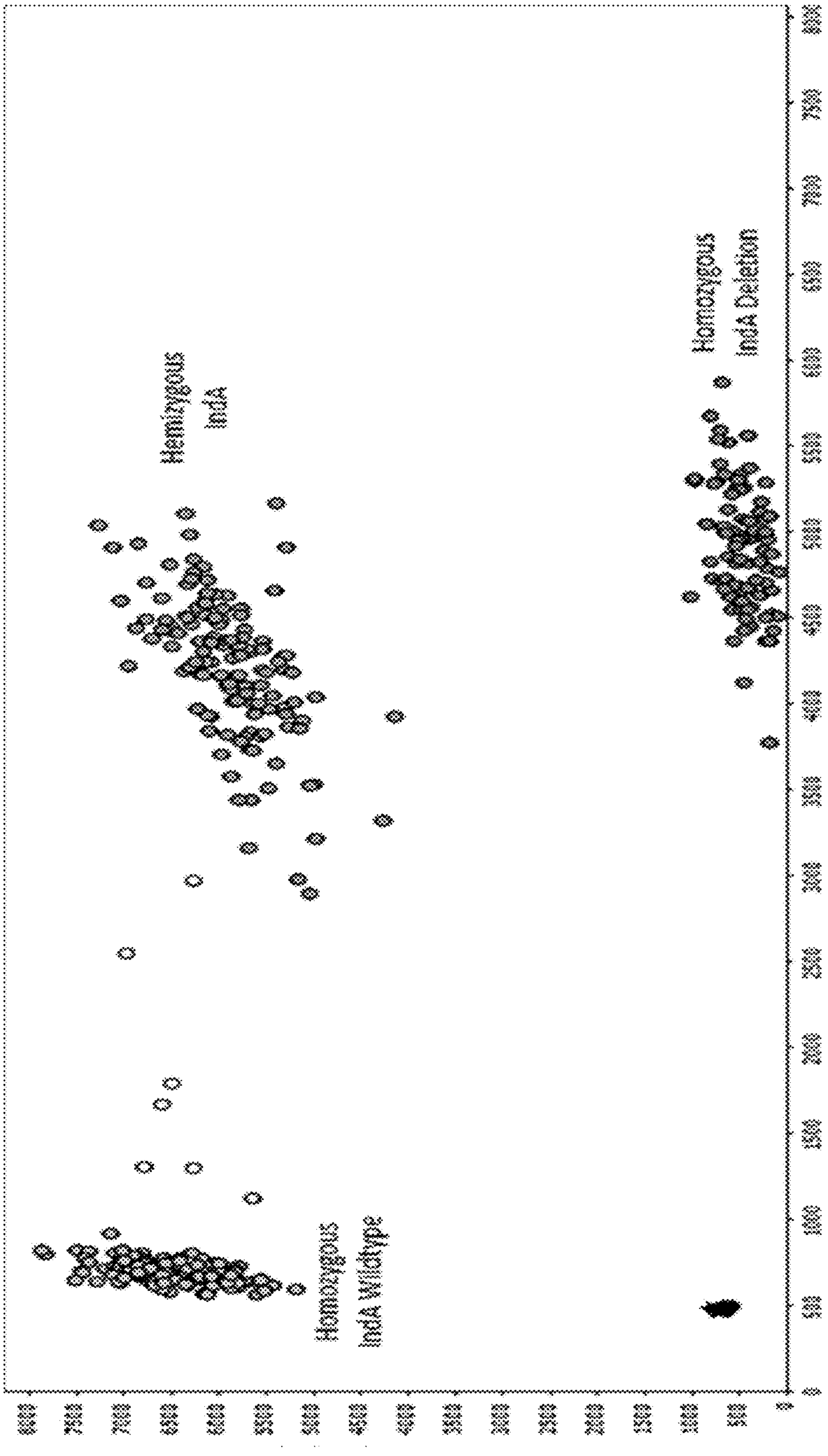
FIG. 3 is a scatterplot showing the results of using a TAQMAN™ assay to screen *B. napus* germplasm segregating in a mapping population for the native BnIND-A deletion disclosed herein.

The combination TAQMAN™ assay included 13.6 μl of a primer probe mixture (18 μM of each probe, 4 μM of each primer) and 1000 μl of master mix from ToughMix™ kit (Quanta Beverly, MA). A liquid handler dispensed 1.3 μl of the mix onto a 1536 plate containing ~6 ng of dried DNA. The plate was sealed with a laser sealer and thermocycled in a Hydrocycler device (LGC Genomic Limited, Middlesex, United Kingdom) under the following conditions: 94° C. for 15 min, 40 cycles of 94° C. for 30 secs, 60° C. for 1 min. PCR products are measured using at wavelengths 485 (FAM) and 520 (VIC) by a Pherastar™ plate reader (BMG Labtech, Offenburg, Germany). The values are normalized against ROX and plotted and scored on scatterplots utilizing the Kraken™ software. FIG. 3 shows results of using this TAQMAN™ assay to evaluate a mapping population segregating for the native BnIND-A deletion disclosed herein. FIG. 3 demonstrates that the disclosed assay can identity and distinguish between clusters of plants that are homozygous wildtype for BnIND-A, homozygous BnIND-A deletions, and hemizygous deletions (wildtype/BnIND-A deletion).

This example describes the development of diagnostic assays useful in methods of detection of and introgression of the BnIND-A native deletion disclosed herein.

Example 3

Survey of Elite Germplasm

Figure 4A:
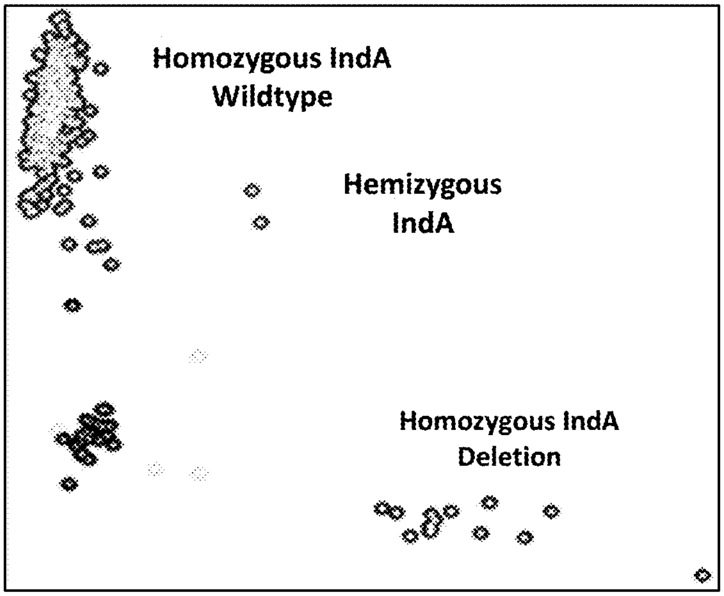
FIG. 4A is a scatterplot showing the results of using a KASPar™ assay to interrogate global elite *B. napus* germplasm for the native BnIND-A deletion disclosed herein.
Figure 4B:
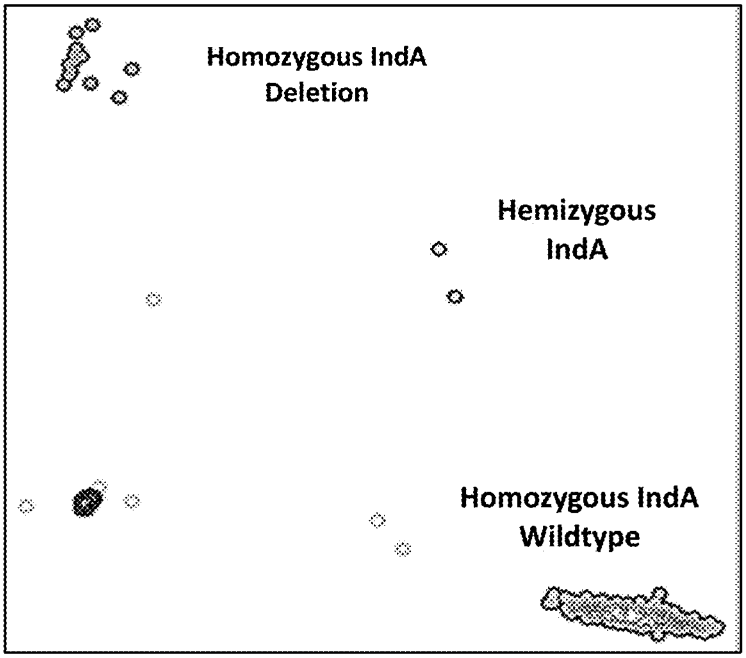
FIG. 4B is a scatterplot showing the results of using a TAQMAN™ assay to interrogate global elite *B. napus* germplasm for the native BnIND-A deletion disclosed herein.

Publicly released and proprietary collections of elite germplasm lines from North America, Australia, and Europe were analyzed using molecular assays described in foregoing Example 2 herein. Results of the KASPar™ assay and combined TAQMAN™ assays for BnIND-A deletion are shown in FIG. 4A and FIG. 4B respectively, which indicated that IndA native deletion can be found in public and proprietary elite global germplasm, although its prevalence is rare: 22 of 947 tested lines were found to contain the BnIND-A native deletion disclosed herein.

The foregoing demonstrates the usefulness of molecular assays disclosed herein for the detection of native BnIND-A deletion. It also confirms that the KASPar™ and combined TAQMAN™ assay produced the results of a co-dominant assay and were able to distinguish and display sample clusters that are homozygous wildtype for BnIND-A, homozygous BnIND-A deletions, and hemizygous deletions (wildtype/BnIND-A deletion). See FIG. 4A and FIG. 4B.

Example 4

Pod Shatter Phenotype of *B. napus* Line with Native BnIND-A Deletion

A laboratory assay was developed to evaluate the shatter resistance of pods subjected to mechanical agitation at a specific speeds and times. GENO/GRINDER device (SPEX®SamplePrep, Metuchen, NJ) was used to mechanically break canola pods and thereby assess shattering tolerance or susceptibility. Different speeds (rpm) and times were tested with intact pods from inbred NS1822BC grown in controlled environment growth chamber (Conviron, Winnipeg, Canada). Fully shattered pods (both valves detached from the replum and seeds dispersed), half shattered (one valve detached from the replum and about half seeds dispersed) or unshattered pods (both valves attached and containing seeds) were measured. Fifteen pods were used for each data point. Results showed a linear relationship between the mechanical speed at which pods are agitated and the number of shattered (full+half shattered) pods ($r2=0.944$).

In another experiment, a group of 15 pods (ranging from 3 cm to 6 cm in length) for three different inbred lines, NS1822BC, G00010BC, and G00055MC grown in a controlled environment were tested. Results indicated a direct relationship between speed of mechanical agitation and pod shatter for the inbreds that were tested. Pods of all three inbreds were almost fully shattered at speeds equal to or greater than 1200 rpm.

At 750 rpm, pod shattering of G00010BC was found to be significantly lower than the other two inbreds. Thus, compared to the other two inbreds evaluated under the foregoing conditions, the native BnIND-A deletion line (G00010BC) provided an improved shatter tolerance phenotype.

Figure 5:
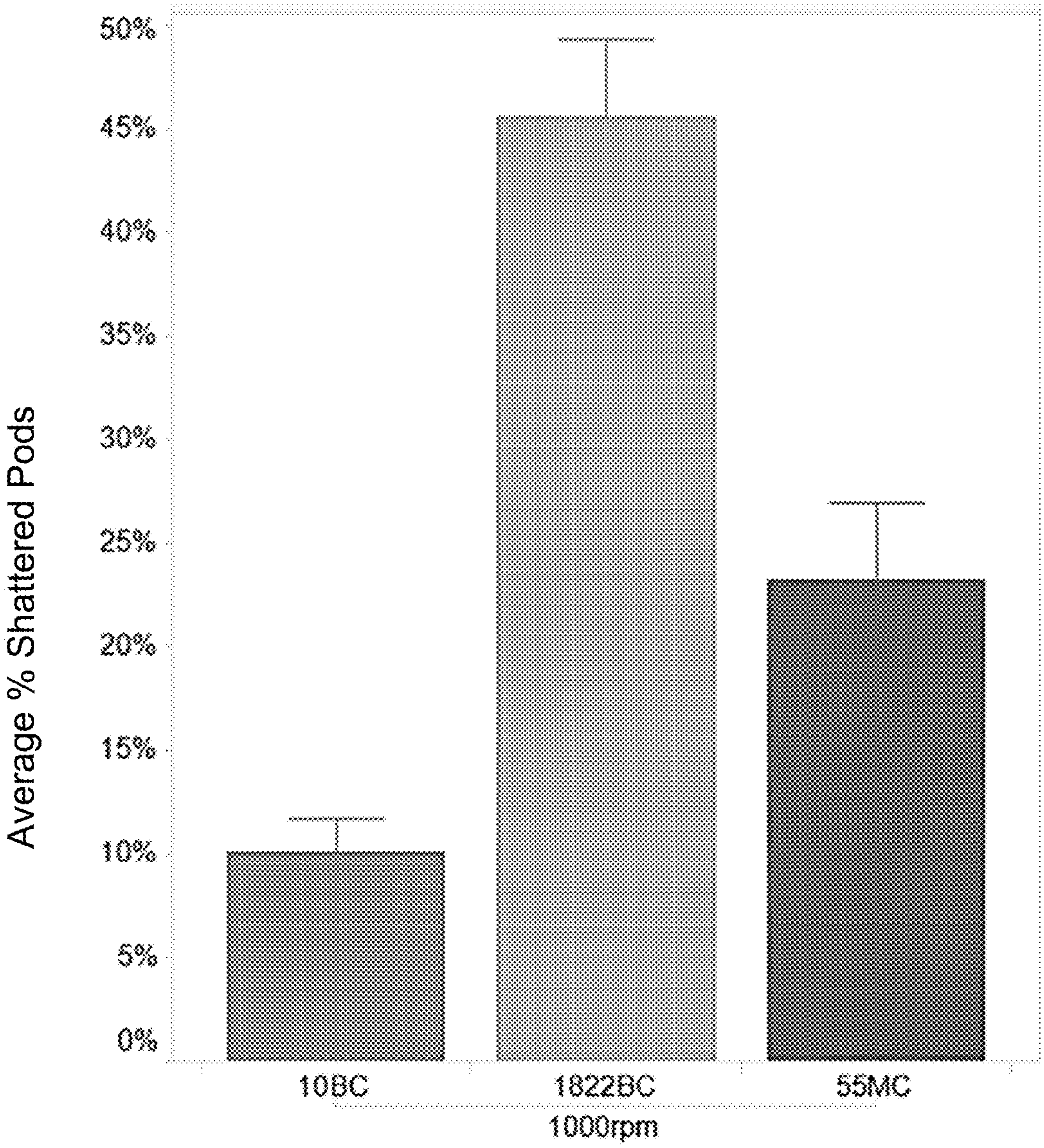
FIG. 5 is a bar graph showing the average percentage shattered pods of *B. napus* inbreds G00010BC, NS1822BC, and G00555MC, which were evaluated using a method for laboratory phenotyping pod shatter tolerance as disclosed herein.

A second laboratory assay phenotyping experiment was conducted using 5 to 6 plants of each the foregoing three genotypes. As described above, plants were grown in a growth chamber, and pods collected at maturity were phenotyped using the Geno/Grinder assay (15 pods at 1000 rpm for 30 sec). Percentage shattered pods (SHTPC) was recorded for each assay repetition. The results shown in FIG. 5 demonstrated statistically significant differences (t-test: two-sample assuming unequal variances, $p<0.01$) between indicated genotypes. Pods collected from G00010BC were found to be on average significantly more shatter tolerant than pods collected from the other two phenotypes. These results provide additional evidence that the presence of the IND-A native deletion in G00010BC contributes to higher mechanical resistance and an improved shatter tolerance phenotype as compared to the other two genotypes tested.

This example describes a laboratory assay to induce pod shattering and evaluate pod shatter tolerance. Results of two studies using the assay showed increased shatter tolerance for G00010BC relative to lines NS1822BC and G00055MC and provides evidence that the native BnIND-A deletion in G00010BC contributes to increased shatter tolerance.

Example 5

Pod Shatter Phenotype of BnIndC Dropout Combined with the Native BnIND-A Deletion CRISPR-Cas9 gene editing was used to generate a targeted genomic deletion ("dropout") of the INDEHISCENCE gene in the C genome (BnIND-C) in lines G00010BC having the native BnIND-A deletion disclosed herein. *Agrobacterium* transformation was done according to Moloney et al. (1989) *Plant Cell Reports* 8:238-242. Second generation (T2) G00010BC BnIND-C homozygous dropout variant and wildtype control plants were grown in controlled environment growth chambers (Conviron, Winnipeg, Canada) under standard conditions. BnIND-C genomic dropout sequences are disclosed herein (SEQ ID NOs:4, 14, and 25).

Pods were harvested at maturity after 2 weeks without water. Pods were left to acclimate in the laboratory at 23° C. for 5 days. Fifteen pods of similar sizes were harvested for 5 individual G00010BC homozygous dropout plants and 5 segregating wild-type plants. Pods from individual plants were placed in plastic boxes of 12×8.5×6.5 cm and mechanically agitated at 1700 rpm for 30 seconds using GENO/GRINDER device. After disruption, individual pods were scored according to half shattered, fully shattered, and unshattered phenotype. Total number of shattered pods was calculated as the sum of the half shattered and fully shattered pods. The average percentage of shattered pods for G00010BC homozygous BnIND-C dropout variants was near 0.00%, as compared to an average of 92.00% shattered pods for G00010BC plants.

This example shows that non-functional gene deletion of the IND gene in the C genome, combined with the native BnIND-A deletion disclosed herein produced a fully controlled genetic trait imparting shatter tolerance in *B. napus*.

Example 6

Pod Shatter Phenotype of Heterozygous and Homozygous T3 BnInd-C Combined with Native BnIND-A Deletion Sixty-four T3 seeds from two T2 G00010BC plants heterozygous for the BnIND-C dropouts (generated as described in Example 5 herein) were planted and genotyped using a dropout specific PCR assay followed by NextGen sequencing. Plants that were homozygous (9), heterozygous (10), and wildtype (8) for the BnIND-C dropout were identified and grown to maturity in a growth chamber in 16 hour light (23° C.) (~360 μE light intensity) and 8 hour dark (20° C.) regimen at ~55% humidity. At maturity, plants were allowed to dry. Pods were harvested and phenotyped using the GENO/GRINDER laboratory assay at 1100 rpm for 15 seconds. For each replication using 15 intact pods, pods were visually inspected after the assay and classified according to fully shattered, half shattered or unshattered pod phenotype.

FIG. 6 shows shatter tolerance of G00010BC plants segregating for a BnIND-C dropout calculated as the average percentage of shattered pods from replicated assays. The number of knocked out alleles (KO) are indicated for each zygosity category, where 4 KO are homozygous for the BnIND-C dropout, 3 KO are heterozygous for the BnIND-C dropout, and 2 KO do not include any BnIND-C dropout alleles. Since G00010BC background has a native ~200 kb-300 kb deletion on chromosome 3 that affects BnIND-A, G00010BC has 2 deleted alleles (2 knockouts or 2 KO). Plants heterozygous for the BnIND-C dropout have three deleted alleles (or 3 knockouts and thus 3 KO) and homozygous plants have four missing alleles (or 4 knockouts and thus 4 KO). *B. napus* plants with 4 KO showed a strong shatter tolerant phenotype, and plants with 3 KO showed a significant reduction in the percentage of shattered pods compared to unmodified G00010BC plants (t-test, $p<0.05$).

This example shows that the number of knocked out IND alleles can correlate with pod shatter tolerance, including in backgrounds having the native BnIND-A deletion disclosed herein. Double knockout plants (all A and C alleles knocked out) showed higher shatter tolerance than plants with 3 knocked out alleles (2 KO for A and 1 KO for C).

Example 6

Validation of Field Phenotyping Study for Pod Shatter Tolerance

Plants were grown in a replicated trial in Rockwood, Ontario, Canada. Plants in the field received a shatter-inducing treatment in the form of 135 km/h wind generated by a blower mounted in front of a tractor. The treatment was applied 12 times at a tractor speed of ~5 km/h four months after planting. Wind angle compared to planted rows was varied from perpendicular to oblique for maximum effect. The trial saw additional shatter pressure for another two weeks after this shatter inducing treatment due to weather related events such as moisture, rain, dryness, temperature and natural wind. Percent shattered pods (SHTPC) was determined using visual evaluation of plants from 5 replications. Intensity of shatter pressure was evaluated using the following reference lines: 45H33 is a moderately susceptible check line; 45CM39 and 45M35 were used as shatter resistant checks. Results showed statistically significant separation between SHTPC of the most shatter susceptible hybrid 45H33 (60% shattered pods), and shatter tolerant HarvestMax hybrids 45M35 and 45CM39 (~30% shattered pods). A statistically significant difference was also found between susceptible (wildtype G00555MC and G00182MC) and tolerant (N00644BC and NS7627MC) inbreds, both indicative of significant shatter pressure on the trial.

The foregoing provides a validated field method for phenotyping pod shatter under controlled conditions that induce pod shatter. The method successfully distinguished between shatter susceptible and shatter tolerant lines of *B. napus* plants.

Example 7

Laboratory Phenotyping Native BnIND-A Deletion in Combination with BnIND-C Dropout Pods were collected at maturity from multiple plants grown in one of the six field replications described in Example 6 prior to the field shatter inducing treatment and phenotyped in the laboratory using the GENO/GRINDER assay.

Intact pods of similar sizes were collected from G00010BC plants having the native BnIND-A deletion disclosed herein and gene edited G00010BC plants that were homozygous or heterozygous for an IND-C dropout. The mechanical resistance of these pods was compared to that of a commercially released pod shatter tolerant (PST) line check, which is referenced herein as PST Check 1. Pods were shaken in the GENO/GRINDER at 1500 rpm for 15 sec and results are presented in FIG. 7. At this speed, only about 1% of PST Check 1 and G00010BC BnIND-C homozygous (4 KO) dropout pods shattered. Pods of G00010BC BnIND-C heterozygous plants (3KO) produced approximately 4% fewer shattered pods than G00010BC (2 KO) controls, though this difference was not statistically significant (t-test, $p<0.01$) because the GENO/GRINDER assay applies significantly higher forces than the forces used in the field phenotyping experiment of Example 6. Because higher forces overcome the mechanical resistance in more pods of both G00010BC plants (2KO) and G00010BC plants with a heterozygous BnIND-C dropout (3KO), the GENO/GRINDER assay did not detect the significant difference in pod shatter tolerance that was observed with this material in the field phenotyping study. Compare the results shown in FIG. 6 with those in FIG. 7.

This example demonstrates that combining native BnIND-A deletion with a second homozygous loss-of-function IND allele improved pod shatter tolerance even under high force shatter-inducing conditions.

Example 8

Field Phenotyping of Native BnIND-A Deletion Plants

Plants in five of the six field replications described in Example 6 were subjected to pod shatter inducing treatment. Plant pods were scored in the field.

Wildtype and inbred G00010BC plants with different BnIND-C gene-edited dropouts were grown in the same field and characterized. G00010BC plants homozygous for BnIND-A native deletion and heterozygous BnIND-C dropout have three loss of function IND alleles (3 KO). Following shatter inducing treatment in the field, these 3KO plants had significantly reduced SHTPC scores as compared to G00010BC control (2 KO) and segregating plants "Recovered" (2 KO) with homozygous native BnIND-A deletion. SHTPC scores of heterozygous plants were reduced by 40% to 45% compared to the (2 KO) controls. See FIG. 8 and Table 9. Plants homozygous for the BnIND-C dropout did not shatter confirming the previously observed strong shatter tolerance of BnIND-A and BnIND-C double homozygous knockout.

TABLE

| INDEHISCENCE Genotype | SHTPC (approx.) | SHTPC Reduced vs 2KO (approx.) |
|---|---|---|
| G00010BC (2 KO) | 50% | — |
| Recovered Segregants with Homozygous BnIND-A deletion (2 KO) | 48% | — |
| G00010BC/BnIND-C Dropout Heterozygous (3 KO) | 28% | 40-45% |
| G00010BC/BnIND-C Dropout Homozygous (4 KO) | ~0% | ~99% |

This example demonstrates that combining native BnIND-A deletion with a second loss-of-function IND allele improved shatter tolerance in the field.

Example 9

Phenotyping Hybrids with Native BnIND-A Deletion

G00010BC plants and G00010BC plants homozygous for an BnIND-C dropout were crossed with wildtype plants and plants containing homozygous BnIND-A dropouts to create hybrid plants with different allelic combinations of dropout and wildtype alleles. A small amount of hybrid seed was generated to grow plants for laboratory assay pod phenotyping. Specific allelic combinations of BnIND dropout variants are shown in Table 10 (for hybrid genotypes: first letter designates male parent allele, second letter G00010BC female parent allele; upper case designates wild-type allele, and lower case indicates a gene-edited dropout allele, except for the bold and underlined "a" which designates G00010BC BnIND-A native deletion allele).

TABLE 10

| Male parent | G00010BC female parent | Hybrid genotype |
|---|---|---|
| IND-A HO Dropout | IND-C HO DO | a**a**/Cc |
| IND-A HO Dropout | IND-C WT | a**a**/CC |
| IND-A WT | IND-C HO DO | A**a**/Cc |
| IND-A WT | IND-C WT | A**a**/CC |

The resulting hybrid plants and checks were grown in a growth chamber for comparison with hybrid checks. The moderately susceptible to pod shatter check used was 45H33. Shatter resistant checks were HARVESTMAX Hybrids 45CM39 and 45M35. Four plants were grown for each entry except for 45CM39 for which only 3 plants were grown. Intact pods were collected from individual plants and Geno/Grinder assays were conducted using 10-15 pods per assays as described in Example 4. Percentages of shattered pods were calculated. Pods from each hybrid ranged from 3 cm to 7 cm in size and hybrids showed comparable pod size distributions except for 45H33, which had a higher number of smaller pods on average. Results of the phenotyping experiment are shown in FIG. 9.

HARVESTMAX hybrids (45CM39 and 45M35) showed a ~50% reduction in percent shattered pods compared to 45H33 in this assay. This is similar to the difference in SHPTPC observed in the field for these hybrids. Accordingly, these results indicate that the laboratory assay results are sufficiently predictive to identify and distinguish shatter tolerant plants (HARVESTMAX hybrids) from moderately shatter susceptible plants (45H33) in a manner that is consistent with their shatter tolerance performance in the field.

The results in FIG. 9 for the hybrid with 3 dropout alleles (aa/Cc allelic combination) also show that native INDA deletion in G0010BC can be used to breed hybrids having a shatter resistance phenotype comparable to commercial shatter tolerant HarvestMax hybrids and that introgression of the native BnIND-A deletion of G00010BC in combination with other loss of function alleles contributed to shatter tolerance that is comparable to that of commercial shatter-tolerant hybrids.

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls.

The invention claimed is:

1. A method of identifying a *Brassica* plant, cell, or germplasm thereof comprising a BnIND-A genomic deletion that contributes to a pod shatter tolerance phenotype, the method comprising:

a. obtaining a nucleic acid sample from a *Brassica* plant cell, or germplasm; and b. screening the sample for genomic sequence comprising a deletion of the BnIND-A gene on chromosome N03, wherein the deleted genomic segment results in a breakpoint locus corresponding to positions 10,002-10,003 of SEQ ID NO:2, and wherein the BnIND-A deletion contributes to pod shatter tolerance phenotype in *Brassica*.

2. The method of claim 1, wherein the method comprises screening for the absence of the deleted genomic segment at the breakpoint locus corresponding to positions 14,989,780 to 14,989,781 of *Brassica napus* line G00010BC N03 genome.

3. The method of claim 1, wherein the method comprises screening for the absence of the deleted genomic segment at the breakpoint locus corresponding to positions 10,002-10,003 of SEQ ID NO:2.

4. The method of claim 1, wherein screening for the presence of the genomic deletion comprises whole genome sequencing.

5. The method of claim 1, wherein screening for the presence of the genomic deletion further comprises DNA sequencing the amplicon to determine the presence of the deletion breakpoint locus in the amplicon sequence.

6. The method of claim 1, wherein the method comprises amplifying or sequencing from 10 to 300 bases upstream of the BnIND-A deletion breakpoint locus at positions 10,002-10,003 of SEQ ID NO:2, and thereby detecting the absence of the deleted genomic segment.

7. The method of claim 6, wherein the method comprises isolating genomic DNA from the DNA sample and the amplification comprises:

c. contacting the isolated genomic DNA with a deletion forward primer and deletion reverse primer to selectively produce an amplicon comprising the BnIND-A deletion breakpoint locus at positions 10,002-10,003 of SEQ ID NO:2, and d. optionally, contacting the isolated genomic DNA with a wildtype forward primer and wildtype reverse primer capable of selectively producing a second amplicon of wildtype genomic BnIND-A that includes sequence from the deleted genomic segment.

8. The method of claim 7, wherein the mutant forward primer comprises SEQ ID NO: 34, the mutant reverse primer comprises SEQ ID NO:35, the wildtype forward primer is SEQ ID NO: 32 and the wildtype reverse primer is SEQ ID NO:33.

9. The method of claim 7, wherein the method further includes e. contacting the amplicon with a deletion probe to detect amplified BnIND-A genomic sequence comprising deletion breakpoint locus at positions 10,002-10,003 of SEQ ID NO: 2; and f. optionally, contacting the amplicon with a wildtype probe capable of detecting a second amplicon comprising wildtype BnIND-A allele that includes sequence from the deleted genomic segment.

10. The method of claim 9, wherein the deletion forward primer comprises SEQ ID NO: 39, the deletion reverse primer comprises SEQ ID NO:40, the deletion probe comprises SEQ ID NO: 41, the wildtype forward primer is SEQ ID NO:36 and the wildtype reverse primer is SEQ ID NO: 37, and the wildtype probe is SEQ ID NO: 38.

11. A method of selecting a *Brassica* plant, cell, or germplasm thereof, the method comprising identifying *Brassica*, plant, cell, or germplasm in accordance with claim 1 and selecting the *Brassica* plant, cell, or germplasm identified as having the BnIND-A deletion.

12. A method of introducing a deletion of the BnIND-A gene into a *Brassica* plant, the method comprising:

a. crossing a first parent *Brassica* plant comprising a deletion of a BnIND-A gene on chromosome N03 with a second parent *Brassica* plant that does not have the deletion to produce hybrid progeny plants; and b. obtaining a nucleic acid sample from one or more hybrid progeny plants; and c. selecting the one or more hybrid progeny plants having the BnIND-A deletion in accordance with the method of claim 11.

13. The method of claim 12 further comprising:

d. crossing the one or more selected progeny plants with the first or second parent *Brassica* plant (the recurrent parent plant) to produce backcross progeny plants;

e. obtaining a nucleic acid sample from one or more backcross progeny plants; and f. selecting the one or more backcross progeny plants having the BnIND-A deletion to produce another generation of backcross progeny plants.

14. The method of claim 13 further comprising:

g. repeating steps (d), (e), and (f) three or more times to produce backcross progeny plants that comprise the native deletion of the BnIND-A gene and the agronomic characteristics of the recurrent parent plant when grown in the same environmental conditions.

* * * * *

SEQUENCE LISTING

```
<160> NUMBER OF SEQ ID NOS: 159

<210> SEQ ID NO 1
<211> LENGTH: 182
<212> TYPE: PRT
<213> ORGANISM: Brassica napus

<400> SEQUENCE: 1
```

```
Met Ser Gly Ser Lys Ala Asp Ala Ala Ile Ala Pro Ile Val Met Met
1               5                   10                  15

Glu His His His Leu Leu Met Asn Trp Asn Lys Pro Ile Asp Leu Ile
            20                  25                  30

Thr Glu Glu Asn Ser Phe Asn His Asn Pro His Phe Ile Val Asp Pro
        35                  40                  45

Pro Ser Glu Thr Leu Ser His Phe Gln Pro Pro Pro Thr Ile Phe Ser
    50                  55                  60

Asp His Gly Gly Gly Glu Glu Ala Glu Glu Glu Glu Gly Glu Glu Glu
65                  70                  75                  80

Met Asp Pro Met Lys Lys Met Gln Tyr Ala Ile Ala Ala Met Gln Pro
                85                  90                  95

Val Asp Leu Asp Pro Ala Thr Val Pro Lys Pro Asn Arg Arg Asn Val
            100                 105                 110

Arg Val Ser Asp Asp Pro Gln Thr Val Val Ala Arg Arg Arg Arg Glu
        115                 120                 125

Arg Ile Ser Glu Lys Ile Arg Ile Leu Lys Arg Met Val Pro Gly Gly
    130                 135                 140

Ala Lys Met Asp Thr Ala Ser Met Leu Asp Glu Ala Ile Arg Tyr Thr
145                 150                 155                 160

Lys Phe Leu Lys Arg Gln Val Arg Leu Ala Ser Ser Ala Ser His Ser
                165                 170                 175

Ala Trp Ser Ser Tyr Val
            180
```

<210> SEQ ID NO 2
<211> LENGTH: 20001
<212> TYPE: DNA
<213> ORGANISM: Brassica napus

<400> SEQUENCE: 2

```
tgcggaggtt tttgaaattc gcaaagtcgt tccagaacat caatgttcaa tagacgaacg      60

tgggggttac gaaacacaag ctacagctgc ggtaattggt gagcttctga aaaacaagtt     120

tggggcgaca ggatcaggtc ccaaacctcg ggagatccgt cacatgatgc gtggtgacct     180

aaacgtcaat atatcatact ggaaggcatg gcggtcgagg gacgtcgcaa tggagaacac     240

gaaagactca gatgtgactg cttacgcaaa actcccagat taccttaaca agctagtgaa     300

gtctaatcca ggttctctcg tcgaactctg tacagaacca cagcaaaatg gtggccaccg     360

tttcaaatat ttatttgttg cattggaggc ttctatcaag ggatacgagt acatgaggaa     420

agttgtggtt gtagatggaa cccacttgaa aggcaagtat ggggggtgtt taataacagc     480

atccgcccaa gatggaaatt atcagatttt tccactggct tttgccattg ttgatggtga     540

gaatgatctg tcatgggaat ggttcttcac tcagctttcc aaattagtac caaaccatga     600

agatttggtg tttgtatctg ataggcatgc ttctattttg aaaggaatta gcaaggttag     660

taacattatc caatttattt tagaaacatt tttaacgtaa tcggaaaaca aggaagatgt     720

aggttatgaa tctttctggt tctcgttgtt acaattattt ttcgtataat atataacgtt     780

tgcttaaaac ataatctcag gtatatccct cggccggtca ttgcatttgt attgtccacc     840

tgaagagaaa catccgctca aactttaaag gacgacatct cgagtacttg gtggccaaag     900

ccgcaagaag cttcagacta gaagattttt acacatcgtt caacgagatt aagagtattg     960

atcctagctg tgcggagtat ctgctcgaga ttgggcttga tcattgggct agagcccaat    1020
```

ttcctggaaa acgatataat gtgatgacaa gcaatcttgc ggagtcttgg aatggagttt 1080
tgcgtgaggc gagagaacta ccggtcatac gattggtcga gttcattcgt agtaagctga 1140
tgacatggtt tgcgagtcgt cgtgaggcgg caaataaaaa taaaggtaac ctatccaaaa 1200
aggtgttagg tattgtaacg aaaaactttg acaactctgg tgggtatgag gtattggaga 1260
ttgcagagaa ggagtttgag gtccgacaga aagaaggtgg aggtttccat gtcaaccttg 1320
ccaatatgac ttgtacgtgc tttgaatttc aaatgctggc aatgccctgt tctcatgcca 1380
tagctgcagc cttaaaagga aagatagcgg tagaatcgtt ggtggcacca gtgtatgggg 1440
ttactcaact tcaagcagca tacgggggga gtatatatcc tgtcgaagga tacagcggaa 1500
ttgcagattt ggtcgccaat gttggtggcg tccaaatctt tcccccaaat acccgacgtc 1560
ctccgggaag gccaaaaaag cagagatact tttcaaaggg agaaaaagtg gtaatctaca 1620
atacgtatca ttcaaacgtg ttcattcttg gtaactaata tacaacttct gcacttatgt 1680
ataacagctt aaacgagggc gtcgcaggac agcttgtagc aggtgcaaaa agttgggaca 1740
caacaaagca acctgcaagg aacctatata agaagaagaa ggttggtggg taaggggaat 1800
ttagggtcag agggaagatg taagtgagac tggttgtagt atgggaaagc tgtatggaac 1860
ggtgaaggat ttaagatggt agaataatga tgtgtgtgta tgtttgtgaa atagtcatgt 1920
aaacaaaatc catcaacgga agtggtggcg gtggacgtta tatatttctt ataagaattc 1980
ccctctctgt atactgtgat ttctatattt tcagcaataa actaatattg acagtaccaa 2040
atatgtagcg aatgaatttc tactaaaatt ctttatggga aaggataacc ggctaacact 2100
taaaataaga cttgtaacat aattgcctaa ccagatttgt aagaaatctg gaaaccaatc 2160
ccaaatactc tgatcgtcac aaactctaaa ttacgggaaa aggctgtaga gaaggttaca 2220
ccgccaactt gatcttagct aataccgtaa agacaacatt acgaaaaatt aatataaatc 2280
aaatgttttt gacatatatt ttttgtaacg agctactaga gttaatctct aaactctaaa 2340
cctttaaccc gaaaacaata aacccaaaac ctaaacaata taccgtataa ccgttgcagt 2400
atcacctata ccctaaacca tagacaatac accctagact gtgatcataa atctgtaggc 2460
ggctacatgt ttgcttatgc gtagacaaag atatgttaac ctgctaaatc atgtaacgct 2520
aaacaataaa ctctataccg ttaaccatta accctaaaaa cataaagcct ataccataaa 2580
ccctaaaccc taaaccagat acggaaaaac ttaaacccta taccctaaac aataaactct 2640
ttacggtatt ccataaaccc ttaccctaaa tcatgtaacg ctaaaccata aacccttacg 2700
ctgtagccgt ctacattatt tcttatccgt ttaaaaatat atgttaacct gctaaatcat 2760
gtaacgctaa accataaact ctataccgtc aaccatttac cctaaaacca taaagcctat 2820
accataaacc gttaaccgta aacctaaaac ccataattcg aaaacactaa accctaaaca 2880
ataaacccta aaccgaatac cgtaaaccct agccaattta accattaacc ctaaaccctt 2940
aacactaaac cctaaaccct aaaacataat aagaaaacac tataccctaa accctaaccc 3000
agaattggaa aacactaaac cctaaaccct aaaccatata ccccaaaccc taaacccaaa 3060
accttaaccc taaaccatat accccaaacc ctaaacccaa aacctaaacc ctaaacactc 3120
aaccataaac actaaaccct aaaccctaaa ccctaaaccc taatccgtaa aacataatac 3180
gtaaacccta aaccctaaac ctaacccata atttgaaaac actaaaccct aaacccaaac 3240
cctaaaccct aaacccgaac ccacaaagct ctgccttcgt agtaactatg tagccggcta 3300
ggacctaaac cgtaaaccta aaacccataa ttcgaaaaca ctaaacccta aaccctaaac 3360
ccttacccaa accctaaacc gaataccgta aatcctagcc aatttaacca ttaaccctaa 3420

```
accettaaca gtaaacccta aaccctaaaa cataattaga aaacactaaa ccctaaacct   3480
aacccagaat tggaaaacac taaaccctaa accctaaacc ccaaacccta aaccccaaaa   3540
cctaaaccct aaacaataaa ccctaaaccc taaaccctaa accctaatcc atataccctc   3600
aaccataatc cgtaaaccct aaaccctatc cactataccc taaaacgttt acaattatac   3660
gtaaacccta aaccctatcc agcggaccct aaaacgtata cgagtaacct aaaaagctaa   3720
aacctccgcc ggcatagtaa ctctgtagcc gggtccatat taacctatcc gtaaatttac   3780
tccgtagccg ggaacatata aactgatccg taaacaaact ctatagccgt catcgtaact   3840
atgtagcccg ctacatattt acttaaccgt aagtaaatat atgtaaacca gctaattcat   3900
gtaacgctaa accatacacc ctaaacccaa atatctaaac cctaaacact aaacactaaa   3960
cgctaaacac taaaccctaa accctaaacc taaaccctaa accctaaacc taaaccctaa   4020
accctaaacc ctaaacacta aaccctaaac cctaaaccct aaacactaaa ccctaaacac   4080
taaacactaa accctaaacc ctaaacccta aaccctaaac cctaaaccat acaccctaaa   4140
cccaaatatc taaaccctaa acactaaaca ctaaacacta aaccctaaac cctaaaccat   4200
ataccgtaaa ccgtaaccaa taccctaaac cctaaaactg taaaacctag ccaaattaaa   4260
ccaaatctta aagcctaaac cataaaccgc aaaccttaaa ccctatccag tcaacacaaa   4320
acataaagca taaacctata acccaaaaac cgccgccgtc atagtaacta tgtagcccgc   4380
tacttatttt cttattcgtg aaaatatata tgttaacctg ctaaagcctg taacgctaaa   4440
ccggctaatt catgtaacgc aaaaccccaa aacaattact ctttagccgt ctttataatt   4500
gcttatccgt aaaaaaaata tgttaacctg gtaaattatg taacagtaat caataaaccc   4560
tataccgtta accattaacc ctatacccta taccctaaaa tctaaaccct aaaccctaaa   4620
ccctaaaccc tcaaccctaa accctatacc gttaaccatt aaccctatac cgtataccct   4680
aaaccctata cgctaaaccc taaactctaa accctaaacc caaaaaccct ataccctaaa   4740
cgctaaaccc aaatccctaa atcgtaaacc ctaaacccaa acctaaaccc taaaccatta   4800
aaccgtattc cttatccagt taaccgtaat ccttatacct tcgaccatag taactctgta   4860
accggctaca tattaactta tccgtaaatt tactccgtag ccggctacat attaactgtt   4920
ccgtaaatta actccgtagc cgtcaaagta actctgtagc ccgctacata ttaacttaac   4980
cgtaaaccct aaaccctgaa cgctaaaccc taaaccatat accatatacc atataccata   5040
taccatatac catataccct aaaccataaa aactaaaccc taaaccataa accctgagtg   5100
aaccccataa tagtaactcc atacgcggct atgcattttc atagggggat ttttaaatat   5160
gttcacctgc taaccatgac attgttatac ccgactatat aatttttaac cgtatgcatg   5220
tatatattaa gctggtaacc atctatttaa caaaattaaa catgtccaaa tattcataca   5280
aacatatcga acatccatac tagcctttaa aaggcgtcat aaaagtctta aagggcaaca   5340
ataattacga aaattatgca aattttacag cacaacacag cagcccctca tgttcatctg   5400
ggattcaatc agcatcttcc cccgttcaat atctttctgc aatccaccaa tttcccctct   5460
taagtcagct atatctccct tcaaatgggt caccatctcc tttagatcgt aaatctcctc   5520
caccatacat tcatcagtcc aggaaaagag gtgagatttg tcctgcacaa attagccaaa   5580
tccggatcgc cttgtttcgg aaagtacttc cattgaaata gaaaaacata aacgatctta   5640
agtacctctt cagatccata cggacaacaa tggaaaagcc ttccagggtt ctttgctgtt   5700
ccggaggttt taatgacagc ctcttcccca caccgacaaa atgtagggaa ccctctctct   5760
```

```
cttgcccgcc gcccccgcct cgagcttact ccccctgcaa aaatgtgggt tatggtaatg   5820
gatagtcaga acaaagaaac tttaaatcca ggttaattac ataccagacg tagaggacga   5880
gcttgccttc cctgattgcg acattcttct tcctctatct ttctcctcct taacgatttt   5940
gtaacttaac ctcttccgga tcgtcgcttt gtcggccaat aagagaggaa ccaaatacga   6000
ctagaaaaag gggaacattg aatttaggtt acagtattag acgttggccc gaatattatg   6060
agcccaagcc caattaatga aaataggtga tattaaataa attacttgac cggctactcg   6120
attttgtaac ctccacacag tttccactta attaggtcga tcataacata tgttttcaaa   6180
caaacaacaa cactggctga gttaaaacat acgggaatgt gaaaaaaata cattacaaac   6240
taggaatgag ttcatatgat gccgtggtat ctctccacaa tggtgacagc aacacgttga   6300
agctctgact cgacaacgtt gggggatatg cacttgcaga tttctaatcc gccaaatgcg   6360
tgtgcttgta taaggagaac cgcattaaca gccgaataca aatgattctc taattgcggc   6420
accagacgtg gtctatcaat cggtaaagcc ttaagatctt tactggaaat ttgtttcccg   6480
gcttgtctaa gtaaataagg aaacatggct gcaattgggg caatctcttt gcacatcata   6540
acatcagtgc ggatagagat gttgcagtcc agaacatgga gctgccaact ggtggcgtca   6600
atgcacaaac caacccaatg tgtcttatcc aagttaaaag ggaagtagaa cctggaagcc   6660
gcacctacgc tcctgcaact tgtagaaaaa ctctccaaca aagttgttgg aaatttgaaa   6720
ccatccattt tcgccttgtt gaaccttcca taactcttgg ataactgaga tacgaacttg   6780
gtgtcgaaga aaactgcgtg atttgttgtt atctgaggag aggcactgtt atataccgaa   6840
cgtgtatgat gaataagcag atcaacaacc tagcaataac catacgttca atatagtgga   6900
ccctcattag gcacgatata ggtataacaa tattataaac aaataacgga agacagacct   6960
tcgccggtac ttgtgcagac ttttccacca gggccattat atccttgctt tcaattttaa   7020
ctccgtgaac gatgaacgaa ctaagataaa atgtgtgaac cactaagtta ccataatccg   7080
acatttcacg tgtgggaaaa tagaagtttg ttggagatac ttacaacggt gttttaagaa   7140
tgtctctcag tttttcgaat ttgtactcag cttccatgtc atcaccggta cgattagccg   7200
caacatgtgc ttcccatgct cttgttagaa ttttcttgtc acattcgtag tcacccacta   7260
acgcttttgg aacaaccttc tggcgcttgc ttttcctgaa agggtgacaa ggcgcatccc   7320
cttcttctgc tgtaagaaca tcatccttgt tcaattgtat cactagagtt tcctcattta   7380
cggcatcaca cccttcgatt tgataatttc gctcttcctg actcagtccg agcgagaatg   7440
taggtttagg gaacaggagg gcagggtcga gaatctgcgg ataaaacata tgaaataggt   7500
tctgatcaga taataaaata tgttaaaatt aacaactcat acggtttcat ctgcggcagc   7560
agaaatattg gaatcaggtt cagaaccatt caagttagcc cttccgaggg tgtgcatctc   7620
cgtgttaact cccacggtat ctacctggag aacgacaaca aattcacttg aagactatcc   7680
gtacggctgt aagtattctg caaaatatcc tcactacccc gctaacattg ttattagcta   7740
cctaactttt gactatcaca tatttacttc cgatgtcaac tacataacct tgttaggtgg   7800
cattatttac acactgctga aagaaacaca ataaaaaaca tacattggga agttgaaacc   7860
cttcctcctg cgcgaaccgc aatgcgctgt cgatgatttt tgaagcatca agttcaccat   7920
tagttgaagc tgggggttga ttgaggacct catttaagcc tacatgtgaa taattggact   7980
gatcctctcc agtcctccga acctgcggag atgttagggg taaatataaa ttattacttt   8040
cacgtacaat tatgcatata tacttacagc tatagacggt cgaacatgtt gtatggccgg   8100
agcaggggaa tgattcatct gattacttat actctggaat gtctcagcgt gaaatgactt   8160
```

```
taacatatct tctactttgg aaacaatggt ggtttcgaga cttgtaaagg cagcaccaaa   8220
actcttaaat tctgtggcga ggaaggaaag ttctgcggaa acacggttga gctcttctga   8280
tacacgactc agatctcctg aaatgcgacc tttcacagaa ctagctatgg attctgcgtc   8340
cacatgatcg ccacaactcg ggtttgattt ctgctttgtt gttttcttct tctctgcttc   8400
agttcttgtt tcttcacgca ttctcacaac gtccgatttt gaaacacctc ccgtaaaaaa   8460
tgaatggctg aacgaaaatc cctcgtcaat taacttcagc aaattttgta cacccacatc   8520
ttcttcatca tcagtaaacc caacctcaga atccccattc acttcctcgt tcccgaccga   8580
aataattgaa aacacctccg cctgccgtta catttgttgt cagtcacgat tacacaaaca   8640
ttttatacca gttgttattt tcctaccata ttacctttcc tgagcagtca gtctcccggg   8700
catgccctgg acttatactt cgcttccctt tcctttcttc ttctgaaagg tcgtcgtcgt   8760
ccgcaaagtc gccttcagaa cccgacgacc cggcttcatg aacggcttcg gtaagagcag   8820
gtacagcttc aatcattaca agctgtaaag ctagcacaaa tccctttaaa gctattgtgt   8880
tttgcgaaag agaaagttcg ttcctctctt tgatactgct tatcagcaac tcgaatgaaa   8940
cgcgtcccca aggatatgca agaaacgcat ccaaatcttt aattttctcc gcatgctcgt   9000
gtgaaatccg aggtgtatga gtggttggga gaacaacaga agcaaggagt gcaaggaacg   9060
catactttat ccttgtttct tttgcagtta cacttctctt tttcagcatc cttacaacac   9120
agctgacaga aacttcttcc atggttccga atagctcacc ccagtatggc ttctcgttga   9180
tatccctctt tgcctttttt ctggaacgag ctggatactt acaacaattc agacctgtta   9240
ctttagcaaa ttccttcaca gaaaaccgga ttggtttgcc agcaaacaag aaccaggctt   9300
catgtttctt cttcaccttc aattgcctcg atataatgta tctcccaaaa cgtccagaga   9360
atgttggttt ctccgcgatt tctacaagcc taccgaacgg tgatcggcgc agagcttcaa   9420
cttcatcttt ttccagtgcc ccgagtatgt tacttattgc gaagggtttg tggtaagggg   9480
ttactctcac cccaacgggt tcctcgccca atgcgaacat cctctccggt atcctttgcg   9540
aagactccac ttctcgtcgg ttttccatct ccatcgtcgg taccgaaatc ttccgtctca   9600
gatgattgcc aaaaaactta aggagagagt ttccagattt gaggcttgtt atacaaaaca   9660
gattgattta agagatgagg atttcgattt tcgaatttca aaattacaca agatgctcta   9720
taatctttta agatttgagt tttctgacac aagatactca agatacggaa atgatacaga   9780
atatcaagga tacgcaaaat ataaaggata cgcaaatctt gaaatatttc actttatacg   9840
caaatcttga aatatctcac cctaaagatt acgtaatctt tttctgcctc gatatcgata   9900
agggtaggga ggtctttaac atctgctcaa cagtactaaa tagtactaat aggtatatgc   9960
ctaaatacgt aatatgtcga gtatagggag cgcaatttct ctatttgttt ttggatgaat  10020
gagcgagaga cagaaagcgc aacaacaatc aatacatttt tttaattaaa ttattaataa  10080
atgattgggc cttttctctt atatctgagt gcaagctttt tttttgaaag atggcccatt  10140
ataaatgggc tatcgtttga attaaaacgt gggccattac tcattttagt agtttactta  10200
cagttaaatt ggatagacgt gtgagtgatc agatcccctc tccgattgat tgattctctc  10260
ctcctccaaa caagccaagc caaggtatgc cttctctctc tctgcaatga gatcggtttt  10320
tcagccggaa gtcaaaacgt atcttcgtat tgttgactac ttcttagatc tattttgctt  10380
ttttttcac ttgttatgga ttgctgctag atttaacaca tgatctgctt tcatttaacg  10440
gatcaagtta tgattctccg accgaacctc taaaccaaca ctttgaaaca ttaatagtcc  10500
```

-continued

```
tttttagtac tttctgatta atattttacg ccaaatagtg atcagttagt tggatcacct  10560
attagcttgc gtcaaaaaaa tgttcagaag ttctattttt gggttgatcc acaaacttca  10620
tttatctaac aagacttata gtttgtgtag gagaaaagag agatggaatc gagcagagga  10680
ggaggtcaag gtgggatcca gcagttgctt gctgctgaac aggaagctca acacattgtc  10740
aatgctgcca gaaccggtaa tttctcttat ttttctactt tcttagtttc ccccacatgc  10800
ttgcattctg aatctaaaca taaatagtta aatacagatg atcttgtggc cgaaaattat  10860
ccaaacttgt atatttataa atgataagca cttgttgagg ataatgcata gtgtccaatt  10920
tgtcttgctg gagctttgat tataaatgtt tggagtttga tttgtgatct tgtgttgcag  10980
caaagatggc aaggctgaag caagccaaag aagaggctga gaaggagatt gccgaataca  11040
aggctaaaac tgagcaagac tttcagagaa aacttgagga ggtaatatat attctacaaa  11100
gtgatataag acaatctagt gttctttttt cttcttcttt gtaataataa tccatgtata  11160
tacatacatc tgggggaaaa caaacagaca agtggagact caggtgcgaa tgtgaagagg  11220
ctggagcaag agactgatgc caaaatcgaa cagctcaaga acgaagcttc caggatttcc  11280
aatgatgttg tggagatgct cctcaaacac gtcaccactg tcaagaactg agtctcacac  11340
tcttatttat ttctctgctt tttgtaattt ctctcttgtt gttgtattca tatcttgttt  11400
gttgttgttg gatgcgaggc ttgagatgtt atgtaaccaa atacacgaaa caataatgtt  11460
ttgagtcttt tgcaagaaat atttcttgat gaataaatct cttttgagaa aacatgtctt  11520
tctcctaacg gtttgctact taagtttagt aaagttggat caatcgtgaa atcttttggc  11580
aaacagttag tttaagtctg tctgtgtcaa agtcatgggc tcggttcggt tgttcagcct  11640
aaaagccata gttaatgagc catagaggtg ttatatattg ggagttatga aaaagcccat  11700
attccaccac tatttgctag ggtttctcct cgtcaccgcc ggtgacacct actttaaata  11760
tgaatcatct ctctcctcca acttagactt ctctctatct ctctttcagt ttttttggtt  11820
catcttcatt atttttccta tctagatgtt ttatttatgt gtgagaaagt acaatgagaa  11880
tagatcagat gatgagataa taactgcaac aatatgatct tcttgatgtt cagtattttt  11940
ttttttaata caatgttatc ttcgttttca aaatttgtat tggttttgat ttttgaggat  12000
aagagaaaga agagatatga tgagcaacta aattggtccg tgtttcagat taaccgtgac  12060
cgaaaacttt cttaaccaaa ctctgatctc tagctaacat ctatcttcct tttaaacaat  12120
aatttgattt tatttattta tcttgcttgg ttcctgcggt gatgatttta tgaaatattc  12180
acatgtcaga cttcagagat tcttgacgaa tcagtgagaa tgtattcata tttctgagca  12240
gaagactagt gtttttccaa gcctcataga aagttttcaa ccgttgaaga aattggacaa  12300
gaacaaatac gacttaatca ctttaagaac atgattattg ccgcgcagaa agaagaaaca  12360
aaacttaata ttgctgagtt gtatcatcgt ggaagttata cattatctaa tacataagtg  12420
cttgaagtac gagctaatca ctttgagaat gtgacaattg catttgtttg ccttttatgt  12480
taaattataa tgagtcaaca aagatctaca atagtctcca aagatgatca agagcccgtt  12540
tgttaagagt ctaagaccgt agcggaacaa ctaaagaata ccctatggac tgttgtggtc  12600
gtttatggat ccaaaatgtt gtcctgtctt caaaatatga tggtataatt aggggttcca  12660
aatatttctt gaataacaag gcacctccgt gtattacatt ttaacagggt ttaattgtta  12720
cgaaactcaa actacattta atttgtttga tatcaagtat tctttctttt tgggaaaatt  12780
ggaaaaatgc aaaatgtaat caggtccttc aaaacattat taggtttctt gcttaacaag  12840
ctatgtgtta ttcatgatat catgtgataa acaaggtact tcaaacctta cccgaaaagt  12900
```

gtaagtcgaa tgcatcggcc gagtggagcc tataattaag taacacagaa tgtgaacaaa 12960
atttactgaa caggttttat aaaacatttc tttaagtcta gttaaacctg ctttcagaca 13020
ctttcatatt acaaatctaa aagtgtataa ctaaaagacc aaaataaaat caaactttag 13080
taaattttct gtaaatcttc agactgaata tatcagatta gatcatacct aacaaatcag 13140
ttcttagcag aattttataa taaacaaatg tagtatgaaa gcctgatatg tcagctactg 13200
tgttttgatt ataacctttt taactctttg cacaaatggt ttagaataag aaaaagctcg 13260
aaagcaacca aaaagctaaa ttacattttt ctcttctgca tattctggaa tccttggatt 13320
ttattctttc acagttttta ttttttattt tcttttcttg accaaaaatc acaccagaac 13380
gctaataacg acagatagat ttttatgtaa acattgataa gtgacacagt ggaccatgtg 13440
atacgttagt ttgttagtaa tcacatttaa taaaaagttt cccatcacta tcagctcacg 13500
gacgatatta cgctatagcg tcaagtcgtg gctccatttt gactagaaat taaaaaaacaa 13560
taaagcatat ttttatttat tttaggtatt agtcttaacg gcacggccag tgacgattga 13620
ttgtcccttt tatgtcctcg tgcttaatca gcgttcgtta gatattctta atatatttac 13680
tttccaaagt ctatctatgt tttgccttct tcacaagcat tatatattgt cgtcgctatt 13740
gctctgcctt gtgatcatca ttgttttact ggtaactctc tctttgtctc cttcatcttg 13800
ttctctgcga gagaggagta gatatggaag tagaagaagg agcgagtgtt gatgttggtg 13860
gtgggaagat aaaggttgga gtatgcgtca tggaaaagaa ggtgaaatgc ggctccgatg 13920
ttatctttca tttttttaaa aaaaaattgt tactgctcga tgttttcttc tactgaccaa 13980
cagactcgga tggttggttt gtagtttatt ttggagtcct cttgttttta ctatgtgttc 14040
ttctcgatcg ctcaaagata gctcgttgtg gatttatagg tctcctcaag tcccatgggt 14100
caaattttgg acagactgga gtcgtttggt gaatttgagg taactttgta ctcacgggtt 14160
tcttctttgt tccaagattt ttatatgcta taattttctg gtttgtagta ctctatatat 14220
agtttactat ttaacctgga gagaggttgc ttttgattag atggcttgtt atttagcttg 14280
ggagatgctc tttttgtgtt cattttccaa gttgttgaat tagtttgcga ctagaaatgt 14340
tgttgactaa tttgtctttg tatattctct ggtgtattct ttatattttt catgtcatgg 14400
acaactttat ccgcagatct tacattttcg ggataaagtc atacttgaag atccaataga 14460
aaggtttgtt gtactaaaga gtttactttt tcccttttcc agttatgaat gacgtcccat 14520
tattagtgta ctaggagaaa tagtagttaa tctctatata tatcaagtac tttctccaat 14580
atatatatat atatatatat atatatatat atatatatat atatcaagta caaaaaacctg 14640
acatgagaat ttgctgtttc agctggccca tttgtgattg cttgattgct ttccattcca 14700
ctggatatcc tcttgaaaag gctcaggctt atgctgcttt aagaaagtga gttttttttca 14760
cctttttat ttcttgattt tggctcccat ataaaagctt tctcatgact ccggcttctg 14820
aggttgacaa cttttcaaac ttgtcttgtt caggccattt ttagtgaatg aactagatcc 14880
acagtatctt cttcatgatc gccgcaaggt gtacgaggta ttgcatatta ggatgcaata 14940
agttggttct gtgtactttt gataattttt caaagtttcc agggctaatg agacaaagaa 15000
gagctactac atatatttta tttttccttg ctactaacaa atagcttttg tgtgcatttt 15060
tcagcatctt gagatgtatg gaatcccagt tcctaggtat gcttgtgtca acagaaaggt 15120
accaaatgaa gaagtagatt attttgtcga ggaagaagat tttgttgagg ttaatggtga 15180
acgcttctgg aagccatttg tggaaaagcc tgtcaatggt gatcttctct tttttgcctc 15240
ttgctctctc tttttcatgc cagcttatta tctatttatc cataagtcta aagtagaaaa 15300
ataaccatag gagtgtgttt tgtattttcc tctgatattt cgtaaccaat ttcacttgaa 15360
tctgttatct catatgagtt aaatattgag gtacaatgaa tataaacaga ggtgattttt 15420
caaggctata ttctcattta atgttcttag ttgttatatg atgatggcta tcctcgttat 15480
atttatcttc cgacagttaa cattctttgt gcgtttgtag gagatgacca tagtatcatg 15540
atatactacc ctagctcggc aggtggaggc atgaaagaat tgttccgcaa ggtatctctc 15600
cagaagaatt tggctgctat ggattcaatt gttgatattc taatatattt ttcataataa 15660
ttagtgtcat attcctctgg gactcgtttt cagctaatgt atctcgttcg tctccatttt 15720
actttaagat tgggaaccga tcaagtgagt ttcatccaga cgtcagaaga gtaaggagag 15780
agggttcctt tatatatgaa gagtttatgt ccaccggagg aactgatgtc aaggtatgtg 15840
tttattttcc ttctgcatgt ttctctatta gctcatttca tcttttagac cacattaatc 15900
tttctgagaa tatcgtacta ttcttggtgt caagtgtcct acatttataa ggttatcatg 15960
ttaatggcct atatgtttat atgacttagc tcctatttgc tggttgtttt tttgtctggt 16020
gaacattttt tcgtgaagtt ttggctttca cgagctctgt actgacaatc tggatgctgg 16080
cttaaataca ggtatacaca gtgggtcctg aatacgcaca tgctgaagca agaaagtcgc 16140
ctgttgttga tggtgttgtt atgaggaata ctgatggcaa ggaagtacgt cgtctaccga 16200
tcatttacct taaatagaat gaaatttgac actatctcat tttcttatgg agagagggct 16260
atattttagg tgcacaaaaa aaaagaagag gggctatatt ttgaatagaa tatcaaagtc 16320
tattgattat gatttggtaa atgtttcatg atggtgtaac actattattt tattttttta 16380
ttgaacaggt gagatatcca gtgttgctta cccctgcaga aaagcaaatg gctagacaac 16440
tttgcattgc atttaggcaa actgtatgtt gtgaatccaa tccctctggc tctcgcagag 16500
ttttattttc tttataatgg tactaaatta tttttatttt ttttacaaat ttcatcaggt 16560
gtgtgggttt gatcttctac gatctgaggg atgttcatat gtttgtgatg taaatggatg 16620
gagttttgtc aagaactctt acaagtaagc taatagcatt cttcacttta ttttaactct 16680
ctaaaatgtg caccgttaaa gtattattca caaacctctc atactatact atgtaaggta 16740
ttacgacgat gctgcttgtg tgctaagaaa aatgtgtttg gacgtaaagg ctcctcatct 16800
gtcatcgact ctccctcaca ctttgccttg gaagttcagt aagcctgtac agcctaataa 16860
aagactaacc cgtcaaggga atggacagtc agaagagttg cgttgtgtca ttgctgttat 16920
tcgacagtat gtttttttta gcatataaat cacctatatc tcatctatac ttctctctgt 16980
taaaattttg ttattacatg acagtggtga tcgaactcca aaacagaagg tgaaactaaa 17040
tgttacagag gcgaaactgt taaacctgat gttgaagtac aatggtggaa agccaagagc 17100
tgaggtgagg agatcgactt tttctgtcat ccatctttta tctgccttgt tcattttata 17160
tattttgtca aattttgcag acaaaactaa aaagtgcagt ccagttgcaa gacctattag 17220
atgccacaag aatgttagtt ccccgtacaa ggtacaaccc tgaactctat cttctctcca 17280
aaaagcatgt ctggtctacc ttttccatgt gttgaatact cgtaccgaca atatggtctt 17340
tctttttta tatgtagacc aggtcgtgag agtgatagtg atccagaaga ccttgaacat 17400
gctgagaagc ttcgccaagt taaagcagtt cttgaagagg ttctttagta ctttctcttt 17460
ttttttttg aatatagtcc gtggaaagta ttacatagta tcatttaggg agttaaaact 17520
cttataagta agctagcatt atgcattttt tatttaattc atgaggtcat attcttatag 17580
cagaaaacct tttggtatgg cgcagggagg aaatttttct gggatataca ggaaggttca 17640
gctgaagccg ctgaagtggg atggtgaagg cgaagaagaa agacctgtag aggcccttat 17700
gattcttaaa tacggcggtg ttctaactca cgctggtaga aaacaggtgc ttacatactc 17760
taccatttaa tttgtcattg ctatatatat atatatatgt ttcccaaata tggaaaattg 17820
tttaacttat tgatgtttgc ttcatctgca tgcaggcaga agagcttggt agattcttcc 17880
gatacaatat gtatccaggt aaggccgcct aatctgtttt tttttatttg ttactttttt 17940
tttggagtat ttgacgatga aatggcttta ctatatgttt tttcaggtga agggactggt 18000
ttgcttcgtc tccatagtac ataccgtcat gaccttaaaa tttacagctc tgacgaggga 18060
cgtgttcagg tacgtacacc ttttacattg atactactca agataattaa acatatgtgt 18120
tggaaaaaat aattattgaa ttggtttgca tatgttgacc agatgtctgc agctgctttt 18180
gctaaaggtc tgcttgacct agaaggacag ctgacaccaa tcctggtttt tctttctttt 18240
tttaaatctt gttggtgctt aatttgcaat gtcatcatgt gtattactaa taatattttt 18300
atctgtcttg cttctctagg tttctttggt tagcaaggac tcttccatgt tggatggtct 18360
tgatactgcc agcattgaaa tggaagcggc caaggtttgt cccatgatga atcattttct 18420
gaatagtcca ccttaaatat gttaacagtt ttgatttcac tacttggact atgcaggcta 18480
gattgaatga gattgtaacg tgtggcaaaa aaatgaccaa tgagcatggc tcctctgaag 18540
aattcccttg gatgactgat ggagctggag ttcctcccaa tgctaatgga ctcctccgtg 18600
aattggtact cacacttttc catctagtct tagtttacta ctggtgtgaa gtacatcacc 18660
aacctttttt ttttagagtt ttgtttgcac aacaacgtac tattgcatag gcactgatga 18720
gcacattggt aacctctgtg ggtattgctc tcatttttgt ggctccctca ttaggtgaca 18780
ttgaccaaga atgtgactga acaagtaaga atacttgcaa tggatgagaa ggagaacctc 18840
actgagccat atgatatgta tgatcaagca aaggctcttg gaaagacaaa cattgacagt 18900
gataggattg cttctggatt accatgcggt agtgaagggt ttcttctcat gtttgctcgg 18960
tggataaaac tcgcaaggga tctctataat gaaagaaaag agtaagtttc ttatcaaatt 19020
ttttaaacat tatttagagg cttgtgagtg agtgagagta gcactaatag ttcagtttta 19080
acttgcagcc gatttgacat cacgcagatt ccggatattt atgattcatg caagtaagtt 19140
atatatgtta tggtggtttt ttggtgtatc tcgtttatga atttacttta atatgtctgt 19200
taacgtcacc aggtacgacc tgttgcataa ttcccatcta ggtctacaag gattagatga 19260
actcttcaaa gttgcacagg tacaaactgt attttctctt ttccagtttt cacttacaat 19320
aatactttgt tatcttccaa ggcatactaa tgaacatgac ctttcttggt agatctctgt 19380
attgcgttga ctgtgttagc aattatgact aaataatgtg ttttgtggtt gcagttgctt 19440
gcagatggtg tgatcccaaa cgagtatgga atcaatccac aacagaagct taaaatcggt 19500
tcaaaggttg acattttata ggctagctac gagagtagtt tatatatggt gtttccagtg 19560
gatctctcac atctttatca aaatctattt ttccgtgaaa aaaggttgct aggcgcttaa 19620
tggggaaaat cttgatagac ttgaggaata ctcgagaaga agcaatgagt gttgctgaac 19680
tcaaagaaca acatgtcaca ttgtcattat ctgcctcgaa aaaacaacaa gacaaaaata 19740
ttcaaccaaa gagagatgat ttgagacgac ctggcactgg tgataaggat gaagatgatg 19800
acgataaaga aaccaaatac cgattagatc ctaagtaata gcttactctc tgcttgtata 19860
gtttctttct tcttctcctt ttcttggttt ttgcatattc ttaagtgttt tatactaatt 19920
gcttttcatt ttcccatttt aggtatgcaa atgtcaagac acctgaacgt catgtgagga 19980
ctcgactcta cttcacatct g 20001

<210> SEQ ID NO 3
<211> LENGTH: 6454
<212> TYPE: DNA
<213> ORGANISM: Brassica napus

<400> SEQUENCE: 3
aagccagaaa aaaatgtgga agtgtaataa aacaattttc tccaggaaga agatatttca 60
gccattcgcc tatttatgtg tatgagatcc cattcaagga catactgttt tccgtgagct 120
actgaatgaa tacgatgctt ttgttgtaaa cgcaacctat tggttttttt tttccgccaa 180
gttttgtttt tattaatcaa acgggccaag cccaaacggt cgaagcccaa atacactaag 240
taccaaacaa aaggcccaca gacacaacgg gctacaacat taatggctga agcccaagta 300
aactaaacgg cccaaaggcc caaacattga aaccggacag cttgacctag gcgcgcgata 360
aggagactgg ggtttgaaca cgtgtaagaa tctgggccat tagtatgaca cgcgtcgccc 420
gcctcgactt gatcgaaacc tcttcgcaca gccgcatgaa cttgccaccg acgacctcgt 480
ttcgccggag ctcagagact gaagagcctc caacgaaacc atagctattc tacgccgctc 540
tgtcttcacg ccggagagtt ccatcgatct aacgagatct cctccgacta tgtatcacca 600
caaaccctag acaggcgagc cgagaaccac tgatatcctc ctcttgtacg tcctcgccgt 660
tgtcggagag tttcatcatc atccgagatc tcatccgcga tggcccacga ccccatacct 720
gaccacaaga accacaccgc acttatctca cctcgatcta atcaccacaa cccaaaggac 780
atcgggttcc aagacggcag cgcggagctt tgcaagcctc cactctccgt gaccaaaagc 840
cggcgaagac ggagctgaat gagcctcccc ttcccggaag ctaaagcggc gacggtggat 900
ctgagaaagc ctccacctcc cgcataaaga ccggcgacga tggatctagg gtagcctcca 960
tctcccggaa aaaacaccac ctgaacatgc aagccgctcc atctccaccg ggagcctcca 1020
attgatcgcg tcgttactcc aaaggccgag ccaccgttga tggatggttg cggtcccaga 1080
gctccgacaa ggcgatcgat gacgggactg cgaagaagga gcggagagtg acaactacaa 1140
aggaagggaa agagctctgg cgacagcacg gacgctcacg cgccagccgt acgccgaacc 1200
caaaagtaga tctggtttct ctcttttctc tctctcgcaa aagaaaacac gcaacctatt 1260
gttctccatt ttgaatttga agtgttacat tattaataaa aaggaagaaa gtacaaagct 1320
tttcatttag tggttgttgc atatatagta tacttatttg atgggcttat gataagtatg 1380
aacatttcac gtaacgggtt tattttgtcg tcaacacatt accggcaatg tgaaaagaag 1440
gggcgaggta tctccatttc aattcttctc tttatagatt aatcgaatta tttacatatg 1500
aaatgagcgt ttatatagaa ttttcgtgtg gaaaacgaca tgtacacggc atcgaaagac 1560
caattagtaa tatactttag tggtgattac atgtttactt atccaattga gaatttaaag 1620
catcgacaat accttaatgt cgattaagcc gtccccactt catgtaatga gttatggggg 1680
gagagagagg tcccgaaatt cgtcaaataa aacaacttag aactaaaaac cgacaccaag 1740
tatcataaag gaaacgttga agaagtcatt tatcgtatcc agctcacaat tcctaagatt 1800
aaatcatgac cgttggaaga gcttataaga ttaaattgaa gaaattgtgg gttttagaag 1860
aaagacaaga aagagaagaa catgatctta cattgcctat tttggtgtat aggagttgtc 1920
aaaaagagga gagagaggag acaattaggt caaataaatg agcactaaaa atggagacat 1980
gtgttgagta actattacaa gagcgactta tgcttctata tggcaatgat atcatcacca 2040
aagtgcaatg ccccttttg ccctagtttc gtaaagtctc tttccttctt catccttagg 2100

```
aaaaacccta aattaaatcc tgtgttcttg atcttgcttt ttgagtaacc atgattttga   2160
ccacacacta gttcttctat attttgtggt ctataggatt ttgctttata tgtgtttctt   2220
gtattgcacc gtacgtgcgt atataaattt aaatggttac aacaaggttt attataaaca   2280
ggcacaaatt agtccatgag gttatttagc ttgcacaaga ggtatataaa tgtgtgtgtg   2340
tgtgttaagt atttaaatat ataaatttgc tacaaaactt aattaacttt atctgattat   2400
attttcttta gtgttcttca tttgccaacg ttgaggtagc tattattatt attattatta   2460
ttattattat tattattatt attattatta ttattattat tattattatt attattattt   2520
tgaacattat gtactatgta cgtagttatt ttggctagtt atgattcaaa ttcttaattt   2580
ggataacact taacagtatt taaaaaaaaa atactattta aaatattctt agtactaaaa   2640
taattaagat ttaacttgaa attgaagtat tcgtgttaaa cagaaactac aataaacaaa   2700
tgattgcatg ttaatttttt tttcgattat cctatatatc agaataaaca catgattgca   2760
tgcaaatttt gtttttgatt atgtcatctt ttgtttattt tagttttgat gctaattaat   2820
atttttttta ttaacaactt ccatacattc tacctgattc taggtcagat aatgacacag   2880
cgcaacaaaa ttatacaaaa ctttcggaaa gtagattacc gcggaagtaa catttttggg   2940
tagacatacg aagtagtttg aatcttcaaa aatcatgcca tacataacca cggatcatag   3000
tcgacacctc aacgtgaagc aaatttgaca atctacatac ataaccaaca aaaagtagaa   3060
taccgtgaaa acctaaaccc aaaatatgat gtaaaactca agcttggtcc agagcataaa   3120
aaaattaaag ccatcgcttt ggtatcacat atttaaacgt cagttttttt ttggggaagt   3180
aatataaaaa tataattaac aagaaaattt atgaaataat tagcatgtaa aacactagtc   3240
ttttggttgt gacaaaacgt tttcacaaat gttctataaa taaattcaag cacattttat   3300
ctgcaaaata tatactttca ctcataaaat aagagcgttt aaaacattca tatacgcact   3360
acattgacat gacaaaagaa atccgcaaat acaaacatat ttagttcgga tatatctagg   3420
aaataagact atattatata tataaagaaa ttagaaaaaa agaaaattgg tatgtataaa   3480
agaaaggtct atgcgtctct agtccaaaaa ctctatatgt ctggttcaaa agcagatgca   3540
gcagccatag ccccaatagt catgatggag cctcatcatc tccttatgaa ctggaacaaa   3600
cctattgatc tcattacaca agaaaactct tttaaccaca atcctcattt catggtagat   3660
ccaccttccg aaaccctaag ccacttccag cccccgccga cagtcttctc cgatcccgga   3720
ggaggagagg aagcagaaga cgaagaagga gaggaagaga tagatgagat gaaggagatg   3780
caatacgcga ttgctgccat gcagcccgta gacatcgatc cagccaccgt tcctaagccg   3840
aaccgccgta acgtaagggt aagcgaggac ccccagacgg tggtggctcg tcggcgtaga   3900
gaaaggataa gcgagaagat ccggatattg aagaggatgg tgccaggcgg tgcaaagatg   3960
gacactgcct ccatgcttga cgaagccatc cgctacacca agttcttgaa acggcaggtg   4020
aggcttcttc agcctcacac tcagcttggg gctcctatgt ctgacccttc tcgcctttgt   4080
tattaccaca actcggatac ctaattataa ttctatcacg cgtttcatgt tgatatatat   4140
agataaatgg ttgaataagg atttcgatcg aagattgtat ggctattgat tacattatat   4200
attgtacaat aaatgatgtg tgtatttcta ttaatgtata tatgatatat atctgtttgc   4260
agtatgcatt tatattctat tctttatagg gaggcaacat gccggattag ggctttgatc   4320
gtatgcaagt tttccgacca aaaatatgaa atacttgttt ggatataaca tatgaatcgg   4380
ataagtgtta ctagttatat aactggaaaa aaattgtttg gtataagaat tcccgggaga   4440
```

accaagcctt tctctaatcc ctaagatcat agctactgaa ataatgaaaa aaaacaaaaa 4500
aaaaacaatg aagaatcagt tgggcattag tccaaaaaaa aaaaagaatc agttggattg 4560
cttataaaat tttgttataa aatttatgtc gtatgtgtgt tagccgtagc tgtaaattta 4620
tttcctttgt atgttaattg taaaatttaa tttattattc ccgatgtttt taatgatgta 4680
agtttacatc aagaaaacat attaagttct gttaataaat gtattatttt tgtttactaa 4740
tttccaataa ttttttcaag aagtacaatt ttttgtttga aatttctaat ttatcaacat 4800
acctaaaaac cataaacatg tattttttga aacatttttt taatataaaa attatttttt 4860
aggagcaggt gaagtatttc ttttaataaa attgttagtg tatttacgtt ggttatagtt 4920
gtagatattt tgcataataa ttaataatat ataagatgtg taatgtatat atgtgagaga 4980
aataccatat ttactaagag tttttcgcaa tattgactca aaattcaaag tcaatcacaa 5040
aactaacata tgtttctttt tagacatttc ctttgcctta ttcactccac gggttcagat 5100
tattcacgaa aatgtcatta aattttttt cttttcgaaa atggcatttt tactctctca 5160
atttcatcct cttcaagtat ttacaagatt tccattgcca tcaatacacc aaccacaatg 5220
aacaaccaat ttgaagctct taatgcacct caaatcgatt tacacttctt ctttttcaat 5280
tcttatgaac taaaaacaac atctctttca atttctcccc atattcatcc aaaaaaccca 5340
agatttttat tctaaaattt taatggttca tagagccatt gaagcttacg attcttggtg 5400
ggtcactttt gttcgagatt ttaggtactt ggagaagact tttgtatgct aaacaagtta 5460
tctcattggc tgaaactatg aaatcagttt tttttccaga tctgttcgcc cggacgactt 5520
ccggataagt cttctggctg tagacgactt acatcgaagt attctggtta atgcagatgt 5580
tagttttgca attgactttt aagatgctta ctcgaagatt agtactcttc tgttcttgta 5640
ccttatgagc attccaatag tattatattt ttcattctaa aatatatttc aatgatattt 5700
tacttttcac tctataatag agtgaaaatg agtttacttt ataatcccct atatattatt 5760
tgtgaaacac tacaacttct ttttgtagcc acatgtcatc actaggatga tttttagaat 5820
tattagagaa ataggttggt ccatctaatt atataataag ttttttatta aattaaccat 5880
aaattcatta ttaatgtcat ttattatttc cttaaataaa gattacggaa ttgcctaatg 5940
tgggtaaagt atatatgaca attaatgatc ttgaataata aagatatgat aaaaaaaatg 6000
tatcttctat caaatttgtt taatttaaaa ctattaaaat aatttttaaa aaaacacaat 6060
aaccatatta taaaaattta gatttttctg tatattttta tattttgaac tttaaaaaat 6120
gacgataaat tactaaaact gttaaaagtc tcacattcaa attttgctat ccatgtttta 6180
aaatttttgt tatgacaaaa tacaaatgat tacaaaatca tataagtaaa agtctaattt 6240
aattaatcat taagatttaa aatatatatg tatatatatc attctaaatt aaactataaa 6300
ccatattgaa taaataaata ttttagtttc aaaattttac tttgaataat tttttttgat 6360
aaaagttttg aactaacatt gataaatgtt tttaaactat caattaccaa aattattgat 6420
cccacaatga aaattttgtt atcagtaatt taaa 6454

<210> SEQ ID NO 4
<211> LENGTH: 4772
<212> TYPE: DNA
<213> ORGANISM: Brassica napus

<400> SEQUENCE: 4
gaattacgaa aacaaaattt gaaaaaaaaa taataaaaaa tttcaaaaaa aaattataaa 60
aagttcgaat ttgaaaacat ataatctgaa actataaaaa ttaattatta ttattattat 120

```
ttgtatttat atatctaggg tattaaaatc tttttactta ttttatgaaa cattttggtt    180
atctttctcc ttacaatcta tttttgtgat aaaaacttga aaatagtcta cttaggagaa    240
ttacccttta cattatctaa taaactgatc ttctagaaga gagaaacgtt aatggtggac    300
gaagcccccca cctcaattga caataaaaga aagtggaaaa gagagaagat agcagagtga    360
aaggtccgaa gagaggagat catgaagaga agaagacaat gtaacctact tatttgcctt    420
gatgaacaat tacgagaaga aataaacata aaatgagaag agagaggtgg gatatacaga    480
agagagaaag atttggcagg aaacccgatt gaccatatat cagatctaga gtggattgga    540
ttagataact cgagcttatt tggttaatct ttttagttta gggaaggtta tgaaaaatta    600
accccgatct gatttttaaa ttttttatct tatattgtgc ccccggctaa caatatatct    660
agatccgtcc ctgatcaggt ccatgagata tatcatattt ttattttttct tatttaatta    720
attatatata taatatttga ggatatattt aaaattttac atatcgttga aagccagaaa    780
aaaatgtgga agtgtaataa aacaatttttc tccaggaaga agatatttca gccattcgcc    840
tatttatgtg tatgagatcc cattcaagga catactgttt tccgtgagct actgaatgaa    900
tacgatgctt ttgttgtaaa cgcaacctat tggtttttttt tttccgccaa gttttgtttt    960
tattaatcaa acgggccaag cccaaacggt cgaagcccaa atacactaag taccaaacaa   1020
aaggcccaca gacacaacgg gctacaacat taatggctga agcccaagta aactaaacgg   1080
cccaaaggcc caaacattga aaccggacag cttgacctag gcgcgcgata aggagactgg   1140
ggtttgaaca cgtgtaagaa tctgggccat tagtatgaca cgcgtcgccc gcctcgactt   1200
gatcgaaacc tcttcgcaca gccgcatgaa cttgccaccg acgacctcgt ttcgccggag   1260
ctcagagact gaagagcctc caacgaaacc atagctattc tacgccgctc tgtcttcacg   1320
ccggagagtt ccatcgatct aacgagatct cctccgacta tgtatcacca caaaccctag   1380
acaggcgagc cgagaaccac tgatatcctc ctcttgtacg tcctcgccgt tgtcggagag   1440
tttcatcatc atccgagatc tcatccgcga tggcccacga ccccatacct gaccacaaga   1500
accacaccgc acttatctca cctcgatcta atcaccacaa cccaaaggac atcgggttcc   1560
aagacggcag cgcggagctt tgcaagcctc cactctccgt gaccaaaagc cggcgaagac   1620
ggagctgaat gagcctcccc ttcccggaag ctaaagcggc gacggtggat ctgagaaagc   1680
ctccacctcc cgcataaaga ccggcgacga tggatctagg gtagcctcca tctcccggaa   1740
aaaacaccac ctgaacatgc aagccgctcc atctccaccg ggagcctcca attgatcgcg   1800
tcgttactcc aaaggccgag ccaccgttga tggatggttg cggtcccaga gctccgacaa   1860
ggcgatcgat gacgggactg cgaagaagga gcggagagtg acaactacaa aggaagggaa   1920
agagctctgg cgacagcacg gacgctcacg cgccagccgt acgccgaacc caaaagtaga   1980
tctggtttct ctcttttctc tctctcgcaa aagaaaacac gcaacctatt gttctccatt   2040
ttgaatttga agtgttacat tattaataaa aaggaagaaa gtacaaagct tttcatttag   2100
tggttgttgc atatatagta tacttatttg atgggcttat gataagtatg aacatttcac   2160
gtaacgggtt tattttgtcg tcaacacatt accggcaatg tgaaaagaag gggcgaggta   2220
tctccatttc aattcttctc tttatagatt aatcgaatta tttacatatg aaatgagcgt   2280
ttatatagaa ttttcgtgtg gaaaacgaca tgtacacggc atcgaaagac caattagtaa   2340
tatactttag tggtgattac atgtttactt atccaattga gaatttaaag catcgacaat   2400
accttaatgt cgattaagcc gtccccactt catgtaatga gttatggggg gagagagagg   2460
```

-continued

```
tcccgaaatt cgtcaaataa aacaacttag aactaaaaac cgacaccaag tatcataaag   2520
gaaacgttga agaagtcatt tatcgtatcc agctcacaat tcctaagatt aaatcatgac   2580
cgttggaaga gcttataaga ttaaattgaa gaaattgtgg gttttagaag aaagacaaga   2640
aagagaagaa catgatctta cattgcctat tttggtgtat aggagttgtc aaaaagagga   2700
gagagaggag acaattaggt caaataaatg agcactaaaa atggagacat gtgttgagta   2760
actattacaa gagcgactta tgcttctacc aagcctttct ctaatcccta agatcatagc   2820
tactgaaata atgaaaaaaa acaaaaaaaa aacaatgaag aatcagttgg gcattagtcc   2880
aaaaaaaaaa aagaatcagt tggattgctt ataaaatttt gttataaaat ttatgtcgta   2940
tgtgtgttag ccgtagctgt aaatttattt cctttgtatg ttaattgtaa aatttaattt   3000
attattcccg atgtttttaa tgatgtaagt ttacatcaag aaaacatatt aagttctgtt   3060
aataaatgta ttatttttgt ttactaattt ccaataattt tttcaagaag tacaattttt   3120
tgtttgaaat ttctaattta tcaacatacc taaaaaccat aaacatgtat tttttgaaac   3180
atttttttaa tataaaaatt attttttagg agcaggtgaa gtatttcttt taataaaatt   3240
gttagtgtat ttacgttggt tatagttgta gatattttgc ataataatta ataatatata   3300
agatgtgtaa tgtatatatg tgagagaaat accatattta ctaagagttt ttcgcaatat   3360
tgactcaaaa ttcaaagtca atcacaaaac taacatatgt ttctttttag acatttcctt   3420
tgccttattc actccacggg ttcagattat tcacgaaaat gtcattaaat tttttttctt   3480
ttcgaaaatg gcatttttac tctctcaatt tcatcctctt caagtattta caagatttcc   3540
attgccatca atacaccaac cacaatgaac aaccaatttg aagctcttaa tgcacctcaa   3600
atcgatttac acttcttctt tttcaattct tatgaactaa aaacaacatc tctttcaatt   3660
tctccccata ttcatccaaa aaacccaaga tttttattct aaaattttaa tggttcatag   3720
agccattgaa gcttacgatt cttggtgggt cacttttgtt cgagatttta ggtacttgga   3780
gaagactttt gtatgctaaa caagttatct cattggctga aactatgaaa tcagtttttt   3840
ttccagatct gttcgcccgg acgacttccg gataagtctt ctggctgtag acgacttaca   3900
tcgaagtatt ctggttaatg cagatgttag ttttgcaatt gacttttaag atgcttactc   3960
gaagattagt actcttctgt tcttgtacct tatgagcatt ccaatagtat tatatttttc   4020
attctaaaat atatttcaat gatattttac ttttcactct ataatagagt gaaaatgagt   4080
ttactttata atcccctata tattatttgt gaaacactac aacttctttt tgtagccaca   4140
tgtcatcact aggatgattt ttagaattat tagagaaata ggttggtcca tctaattata   4200
taataagttt tttattaaat taaccataaa ttcattatta atgtcattta ttatttcctt   4260
aaataaagat tacggaattg cctaatgtgg gtaaagtata tatgacaatt aatgatcttg   4320
aataataaag atatgataaa aaaaatgtat cttctatcaa atttgtttaa tttaaaacta   4380
ttaaaataat ttttaaaaaa acacaataac catattataa aaatttagat ttttctgtat   4440
atttttatat tttgaacttt aaaaaatgac gataaattac taaaactgtt aaaagtctca   4500
cattcaaatt ttgctatcca tgttttaaaa tttttgttat gacaaaatac aaatgattac   4560
aaaatcatat aagtaaaagt ctaatttaat taatcattaa gatttaaaat atatatgtat   4620
atatatcatt ctaaattaaa ctataaacca tattgaataa ataaatattt tagtttcaaa   4680
attttacttt gaataatttt ttttgataaa agttttgaac taacattgat aaatgttttt   4740
aaactatcaa ttaccaaaat tattgatccc ac                                 4772
```

<210> SEQ ID NO 5
<211> LENGTH: 3100
<212> TYPE: DNA
<213> ORGANISM: Brassica napus

<400> SEQUENCE: 5
attatatatg gaccaaaaca tgaatgattt ttcggaatca gatactccat tcagcttcga 60
acagttatta tatggagatg attggcagag gtgggacact tatccgagcg ttgatgttaa 120
tgccaactca atagagccta atcattcgat ggtcgagatg aaccatgatg gtatgacaat 180
agatgctact ccaatttcaa tgatatatcc aatggtaata atctactttc tgcatgtttt 240
ttttagagat attaaagtat ggataaataa tataagactt attgaaaatg tataggaaga 300
aacattcgag cagtggttac agacactggc caatggatca tttgaaatac catcatatga 360
agaactcaac ttcacgtatg aggtatggtg aaagataata tatataaagg tatattttat 420
gtaacatata atcaatttat tggtaactta tttggttata ttgcatttgt acattttttt 480
ctcagtggat atgcatttga atcatagttg aagaaaacaa aaaggaatat atatgctgca 540
attggattgt tgatttttaa aatgatatga cgtccaatga cttatttcat tatttccata 600
aatttttaca gtatttaaca tgaatagaat gaaatactca ttccatcaat tccacaaaca 660
ttccaaaaaa tatacaaaaa atacattcat atgcaatttt aattatgagt gaatagaatg 720
aaaatatttc ttttttaact aattccattc atcttattcc atctattttg attccactaa 780
tttcatttca ttgttaccat tgacaaccat aatgtgcatg gttgtaaatt tagaactctg 840
taaccatata tatatatatt caaaagttta ttagtgtatt tttttctagg aattattgct 900
catgagtgag cagataggag atgtctgcat tggtgtagac gttgatatca ttgaggggaa 960
tctgaaacga agaaagtatg aagatcgttc tggtcaagcg gagaagtgtg tgatatgtct 1020
cgatgaactt aagtgcaatg atgaggcttc tacactggca tgtgggcatg attttcacta 1080
cgagtgtatc aaaaactggc taatggtcaa gaacaagtgt cctctttgca agcaacaagc 1140
tctttaattg tttcatgatg ctgaatattt gaatgtgtta gtattgctaa cattggtttc 1200
ttttgttcaa gtatcggtat tcggtagttt aataaaaaca aatatggaag tttcataaca 1260
aaaaaaaaag tctaccaaaa tttatgcaag ttaattatca ttcaagacaa cacccactgc 1320
aatttgtcaa aaatggtgaa actcttgcaa gaccttacct gtgaagtgat tgtccttttt 1380
catgtttaat aataataatt aattacagta ttatttatga ctttcagaaa actctatcta 1440
tcaaccgttc tttactgatt tttccaccca tcactgctct atttttttatt tatggcatcg 1500 ggaaaaaaag agaagaaaaa gaaatattat atgcaatctt tttttttttt tatgcaatct 1560
taccgggtgt taatacttat aactacattt agtgataaat ctgctttgtt aaatccagta 1620
caaaatcaat tattgaattt atagactata aagttgtgaa caaaatacaa attatcacta 1680
atgggaatat tcatatacag tataataacg taagccacca gattatggct agagtgattt 1740
gccacgcgcc tgcctattta ttatgaaaag cctcagtaac tttgtgatga gaagaattca 1800
cagagagaga gaggagagag atgggtaatt ccgacgaagg tgatcgtctt cctgctccat 1860
cttcttcgga cgaactctcg agcattctcc ggcaggtact gtcccgtgct cccacagctc 1920
aaccttcttt ctcaccgaag aaaatcgttt cctccgctga gatgttcaac cgaaccttcc 1980
ccctcgttcc cggcggagcg gtttcttacg ccgcttgtgc agccgctgaa actggggaag 2040
gcaaatgtgg tttcgaaaac aaggtaaact taacgatgtt agtttccgtg aaactaccct 2100
cgcttttgat taaagaaaaa ataacttagt tgttgttttt gcttggtaat ggttaacaca 2160

```
acactaaaga gaaatggagc tagacagcga aattcattga agagaaacat tgatgcacag   2220
ttccacaact tgtctgaaaa ggtttcgtct ttatcctttt aagattcttg atttggttta   2280
aaaaaaaact agagataata atagaaactg gatatatgca gaggaggagg agcaagatca   2340
atgagaaaat gaaagctttg cagaaactga tacccaattc caacaaggtg gtaaatacca   2400
agttcgcctt tttatccttc agaactcagt tgtgagaacc atttgttttg tttttttatgt   2460
tttgtagaca gataaggcct caatgcttga tgaagctata gaatatctga aacagcttca   2520
acttcagttt caggttcttt ttctatatgt tccttacgct atgatcatga acaactaaat   2580
ttgtaaaacc aaacatctga ttaacttaat gaatgcagac gttagccgct atgaatggtt   2640
taggcctaaa tcctctgcga ttaccaccaa ttctaccgcc tacgcagaca aggatcactg   2700
gaacctcaga acaagggctg aaccttgaga ctctgcttgg tggttctcac tcgatggcta   2760
accgtgaacc acccgaaact caggaaatgt gctttcccac aaccactctg ctttgaagac   2820
aacgttcaga cagtgaagag gatccgaagt cagatttcct ctccacagaa acatgagtcg   2880
aaaatgattt gtagagtcta gtatttggtt atataagtgt tatgctaata agctttagga   2940
ctgaacaaaa ctgagtagct tcattataat gatgtcagaa taaatttaac tacatgatta   3000
agatcaaatg gctatgtctg tgagttgcag ccatccgtac gcacaccggt ctcggatact   3060
tcgagccatg gatgctgctg actgaaccgc aggtcttatc                          3100
```

<210> SEQ ID NO 6
<211> LENGTH: 7672
<212> TYPE: DNA
<213> ORGANISM: Brassica napus

<400> SEQUENCE: 6

```
aacatgaatg atttttcgga atcagatact ccattcagct tccaacagtt attatatgga     60
gataattggc agaggtggga cacttatccg agcgttgatg ttaatgccaa ctcaatagag    120
cctaatcatt cgatggttga gatgaaccat gatggtctga caatagagcc taatccaatt    180
tcaatgatat atccaatggt aataatctac tttctgcatg tttttttgag agatattaaa    240
gtatggatga acaatataag acttattgaa aatgtatagg aagaaacatt cgagcagtgg    300
ttacagacac tggccaatgg atcatttgaa ataccatcat atgaagaact caacttcata    360
tatgaggtat ggtgaaagat aatatatata catagaaaac aatatatata tatatatata    420
taaaaaaata aaagggtata ttttatgtaa catataatca atttattggt aacttaattg    480
gttatattgc atttgtacat tttttcgagt ggatatgcat ttgaatcata gttgaagaaa    540
actaaaagga atatatatgc tgcaattgga ttgttgattt ttggaatgat atgacgtgga    600
atgacttatt tcattatttc cataaaaaat tttcagtatt taacatgaat ataataaaat    660
attcattcca tcaattccac aaacattcca aaaaaaaaca ttcatatgca attttagtta    720
tgaatgaata aaatgaaaat atttcttttt taactaattc cattcatctt attccatcta    780
tttttattcc attaatttca tttcattgtt accattgaca accataatgt gcatggttgt    840
aaatttagaa ctctgtaact atatatattc aaaaatttat tagtgcattt ttttctagga    900
attattgctc attagtgagc agataggaga tgtctgcatt ggtttagacg ttgatatcat    960
tgaggggaat ctgaaaggaa gaaagtatga agatcgttct ggtgaagcgg agaagtgtgt   1020
gatatgtctc gatgaactta agtgcaatga tgaggcttct acactggcat gtggacatga   1080
ttttcactac gagtgtatca agaaatggct aatggtcaag aacaaatgtc ctctttgcaa   1140
gcaacaagct ctttaagtgt ttcattatgc tgaatatttg aatgtgttag tattgccaac   1200
```

```
attggtttct tttgttcaag tatcggtatt cggtagttta atgaatacaa atatggaagt   1260
ttcataacaa aaaaaaaagt ctaccgaaat ttatgcaagt taattatcat tcaagacaac   1320
acccactgca atttgtcaaa aatggtgaaa ctcttgcaag accttacctg tgaagtgatt   1380
gtccttttc atgtttaata ataataatta attacagtat tatttgaaac tctttgtaaa   1440
cttaaagtac ttttcttatt gaatgaaggc aacataagag ttgcttaaat aacaaagcgt   1500
acagatactc ccgacagttt tggtaaagtc ttaaccactt cctatagtag aggaagactt   1560
attcaaataa cttaaagcag aaaataattc aaaactacca actaaagact ctaccaacta   1620
aagactcgat ctttttttatt cattaatccc tcccttaaac ttgaactcct ttataaagtt   1680
taaacttcct ttaagctgac tcccatgtgt gctctcagct tctcaaacgc ttcaagtttc   1740
accggctttg tcatgatatc cgacaattgc ttatgagttg aacaatactc cattgagatg   1800
atgccttcat tcacaagctc tcttaagaaa tgaaacctca catgaatatg cttgcttctt   1860
ccatgtagaa caggattcct tgacaacttg atagctgaac tattatcaca gaaaagaaca   1920
gttccatcac cttgatcaaa cccaatttca gccaacacgt tcctcatcca tacagcttga   1980
caagctccaa ttgctgcagc aacatactct gcttccgtgg tagagagtgt gacaattggt   2040
tgtttctttg agctccagga cacagctcct cctccaaaca tgaaagtgta gcctgatgta   2100
ctctttctgt catcctcatc gcctgcataa tcactgtcca catacccctac aagcttttct   2160
tctccaccac gcaagtactg aataccatag cttgcagttc cttgcacata cctcaaaata   2220
cgcttaacag ccatcatgtg cccttcattt ggattctcca tgtatctact aaccacattc   2280
acagagtata tcagatcagg tcgagtagct gttaagtacc tcaagcttcc cacgagttgc   2340
ttgtaagcgg ttggatcaac ttcttctcca gctcctgtct tggtcagttt gttccctgga   2400
accattggat tcttcacaga gttgcagtct ttcattccat acttctttaa agtctccagt   2460
gcatacttct tttggccaat aaagatccca acctcgtctt gcacaacctc cacgcctaga   2520
aagtacttca tctttcctag atcagtcatt gagaactctt cttgcattga agttttgaag   2580
ctctccagca tgctttccga gttactagtg taaatgaggt cgtctacgta caagctcagg   2640
atcaacgagt tcccttcttc tgtttttacg aacaatgtgt gttcgcaata acatttctca   2700
aagccttcct ttataaagta actctcgatc ctgctatacc aggccctagg agcttgtctt   2760
aatccataca aagccttttt caacttgtag accttctcac tgtcaacctg agactcgaac   2820
cccttaggct gctcaacgta aacgtcctcc ttaagctcac catgtaggaa cgcgctcttc   2880
acatctagtt gatatacact ccatcttctt tgagccgcta agccgagaat cagcctgatc   2940
gtgtcccatc tggccacagg tgcaaaaact tcatggaagt ctactccata ggtttggtga   3000
aagccctttg ccaccagtct cgctttgtac ttatccacct ctccttttc attcaacttg   3060
gtcttgaaga cccatttcac tcctatcacc ttcacattgg caggtagact aaccagctcc   3120
caagtgttgt tatcctctat tgattcaatc tcagtttcca ttgcctttct ccatttgtca   3180
tgttggatag catcttcaaa cttctctgga tcctcatctg acaagaacag cgcaactagt   3240
tcttctccat catcttccat gataagaccc ctcccatcaa ccacgtaatc tttcatccag   3300
actggtctta gtttgcttct tcctgctctg cttgtgtctg atctttcttc tggtgtagag   3360
acagttcttt ctccatcaga ctcagtgtta tctcctcctt ctgtctcttc gttagttgct   3420
ggtgctgtca ccaggttctc accctgattc ctctcttcct cttcttcagc ttctccacat   3480
tcgacaaatt tgtcttcatc aatgttatct tcccagttcc accgcgtttc ttcgtcaaac   3540
```

-continued

```
ctcacgtctt tgcttattat gatcctcttc ccaataggat cataaagtct gtaagccttc   3600
gactccttgc ttacaccaaa catgacacat ctcacacttt tctcatccag cttcacacgc   3660
ttctcataag gtataagtgc ataagccaca cagccaaaca cacggagatg ctctacagac   3720
ggcttgtgct tactccactt ctcacttggc gtcacttctc ccaatatctt tgttggactt   3780
ctgttaagta tatggacagc atactgtgtt gcttctgtcc aatacttgat cggcaccttc   3840
ataccaaaca gcatgcacct gaccatattc agaatgcttc tattcttcct ctctgccacg   3900
ccgttctgct gaggcgtgta tgcggctgtc agctgtcgtt tgatgccgtg ctccacacaa   3960
tagtcctgaa acgcctttga attgtattct ccacctctgt cggttcttag acagacgagc   4020
agctcaccac tctccctctc agcggcattt ttgaactcct tgaaagttct aagtgcctct   4080
gatttctctg ctagaaagaa gctccaacac tttcggctaa actcatcaat gaaattgatt   4140
atgtacctct tgccgctttc agatgtgggt gatattggcc cgcagatgtc actgtgaact   4200
agctccagtc gttgtgttgc tctccataga ctcttctttg gtatcttttc tctgatctgc   4260
ttccccttca tacacacctc acatactgtc ccgttggtgt tgatctttgg tagaccttcc   4320
accatcgcct tttctgctag tgttagcaaa ctgttgtggt tcaaatgtcc gaagcgtttg   4380
tgccaagttt cctccattgt ctccatcgta ttctgaactt ggtttgcctc caacgcttcc   4440
ttaggctccc tgacaatagc agttactaca aacatcctgt ttgtggtcat cagagaatgc   4500
atgatcagtc tccgttgttg tttgtgccag atctcacacg tatctccttc aattataatc   4560
ctcaacccct tctgttgcaa ctgaccgaca gacagtagat tgttcttcaa gccaggcaca   4620
aagtatactg cagtgatcac ttgagtagta ccattgatct ccaatcttag gttacctctt   4680
ccctcaactt gcattcgcct atcatctcca agctttactt gttgtctgaa ctggctatca   4740
aactctgaaa accactcctt ggttccacac atgtggttgc tacaccctga gtcaaggtac   4800
cacacgtgtc tttcttcagt ctcaacttga gtcatcagca aaatatcctc ctctaactct   4860
gcatagttag ctgccttctc ccagctagga cattcgtttt tgaaatgccc catcttgtgg   4920
cacttaaagc actcaatgtt gctcttgtca aagcttgtat ttcctctgtc ttgtcctcca   4980
cgacctcctc tgtaactgcc tcttcctctg gtttgatatc ctcctcgtcc attggagtaa   5040
cctgagtagc cacctcgtcc ccttcctcct tccatcttca ggacttgttc ctctcctgtg   5100
tgtttactca ggttctgctc atgtacgagt aatgagcttt gtaactcatc caccgacagc   5160
tccttgatat cctttgattc ctctatcgca cataccacat atgtgaactt ctccacaagg   5220
gttcttagga tcttctcaac caccttttca tctggcatgt cttctccacg gttccgcatg   5280
tcattagcaa ccaccatgac tctagagaaa tagtctgcga ttgagtcacc ttccttcatc   5340
tccaggactt caaagtttct tctcagcctc tgtaattgcg cactttgaac cctcttgttg   5400
ccttggtact ttgccttcag cgactcccat atgtcttttg cggtgtcctt cttcacaatc   5460
gtcttcagaa cagtcttgtc gatggaggca aagagatagt tcttcacctt gaagtctttg   5520
agcttttgct ccgcaagctc ggttctctga gcttcagaca gtgtcacact actttcatgt   5580
tgaatgattc cggtattgat cagttcccac cactccttgg atctcaacaa attctccata   5640
agcattgccc aatgctcata gtctccatca agctttggta tgctcaacga ggactccttt   5700
tcactcatct ctcttacttt cggattacct agaactcaca acagtttttg ttagagctct   5760
gataccactt gaaactcttt gtaaacttaa agtatttttc ttattgaatg aaggcaacat   5820
aagagttgct taaataacaa agcgtacaga tactcccgac agttttggta aagtcttaac   5880
cacttcctat agtagaggaa gacttattca aataacttaa agcagaaaat aattcaaaac   5940
```

taccaactaa agactctacc aactaaagac tcgatctttt ttattcatta ttatttatga 6000
ctttcagaaa actctatcta tcaaccgttc tttactgatt tttccaccca tcactgctct 6060
attttttatt tatttatggc atcgggaaaa aaagagaaga aaaagaaaaa ttatatgcaa 6120
ttttaccggg tgttaaaact tataattaca tttggtgata aatctgcttt gttaaatcca 6180
gtacaaaatc aattattgaa ttcatagact ataaagttgt gaaccaaata caaattatca 6240
ctaatgggaa tattcatata cagtatagta acgtaagcca ccagattatg tctagagtga 6300
tttgccacgc gcctgcctat ttattatgaa aagcctcagt aacttgtgat gagaagaatt 6360
cacagagaga gaggagagag atgggtaatt ccgatgaagg tgatcgtctt cctgctccat 6420
cttcttcgga cgaactctcg agcattctcc ggcaggtact gtcccgtact cccacagctc 6480
aaccttcttt ctcaccgaag aaaatcgttt cctccgctga gatgttcaac cgaaccttcc 6540
ccctcgttcc cggcggagcg gtttcttacg ccgcttgtgc agtcgctgaa actggggaag 6600
gcaaatgtgg tttcgaaaac aaggtaaact taacgatgtt agttgccgtg aaactaccct 6660
cgcttgttga ttaaagaaaa aaataacttt attgtgtttt tggttggtaa tggttaaaaa 6720
acactaaaga gaaatggagc tagacagcga aattcattga agagaaacat tgatgcacag 6780
ttccacacct tgtctgaaaa ggttttgtct ttatcctttt aagattcttg atttggttta 6840
aaaaaaaaac tagagataat aatagaaact ggatatattg cagaggagga ggagcaagat 6900
caacgagaaa atgaaagctt tgcagaaact gatacccaat tccaacaagg tggtaaatac 6960
caagttcgac tttttatctt tcagaactca gttgtgagat acatttgttt tggttttttt 7020
ttatgttttg tagacagata aggcctcaat gcttgatgaa gctatagaat atctgaaaca 7080
gcttcaactt cagtttcagg ttctttttct atatgttcct tacgctatga tcataaacaa 7140
ctaaatttgt aaacccaaac atctgattaa cttgatgaat gcagacgtta gccgctatga 7200
atggtttagg cctaaatcct ctgcgattac caccaattct accgcctacg cagacaggga 7260
tcactggaac ctcagaacaa gggctgaacc ttgagactct gcttggtggt tctcactcga 7320
tggctaacct tgaaccaccc gaaccaactc aggaaatgtg ctttcccaca accactctgc 7380
tttgaagaca acgttcagac agtgaagagg attcgaagtc agatttcctc tccacagaaa 7440
catgagccga aaatgatttg gttatatttc aaagtgttat gctaataagc tttaggactg 7500
aacaaaactg ctactggtta tatttcaaag tgttatgcta ataagcttta ggactgaaca 7560
aaactgagta gcttcattat aatgatgtaa gaaaaaaaat gtataaattt aactacatga 7620
ttacgatcaa atggctatgt ctgtgagttg cagccatccg tacgcacacc gg 7672

<210> SEQ ID NO 7
<211> LENGTH: 7235
<212> TYPE: DNA
<213> ORGANISM: Brassica napus

<400> SEQUENCE: 7
atataagcat gttgagtcct attcatcaga aaattttctc caaaggatga acaataacct 60
acaattaagg aaacttatta taacaacgac caagaagttt tcccataagt catgctttcg 120
tccatacctt cgggtctttc aagcaagctt cacacatgcc ttatcgtata tttgtatacg 180
ttttcatttt gtgtacgtct attaattagt atatgcctag attatatatt tatatagtcg 240
acaattacct atcctaaagg tttattttaa tttttattca gaaagatatg cacgtagggc 300
cactagtgtt tcccgttgtt attggaaatt ccatgtgttg aactgtttga ttaagttttt 360

```
gaacccgtaa gtcaaattta tttaggttta acagggtttc attactgtta taagcttgtc    420
aagaaagaat ttgtcacaaa tttcgagact catgcatgca tgcatgtttc ttaactttcg    480
agaaacatga agtgtggttt taccagctga agtttgtgtt aaaacacatt tttaatttga    540
ccacgtgtga tattcaaata tcaacaattc tgttcaacgg gagattcata catatgttca    600
gatgttcttt aatcttgagc acctaacttt gcttcccata cgcaaatgtg tgtgccgcga    660
actatggtga atgtacggca tcgtttttct ttttggagca tttttaaaag aaaatataat    720
ttagttattt ccgttttgat tgatatagat gcattaataa accgacttac gtgggtgatg    780
ggatgagcaa aattaaaata tgcattttag taaccaatta cggtccatct tgacaaacta    840
acaaacaaaa agtctattat gacgttgatt tgtgaccttg ccatataaat gccaaaattt    900
cattctttca ataagcaacg agatcaataa gatgtggcag tcacgtgaac gttagttatc    960
gccatttcaa ctgaaccttc acgaacatat aaagttcatt tgttctttgc taaaattacg   1020
caaatctctg ttgtgcacga aattacgact attttttaat gacaactcct gttcttgtat   1080
cgtgtatcta gcacgtaaat ttgaattatg gcggcattat cgataaaata tgtaaagaat   1140
atattttcat catacaccac aaacaaatgt tctggaaata tcacctttta tcacatatac   1200
aaagctgacc ctgaattttt ggaaactaca agccaaaaaa aaatggacaa aagaaaaatt   1260
atgcacaaaa gtggactcgt cctaactctt tttataatga taattaacct ttgaacaact   1320
aattaataca tacaatatgt tttttttttc taaaaattgg tcgattaaat attcatatat   1380
aatcctcatc atcatttatt agccttttgt agcttactta aaaaatcact tcccaccaaa   1440
ttgattattt tttcacttca tacgttgatc aatttaaaaa aaaaataata ataatatatg   1500
cacgtccggc gtcccatgac ttcagacgct tttctgtttc cttgatttta taggttagaa   1560
atttccaaaa tgctcatatt tttcactgat atgtattata cgcacaaaat agtaaagtca   1620
taaaaattta tgatggttct tttatatgta tagagtagtg aaaatttata tatattgtag   1680
ttccgcttaa aataaattaa tatttttctt ttatcgccca tatttaagtt actaaacgta   1740
tataattaaa aactgaaatg caatatgtag aaatccgggc attgattgtt gattaacatt   1800
gatataccca tgcgactggc ttatgatgaa ccatacctgc taatactcat tgttacaaac   1860
tcgcagcaac atcataaatc catcactcgc cacaataatt ttcttcagtg tatgttcaat   1920
tgatcacatt ttgacccttc actttcttga atgagaaatt atacaagaaa gtgatttgag   1980
tgtgttaaaa aatgatttgt cattctgacc aattatctgg cagagagtat aataaaatac   2040
ttctaattac cttaaatcat taggcgttgt ttcttgccga atatatgatg gagcatggtc   2100
tcgctaagag acaacaaaat ctttaaataa attaaagaaa ttgtttagca aaaaaattaa   2160
ataaattaaa caagagagag tacaaatata aaacactcta acggaagata aatatataaa   2220
atacaaaata tagaatagag gcctcaagta gtgtttacgt gacaatctca atttcactcc   2280
atacctcgaa ctcattcaag cttagaaacc taacttctac tgttcctttt gatttgccta   2340
taaatacacg ttggtccata cttctctaat ttcaaatata caaagcaaaa cacagagaca   2400
agaatcataa ataacaaaca ttttcaacat aatcccaaaa aacgacacgc gttccttttc   2460
caaaaattca cttctctacg taccaaccac aatggctcat tgttgcacag ttcttaccgg   2520
tttactagta tggtctcttt ttatgctctc atggtgtgaa gcttcaagaa acaacattaa   2580
tagatatgat cattcttatg gaacgttcaa atccaatagc ttaatcaagc gaagagacga   2640
tataactcgt ctgaaaagtg ttgcaagagc ctctttgcgg cttccaacca ccgttagtgt   2700
ttctgatttt ggagctaaag gagatggaaa aaccgacgac acgcaggtat atacgcatat   2760
```

acacatatct acatgactta taaatatttt gagacggtca cgcatataaa tttacgttgt 2820
ttgtactaat gatccatgca tgcgcatgca tatgatcagg cgttcgtgaa tgcatggaag 2880
aaagcttgtt cttcaagtgg agctgtaaat ctcttagttc ctgaaggaaa aacttatttt 2940
ctcaagtctc ttcgattaaa tggcccatgc aaatcagttc ttaccgttca ggtaaattac 3000
aaagtttttt tttcttaaat ttgggtaaat tacaaagttg actatttgtt aattaaatac 3060
gtatactaca tgtgatcacg tatatggttt tgaatattta aatgagcggt tgatgaatgg 3120
aacgacagat tttaggaacg ttatcggctt ctcaacaacg atcggattat gaagatctca 3180
gcaaatggat tacgtttgac ggcgttaaca gtctaacggt tgatggcgga gccaccggaa 3240
ctgtcaacgg aaacggcgaa acgtggtggg aaaactcatg caaacggaac gaagctaagg 3300
tgtgtgtttg tacatgtttc atttacttaa tatatatcta ctgtctacat gtcatcttga 3360
tatattaaca ctcttttatt gttattgttt tgaagaaatg cacaaaagcc cctacggtac 3420
gtagaaacat atttgacatt ttcatgtaat actgacgatg gcggtgatca tgattggaca 3480
aatgttttac atgcatgaat atatgtattt tatatgcagg ctcttacttt ctacaactcg 3540
aagaatttaa gagtgaataa tctgagggtg aaagatgcgc aacagattca gatttcgatt 3600
gagaaatgct ccaacgttca ggtctcaaat gttgaggtca ctgcacctgc tgatagtcct 3660
aacactgatg gtatccacat cactaacact caaaacattc aagtctccaa ttccatcatt 3720
ggaacaggtt agtagttata tcctcgttat ttaaaagagt tgcgtgcata tccagaaaac 3780
taaaatttaa gagtatcgtt ataatttata attttataga gattggtctt aaaagagttt 3840
ttaatggttg cttttctttg caggtgatga ttgtatatct attgaaagtg gatcacaaaa 3900
cgttaaaatc aacgatttaa cttgcggccc aggccacggt atcaggtatc aatgaattgt 3960
tttcagtata tgtacctaag aaattcaacc gtaatctttt aaattaacat agaaatttga 4020
tatttccata taaaacatga gcagcattgg gagcttagga gatgacaatt caaaggcatt 4080
tgtatcaggc gtgactgtgg atggtgctaa actttccggt acagacaatg gagttaggat 4140
caaaacttac caggtgaaaa tcacaaacta gaccttcaat tttaactagc ctattgacaa 4200
gttcatctca atttaacttt taaacccaat tcaatatagg gagggtctgg aactgctagc 4260
aacattatat ttcagaacat tcagatggag aatgtgaaga atccaatcat aattgaccaa 4320
gattattgcg acaagagcaa atgcactgaa caagttcgtt tgaatctgat caaatctccc 4380
attactaatc atcatgataa taaacactat tgtctctaat catttactac atatattttc 4440
agaaatcagc ggtccaaata aagaacgtgg tgtaccggaa cataagcggc acaagcgcat 4500
cggacatagc aataactttc aactgcagca agaactatcc atgccaagga attgtactcg 4560
acaaagtgaa cattaaggga gggaaagcca gttgcagcaa tgctaatgtg atggataaag 4620
acggtgtttt acctcagtgc aaatccactt gattaataag acctataaaa aaaactcaca 4680
tagatgtata aaaatacata tataccgata caaagtatac aaaattatga tatacacttg 4740
tggatatata catggacaat gaatttaaac atattgtcta tatgtcaaaa atagtttatg 4800
aatatacata tagacaacat ggtcaagaga tttattgttt taatgtatat atatactact 4860
aaactacttg tctaaaattt catgaataaa ggattacgtt tttaagtggt tatgtatcat 4920
gatgtggtta cagtatgatg tgtattgtag attttcaatt aaatacataa aaatgaaaaa 4980
gatgacatgg ctggtcaatg atgttacttg accaactaat tcaagctaat tgatacacga 5040
tgaacatcta acgaaacaga agcgactttc atattgttta gttgtgctca aaccaggccg 5100

```
ataaactcat tgggcctata agcccattaa tatttatccg tgagagcgaa gtctgttact   5160
tgggttacta aacaaagagg cctttagaaa accctaactc ttaccgtagc acctgagcta   5220
tatattgccg cagctagggt ttccactccc tcacgctaac acacatcacc gcagccattt   5280
ccatctctca accaacttca aacaatggct gaacgaggcg gagaacgagg tgccgagcga   5340
ggaggagacc gcggcggttt cggacgcgga ttcggaggag gtcgcggcga cagaggaggc   5400
cggggaggtc cgagaggccg aggcggcaga cgcggaggac gtccgacaga ggaggagaag   5460
tggaccccag tgaccaagct cggccgtctc gtgcaagccg gaaagatcca gaagctcgag   5520
cagatctacc tccactccct ccccgtcaag gagtaccaga tcatcgacct cctcgtcggc   5580
cccaccttga aagacgaggt gatgaagatc atgccggttc agaaacagac cagggccggt   5640
cagaggacga ggttcaaggc ctttgtcgtc gtcggagaca cgaacgggca cgttggtttg   5700
ggtgtgaagt gctccaagga ggtggcgacg gcgatcagag gtgggattat attggcgaag   5760
ctgtcggtta ttcccgtgag gagagggtac tgggggaaca agattgggaa gccgcatacg   5820
gttccttgta aggttacggg gaagtgtggg tctgttacgg tgaggatggt gcctgctccg   5880
aggggtgcgg ggattgtggc ggctagggtt cctaagaagg tgcttcagtt cgctgggatt   5940
gatgatgtgt ttacttcgtc gagggggtct actaagactc ttggaaactt cgtaaaggtt   6000
tgaactttct tcatttattt agagtttgga gttgtgtatg gattgaaagt tgattccttt   6060
ttgatggttg cgtgtggagt tgttttgggt aatttagctt gttgtagttg atgtaaagtg   6120
agaattgcta agcttgatta gtttgaataa gctgtctgtg ttaaatgatg atttgtttgt   6180
gttgtattga gctgtctgaa tttcattatt tgtttgtgtt attgctaaat tacaagctta   6240
aatttgataa cttttgattc tttcgtgaga gtttttttg ggtaatatag cttgatgtag   6300
ttgatggaag taaattgtta acctttagag ctgtctgtta atggtgattt gtttgtgttg   6360
tattgagctg tctgaattat aatttgtttg tgtttattgc taaatcacaa agctttgaag   6420
tcgtttgtac atattcatca tttttgtgtt tattgacttg tttgtgttta ttgctaaatc   6480
acaagtttct atgattaatc ttcatgattt ggttgtgttt attactaaat cacaagtttc   6540
tatgattaat cttaatgatt tggttgtgtt tattgctaaa tttgagatta cattataatc   6600
ttagtttata catgtataac atcatttcac ttgaattttc acagacgagc tggtgatatg   6660
ttttttagt attttccatg tattgctttg taagaacttt taaatgtttg ttttcttcct   6720
ttgaagaaca attaaatgtt tgttcagtat ttttgaatca ttcattggtt aatcatgtgt   6780
aattttattt ttgtaggcta cattcgactg tctccagaag acttatggat tcctgacacc   6840
agagttctgg aaagagacga gctttaaaaa gtcaccgtac caggagtaca ctgatctgct   6900
ggccgagaag ggaattgcaa ccaaagccat caccgaggtt gaagaccaag ccgcctccta   6960
aataaacaaa caaacaatgt ccccctgtt ttgtttttgg atgatccttt cttgagtttt   7020
attttgttcg aacctttagt atatgttgtt tgctggattg ctgctttctt atgttttcat   7080
catctccccc aaacaaagtt atttttgctc tagttttttt ttataatcga tggttatgcc   7140
ctctagtatt ttttttactt gaatttttca ctaattttct atcaacttcc ctatgttaca   7200
ctttctaagg ttgattacat aggtggattg ttgtg                              7235
```

<210> SEQ ID NO 8
<211> LENGTH: 4453
<212> TYPE: DNA
<213> ORGANISM: Brassica napus

<400> SEQUENCE: 8

```
ttaaacgtaa acgtctccgc tgtatttata taaacttttc aaaatcacgg tgtcgctcgt     60
gttaagattt ggatttctaa tccaactttc agaaagttta tgtgaaagat aatactcaaa    120
cacaatagtt cgtttagaac gctcttaaga ttaatgtcac acacacaaaa ttgatgtcac    180
tagatttata tgttttgtcg tttaagggga tccatcaact acacatggaa gaatagaaaa    240
cactggtcac acacaaaaaa taatataagc atgttgagtc ctattcatca gaaaattttc    300
tccaaaggat gaacaataac ctacaattaa ggaaacttat tataacaacg accaagaagt    360
tttcccataa gtcatgcttt cgtccatacc ttcgggtctt tcaagcaagc ttcacacatg    420
ccttatcgta tatttgtata cgttttcatt ttgtgtacgt ctattaatta gtatatgcct    480
agattatata tttatatagt cgacaattac ctatcctaaa ggtttatttt aatttttatt    540
cagaaagata tgcacgtagg gccactagtg tttcccgttg ttattggaaa ttccatgtgt    600
tgaactgttt gattaagttt ttgaacccgt aagtcaaatt tatttaggtt taacagggtt    660
tcattactgt tataagcttg tcaagaaaga atttgtcaca aatttcgaga ctcatgcatg    720
catgcatgtt tcttaacttt cgagaaacat gaagtgtggt tttaccagct gaagtttgtg    780
ttaaaacaca tttttaattt gaccacgtgt gatattcaaa tatcaacaat tctgttcaac    840
gggagattca tacatatgtt cagatgttct ttaatcttga gcacctaact ttgcttccca    900
tacgcaaatg tgtgtgccgc gaactatggt gaatgtacgg catcgttttt ctttttggag    960
catttttaaa agaaaatata atttagttat ttccgttttg attgatatag atgcattaat   1020
aaaccgactt acgtgggtga tgggatgagc aaaattaaaa tatgcatttt agtaaccaat   1080
tacggtccat cttgacaaac taacaaacaa aaagtctatt atgacgttga tttgtgacct   1140
tgccatataa atgccaaaat ttcattcttt caataagcaa cgagatcaat aagatgtggc   1200
agtcacgtga acgttagtta tcgccatttc aactgaacct tcacgaacat ataaagttca   1260
tttgttcttt gctaaaatta cgcaaatctc tgttgtgcac gaaattacga ctattttta   1320
atgacaactc ctgttcttgt atcgtgtatc tagcacgtaa atttgaatta tggcggcatt   1380
atcgataaaa tatgtaaaga atatattttc atcatacacc acaaacaaat gttctggaaa   1440
tatcaccttt tatcacatat acaaagctga ccctgaattt ttggaaacta caagccaaaa   1500
aaaaatggac aaaagaaaaa ttatgcacaa aagtggactc gtcctaactc tttttataat   1560
gataattaac ctttgaacaa ctaattaata catacaatat gttttttttt tctaaaaatt   1620
ggtcgattaa atattcatat ataatcctca tcatcattta ttagcctttt gtagcttact   1680
taaaaaatca cttcccacca aattgattat tttttcactt catacgttga tcaatttaaa   1740
aaaaaaataa taataatata tgcacgtccg gcgtcccatg acttcagacg cttttctgtt   1800
tccttgattt tataggttag aaatttccaa aatgctcata tttttcactg atatgtatta   1860
tacgcacaaa atagtaaagt cataaaaatt tatgatggtt cttttatatg tatagagtag   1920
tgaaaattta tatatattgt agttccgctt aaaataaatt aatatttttc ttttatcgcc   1980
catatttaag ttactaaacg tatataatta aaaactgaaa tgcaatatgt agaaatccgg   2040
gcattgattg ttgattaaca ttgatatacc catgcgactg gcttatgatg aaccatacct   2100
gctaatactc attgttacaa actcgcagca acatcataaa tccatcactc gccacaataa   2160
ttttcttcag tgtatgttca attgatcaca ttttgaccct tcactttctt gaatgagaaa   2220
ttatacaaga aagtgatttg agtgtgttaa aaaatgattt gtcattctga ccaattaggg   2280
tttccactcc ctcacgctaa cacacatcac cgcagccatt tccatctctc aaccaacttc   2340
```

-continued aaacaatggc tgaacgaggc ggagaacgag gtgccgagcg aggaggagac cgcggcggtt 2400
tcggacgcgg attcggagga ggtcgcggcg acagaggagg ccggggaggt ccgagaggcc 2460
gaggcggcag acgcggagga cgtccgacag aggaggagaa gtggacccca gtgaccaagc 2520
tcggccgtct cgtgcaagcc ggaaagatcc agaagctcga gcagatctac ctccactccc 2580
tccccgtcaa ggagtaccag atcatcgacc tcctcgtcgg ccccaccttg aaagacgagg 2640
tgatgaagat catgccggtt cagaaacaga ccagggccgg tcagaggacg aggttcaagg 2700
cctttgtcgt cgtcggagac acgaacgggc acgttggttt gggtgtgaag tgctccaagg 2760
aggtggcgac ggcgatcaga ggtgggatta tattggcgaa gctgtcggtt attcccgtga 2820
ggagagggta ctgggggaac aagattggga agccgcatac ggttccttgt aaggttacgg 2880
ggaagtgtgg gtctgttacg gtgaggatgg tgcctgctcc gaggggtgcg gggattgtgg 2940
cggctagggt tcctaagaag gtgcttcagt tcgctgggat tgatgatgtg tttacttcgt 3000
cgagggggtc tactaagact cttggaaact tcgtaaaggt ttgaactttc ttcatttatt 3060
tagagtttgg agttgtgtat ggattgaaag ttgattcctt tttgatggtt gcgtgtggag 3120
ttgttttggg taatttagct tgttgtagtt gatgtaaagt gagaattgct aagcttgatt 3180
agtttgaata agctgtctgt gttaaatgat gatttgtttg tgttgtattg agctgtctga 3240
atttcattat ttgtttgtgt tattgctaaa ttacaagctt aaatttgata acttttgatt 3300
ctttcgtgag agttttttt gggtaatata gcttgatgta gttgatggaa gtaaattgtt 3360
aacctttaga gctgtctgtt aatggtgatt tgtttgtgtt gtattgagct gtctgaatta 3420
taatttgttt gtgtttattg ctaaatcaca aagctttgaa gtcgtttgta catattcatc 3480
atttttgtgt ttattgactt gtttgtgttt attgctaaat cacaagtttc tatgattaat 3540
cttcatgatt tggttgtgtt tattactaaa tcacaagttt ctatgattaa tcttaatgat 3600
ttggttgtgt ttattgctaa atttgagatt acattataat cttagtttat acatgtataa 3660
catcatttca cttgaatttt cacagacgag ctggtgatat gttttttag tattttccat 3720 gtattgcttt gtaagaactt ttaaatgttt gttttcttcc tttgaagaac aattaaatgt 3780
ttgttcagta tttttgaatc attcattggt taatcatgtg taattttatt tttgtaggct 3840
acattcgact gtctccagaa gacttatgga ttcctgacac cagagttctg gaaagagacg 3900
agctttaaaa agtcaccgta ccaggagtac actgatctgc tggccgagaa gggaattgca 3960
accaaagcca tcaccgaggt tgaagaccaa gccgcctcct aaataaacaa acaaacaatg 4020 tccccccttgt tttgttttg gatgatcctt tcttgagttt tattttgttc gaacctttag 4080
tatatgttgt ttgctggatt gctgctttct tatgttttca tcatctcccc caaacaaagt 4140
tatttttgct ctagtttttt tttataatcg atggttatgc cctctagtat ttttttact 4200 tgaattttc actaatttc tatcaacttc cctatgttac actttctaag gttgattaca 4260
taggtggatt gttgtgaaac aaatactaat aataaactaa tacttttaga ataatataat 4320
tagtgggatt aaattataaa ttataaatta aaaagacaag tctgaaatgg attgtttaac 4380
tgtaaaaggt aaagagactt tgaatagaag agaataaatc aaaagttgac gtatcttctc 4440
cgaaatttca gct 4453

<210> SEQ ID NO 9
<211> LENGTH: 7172
<212> TYPE: DNA
<213> ORGANISM: Brassica napus

<400> SEQUENCE: 9

```
gtgacctggc catataaatg ccaaattttc attctttcaa taagcaacga gatcaataag     60
atgtggcagt cacgtgaacg ttagttatcg ccatttcaac tgaaccttca cgaacatata    120
aagttcattt gttctttgct aaaattacgc aaatctctgt tgtgcacgaa attacgacta    180
ttttttaaag acaactcctg tgtcttgtat cgtgtatctc gcacataaaa tttgaattat    240
gggggcatta tcgataaaat atataaagaa tatattttca tcatacacca caaacaaatg    300
ttctggaaat gtcacatttt atcacagata caaagctgac cctgaatttt tggaaactac    360
aagccaaaaa aaaatggtca aaagaaaaat tatgcacaaa ggtggactcg ccctaactct    420
ttttataatg ataattaacc tttgaacaac taattaaaga tacatacaat atgttttttt    480
tctctaaaaa ttggtcgatt aaatattcat atataatcct tatcatcatt tattagcctg    540
ttgtagctta cttaaaaaat cacttcctac caatgttttt aaactcgacg cgaaccggac    600
gatttaccgg gtcgctgggt cactgtatcg accgcgagcg aaccgcgggt taataaataa    660
actaaaattt aaaataatat atcagctatg taaataaaaa tatagaaact aaaatttaat    720
attttctaaa tgttcttata aacataaaat aatagtctgg atgtgtatat ttttatgttt    780
aataacattt agaaaatact taactttaat ttttatattt ttattttcat ttgatataca    840
aaatatcaaa aaatagttta gattatttat aattttgtct aacaaggtaa gagttatggc    900
atctaagaaa atcaagacat aaaatttata aatatttaaa tgtttaatgt gaataataaa    960
ttaaatttca aatacaaaat aaaccaaaag tgaaaaatca ttataaaaaa ttatcaataa   1020
cagaaataaa ccaactccaa atcacatcaa ctagttttgg ttctgtctac cattgttcac   1080
ttttattttc ttcaagtggc atagtgaaat cttcattaaa atctaaaaat cacaaatata   1140
aaactgaaaa ggaaaaactt aacttttttt tgtcggtata tcacttctta attagaaatt   1200
tagaatataa aacataatct aaaaacataa ttaaaaatta aaaatgaagt aaacgttatt   1260
tattggttca accagtggtt caaccggtat cgggttccgg gttctattgg gtttttgcgg   1320
gtttctaaat attgtgtttt tcacaaaact caaaccggat ttttttaggg ttgccgggtt   1380
taccggttca accgcaggtt cgggtcgggt ttcaaaacac tgcttcccac caaattgatt   1440
aatgtagatt gattattttt tcacttcata cgttgatcaa tttttaaaaa gaaataatat   1500
atgcacgtcc ggcgtcccat gacttcagac gcttttctgt ttccttgatt ttataggtta   1560
gaaatttcca aaatgctcat atttttcact catgtattat acgcacaaaa tagtaaattc   1620
ataaaaattt atgatggttc tttatatgta tagagtagtg aaatttatat atattgtagt   1680
tccgcttaaa ataaattatt atttttcttt tatcgcccat ttttaagtta ctaaacgtat   1740
ataattaaaa actgaaatgc aatatgtaga aatccgggca ttgattgttg attaacattg   1800
atgatgatac tcatgcgact ggcttatgat gaaccatact aatactcatt gttacaaact   1860
cacagcaaca tcataaatcc atcactcgcc acaataattt tctttagtgt atgttcaatt   1920
tcacattttg acccttcact ttcttgaatg aaaaattata caagaaagtg atttgagtgt   1980
gttagaaaaa aaaaagattt gagtcattct gaccaattat ctgggagaga ctataataaa   2040
atacttccaa ttaccttaaa tcatcaggcg ttgtttcttg cctaatatat gatggagcat   2100
ggtctcgcta agagacaaca aaatctttaa ataaattaaa caagttgttt agcaaaaata   2160
aaaaaaataa attaaacaag agaaagtaca aatataaaac tctaaaggaa gataaatgta   2220
taaaatacaa gatatagaat agaagcgttt acgtgacaat ctcaatttca ctccatacct   2280
cgaactcatt caagcttaga aacctaactt ttactgttcc ttttgatttg cctataaata   2340
```

```
cacgttcgtc catacttctc taatttcaaa tatacaaagc aaaacacaga gacaagaatc   2400
ataaacaaca aacattttca acataatccc aaaaagacga cacgcattcc ttcttccaaa   2460
aatccacttc ctacgtacca accacaatgg ctcattgttg cacagttctt accggtttac   2520
tagtatggtc tcttttgatg ctctcatggt gcgaagcttc aagaaacaac attaatagat   2580
atgatcattc ttatggaacg ttcaaatcca atagcttaat caagcgaaga gacgatatca   2640
ctcgtctgaa aagtgttgca agagcctctt tgcagcttcc aaccaccgtt agtgtttctg   2700
attttggagc taaaggagat ggaaaaaccg acgacacgca ggtatatacg catacacaca   2760
tatctacatg acttataaat attttgagac ggtcatgtat ataaatttac gttatttgta   2820
ctaatgatcc atgcatgcat gcatatgatc aggcgttcgt gaatgcatgg aagaaagctt   2880
gttcttcaag tggagctgta aatctcttag ttcctgaagg aaaaacttat ttccttaagt   2940
ctattcgatt aaatggccca tgcaaatcaa ttcttaccgt tcaggtaaat tacaaagttg   3000
acaaaaaaac aattacaaag ttgactattt gttaattata tacgtatact acatgtgatc   3060
acgtatatgg ttttgaatat ataaatgagc ggttgacgaa tggaatgaca gattttagga   3120
acgctatcgg catctcaaca acgatcggat tataaagatc tcagcaaatg gattacgttt   3180
gacggcgtta acagtctaac ggttgatggc ggggccaccg gaactgtcaa cggaaacggc   3240
gaaacgtggt gggaaaactc atgcaaacgg aacgaagcta aggtgtgtgt ctgtacatgt   3300
ttcatttact taatatatat ctactattta catgtcatct tgatatattg acacttttta   3360
ttgttattgt tattgttttc aagaaatgca caaaagcccc aacggtacgt agaaacatat   3420
ttgacatttt catgtaatac tgacgatggc tgtgatcatg attggacaaa tgttttacat   3480
gcatgaatat atgtatttta tatgcaggct cttactttct acaactcaaa gaatttgaga   3540
gttaataatc tgagggtgaa agatgcgcaa cagatccaga tttcgattga gaaatgctcc   3600
aacgttcagg tctcaaatgt tgaggtcact gcgcctgctg atagtcctaa cactgatggt   3660
atccacatca ctaacactca aaacattcaa gtctccaaat ccatcattgg aacaggttag   3720
taattacatc ctcgttattt aaaagagttg cgtgcatatc cagaaaacta atatttaagg   3780
gtttatcgtt ataatttata gagattggtc ttaaaagagt tttttaatgg ttgcttttct   3840
atgcaggtga tgattgtata tctattgaaa gtggatcaca aaacgttaaa atcaacgatt   3900
taacttgcgg ccccggtcac ggtatcaggt atcaatgaat tgttttcagt atatttacct   3960
aagaaattca accgtaatct tttacatata aatttgaaat ttccttataa aacatgagca   4020
gcattgggag cttaggagat gacaattcaa aggcatttgt atcaggcgtg actgtggatg   4080
gtgctaaact ttccggtaca gacaatggag ttaggatcaa aacttaccag gtgaaaatca   4140
caaactaaac cttcaatttt aactagccta tcaagttcat ctcaatttaa cttttaaacc   4200
caattcaata tagggagggt ctggaactgc tagcaacatt atatttcaga acattcagat   4260
ggaaaatgtg aagaatccaa ttataatcga ccaagattat tgcgacaaga gcaaatgcac   4320
tgaacaagtt cgtttgaatc tgatcaaatc ttccattact aagcgtcata ataatataaa   4380
cttttctcta atcatttact acatattttc agaaatcagc ggtccaaata aagaacgtgg   4440
tgtaccggaa cataagcggc acaagcgcat cggacatagc aataactttc aactgcagca   4500
agaactatcc atgccaagga attgtagtcg acaaagtgaa cattaaggga gggaaagcaa   4560
gttgcagcaa cgctaatgtg atggataaag acggtgtttt gcctcagtgc aaatccactt   4620
gattaactag acctatcaaa aactcacata gatgtataaa tacatataga ccgatacaaa   4680
gtatacaaaa ttatgatata tacttgtgga tatatacatg gacaatgaat ttaaacatat   4740
```

tgtttatatg tcaaaatagt ttatgaatag acatataaac aacatgttca agagatttat 4800
tgtcttaatg tatatactgc atactaaatt gtttgtctaa aacttcatat aataaaaact 4860
gttaatcttc atgatggtgt gatttgttgt gataacagta tgatgtctat atttgtaaaa 4920
aaaaaaacag tatgatgtct attgtagatt tttatctaaa tacataaaaa ttgaaaaaaa 4980
aaaaatgaca tggctacttg accgattgat tcaagttaat tgttactaac caggccgata 5040
aacaaattgg gcctttaaag cccgttaata tttatcagtg aaagcgaagt ctgttacttg 5100
ggttactaaa caaaggcctt tagaaaaccc taactcttat cgcagcacct gagctatata 5160
ttgccgcagc tagggttttc gctagctcac gctaacacac aaagccgcag ccatttccat 5220
ctctctcgca actcaacttc gaacaatggc tgaacgaggc ggagaacgag gcgccgagcg 5280
aggaggagac cgcggcggtt tcggacgggg attcggagga ggtcgcggcg acagaggagg 5340
ccgcggaggt ccgagaggcc gaggcggcag acgcggagga cgtcccacag aggaggagaa 5400
gtggacccca gtgaccaagc tcggccgtct cgtgcaagcc ggaaagatcc agaagctcga 5460
gcagatatac ctccactccc tccccgtcaa ggagtaccag atcatcgacc tcctcgtcgg 5520
tccaacttta aaagacgagg tgatgaagat catgccggtt cagaaacaga ccagggccgg 5580
tcagaggacg aggttcaagg cttttgtcgt tgtaggagac acgaatggtc atgttggttt 5640
gggtgtgaag tgctccaagg aggtggcgac ggcgatcagg ggtgggatta tattggcgaa 5700
gctgtctgtg attcccgtga ggagagggta ctgggggaac aagattggga agccgcatac 5760
ggttccttgt aaggttacgg ggaagtgtgg gtctgttacg gtgaggatgg tgcctgctcc 5820 gagggggggct gggattgtgg cggctagggt tcctaagaag gtgcttcagt tcgctgggat 5880
tgatgatgtg tttacttcct cgagggggtc tactaagact cttggaaact tcgtaaaggt 5940
ttgaacttta ttattttact tggtgtttgg agttgtgtat ggattgaaag ttgattcctt 6000
tttgatcgtt gcttgtggag gtgttttggg taatattgct aaatgtaaaa attgccaagc 6060
ttgattagtt tgaataagct gtctgtgtta aatgatgatt tgtttgtgtt gtaatgagct 6120
gtctgaattt cattatttgt ttgtgttatt gctaatttac aagcttaaat ttgattcctt 6180
ttgatcgttt cgtgtgagtt gttttgtgta atttagcttg atgtagttga tggaagtaag 6240
aattgttaag ctttagagct gtctgttaat gttgaattgt ttgtgttgta ttgagctgtc 6300
tgaattataa tttgtttgcg atttattgct aaatcacaaa gctctaaagt cgtttgaaca 6360
tatgcatcat ttggttagtg tttattgctg aattttcatg atttggttgt gtttattgct 6420
aaatttgaga ttacattata atcttaattt gtacatatat tcatcatttt tgtgtttatt 6480
gatttgtttg tgtttattga tgaatcacaa gtttctatga ttaatcttca tgatttggtt 6540
gtgattattg ctaaatttga gattacatta taagcttagt ttgtacatgt atacatcatt 6600
tcacttacat ttcacttggt ggtgatatat attttttttt tagtattttc catgtattgc 6660
tttgtaagaa cgtttaaatg ttagttttct tgaatgtttt tttctttgta agaacaatta 6720
aatgtttgtt cagtattttt gaatcattca atggttaatc atgttcaaca tgtatttttt 6780
gtaggctaca tttgactgtc tccagaagac ttatggattc ctgacaccag agttctggaa 6840
agagacgagc tttaaaaagt caccgtacca ggagtacact gatttgctgg ccgagaaggg 6900
aactgcaacc aaagccatca ccgaggttga agaccaagcc gcctcctaaa taaacaaaca 6960
agcaatgtcc accttgtttt gtttttggat gatcctttca tgagttttat tttgttcgaa 7020
ccttttagta tatgttgttt gctggattgc tgctatctta agttttcatc atcttcccaa 7080
acaaagttat ttttgctcta gttttttttt ttttaataat cgatggttat actctagtat 7140 tttttactt gaatttctct aattttctat ca 7172

<210> SEQ ID NO 10
<211> LENGTH: 188
<212> TYPE: DNA
<213> ORGANISM: Brassica napus

<400> SEQUENCE: 10
cattttgacc cttcactttc ttgaatgaaa aattatacaa gaaagtgatt tgagtgtgtt 60
agaaaaaaaa aagatttgag tcattctgac caattagcta gggttttcgc tagctcacgc 120
taacacacaa agccgcagcc atttccatct ctctcgcaac tcaacttcga acaatggctg 180
aacgaggc 188

<210> SEQ ID NO 11
<211> LENGTH: 15000
<212> TYPE: DNA
<213> ORGANISM: Brassica napus

<400> SEQUENCE: 11
gtagttccaa tactaaatcc tcaactctaa tcagtgaacc ctaaacttta tcccaacccc 60
accccatccc ctaaaatact aaaccctaaa cactaatcag cgaacctaaa cccaaatata 120
aaccataaat ccaaatataa accctaaacc caaatagaat ggaacaacta tgaacccaaa 180
tatcaaaatc taaaccttaa ccagtgttta accccaattt tccataaact aaattcaaat 240
tttaaaatgc cagtaaaata cattaccatt ctacatgagt catatagaat agaaatagag 300
aaaatgtagt tccaatacta aatcctcaac tctaatcagt gaaccctaaa ctttatccca 360
accctacccc atcccctaaa atactaaacc ctaaactcta atcagcgaac ctaaacccaa 420
atataaacca taaatccaaa tataaaccct aaacccaaat agaatggaac aaaataaata 480
gaatagtaca tactggtgaa attatgaaat atctatgatt gcatgaaaga agttaataat 540
gactccaacc ataacccctc accttctaat tagtaaaccc taaactataa tcactaaacc 600
ctaaacgcaa atatcaaaat ataaaaatgt atgcaatatt atgcaatatt aaatcatatt 660
atataatatt aaactataca atataaatca tagtacggtt tttacagatt caaaacatgt 720
aatgatagtt agatattaag aaaattacaa aatatatttt taaacaaaat agaacactct 780
ttattaatca tcaaatggaa tataacataa ttaaatagta tagtaacaaa aaggtagaaa 840
acaacaagac acatctggga agaagaactg gccgttgtta cttcatgttg ccgtgtctcc 900
tcttccgtca aacaagacac catcgatttc acaatcagag aaacctcccc ttcagccacc 960
caccgagaat gcaaagatgt tatactcttg caaaaatcaa ctctgataat cgtgtccgtc 1020
tcattgctct ctcccaaatc tgagaatcaa acgatttaat ttctcgaaaa agaagaaagg 1080
taaaaattac ggagatgatg acggagcaaa tacggtggcg gcgatgaaac aaacgatgat 1140
gatgatggtt gtgctggttg tacatgtaga gatgattgaa gctatgtgac agagatttat 1200
gtgttcgtcg tataaaaaaa cagaaatttg agagagagag agagagagag aggaacacga 1260
agaaacaggg aagaagaaga aaaaattatg tgtggatgtg tgactttcta ctggacacaa 1320
attattttta aaatataatg attattaatt ttttttctg caggttttac cggttacaac 1380
agagggcaat acggcaatat tatataaaag acacatgata cagtgaaaaa atagggtttt 1440
tagttataga ttgaattata atttttttgg tggttataca gcccaatttc ccttaaaatt 1500
ttacatatcg ttgaaagcca gaaaaatatg tggaagtgta ataaaacaat tttctccagg 1560
aagaagatat ttcagccatt cgcccatcta tgtgtatgag atcccattca aggccatatt 1620
ctaagattga ctttatctaa tttactgtat tttccgtggg ctactgaatg aatacgatgc 1680
ttttgttgta aaacgcaacc tattgttctc cattttgaat ttgaagtgtt acattgttga 1740
taaaaaggaa gaaagtacaa agcttttcat ttagtggttg ttgcatatat atatacttat 1800
ttgatgggtt tatgataagt atgaacatta ttagattatg gttaagtgat ggtttaataa 1860
ctggtttagc ttccttttac taaaccggtt gtataaatac atcctcttgt acattgtaaa 1920
ctttaacttg agcaatatac tttttccttt tcatcgtaac aaactttctc cattgatctt 1980
gagctcaagt tctaatatgg tatcagagcc aatctgatct tcgttcttcc gcttcgttct 2040
ttctggattc aagcttctgt agctgcgatt cagtctgatt tcatcttctt tttcgttttc 2100
tcacttcttt ttctcgggaa aatcagctcg atcttcttcg cttaagcgca ttcttcatct 2160
caatgagtct ctcgttacgg cgcctgatcg atctttttgt tgagctgtat cttcccatcc 2220
tttttgcgat ttatcagtcg gtttctatga taatcgcgat tctgtttctt tcttttcttt 2280
ctctttgatc ttcgatttgc gtattctctt ctcgcgcaat cgttttctgg ttttccaaat 2340
tgattcttgt tttctcatga cgactcctgc atcaacgatc cctctctccg acgataatcc 2400
acctgtttcg gcgtcacttc ttgatcccaa ttccaatcct ctgtatgttc acaatgccga 2460
tcacgctggt atctctcttg tttctgaaaa gctagctggt ttggggaatt ttaatacttg 2520
gcgtagatcg atgatcatgg cactgggagc taggaataag gcagtttttg tggatggtac 2580
ttatctggaa ttatctgaaa cgcatccgga ttatgcatct tggtcacgtt gtaacaatat 2640
cgtttgcaca tggattgtga atgctgtcga gaaatccatc gccaagagca taatgtacct 2700
tcctacggct cgtcaaatgt ggcttgacat ccatgatcag tttaagcaga gtgatggacc 2760
aagaacagcc gagataaagc aacaaatttt tgcggaggtg cagggctctc aaactgttag 2820
tgaatactac actcgtttga agcaacaatg ggaggagttg aagaatcatg agagtcctta 2880
tacttgctgt tgtggacgtt ttgattgttc gagcatgaag aggattgatg agggagagga 2940
acaggacaag atcttgaagt ttctcacggg gttgaatgat acattcactg ctactcgggg 3000
tcagatactg atgatggatc caaaaccgaa catttctaga gtgtttaatc ttgtttcaca 3060
agaggagcga cagaggtcta tgaagagcac aagtgtggta gcgtttcaag tttctcaagg 3120
agcatctaat gatgagatgg ttgctgcata tcactctggt tataacaaac agaagcagcg 3180
ctcgatatgc tctcactgtg gcattgctgg tcacactgtt aaccgctgct acaagcttca 3240
tggttatcca caaggatata gaggtgctac gggttcctcc aagttctcta ctcaggcttc 3300
ttcttcatct tcttctgtga agagtcaacc agctggtggg attgatcttt tggaccatca 3360
aggtgcgtgc ttggggtctg tcactacagc acaagtcagt cgatttctaa gtgtcttggg 3420
ggctcatccg tcgagtctca atgacaatgt ttctcaggct tcagctagca ctattaatca 3480
ttctgatgga acagtctcta caccaaaacc acaaccccac ctcgtccccc atttaccgtt 3540
acctcaccct tcttcaggta ccactcatta catcaattct cattttgttt ctgctggaac 3600
caataatggc cttacctttc taagtgatgc gtggatcata gatactggtg ctagttgtca 3660
cgttagttcg aacttaggtt tgtttcattc aactagaacc attagtaaca catctgtcac 3720
tcttcctgat ggaacccaaa ttccggtcac aacttctggt tccattactc tctctgaaca 3780
tttaactctt cttgatgtct tatacattcc gcattttcaa ttcaatcttt tgagcattag 3840
tgctctcact cgcaacagta ctattgctgt tttgttttct tctcattcat gtttcatttt 3900

-continued tcctaacaat ccatttctcc tccaggagca tactctggat tgcacgattg ggaagggtaa 3960
cctcctgcgc aatctgtatg tcctggagtc tcctacactt tcttcacatt ccgcgcattc 4020
tttgtcggtt tctacacctt cttctatgga tcttcctctt ttacaagtct ctgctgatgt 4080
gtggcatcaa cgccttggtc atccttctca aaacaagatt caagctcttt caaaactttt 4140
gaagatttct tcggctaaga ttgatcatag tagtttgtgt tctgtgtgtc cattagctaa 4200
gcaaaagcgt ctgtcgtttc ctttgtctcc tcatttgtcc aaaactcctt tcgatcttat 4260
tcatatagat atatggggtc ctttctcgac tactacacat gatggttata gatatttttt 4320
aactttggtc gatgattgta ctcgtgctac ttggttatat cttttaaagg ataagagttc 4380
ggtttcaaca atttttcctg agtttcttgc ttttgttcat actcaatata agactcatgt 4440
taaatccatt cgttctgaca atgccccaga gcttgccttt actgatctgt tgcgtgaaaa 4500
aggaattatg cattactttg catgtccata cacacctcaa cagaattctg tagttgaacg 4560
aaaacaccaa catattctaa atgtcgctag agctttgctg tttcaatcaa aagtaccatt 4620
gatatattgg ggagattgtg ttcaaactgc tgtgtatttg ataaatagga ctccctcacc 4680
gcttttgaat gataagtctc catttgaact tctctcaaaa cagattcctt catatgatca 4740
tctaaaagtg tttggttgct tatgttactc ttctacacta gctaaagata gaaataaatt 4800
tactcctcgt gctgacgcat gtatttttct tggttatccg aatggctata aagggtacaa 4860
agttttaaat ctcacgtctc attcgataaa tgtcactaga aatgttgttt ttcatgaaac 4920
agttttccca tttcataaat ctactgattc ttctactcat gatgatttct ttgctcagga 4980
tgtcttacca ttacctgttc cggattctat gtttcctgct ttctttgact tgggttctga 5040
tattgattct tcaatgtttc ctgatccaac tactattagt tcttccaaca tttctaatca 5100
ttcgtttgat gcgtctcttc atccttctgt ttctacttct gttccttctt cttcttcttc 5160
attaccatca ggaactagaa atgaaactag gactcgtcgt caggttaagg caccagctta 5220
tctagatcaa taccattgct atcttttaca aaaagtgcct atggaaccag ttcatcctac 5280
tcatacgact tcataccta tatctgcatt tctttcttat gataaatttg atgaaacaca 5340
ccgaaacttc attctttcca taaccaccac caaaccaccc caaacttacc aagaggctgt 5400
tctatctgaa gaatttaaga atgctatgaa gtctgaaatg acttctctag aagagacagg 5460
gacttggact gtttgtgagt tgcctgcagg taaacacccg gttggttgca aatgggttaa 5520
tacttacaag tataaagctg atggtactgt ggaaagaccg aagtctcgtc ttgttgccaa 5580
gggctatact cagttggagg gtcttgatta tcttgacact tttctccgg ttgcgaaact 5640 tggtacactt cgtcttctct tagctgttgc agcagctaaa ggatggtcta ttcaacagct 5700
ggatataagc aacgcatttc tcaatggtga cttggatgaa gagatatata tgcggcttcc 5760
tcagggatat gaagaactca ctggaaagaa gtgtcctcca aactctgttt gtcggctcca 5820
taagtctctt tatggcctta aacaggcttc aagacaatgg aatcacaaac tctctagtgt 5880
gatcttgggt gatggatttg ttcaaacaca ctctgaccat tctctcttca tcaaacacaa 5940
tgagaaggct tttctagcag ttttggtcta tgtcgatgac atattgatcg tctccaacga 6000
tgactctgct tctgctacat tcatgaatgt cctcaagtcg gcattcaagt tacgtgatct 6060
tggtcaagct aggtacttct taggctttga gattgcacgt aactcctctg gaatttcttt 6120
gaatcaacgg aagtattgct tggagctatt ggaagaagct ggaatgctgg gttgcaagcc 6180
tgtatctgtt cctatggaac ctaatctgaa gctttcggct actcctggtg acgttttacc 6240
ggatgcttct gtttacagga ggctagtggg tcgcttatta tacttgactc acacaagacc 6300
tgacatcact tatgctgttc ataagctaag tcagttcatg tctgcgccta cgactgatca 6360
tctacaagca gcatacagag ttcttcgcta tctcaagaat gatccagctc agggtctttt 6420
ctattctgca acttctgcga tcaaactcac agcttattct gatgctgatt gggcttcatg 6480
tccagattct cgtcaatctg tcacaggtta ctgcatgttc ttaggtgact cgttgatatc 6540
ttggcgtgca aagaaacaac ctactgtttc ccggagtagc tcagaggcag aatacagagc 6600
catggctgat gctacttgtg aacttatctg gttgactgcg ttgttgattg agatgcattg 6660
tgctcctgtt gctcctgcaa ccttgttttg tgacaatcag tcagcgttat acattgcgtc 6720
taacccggtc tatcatgaac gcaccaagca tgttgagatc gactgtcaca ttgttcggga 6780
gcggttgcag agcggcttca tgaaggctct acacgtccgg tctgagcttc agttagctga 6840
catattcact aaggttgttc aaccaggctt gttcaagagt ttagtaagca agattggaat 6900
tcatagtcta tgcattccat cttgaggga gggtattaga ttatggttaa gtgatggttt 6960
aataactggt ttagcttcct tttactaaac cggttatata aatacatcct cttgtacatt 7020
gtaaacttta acttgagcaa tatacttttt ccttttcatc gtaacatact ttccccattg 7080
atcttgagct caagttctaa taaacatatt acgtaacggg tttattttgt cgtcaacaca 7140
ttatcggcaa tgtgaaaaga aggggtgagg tatctccatt tcaattcttc tctttatata 7200
ttaatcgaat tatttacgta tgaaatgaac gtttatatag aaatttcgtg tggaaaacga 7260
catgtacacg gcatctcaag accaattagt aatatacttt agtggtgatt acatgtttac 7320
ttatccaatt gagaatttaa agcatcgaca ataccttaat gtcgattaag ccgtccccac 7380
ttcatgtaat gagttatggg gggagagaga gatcccgaaa ttcgtcaaat aaaacaactt 7440
agaactaaaa accgacacca agtatcataa aggaaatgtt gaagaagtca tttatcgtat 7500
ccagctcaca attcctaaga ttaaatcatg accgttggaa gagcttataa gattaaactg 7560
aagaaattgt gggttttaga agaaagacaa gaaagagaag aacatgatct tacattgcct 7620
attttggtgt ataggagttg tcaaaaagag gagagagagg agacaattag gtcaaataaa 7680
tgagcactaa aaatggagac atgtgttgag taactattac aagagcgact tatgcttcta 7740
tatggcaatg atatcatcac caaagtgcaa tgcccctttt tgccctagtt tcgtaaagtc 7800
tctctccttc ttcgtcctta ggaaaaaccc taaattaaat cctgtgttct tgatctttct 7860
ttttgagtaa ccatgatttt gaccacacac tagttcttct atattttgtg gtctatagga 7920
ttttgcttta tatgtgtttc ttgtattgct ccgtacgtgc gtatataaat ttaaatggtt 7980
acaacaaggt ttattataaa taggcacaaa ttagtccatg aagttattta gcttgcacaa 8040
gtataatttg ttaagtattt aaatatataa atttgttaca aaacttaatt aaatttatct 8100
gattatattt tctttagtgt tcttcctttg ccaacgttga ggtagctatt attattatta 8160
ttttgaacat tatgtacgta gttatcttgg ctagttatga ttcgaattct taatttggat 8220
cacacttaac agtatttaaa atattcttag aactaaaata attaagagtt acctttaaat 8280
tgaagtattc gtgctaaaca gaaactagaa taaacaaatg attgcatgtt aatttttttt 8340
ttcgattttc ctatcagaat aaacacatga ttgcatgcaa attttgtttt tgattacgtt 8400
atcttttgtt tattttagtt ttgatgctaa ttaatatttt ttattaacaa ctcacataca 8460
ttctacctga ttctaggtca gataatgaca cagcgcaaca aaattaatac aaaaccttcg 8520
gaaagtagaa taccgcagaa gtaacttttt tgggtacata cgaaatacag tgaaatctct 8580
ataaattaat aatgttggga ctataccaaa actataattt tttattaatt tatagagatt 8640
aatttatcga tatactaatt gaatcaaaaa cttaatttga gactaaaaaa ttatattatt 8700
ttatagagat ttttagtgta tattaattta tagaatatta ttttataaaa aattttagtg 8760
tgtattaatt tatagagtat taatttaaag aggttatact gtaatgtgaa tcttcgaaaa 8820
acatgccata cataaccacg gatcatagtc gacacctcaa cgtgaagcaa atttgacaat 8880
ctacatacat aaccaacaaa aagtagaata ccttgaaaat ctaaaaccca aaatatgatg 8940
taaaactcaa gcttggtcca gagcataaaa aaattaaagc catcgctttg gtatcacata 9000
tttaaacgtc agtttttttt ttttttttgg gggggggggg gggggggta atataaaaat 9060
ataattaaca aaaaaaaatt atgaaacaat tagcatgtaa aacactaatc ttttggttgt 9120
gacaaaacgt tttcacaaat gttctataaa taaattcaag tgcattttat ctgcaaaata 9180
tatactttca ctcataaaat aagagcgttt aaaacattca tacacgcact acattgacat 9240
gacaaaagaa atccgcaaat acacatgatg tatgtcgaaa aaaacaaaaa atacacatga 9300
tgtatatata gagaggatag tatctaggaa ataagactat attatatata taaagaaaat 9360
agagaaaaga taaaaatata aattggtatg tataaaagaa aggtctatgc gtctctagtc 9420
caaaaactct atatatgtct ggctcaaaag cagatgcagc catagcccca atagtcatga 9480
tggagcatca tcatctcctt atgaattgga acaaacctat tgatctcatt acagaagaaa 9540
actcttttaa ccacaatcct catttcatag tagatccacc ttccgaaacc ctaagccact 9600
tccagccccc gccgacaatc ttctccgatc acggaggagg agaggaagca gaagaagaag 9660
aagaagaaga aggagaggaa gagatggatc cgatgaagaa gatgcaatac gcgattgctg 9720
ccatgcagcc cgtagacctc gatccagcca ccgttcctaa gccgaaccgc cgtaacgtaa 9780
gggtaagcga cgaccctcag acggtggtgg ctcgtcggcg tagagaaagg ataagcgaga 9840
agatccggat attgaagagg atggtgccag gcggtgcaaa gatggacact gcctccatgc 9900
tcgacgaagc catccgctac accaagttct tgaaacggca ggtgaggcta gcttcttcag 9960
cctcacactc agcttggagc tcctatgtct gacccttctt gcctttgtta ttaccacaac 10020
tcggatacct aattataatt ctatcacgcg tttcatgttg atatatatag ataaatggtc 10080
gaataaggat ttcgatcgaa gattgtatgt acaataaatg atgtgtgtat ttcaattaat 10140
gtatgatata tatatatata tgtatgcagt atgcatttat attctattct ctataaggag 10200
gcaacattgc cggattaggg ctttgatctt atgcaagttt tccgaccaaa aatatgaaat 10260
acttgtttgg atataacata tgaatcggat aagtgttact agttatataa ctggaaaaca 10320
aatgtctgga ataagaattc ccgggagaac caagcctttc tctaatccct aagattatag 10380
ctactgaaac aatgaaacaa tgaagaatca gttgggcatt agtaaaaaaa aaagaatcag 10440
ttgggttgct tataaaattt tgttataaaa tttatgtcgt atgtgtgtta gccgtagctg 10500
taaatttatt tcctttgtat gttaattgta aaagtaaatt tattattccc gatgttttta 10560
atgatgtaaa tttaaatcaa gaaaacatat taagttctgt taataaatgt attatttttg 10620
tttactaatt tccaataatt ttttcaagaa gtacaatttt ttgtttgaaa tttctaattt 10680
atcattattg aataatagaa catacctaaa aaccataaaa catgtattcc ttgaaacatt 10740
ttttttaata taaaaattat cttttaggag caggtaaagt actttttttt ataaaattgt 10800
tagtgtattt atgttcgtta tagatgtaga tattttgcat aataattaat aatatatgag 10860
atgtgtaatg tatatatgtg agagaattgc catatttatt aagcggtttt tgtaaaattg 10920
actcaaaatt taaagtcaac cacaaaacta acatatgttt ttttggacat ttcatttgcc 10980
ctattcactc cacaagttca gattatttac gaaaatgtca ttaatttttt ttctttctga 11040
aatggtattt ttactctctc aacctcatca tcttcaagta tttacaagat tgtcattgcc 11100
atcaatacac caaccaccat gaacaaccaa tttgaataat gcaccttaaa tcgatttaca 11160
cttcttcctt ctcaattctt atgaactaaa aacaacatct ctttcacttt ctctccatat 11220
tcatccaaaa aatctaagat ttttattcaa aaatttttat ggttcataga accattgaag 11280
cttacgattc ttggtgtgtc acttttgttt gagattatag gtgcttggag aagacttttg 11340
tgtgctaaac aagttatctc aatggttgaa ctatgaaaat cagtgttttt tccagatttg 11400
ttcgcccaac cgactttcgg gtaagttttc tggctgtaga cgactaacat ggaagtcttc 11460
tggtcaatgc acttctcttt gattgtcttc ttctgattta cattatgtag aatgaacaag 11520
agatgggagg aactaggggt aggtaaaaaa aacggaaccg aattatcgaa ccgaacagac 11580
ccgaaaaaaa ccgaaccaaa tttatgaatt atccaattgg atactgaaat tgtatacccg 11640
aagaattaga atcgaactcg taccgaaccg aaaaccgaat aatacccata tagaaccaga 11700
tgaaaaacct ttatacacta cttatacgta tatctttata gtttatattt tatacacttg 11760
tttttttat tgatcaacgc ttgttttata ggagaacctt gtattgtttg gatattttat 11820
cctcataatt taagttttgg tttctgaatg ggaaaatcat ttgaatgtta ttttggtgtt 11880
ggttttaatt catttatttg caagtacatc agattaattt ggataaatatg gttacaaagt 11940
aaaaagaaaa aactgaactt caggaaccta aaaaaccgag aaccgatctg atctgatccg 12000
aaatttttat ggttctttaa tggttaccaa tttcaagaac cgaaagaaac gagaaccgaa 12060
agaaccaata accgaagaac cgagcgccca ctcctaggag gaaccaaaca atactttgat 12120
ttgaagccca agataattgg aaccatgtta tattacgcag cttatctgat gtgggcttta 12180
tgtagaactg ataatgggct ttaaggcagc ctatttcggt ccgtcaagaa gattcctcct 12240
aacgtaaggt aggggcaatg agctgctact ctgaccaatt aattacgttt caatagtgat 12300
ctctcatctg ttgtcggtgt gaaaggaatc gtcttttgaa tttatcttca tgcgattcat 12360
tgttttataa ctaccacaca tgtgacataa ctaatagtct cgaatcagga catcaaaatt 12420
tatttttttg tttgtggcaa tgattcaaat cgacggcata gcatactgat taaaaatata 12480
tacaatacac tggttattaa aacgttatag ttgtctagat tttaataaca ggtgataata 12540
gatcaagtat atagtaaatg ttttatctca cccattacat atttcatatt aaacatttca 12600
gatttatttg taaatggatt caactgcctg ttacccttca ctccttttga ttaacatcgc 12660
gtcgcaagtc acaaccacca tttagttggg gcgattcgta tattttggga gtatataata 12720
acatacataa ctatcaaacc aactggtgtc gacctttggt gttaactaat ttgatttaac 12780
tctttttggg aataaataaa ataaaatttc agagcagctg ttcaatagta aaatgacagg 12840
tgggatctag ggtttgtggt ccttacgatc gattgattac tactacttaa cttggcatta 12900
tttggagtca cttttgctta ttaataatta gattttgttt acaaacgtgt ggtgatagtc 12960
tgggacaagt tgacctgttg acacccaatc atttagaaca ccttttacaa atataaatat 13020
tcgcacactg ttacaaacat tatcatcaaa ttattgtgga attttgcaga caaagcatat 13080
gccattgtgt ttccttcgat ttggctttta tgcttattcg tggtgtcata attaattcgt 13140
gaaaacgaat gattttacat actgtaagta gggctgaaag cggatcgaat agtaccatat 13200
tttctactat ttgtgattta ttccatattt cagttttctt cgtaaaaata cgaatatcca 13260
gtttttcgaa tatccggaat ttttttgaca tttgcgaata ttcacagata tttacagatg 13320
attcatccac tttgttcaat acaagtctaa aaaaatatca aattattttt tagaaatatc 13380
ttttacatga taaaaatatt aagtaaaaat taatgaaact aaatgtttta ttaaatttta 13440
aaattagtaa tttttcttat aaaaatgttt ttagaaaaat atgtagtttt gtataaagat 13500
ttatatattt ttaatttaat attttataag tagtttttaa aataaaattt aataaattat 13560
atgttaaata attatataag attatacatt taaaactcta tatttaatcg tagatataca 13620
tctatttgta caactccgat ccgtctctaa tttttttag tatttgtggt ttggttcgtt 13680
tttaacggat attgattttt aatatttgct tttttcagag acttacgaat attcatattt 13740
ttttggatcg agtcgaaaca aataataaat tgaatcaaat ttaacggata aaatgttcag 13800
ccctaactat ggttaactat ggatactgaa accaccactt atcaacaaaa aaaagtagtt 13860
gttcgcttct ggtttagagt gaggttacaa attcaaaaca taataattat tttctcggac 13920
gataaccaga tcctttttag aggctttaaa aggtaaatca tagtcatgtg tagcctatac 13980
atacaaatta aattacaatg gaatatgcat ttattgtcaa tatgtataac acatatgtag 14040
acgtaaggta atatatcatt ttggatttga aggaggaagc tgttgctgca tttgctgata 14100
gaacgcagcc atcctgctat atgcttccat cgtcgttggc tgcatgtcaa tgcttcatta 14160
gatttaaaca aaaatgaagt ataaaagttt tatataaaac aaaaagttgt ataacctgcg 14220
aggagcatgc aagaaaggct gacataggat cggggataag aggagactga aatcgagggt 14280
cgatggaaga ggaggcatcc catgatgtag aagtcatggg cacaaatggg ttctgcatca 14340
tgttggcatg gatattagga gccgttgcag tagcagctcg gttcatagaa ctaaggtcga 14400
caagacctag accgggcatc cccatgcgaa gccctaagcc catggaactg gacatgagat 14460
ttagttgaag ttgttgttgt tgctgctgca tggccatggg aagcatcatg gagggcatgt 14520
tcattctgct catcatgcac acttgtgctt ggagttgctt caagtactct atcacttcat 14580
ccaacatgga cgctttatcc gtctagttcc aaattgtaac ttatcaaacc gttcactcct 14640
tttgatgtat tatttaacca aaccaactca agggatgatc gatgaacaca tgtctacaat 14700
aataatagta cactatacat ttttttttg tcaaacatag tacactatac atatgtaacg 14760
tagattgtgt taattgattg tgttggttga attttgattg accgccaaaa ggtggcatcc 14820
ctttcttatt atttgaggaa cattagataa aactaacatt tacttcatgt gtttattaca 14880
tgtgtgtcat ttcctacgtg gcatcaccac aagctctctc acaccttata ttcaaacacc 14940
ctttcttaac tagactaatt acaaaatttg ccattgctaa ttacattaaa acttcaatat 15000

<210> SEQ ID NO 12
<211> LENGTH: 4081
<212> TYPE: DNA
<213> ORGANISM: Brassica napus

<400> SEQUENCE: 12
ttagctgttg cagcagctaa aggatggtct attcaacagc tggatataag caacgcattt 60
ctcaatggtg acttggatga agagatatat atgcggcttc ctcagggata tgaagaactc 120
actggaaaga agtgtcctcc aaactctgtt tgtcggctcc ataagtctct ttatggcctt 180
aaacaggctt caagacaatg gaatcacaaa ctctctagtg tgatcttggg tgatggattt 240
gttcaaacac actctgacca ttctctcttc atcaaacaca atgagaaggc ttttctagca 300
gttttggtct atgtcgatga catattgatc gtctccaacg atgactctgc ttctgctaca 360
ttcatgaatg tcctcaagtc ggcattcaag ttacgtgatc ttggtcaagc taggtacttc 420
ttaggctttg agattgcacg taactcctct ggaatttctt tgaatcaacg gaagtattgc 480
ttggagctat tggaagaagc tggaatgctg ggttgcaagc ctgtatctgt tcctatggaa 540

```
cctaatctga agctttcggc tactcctggt gacgttttac cggatgcttc tgtttacagg    600
aggctagtgg gtcgcttatt atacttgact cacacaagac ctgacatcac ttatgctgtt    660
cataagctaa gtcagttcat gtctgcgcct acgactgatc atctacaagc agcatacaga    720
gttcttcgct atctcaagaa tgatccagct cagggtcttt tctattctgc aacttctgcg    780
atcaaactca cagcttattc tgatgctgat tgggcttcat gtccagattc tcgtcaatct    840
gtcacaggtt actgcatgtt cttaggtgac tcgttgatat cttggcgtgc aaagaaacaa    900
cctactgttt cccggagtag ctcagaggca gaatacagag ccatggctga tgctacttgt    960
gaacttatct ggttgactgc gttgttgatt gagatgcatt gtgctcctgt tgctcctgca   1020
accttgtttt gtgacaatca gtcagcgtta tacattgcgt ctaacccggt ctatcatgaa   1080
cgcaccaagc atgttgagat cgactgtcac attgttcggg agcggttgca gagcggcttc   1140
atgaaggctc tacacgtccg gtctgagctt cagttagctg acatattcac taaggttgtt   1200
caaccaggct tgttcaagag tttagtaagc aagattggaa ttcatagtct atgcattcca   1260
tcttgagggg agggtattag attatggtta agtgatggtt taataactgg tttagcttcc   1320
ttttactaaa ccggttatat aaatacatcc tcttgtacat tgtaaacttt aacttgagca   1380
atatactttt tccttttcat cgtaacatac tttccccatt gatcttgagc tcaagttcta   1440
ataaacatat tacgtaacgg gtttattttg tcgtcaacac attatcggca atgtgaaaag   1500
aaggggtgag gtatctccat ttcaattctt ctctttatat attaatcgaa ttatttacgt   1560
atgaaatgaa cgtttatata gaaatttcgt gtggaaaacg acatgtacac ggcatctcaa   1620
gaccaattag taatatactt tagtggtgat tacatgttta cttatccaat tgagaattta   1680
aagcatcgac aataccttaa tgtcgattaa gccgtcccca cttcatgtaa tgagttatgg   1740
ggggagagag agatcccgaa attcgtcaaa taaaacaact tagaactaaa aaccgacacc   1800
aagtatcata aaggaaatgt tgaagaagtc atttatcgta tccagctcac aattcctaag   1860
attaaatcat gaccgttgga agagcttata agattaaact gaagaaattg tgggttttag   1920
aagaaagaca agaaagagaa gaacatgatc ttacattgcc tattttggtg tataggagtt   1980
gtcaaaaaga ggagagagag gagacaatta ggtcaaataa atgagcacta aaaatggaga   2040
catgtgttga gtaactatta caagagcgac ttatgcttct gaaccaagcc tttctctaat   2100
ccctaagatt atagctactg aaacaatgaa acaatgaaga atcagttggg cattagtaaa   2160
aaaaaaagaa tcagttgggt tgcttataaa attttgttat aaaatttatg tcgtatgtgt   2220
gttagccgta gctgtaaatt tatttccttt gtatgttaat tgtaaaagta aatttattat   2280
tcccgatgtt tttaatgatg taaatttaaa tcaagaaaac atattaagtt ctgttaataa   2340
atgtattatt tttgtttact aatttccaat aattttttca agaagtacaa tttttttgttt   2400
gaaatttcta atttatcatt attgaataat agaacatacc taaaaaccat aaaacatgta   2460
ttccttgaaa cattttttttt aatataaaaa ttatctttta ggagcaggta aagtactttt   2520
ttttataaaa ttgttagtgt atttatgttc gttatagatg tagatatttt gcataataat   2580
taataatata tgagatgtgt aatgtatata tgtgagagaa ttgccatatt tattaagcgg   2640
tttttgtaaa attgactcaa aatttaaagt caaccacaaa actaacatat gttttttttgg   2700
acatttcatt tgccctattc actccacaag ttcagattat ttacgaaaat gtcattaatt   2760
tttttctttt ctgaaatggt atttttactc tctcaacctc atcatcttca agtatttaca   2820
agattgtcat tgccatcaat acaccaacca ccatgaacaa ccaatttgaa taatgcacct   2880
```

taaatcgatt tacacttctt ccttctcaat tcttatgaac taaaaacaac atctctttca 2940
ctttctctcc atattcatcc aaaaaatcta agatttttat tcaaaaattt ttatggttca 3000
tagaaccatt gaagcttacg attcttggtg tgtcactttt gtttgagatt ataggtgctt 3060
ggagaagact tttgtgtgct aaacaagtta tctcaatggt tgaactatga aaatcagtgt 3120
tttttccaga tttgttcgcc caaccgactt tcgggtaagt tttctggctg tagacgacta 3180
acatggaagt cttctggtca atgcacttct ctttgattgt cttcttctga tttacattat 3240
gtagaatgaa caagagatgg gaggaactag gggtaggtaa aaaaaacgga accgaattat 3300
cgaaccgaac agacccgaaa aaaaccgaac caaatttatg aattatccaa ttggatactg 3360
aaattgtata cccgaagaat tagaatcgaa ctcgtaccga accgaaaacc gaataatacc 3420
catatagaac cagatgaaaa acctttatac actacttata cgtatatctt tatagtttat 3480
attttataca cttgtttttt ttattgatca acgcttgttt tataggagaa ccttgtattg 3540
tttggatatt ttatcctcat aatttaagtt ttggtttctg aatgggaaaa tcatttgaat 3600
gttattttgg tgttggtttt aattcattta tttgcaagta catcagatta atttggataa 3660
tatggttaca aagtaaaaag aaaaaactga acttcaggaa cctaaaaaac cgagaaccga 3720
tctgatctga tccgaaattt ttatggttct ttaatggtta ccaatttcaa gaaccgaaag 3780
aaacgagaac cgaaagaacc aataaccgaa gaaccgagcg cccactccta ggaggaacca 3840
aacaatactt tgatttgaag cccaagataa ttggaaccat gttatattac gcagcttatc 3900
tgatgtgggc tttatgtaga actgataatg ggctttaagg cagcctattt cggtccgtca 3960
agaagattcc tcctaacgta aggtaggggc aatgagctgc tactctgacc aattaattac 4020
gtttcaatag tgatctctca tctgttgtcg gtgtgaaagg aatcgtcttt tgaatttatc 4080
t 4081

<210> SEQ ID NO 13
<211> LENGTH: 14640
<212> TYPE: DNA
<213> ORGANISM: Brassica napus

<400> SEQUENCE: 13
attattattt gtatttatat atctagggta ttaaaatctt tttacttatt ttatgaaaca 60
ttttggttat ctttctcctt acaatctatt tttgtgataa aaacttgaaa atagtctact 120
taggagaatt accctttaca ttatctaata aactgatctt ctagaagaga gaaacgttaa 180
tggtggacga agcccccacc tcaattgaca ataaaagaaa gtggaaaaga gagaagatag 240
cagagtgaaa ggtccgaaga gaggagatca tgaagagaag aagacaatgt aacctactta 300
tttgccttga tgaacaatta cgagaagaaa taaacataaa atgagaagag agaggtggga 360
tatacagaag agagaaagat ttggcaggaa acccgattga ccatatatca gatctagagt 420
ggattggatt agataactcg agcttatttg gttaatcttt ttagtttagg gaaggttatg 480
aaaaattaac cccgatctga tttttaaatt ttttatctta tattgtgccc ccggctaaca 540
atatatctag atccgtccct gatcaggtcc atgagatata tcatattttt atttttctta 600
tttaattaat tatatatata atatttgagg atatatttaa aattttacat atcgttgaaa 660
gccagaaaaa aatgtggaag tgtaataaaa caattttctc caggaagaag atatttcagc 720
cattcgccta tttatgtgta tgagatccca ttcaaggaca tactgttttc cgtgagctac 780
tgaatgaata cgatgctttt gttgtaaacg caacctattg gttttttttt tccgccaagt 840
tttgttttta ttaatcaaac gggccaagcc caaacggtcg aagcccaaat acactaagta 900

```
ccaaacaaaa ggcccacaga cacaacgggc tacaacatta atggctgaag cccaagtaaa    960
ctaaacggcc caaaggccca aacattgaaa ccggacagct tgacctaggc gcgcgataag   1020
gagactgggg tttgaacacg tgtaagaatc tgggccatta gtatgacacg cgtcgcccgc   1080
ctcgacttga tcgaaacctc ttcgcacagc cgcatgaact tgccaccgac gacctcgttt   1140
cgccggagct cagagactga agagcctcca acgaaaccat agctattcta cgccgctctg   1200
tcttcacgcc ggagagttcc atcgatctaa cgagatctcc tccgactatg tatcaccaca   1260
aaccctagac aggcgagccg agaaccactg atatcctcct cttgtacgtc ctcgccgttg   1320
tcggagagtt tcatcatcat ccgagatctc atccgcgatg gcccacgacc ccatacctga   1380
ccacaagaac cacaccgcac ttatctcacc tcgatctaat caccacaacc caaaggacat   1440
cgggttccaa gacggcagcg cggagctttg caagcctcca ctctccgtga ccaaaagccg   1500
gcgaagacgg agctgaatga gcctcccctt cccggaagct aaagcggcga cggtggatct   1560
gagaaagcct ccacctcccg cataaagacc ggcgacgatg gatctagggt agcctccatc   1620
tcccggaaaa aacaccacct gaacatgcaa gccgctccat ctccaccggg agcctccaat   1680
tgatcgcgtc gttactccaa aggccgagcc accgttgatg gatggttgcg gtcccagagc   1740
tccgacaagg cgatcgatga cgggactgcg aagaaggagc ggagagtgac aactacaaag   1800
gaagggaaag agctctggcg acagcacgga cgctcacgcg ccagccgtac gccgaaccca   1860
aaagtagatc tggtttctct cttttctctc tctcgcaaaa gaaaacacgc aacctattgt   1920
tctccatttt gaatttgaag tgttacatta ttaataaaaa ggaagaaagt acaaagcttt   1980
tcatttagtg gttgttgcat atatagtata cttatttgat gggcttatga taagtatgaa   2040
catttcacgt aacgggttta ttttgtcgtc aacacattac cggcaatgtg aaaagaaggg   2100
gcgaggtatc tccatttcaa ttcttctctt tatagattaa tcgaattatt tacatatgaa   2160
atgagcgttt atatagaatt ttcgtgtgga aaacgacatg tacacggcat cgaaagacca   2220
attagtaata tactttagtg gtgattacat gtttacttat ccaattgaga atttaaagca   2280
tcgacaatac cttaatgtcg attaagccgt ccccacttca tgtaatgagt tatgggggga   2340
gagagaggtc ccgaaattcg tcaaataaaa caacttagaa ctaaaaaccg acaccaagta   2400
tcataaagga aacgttgaag aagtcattta tcgtatccag ctcacaattc ctaagattaa   2460
atcatgaccg ttggaagagc ttataagatt aaattgaaga aattgtgggt tttagaagaa   2520
agacaagaaa gagaagaaca tgatcttaca ttgcctattt tggtgtatag gagttgtcaa   2580
aaagaggaga gagaggagac aattaggtca aataaatgag cactaaaaat ggagacatgt   2640
gttgagtaac tattacaaga gcgacttatg cttctatatg gcaatgatat catcaccaaa   2700
gtgcaatgcc cctttttgcc ctagtttcgt aaagtctctt tccttcttca tccttaggaa   2760
aaaccctaaa ttaaatcctg tgttcttgat cttgcttttt gagtaaccat gattttgacc   2820
acacactagt tcttctatat tttgtggtct ataggatttt gctttatatg tgtttcttgt   2880
attgcaccgt acgtgcgtat ataaatttaa atggttacaa caaggtttat tataaacagg   2940
cacaaattag tccatgaggt tatttagctt gcacaagagg tatataaatg tgtgtgtgtg   3000
tgttaagtat ttaaatatat aaatttgcta caaaacttaa ttaactttat ctgattatat   3060
tttctttagt gttcttcatt tgccaacgtt gaggtagcta ttattattat tattattatt   3120
attattatta ttattattat tattattatt attattatta ttattattat tattattatt   3180
attttgaaca ttatgtacta tgtacgtagt tattttggct agttatgatt caaattctta   3240
```

atttggataa cacttaacag tatttaaaaa aaaaatacta tttaaaatat tcttagtact 3300
aaaataatta agatttaact tgaaattgaa gtattcgtgt taaacagaaa ctacaataaa 3360
caaatgattg catgttaatt tttttttcga ttatcctata tatcagaata aacacatgat 3420
tgcatgcaaa ttttgttttt gattatgtca tcttttgttt attttagttt tgatgctaat 3480
taatattttt tttattaaca acttccatac attctacctg attctaggtc agataatgac 3540
acagcgcaac aaaattatac aaaactttcg gaaagtagat taccgcggaa gtaacatttt 3600
tgggtagaca tacgaagtag tttgaatctt caaaaatcat gccatacata accacggatc 3660
atagtcgaca cctcaacgtg aagcaaattt gacaatctac atacataacc aacaaaaagt 3720
agaataccgt gaaaacctaa acccaaaata tgatgtaaaa ctcaagcttg gtccagagca 3780
taaaaaaatt aaagccatcg ctttggtatc acatatttaa acgtcagttt tttttttgggg 3840 aagtaatata aaaatataat taacaagaaa atttatgaaa taattagcat gtaaaacact 3900
agtcttttgg ttgtgacaaa acgttttcac aaatgttcta taaataaatt caagcacatt 3960
ttatctgcaa aatatatact ttcactcata aaataagagc gtttaaaaca ttcatatacg 4020
cactacattg acatgacaaa agaaatccgc aaatacaaac atatttagtt cggatatatc 4080
taggaaataa gactatatta tatatataaa gaaattagaa aaaaagaaaa ttggtatgta 4140
taaaagaaag gtctatgcgt ctctagtcca aaaactctat atgtctggtt caaaagcaga 4200
tgcagcagcc atagccccaa tagtcatgat ggagcctcat catctcctta tgaactggaa 4260
caaacctatt gatctcatta cacaagaaaa ctcttttaac cacaatcctc atttcatggt 4320
agatccacct tccgaaaccc taagccactt ccagcccccg ccgacagtct tctccgatcc 4380
cggaggagga gaggaagcag aagacgaaga aggagaggaa gagatagatg agatgaagga 4440
gatgcaatac gcgattgctg ccatgcagcc cgtagacatc gatccagcca ccgttcctaa 4500
gccgaaccgc cgtaacgtaa gggtaagcga ggacccccag acggtggtgg ctcgtcggcg 4560
tagagaaagg ataagcgaga agatccggat attgaagagg atggtgccag gcggtgcaaa 4620
gatggacact gcctccatgc ttgacgaagc catccgctac accaagttct tgaaacggca 4680
ggtgaggctt cttcagcctc acactcagct tggggctcct atgtctgacc cttctcgcct 4740
ttgttattac cacaactcgg atacctaatt ataattctat cacgcgtttc atgttgatat 4800
atatagataa atggttgaat aaggatttcg atcgaagatt gtatggctat tgattacatt 4860
atatattgta caataaatga tgtgtgtatt tctattaatg tatatatgat atatatctgt 4920
ttgcagtatg catttatatt ctattcttta tagggaggca acatgccgga ttagggcttt 4980
gatcgtatgc aagttttccg accaaaaata tgaaatactt gtttggatat aacatatgaa 5040
tcggataagt gttactagtt atataactgg aaaaaaattg tttggtataa gaattcccgg 5100
gagaaccaag cctttctcta atccctaaga tcatagctac tgaaataatg aaaaaaaaca 5160
aaaaaaaaac aatgaagaat cagttgggca ttagtccaaa aaaaaaaaag aatcagttgg 5220
attgcttata aaattttgtt ataaaattta tgtcgtatgt gtgttagccg tagctgtaaa 5280
tttatttcct ttgtatgtta attgtaaaat ttaatttatt attcccgatg tttttaatga 5340
tgtaagttta catcaagaaa acatattaag ttctgttaat aaatgtatta tttttgttta 5400
ctaatttcca ataatttttt caagaagtac aattttttgt ttgaaatttc taatttatca 5460
acatacctaa aaaccataaa catgtatttt ttgaaacatt tttttaatat aaaaattatt 5520
ttttaggagc aggtgaagta tttcttttaa taaaattgtt agtgtattta cgttggttat 5580
agttgtagat attttgcata ataattaata atatataaga tgtgtaatgt atatatgtga 5640
gagaaatacc atatttacta agagtttttc gcaatattga ctcaaaattc aaagtcaatc 5700
acaaaactaa catatgtttc tttttagaca tttcctttgc cttattcact ccacgggttc 5760
agattattca cgaaaatgtc attaaatttt ttttcttttc gaaaatggca tttttactct 5820
ctcaatttca tcctcttcaa gtatttacaa gatttccatt gccatcaata caccaaccac 5880
aatgaacaac caatttgaag ctcttaatgc acctcaaatc gatttacact tcttcttttt 5940
caattcttat gaactaaaaa caacatctct ttcaatttct ccccatattc atccaaaaaa 6000
cccaagattt ttattctaaa attttaatgg ttcatagagc cattgaagct tacgattctt 6060
ggtgggtcac ttttgttcga gattttaggt acttggagaa gacttttgta tgctaaacaa 6120
gttatctcat tggctgaaac tatgaaatca gtttttttc cagatctgtt cgcccggacg 6180
acttccggat aagtcttctg gctgtagacg acttacatcg aagtattctg gttaatgcag 6240
atgttagttt tgcaattgac ttttaagatg cttactcgaa gattagtact cttctgttct 6300
tgtaccttat gagcattcca atagtattat atttttcatt ctaaaatata tttcaatgat 6360
attttacttt tcactctata atagagtgaa aatgagttta ctttataatc ccctatatat 6420
tatttgtgaa acactacaac ttctttttgt agccacatgt catcactagg atgattttta 6480
gaattattag agaaataggt tggtccatct aattatataa taagtttttt attaaattaa 6540
ccataaattc attattaatg tcatttatta tttccttaaa taaagattac ggaattgcct 6600
aatgtgggta aagtatatat gacaattaat gatcttgaat aataaagata tgataaaaaa 6660
aatgtatctt ctatcaaatt tgtttaattt aaaactatta aaataatttt taaaaaaaca 6720
caataaccat attataaaaa tttagatttt tctgtatatt tttatatttt gaactttaaa 6780
aaatgacgat aaattactaa aactgttaaa agtctcacat tcaaattttg ctatccatgt 6840
tttaaaattt ttgttatgac aaaatacaaa tgattacaaa atcatataag taaaagtcta 6900
atttaattaa tcattaagat ttaaaatata tatgtatata tatcattcta aattaaacta 6960
taaaccatat tgaataaata aatattttag tttcaaaatt ttactttgaa taattttttt 7020
tgataaaagt tttgaactaa cattgataaa tgtttttaaa ctatcaatta ccaaaattat 7080
tgatcccaca atgaaaattt tgttatcagt aatttaaagt ttttgctatt aaaaatacgc 7140
ataataaaac aaaacatatg agtagaaagc atcatttaaa gaaaaataaa aaaataaaat 7200
agacattaat attaaaaata tactgtgtat gttaatatca tttaaattta attacatatc 7260
ctatcaaaaa aaatttaaaa aaatgtttgg attaataaaa ttgatttata cgttcgcacc 7320
aatataatta tatacgtaat agttactgac ttttaattat tcaatatata tttattattt 7380
cataatatgt aagaacatat aatacataaa ataattttta tatataatgt ttatctcgcg 7440
caaggcgcgg atcttaatct agtctatatt ataagagtta ttcttgggtt catcccctag 7500
ggtgaacctc cagccaatag gatttcttta tttcaaatac gatatatttt aaaaaaataa 7560
accaaatatt atcaagttat attatgtttt taaaataaaa aagtaaaaaa aaagtagcag 7620
ttacagaaaa aagaattaaa aaaaaaaatt taacgtcgtc agcaaaacac taaaccctaa 7680
atcataatcc ctaaacccta aatcataaat tctaaaccct tgggtaaacc taaactcttg 7740
ggtaaaccta aactcttggg taaaccctaa accattgggt aaactctaaa cccttgggta 7800
aaccctaaac ccttggataa atcataaact ctaaataaaa actctaaacc ctaaaactct 7860
aaaccataaa tcctaaaccc taaacccttg agtgttttag tgtttagtga ttttgattta 7920
gagtttaaga tttatcctag agtttaagat ttatgctagg gtttatggtt taccaaaggg 7980

-continued

```
tttagggttt aagatttagg gtttagggat taggatttag agtttaatgt tttgctgatg   8040
acgttaaaaa tatttttttt tgtaattact gttttttttt tttttacctt ttaattttat   8100
aaagataata taatttgaca atattggtcg gtgaataagt catattataa tgccaacttt   8160
tctctttcct aaaggagcct gcgtgtgcat tctataaagc atgggggacc cacttaatgt   8220
ctggtttatt ttggtcgaat aggctatagt ttggtttggt cagatttggg ttttctacgt   8280
ttggtttgat tattaagggc ctggctggtt caaccgcagc ggttgcggtt gcggctgcgg   8340
gagtttgcgg atgcgggtgg ttgcggtttc taacggtttt aagagattta tacgactggt   8400
tctgcggtta gaaattggtg cgtttgatac ttatgactgg ttaactacca aacgcaacag   8460
cggttaaata ataaattaac aaaatttaca ttttatatca ttataaaata tcaaaaataa   8520
taatattata ataaatataa aatttatatt tagaaagtta tagtttaaac tttttttaaa   8580
ttatagaaaa tattttcatt ttaaagtttt ataatattaa ttaaaatata atagatatat   8640
tttagtattt ttataattct aatttaaatt ttttattgaa tatttttatt tttgtattta   8700
aattgtttta gaaaaaaaaa aatttatcct cccgcaaccg cccgcaaccg caaacgctag   8760
ttggaaccag tttttgaatt tatgaggttt agagcgattt ggagcggttt ggagcggttt   8820
gagcgattgt tgcaaaacgc caacaaccgc taccaaccgc aaaagctgcg tttgcgggtg   8880
gtagcgggaa aaccagtctt acccttgtca ttagggcttc attagttgtt agcgttcttc   8940
cacacttcga gtgtgattgg taacatcaga gtaaagtgga gtaaaaaaaa gtggtgaaaa   9000
agaggaaaat aaatggtgga aaaatgtgag agagaaaaga atctggaata acatgagtgt   9060
acctaaagct agaggaaaaa taggtgtata tttccctcat aatcaatagt gcctagagta   9120
aatatgaaaa gatagtattt cattttattg gtgacttttt ggcttaactg agagtaaata   9180
tatatctaga gtaatagttt actctataga taccatacaa tcataccctt catcctcgcc   9240
gtgaatctgc aaacctaatg acttctcctc ccatctcttt accttccctt ccgttcaata   9300
tatttctttt aattcagcaa tagttgttat tcacattaaa cccagtaagg atgtcgacct   9360
cttcgttttc ttcacgtcaa cctataaata ggagaaggtt gagagtagga tggatcttca   9420
gaaccactgt ctgttaatct tctttgtcac tctcactcac tctctctctc atctgcaact   9480
ggtttggccc tcccttcgag ttatgtggac cttgtggttt gtctttctcc agtgagaaac   9540
ttggtgagca aacttaatat tattcatctt atgcattact tattgaactg gaagtatctt   9600
atacataata cccgtctcaa gaacctatca aagaggcggg aattttggag ggtcgcaatg   9660
gtataaagga gacatgccgt caggtatgct taccgtggaa gtcatgttgc aacagttaac   9720
aatcatgatt atgtttttaa atttaacttt taaatttgct ttatttctgt gatcacattg   9780
gtgcttttat gtttgttttt aggggatagt ctaattattt tcatatatgg acccatcttt   9840
cttaagtatg ctggttgctc atgtcgtgtt gcatattagg gacagcgccc taagaacccc   9900
ccatgttaga taattctaat taacttaaag agcaagttaa ctcattaaag tgaagtttga   9960
tgggttaagg aaaaaggaaa acatatcgag cttaggaatg tttccatatt attattagga  10020
aaagatgtag cttcgccttt aggaaaagat gtagtttcgc ctttaggaaa agatgtagct  10080
tcttcctata taaagagttc ttatggagag atgttctata aaaaaaaaca cattgaaagg  10140
tttagttttg agagagtttc taaatctaat aagaagtgaa gttcttataa tctttgtgta  10200
tatgcaactt taaattggta tcagagctcc aggtttcgaa ggtcgtttac aagaggagtt  10260
gtaacttcga tcaaaacatg ggagacgatt ctcaagcacg tgataaaggt cttgggatga  10320
agaaggacat acgatgtccg atgctaacat cgaccaacta caccgtatgg tcgatgcgaa  10380
```

```
tgaaagtgat gcttcgttta tacgaagttt gggatacgat tgatccaggg agtaacgatg  10440
caaagaagaa taatatggcg attgctctaa tctttcaatc agtcccggag gcgctaatac  10500
ttcagattgg agaacatgat acatcgaaga agatttggga agctatcaaa tcccgtaacc  10560
taggtgctga tcgcgtgaga gaagcaaggt tacaaacttt gatgtctgag ttcgacaaac  10620
tgaagatgac agacacagac acggtggatg actacgcaga aaaactttca ggcttagcat  10680
cgagagcagc cgcattagga gagataatgg aagcatcaag gctggtaaag aagtttctga  10740
agggacttcc aagaacgaag ttcattcaca tcgtagcttc gttagaacaa gtgctggatc  10800
taaattctac gggattcgaa gacattgttg ggagattgaa ggctttcgaa gaacgcatca  10860
aagaagaaac ccaagatgaa ggtcaatcga agctcatgtt tggaaagaat gatatgcaag  10920
gtagtggaag ccataacaac tcgcgaggaa gaggcatagg tagaggttat ggtagaagag  10980
gaagaggaca aggaaggtct aatgtttctg atggtcataa caaaggagga gaagcttcag  11040
acaagaccaa gaaggactac tctaaggtta gatgttggcg atgcgacaag atggggcact  11100
tcgtgtcaca ttgtcctaca cgaccaagag aagaagctaa cctaacggaa acacaagaag  11160
cggatgcatt atatatgcat gaagtagtat tcctcaacga agagagagtg tttcctaaga  11220
ggtttgatga atgcgatgga aatacgagta tatggtacct tgacaatggt gcaagtaacc  11280
atatgacagg caagagagag ttcttctcaa acctagatga tagcatcaaa ggcaaagtca  11340
aattcggtga tggatcaaac atcaagattg ttgggaaagg ttcgatcacg ttcaccggaa  11400
aaacagggga gagaagagca ctcaaagata tctactacat cccaagtctt aaacacaata  11460
tcataagtct tggacaagca accgagatgg gttgtgaggt taatatgaaa gaagacttac  11520
tgatgctgaa agatccccgt ggaaggttat tagtacaagt cgcaaggcaa ccaaaccgat  11580
tgtacaagac gccaatggag gttgaatatc cgaagtgtct tcaaatacaa gaaactgatg  11640
ttacatggac gtggcatgca cggctaggac atgtaaactt tggagtcatg aagaatatgg  11700
tagacaaaga gatggtagta gggatgcctc aggtgataca cgagaaagat gtgtgcaacg  11760
cctgcttagt tgggaagcaa actcggaagt ctttcctgcc taaagcaaag tatcgagcat  11820
cacacgcatt ggatttggta catggtgact tgtacggtcc gatatcacca tcaacaccag  11880
caaacaatag atatgtatac gtcttaattg atgattactc aagatatatg tggacgatgc  11940
tgctaagaga gaagagtgaa gcgttcgatc ggttcaaaaa gttcaaggag tacgtggaga  12000
atcaaacgaa gctacaactc aagaattttc gcaccgatag aggaggagag ttcacatctt  12060
ctgatttcat tcgtttttgt gaagaaaacg gtgtaattag acatctcacc gcatcatata  12120
cactatcaag aaacgtggac gaagaaccag gatcattcaa gcttcctcat attgatgtta  12180
cagaaggaga tggtgatgag catcaacatc accaacacca cgaagagcaa aacaataatg  12240
aagaagatgt gaacttgttt gtaacgggga cttcgctcag tgttatcaag caattcaaag  12300
atgatatgtc aagaatattt gagatgtcag acctcgagat gcttacatac tatcttggta  12360
tagaagtaac acaaggagct gatggcattc acatcaaaca agaaggatac gcgcaaggta  12420
tacttgtcaa gacgaagatg gagtcatgta actatactca cgttctgatg cacacgagtt  12480
tgaaagtatc aaaggcagag gaggagcctg agattgatgc aacatcgtat cgaagcacca  12540
taggatgctt aagagagagt ataaatgctt cactgcttct ctatgactct ctcttaagca  12600
tcttatggtg cttcgatacg atgttgcatc aatctcaggc tcctcctctg cctttgatac  12660
tttcaaactc gtgtgcatca gaacgtgagt atagttacat gactccatct tcgtcttgac  12720
```

aattatacct tgcgcgtatc cttcttgttt gatgtgaatg ccatcagctc cttgtgttac 12780
ttctatacca agatagtatg taagcatctc gaggtctgac atctcaaata ttcttgacat 12840
atcatctttg aattgcttga taacactgag cgaagtccct gttacaaaca agtcatcgat 12900
gtatatagct atgatcagaa gctccccctt ctgtttcttt tgatataccg caggttccgt 12960
ggtgcacttc gtgaactcca tctccttgag aacacggtcg agtttgatgt tccaagctct 13020
tagagcaact ggtgcaaata attcgtcgaa gtctatgcct tgttgttgca cgtagccttt 13080
tgcgactagc cttgctttgt atttgatcac cgttccatct acattcctct tgatcttata 13140
gatacacttc aaacctatca gtttcacacc tgccggcttc ttgacgagct tccaggtctt 13200
gtttttgatg atagatttga tctctgcctt cattgcatcg atccaagctt gtattactgc 13260
agcttcgatg taactttctg gttcaccatc gatggtgagc aagagtctgc cactttcaac 13320
ttcagcaagt aggatgtaat catcgaaccg ctttggtttt ctgatgttac gaccatatct 13380
tgatgttaca tgctggtctt ggtttgcatc gttgttctct gctacttgct cttgttcacc 13440
tgcgtctaca gcttcttctt cttcattatt gttttactct tcgttctgat gcaacatcgt 13500
atcgaagaaa tgcgatgcac ctagtaacgg tctatggaag ttcatcggag ttcagaagat 13560
caacatacct aagattcaag ttggaattaa gggggagaat gttggataat tccaattaac 13620
ttaaggagca agttaactca ttaaagtgaa gtttgatggg ttaaggaaaa aggaaaacat 13680
atcgagctta ggaatgtttc catattatta ttaggaaaag atgtagtttc gcctttagga 13740
aaagatgtag tttcgccttt aggaaaagat gtagcttctt cctatataaa gagttcttat 13800
ggagagatgt tccatcaaga aaaacacatt gaaaggttta gttttgagag agtttctaaa 13860
tctaataaga agtgaagttc ttataatctt tgtgtttatg caactttaaa ttatatctct 13920
tatttaagag acggttctta acttttctta gttaaagcta agaaccgtct cttagctgaa 13980
gctaagaacc cagtctctta tctggggtta atcatggtcg tctaatgtct catttattag 14040
tgtttttatt tttcacagtc gttaggtact ctcatcatgc tctctcctat ataattcgtt 14100
aatgcatgcg cagataccaa ttatcatgct tgttgtggaa gtcccttgtg atctggtatg 14160
cagtatacag tcaccaaaag atggcccaga ctgtatcacc gttgaccaag acagcaatag 14220
taacactgat gtggttggat ttgaagactc tgcagcagca aactctttac cgacaaaggc 14280
tggaaacttg gcaaatgcaa aatgtgtccg tcttgacatc agtttcaaaa cgccatcgca 14340
tacgtgtctt caaaccacac aattggtgtt tgtttaattc ttctttcaca gcaagatatt 14400
tgtttttctt acattatacc tcttcttgtc tatgtatctc tgtaaccttt tttctttctt 14460
tgggcttatg tttcctaaaa tgttcgtttc tgcaggtgaa agatctgaca gcaatttcca 14520
gctgccacac cacttgcttt ggtgttaaag cagtttttgg ctgatcgtac cctggatcaa 14580
tcatactccg gcggattgag ctcttattgc ctggtgagcc gtgttccttt acattaagta 14640

<210> SEQ ID NO 14
<211> LENGTH: 3781
<212> TYPE: DNA
<213> ORGANISM: Brassica napus

<400> SEQUENCE: 14
agaggagatc atgaagagaa gaagacaatg taacctactt atttgccttg atgaacaatt 60
acgagaagaa ataaacataa aatgagaaga gagaggtggg atatacagaa gagagaaaga 120
tttggcagga aacccgattg accatatatc agatctagag tggattggat tagataactc 180
gagcttattt ggttaatctt tttagtttag ggaaggttat gaaaaattaa ccccgatctg 240

```
atttttaaat tttttatctt atattgtgcc cccggctaac aatatatcta gatccgtccc    300
tgatcaggtc catgagatat atcatatttt tatttttctt atttaattaa ttatatatat    360
aatatttgag gatatattta aaattttaca tatcgttgaa agccagaaaa aaatgtggaa    420
gtgtaataaa acaattttct ccaggaagaa gatatttcag ccattcgcct atttatgtgt    480
atgagatccc attcaaggac atactgtttt ccgtgagcta ctgaatgaat acgatgcttt    540
tgttgtaaac gcaacctatt ggtttttttt ttccgccaag ttttgttttt attaatcaaa    600
cgggccaagc ccaaacggtc gaagcccaaa tacactaagt accaaacaaa aggcccacag    660
acacaacggg ctacaacatt aatggctgaa gcccaagtaa actaaacggc ccaaaggccc    720
aaacattgaa accggacagc ttgacctagg cgcgcgataa ggagactggg gtttgaacac    780
gtgtaagaat ctgggccatt agtatgacac gcgtcgcccg cctcgacttg atcgaaacct    840
cttcgcacag ccgcatgaac ttgccaccga cgacctcgtt tcgccggagc tcagagactg    900
aagagcctcc aacgaaacca tagctattct acgccgctct gtcttcacgc cggagagttc    960
catcgatcta acgagatctc ctccgactat gtatcaccac aaaccctaga caggcgagcc   1020
gagaaccact gatatcctcc tcttgtacgt cctcgccgtt gtcggagagt ttcatcatca   1080
tccgagatct catccgcgat ggcccacgac cccatacctg accacaagaa ccacaccgca   1140
cttatctcac ctcgatctaa tcaccacaac ccaaaggaca tcgggttcca agacggcagc   1200
gcggagcttt gcaagcctcc actctccgtg accaaaagcc ggcgaagacg gagctgaatg   1260
agcctcccct tcccggaagc taaagcggcg acggtggatc tgagaaagcc tccacctccc   1320
gcataaagac cggcgacgat ggatctaggg tagcctccat ctcccggaaa aaacaccacc   1380
tgaacatgca agccgctcca tctccaccgg gagcctccaa ttgatcgcgt cgttactcca   1440
aaggccgagc caccgttgat ggatggttgc ggtcccagag ctccgacaag gcgatcgatg   1500
acgggactgc gaagaaggag cggagagtga caactacaaa ggaagggaaa gagctctggc   1560
gacagcacgg acgctcacgc gccagccgta cgccgaaccc aaaagtagat ctggtttctc   1620
tcttttctct ctctcgcaaa agaaaacacg caacctattg ttctccattt tgaatttgaa   1680
gtgttacatt attaataaaa aggaagaaag tacaaagctt ttcatttagt ggttgttgca   1740
tatatagtat acttatttga tgggcttatg ataagtatga acatttcacg taacgggttt   1800
attttgtcgt caacacatta ccggcaatgt gaaaagaagg ggcgaggtat ctccatttca   1860
attcttctct ttatagatta atcgaattat ttacatatga aatgagcgtt tatatagaat   1920
tttcgtgtgg aaaacgacat gtacacggca tcgaaagacc aattagtaat atactttagt   1980
ggtgattaca tgtttactta tccaattgag aatttaaagc atcgacaata ccttaatgtc   2040
gattaagccg tccccacttc atgtaatgag ttatgggggg agagagaggt cccgaaattc   2100
gtcaaataaa acaacttaga actaaaaacc gacaccaagt atcataaagg aaacgttgaa   2160
gaagtcattt atcgtatcca gctcacaatt cctaagatta aatcatgacc gttggaagag   2220
cttataagat taaattgaag aaattgtggg ttttagaaga aagacaagaa agagaagaac   2280
atgatcttac attgcctatt ttggtgtata ggagttgtca aaaagaggag agagaggaga   2340
caattaggtc aaataaatga gcactaaaaa tggagacatg tgttgagtaa ctattacaag   2400
agcgacttat gcttctagaa ccaagccttt ctctaatccc taagatcata gctactgaaa   2460
taatgaaaaa aaacaaaaaa aaaacaatga agaatcagtt gggcattagt ccaaaaaaaa   2520
aaaagaatca gttggattgc ttataaaatt ttgttataaa atttatgtcg tatgtgtgtt   2580
```

agccgtagct gtaaatttat ttcctttgta tgttaattgt aaaatttaat ttattattcc 2640
cgatgttttt aatgatgtaa gtttacatca agaaaacata ttaagttctg ttaataaatg 2700
tattattttt gtttactaat ttccaataat tttttcaaga agtacaattt tttgtttgaa 2760
atttctaatt tatcaacata cctaaaaacc ataaacatgt attttttgaa acattttttt 2820
aatataaaaa ttatttttta ggagcaggtg aagtatttct tttaataaaa ttgttagtgt 2880
atttacgttg gttatagttg tagatatttt gcataataat taataaatata taagatgtgt 2940 aatgtatata tgtgagagaa ataccatatt tactaagagt ttttcgcaat attgactcaa 3000
aattcaaagt caatcacaaa actaacatat gtttcttttt agacatttcc tttgccttat 3060
tcactccacg ggttcagatt attcacgaaa atgtcattaa attttttttc ttttcgaaaa 3120
tggcattttt actctctcaa tttcatcctc ttcaagtatt tacaagattt ccattgccat 3180
caatacacca accacaatga acaaccaatt tgaagctctt aatgcacctc aaatcgattt 3240
acacttcttc tttttcaatt cttatgaact aaaaacaaca tctctttcaa tttctcccca 3300
tattcatcca aaaaacccaa gatttttatt ctaaaatttt aatggttcat agagccattg 3360
aagcttacga ttcttggtgg gtcacttttg ttcgagattt taggtacttg gagaagactt 3420
ttgtatgcta aacaagttat ctcattggct gaaactatga aatcagtttt ttttccagat 3480
ctgttcgccc ggacgacttc cggataagtc ttctggctgt agacgactta catcgaagta 3540
ttctggttaa tgcagatgtt agttttgcaa ttgactttta agatgcttac tcgaagatta 3600
gtactcttct gttcttgtac cttatgagca ttccaatagt attatatttt tcattctaaa 3660
atatatttca atgatatttt acttttcact ctataataga gtgaaaatga gtttacttta 3720
taatccccta tatattattt gtgaaacact acaacttctt tttgtagcca catgtcatca 3780
c 3781

<210> SEQ ID NO 15
<211> LENGTH: 8640
<212> TYPE: DNA
<213> ORGANISM: Brassica napus

<400> SEQUENCE: 15
tgtgaaattt tgtgtattca ctttagttat aatatctatg tataccaaag agaagaagat 60
aacatatatt atagtattgg tacatactat aatataacat acttaattag taaatttcac 120
accacagcaa aaataatata aaaggtcact ttttaatata caacgtgcca aacttcgtcc 180
atttataatc ttatatattt ttgtcttcgc atatgataga tcataagatt tggagaaaca 240
tataaaatta acctatgaaa ttaaggggat ctatatatta tagtatgtat ccaaagaaca 300
tatatatgaa atatttgaat acatcataag atttggggaa tataaattaa tataaaataa 360
aatcgtccaa ttttaaacgt aaacgtctcc gctgtattta tataaacttt tcaaaatcac 420
ggtgtcgctc gtgttaagat ttggatttct aatccaactt tcagaaagtt tatgtgaaag 480
ataatactca aacacaatag ttcgtttaga acgctcttaa gattaatgtc acacacacaa 540
aattgatgtc actagattta tatgttttgt cgtttaaggg gatccatcaa ctacacatgg 600
aagaatagaa aacactggtc acacacaaaa aataatataa gcatgttgag tcctattcat 660
cagaaaattt tctccaaagg atgaacaata acctacaatt aaggaaactt attataacaa 720
cgaccaagaa gttttcccat aagtcatgct ttcgtccata ccttcgggtc tttcaagcaa 780
gcttcacaca tgccttatcg tatatttgta tacgttttca ttttgtgtac gtctattaat 840
tagtatatgc ctagattata tatttatata gtcgacaatt acctatccta aaggtttatt 900

```
ttaattttta ttcagaaaga tatgcacgta gggccactag tgtttcccgt tgttattgga    960
aattccatgt gttgaactgt ttgattaagt ttttgaaccc gtaagtcaaa tttatttagg   1020
tttaacaggg tttcattact gttataagct tgtcaagaaa gaatttgtca caaatttcga   1080
gactcatgca tgcatgcatg tttcttaact ttcgagaaac atgaagtgtg gttttaccag   1140
ctgaagtttg tgttaaaaca catttttaat ttgaccacgt gtgatattca aatatcaaca   1200
attctgttca acgggagatt catacatatg ttcagatgtt ctttaatctt gagcacctaa   1260
ctttgcttcc catacgcaaa tgtgtgtgcc gcgaactatg gtgaatgtac ggcatcgttt   1320
ttctttttgg agcattttta aaagaaaata taatttagtt atttccgttt tgattgatat   1380
agatgcatta ataaaccgac ttacgtgggt gatgggatga gcaaaattaa aatatgcatt   1440
ttagtaacca attacggtcc atcttgacaa actaacaaac aaaaagtcta ttatgacgtt   1500
gatttgtgac cttgccatat aaatgccaaa atttcattct ttcaataagc aacgagatca   1560
ataagatgtg gcagtcacgt gaacgttagt tatcgccatt tcaactgaac cttcacgaac   1620
atataaagtt catttgttct ttgctaaaat tacgcaaatc tctgttgtgc acgaaattac   1680
gactattttt taatgacaac tcctgttctt gtatcgtgta tctagcacgt aaatttgaat   1740
tatggcggca ttatcgataa aatatgtaaa gaatatattt tcatcataca ccacaaacaa   1800
atgttctgga aatatcacct tttatcacat atacaaagct gaccctgaat ttttggaaac   1860
tacaagccaa aaaaaaatgg acaaaagaaa aattatgcac aaaagtggac tcgtcctaac   1920
tctttttata atgataatta acctttgaac aactaattaa tacatacaat atgttttttt   1980
tttctaaaaa ttggtcgatt aaatattcat atataatcct catcatcatt tattagcctt   2040
ttgtagctta cttaaaaaat cacttcccac caaattgatt attttttcac ttcatacgtt   2100
gatcaattta aaaaaaaaat aataataata tatgcacgtc cggcgtccca tgacttcaga   2160
cgcttttctg tttccttgat tttataggtt agaaatttcc aaaatgctca tatttttcac   2220
tgatatgtat tatacgcaca aaatagtaaa gtcataaaaa tttatgatgg ttcttttata   2280
tgtatagagt agtgaaaatt tatatatatt gtagttccgc ttaaaataaa ttaatatttt   2340
tcttttatcg cccatattta agttactaaa cgtatataat taaaaactga aatgcaatat   2400
gtagaaatcc gggcattgat tgttgattaa cattgatata cccatgcgac tggcttatga   2460
tgaaccatac ctgctaatac tcattgttac aaactcgcag caacatcata aatccatcac   2520
tcgccacaat aattttcttc agtgtatgtt caattgatca cattttgacc cttcactttc   2580
ttgaatgaga aattatacaa gaaagtgatt tgagtgtgtt aaaaaatgat ttgtcattct   2640
gaccaattat ctggcagaga gtataataaa atacttctaa ttaccttaaa tcattaggcg   2700
ttgtttcttg ccgaatatat gatggagcat ggtctcgcta agagacaaca aaatctttaa   2760
ataaattaaa gaaattgttt agcaaaaaaa ttaaataaat taaacaagag agagtacaaa   2820
tataaaacac tctaacggaa gataaatata taaaatacaa aatatagaat agaggcctca   2880
agtagtgttt acgtgacaat ctcaatttca ctccatacct cgaactcatt caagcttaga   2940
aacctaactt ctactgttcc ttttgatttg cctataaata cacgttggtc catacttctc   3000
taatttcaaa tatacaaagc aaaacacaga gacaagaatc ataaataaca aacattttca   3060
acataatccc aaaaaacgac acgcgttcct tttccaaaaa ttcacttctc tacgtaccaa   3120
ccacaatggc tcattgttgc acagttctta ccggtttact agtatggtct ctttttatgc   3180
tctcatggtg tgaagcttca agaaacaaca ttaatagata tgatcattct tatggaacgt   3240
```

-continued

```
tcaaatccaa tagcttaatc aagcgaagag acgatatcac tcgtctgaaa agtgttgcaa   3300
gagcttcttt gcggcttcca accaccgtta gtgtttctga ttttggagct aaaggagatg   3360
gaaaaaccga cgacacgcag gtatatacgc atatacacat atctacatga cttataaata   3420
ttttgagacg gtcacgcata taaatttacg ttgtttgtac taatgatcca tgcatgcgca   3480
tgcatatgat caggcgttcg tgaatgcatg gaagaaagct tgttcttcaa gtggagctgt   3540
aaatctctta gttcctgaag gaaaaactta ttttctcaag tctcttcgat taaatggccc   3600
atgcaaatca gttcttaccg ttcaggtaaa ttacaaagtt ttttttctt aaatttgggt   3660
aaattacaaa gttgactatt tgttaattaa atacgtatac tacatgtgat cacgtatatg   3720
gttttgaata tttaaatgag cggttgatga atggaacgac agattttagg aacgttatcg   3780
gcttctcaac aacgatcgga ttatgaagat ctcagcaaat ggattacgtt tgacggcgtt   3840
aacagtctaa cggttgatgg cggagccacc ggaactgtca acggaaacgg cgaaacgtgg   3900
tgggaaaact catgcaaacg gaacgaagct aaggtgtgtg tttgtacatg tttcatttac   3960
ttaatatata tctactgtct acatgtcatc ttgatatatt aacactcttt tattgttatt   4020
gttttgaaga aatgcacaaa agcccctacg gtacgtagaa acatatttga cattttcatg   4080
taatactgac gatggcggtg atcatgattg gacaaatgtt ttacatgcat gaatatatgt   4140
attttatatg caggctctta ctttctacaa ctcgaagaat ttgagagtta ataatctgag   4200
ggtgaaagat gcgcaacaga ttcagatttc gattgagaaa tgctccaacg ttcaggtctc   4260
aaatgttgag gtcactgcac ctgctgatag tcctaacact gatggtatcc acatcactaa   4320
cactcaaaac attcaagtct ccaattccat cattggaaca ggttagtagt tatatcctcg   4380
ttatttaaaa gagttgcgtg catatccaga aaactaaaat ttaagagtat cgttataatt   4440
tataatttta tagagattgg tcttaaaaga gtttttaatg gttgcttttc tttgcaggtg   4500
atgattgtat atctattgaa agtggatcac aaaacgttaa aatcaacgat ttaacttgcg   4560
gcccaggcca cggtatcagg tatcaatgaa ttgttttcag tatatgtacc taagaaattc   4620
aaccgtaatc ttttaaatta acatagaaat ttgatatttc catataaaac atgagcagca   4680
ttgggagctt aggagatgac aattcaaagg catttgtatc aggcgtgact gtggatggtg   4740
ctaaactttc cggtacagac aatggagtta ggatcaaaac ttaccaggtg aaaatcacaa   4800
actagacctt caattttaac tagcctattg acaagttcat ctcaatttaa cttttaaacc   4860
caattcaata tagggagggt ctggaactgc tagcaacatt atatttcaga acattcagat   4920
ggagaatgtg aagaatccaa tcataattga ccaagattat tgcgacaaga gcaaatgcac   4980
tgaacaagtt cgtttgaatc tgatcaaatc tcccattact aatcatcatg ataataaaca   5040
ctattgtctc taatcattta ctacatatat tttcagaaat cagcggtcca aataaagaac   5100
gtggtgtacc ggaacataag cggcacaagc gcatcggaca tagcaataac tttcaactgc   5160
agcaagaact atccatgcca aggaattgta ctcgacaaag tgaacattaa gggagggaaa   5220
gccagttgca gcaatgctaa tgtgatggat aaagacggtg ttttacctca gtgcaaatcc   5280
acttgattaa taagacctat aaaaaaaact cacatagatg tataaaaata catatatacc   5340
gatacaaagt atacaaaatt atgatataca cttgtggata tatacatgga caatgaattt   5400
aaacatattg tctatatgtc aaaaatagtt tatgaatata catatagaca acatggtcaa   5460
gagatttatt gttttaatgt atatatatac tactaaacta cttgtctaaa atttcatgaa   5520
taaaggatta cgtttttaag tggttatgta tcatgatgtg gttacagtat gatgtgtatt   5580
gtagatttc aattaaatac ataaaaatga aaaagatgac atggctggtc aatgatgtta   5640
```

```
cttgaccaac taattcaagc taattgatac acgatgaaca tctaacgaaa cagaagcgac   5700
tttcatattg tttagttgtg ctcaaaccag gccgataaac tcattgggcc tataagccca   5760
ttaatattta tccgtgagag cgaagtctgt tacttgggtt actaaacaaa gaggccttta   5820
gaaaacccta actcttaccg tagcacctga gctatatatt gccgcagcta gggtttccac   5880
tccctcacgc taacacacat caccgcagcc atttccatct ctcaaccaac ttcaaacaat   5940
ggctgaacga ggcggagaac gaggtgccga gcgaggagga gaccgcggcg gtttcggacg   6000
cggattcgga ggaggtcgcg gcgacagagg aggccgggga ggtccgagag gccgaggcgg   6060
cagacgcgga ggacgtccga cagaggagga gaagtggacc ccagtgacca agctcggccg   6120
tctcgtgcaa gccggaaaga tccagaagct cgagcagatc tacctccact ccctccccgt   6180
caaggagtac cagatcatcg acctcctcgt cggccccacc ttgaaagacg aggtgatgaa   6240
gatcatgccg gttcagaaac agaccagggc cggtcagagg acgaggttca aggcctttgt   6300
cgtcgtcgga gacacgaacg ggcacgttgg tttgggtgtg aagtgctcca aggaggtggc   6360
gacggcgatc agaggtggga ttatattggc gaagctgtcg gttattcccg tgaggagagg   6420
gtactggggg aacaagattg ggaagccgca tacggttcct tgtaaggtta cggggaagtg   6480
tgggtctgtt acggtgagga tggtgcctgc tccgaggggt gcggggattg tggcggctag   6540
ggttcctaag aaggtgcttc agttcgctgg gattgatgat gtgtttactt cgtcgagggg   6600
gtctactaag actcttggaa acttcgtaaa ggtttgaact ttcttcattt atttagagtt   6660
tggagttgtg tatggattga aagttgattc ctttttgatg gttgcgtgtg gagttgtttt   6720
gggtaattta gcttgttgta gttgatgtaa agtgagaatt gctaagcttg attagtttga   6780
ataagctgtc tgtgttaaat gatgatttgt ttgtgttgta ttgagctgtc tgaatttcat   6840
tatttgtttg tgttattgct aaattacaag cttaaatttg ataacttttg attctttcgt   6900
gagagttttt tttgggtaat atagcttgat gtagttgatg gaagtaaatt gttaaccttt   6960
agagctgtct gttaatggtg atttgtttgt gttgtattga gctgtctgaa ttataatttg   7020
tttgtgttta ttgctaaatc acaaagcttt gaagtcgttt gtacatattc atcatttttg   7080
tgtttattga cttgtttgtg tttattgcta aatcacaagt ttctatgatt aatcttcatg   7140
atttggttgt gtttattact aaatcacaag tttctatgat taatcttaat gatttggttg   7200
tgtttattgc taaatttgag attacattat aatcttagtt tatacatgta taacatcatt   7260
tcacttgaat tttcacagac gagctggtga tatgtttttt tagtattttc catgtattgc   7320
tttgtaagaa cttttaaatg tttgttttct tcctttgaag aacaattaaa tgtttgttca   7380
gtatttttga atcattcatt ggttaatcat gtgtaatttt atttttgtag gctacattcg   7440
actgtctcca gaagacttat ggattcctga caccagagtt ctggaaagag acgagcttta   7500
aaaagtcacc gtaccaggag tacactgatc tgctggccga gaagggaatt gcaaccaaag   7560
ccatcaccga ggttgaagac caagccgcct cctaaataaa caaacaaaca atgtccccct   7620
tgttttgttt ttggatgatc ctttcttgag ttttattttg ttcgaacctt tagtatatgt   7680
tgtttgctgg attgctgctt tcttatgttt tcatcatctc ccccaaacaa agttattttt   7740
gctctagttt ttttttataa tcgatggtta tgccctctag tattttttttt acttgaattt   7800
ttcactaatt ttctatcaac ttccctatgt tacactttct aaggttgatt acataggtgg   7860
attgttgtga aacaaatact aataataaac taatactttt agaataatat aattagtggg   7920
attaaattat aaattataaa ttaaaaagac aagtctgaaa tggattgttt aactgtaaaa   7980
```

ggtaaagaga ctttgaatag aagagaataa atcaaaagtt gacgtatctt ctccgaaatt 8040
tcagctattt ctaaatacgc ggattctgat tactctgttc tctctcgcct gataaacctt 8100
agaattgagt ttttttttt tttatctttt tggttctttt ttagttcttg tcggaatcgt 8160
gagaagctct gtctctctgt cggaaccaat ggggactccg gagtttccag atctggggaa 8220
acactgctcc gtcgatatct gcaagcaaat cgatttcttg cctttcacct gcgaccgttg 8280
tctccaggtt cctctctctc tatctctgtt ttgaatcaca tgcaaaaaag aatcgtcttt 8340
gttgcgaata gttgtgtcgt atgactgtct gaatcgcctg tcttcgatcc tgggaactac 8400
tatatcatca tccttgttct tttgtcgttc gtgttctggg agaaccaagt gaaaagtctc 8460
cgtctttctc ttaattaccg cgaggaaaat tcatcttttc tacatgcgac cagtttgatt 8520
tgatttgttc cgacattaag tttatcactt aagttcttgt aattacgaac caacgtgttg 8580
agccatctgt catttcgagc ttaatcatcg acatttcgca attctccgca cttaaattca 8640

<210> SEQ ID NO 16
<211> LENGTH: 5668
<212> TYPE: DNA
<213> ORGANISM: Brassica napus

<400> SEQUENCE: 16
tggtgttaag atttgattta tggatgcaca tagttggata cattttatgt ttaaaatgtg 60
tttttaatat tattattgct gtggtgtgaa attttgtgta ttcactttag ttataatatc 120
tatgtatacc aaagagaaga agataacata tattatagta ttggtacata ctataatata 180
acatacttaa ttagtaaatt tcacaccaca gcaaaaataa tataaaaggt cactttttaa 240
tatacaacgt gccaaacttc gtccatttat aatcttatat atttttgtct tcgcatatga 300
tagatcataa gatttggaga aacatataaa attaacctat gaaattaagg ggatctatat 360
attatagtat gtatccaaag aacatatata tgaaatattt gaatacatca taagatttgg 420
ggaatataaa ttaatataaa ataaaatcgt ccaattttaa acgtaaacgt ctccgctgta 480
tttatataaa cttttcaaaa tcacggtgtc gctcgtgtta agatttggat ttctaatcca 540
actttcagaa agtttatgtg aaagataata ctcaaacaca atagttcgtt tagaacgctc 600
ttaagattaa tgtcacacac acaaaattga tgtcactaga tttatatgtt ttgtcgttta 660
aggggatcca tcaactacac atggaagaat agaaaacact ggtcacacac aaaaaaataat 720 ataagcatgt tgagtcctat tcatcagaaa attttctcca aaggatgaac aataacctac 780
aattaaggaa acttattata acaacgacca agaagttttc ccataagtca tgctttcgtc 840 catacettcg ggtctttcaa gcaagcttca cacatgcctt atcgtatatt tgtatacgtt 900
ttcattttgt gtacgtctat taattagtat atgcctagat tatatattta tatagtcgac 960
aattacctat cctaaaggtt tattttaatt tttattcaga aagatatgca cgtagggcca 1020
ctagtgtttc ccgttgttat tggaaattcc atgtgttgaa ctgtttgatt aagtttttga 1080
acccgtaagt caaatttatt taggtttaac agggtttcat tactgttata agcttgtcaa 1140
gaaagaattt gtcacaaatt tcgagactca tgcatgcatg catgtttctt aactttcgag 1200
aaacatgaag tgtggtttta ccagctgaag tttgtgttaa aacacatttt taatttgacc 1260
acgtgtgata ttcaaatatc aacaattctg ttcaacggga gattcataca tatgttcaga 1320
tgttctttaa tcttgagcac ctaactttgc ttcccatacg caaatgtgtg tgccgcgaac 1380
tatggtgaat gtacggcatc gtttttcttt ttggagcatt tttaaaagaa aatataattt 1440
agttatttcc gttttgattg atatagatgc attaataaac cgacttacgt gggtgatggg 1500
atgagcaaaa ttaaaatatg cattttagta accaattacg gtccatcttg acaaactaac 1560
aaacaaaaag tctattatga cgttgatttg tgaccttgcc atataaatgc caaaatttca 1620
ttctttcaat aagcaacgag atcaataaga tgtggcagtc acgtgaacgt tagttatcgc 1680
catttcaact gaaccttcac gaacatataa agttcatttg ttctttgcta aaattacgca 1740
aatctctgtt gtgcacgaaa ttacgactat tttttaatga caactcctgt tcttgtatcg 1800
tgtatctagc acgtaaattt gaattatggc ggcattatcg ataaaatatg taaagaatat 1860
attttcatca tacaccacaa acaaatgttc tggaaatatc accttttatc acatatacaa 1920
agctgaccct gaatttttgg aaactacaag ccaaaaaaaa atggacaaaa gaaaaattat 1980
gcacaaaagt ggactcgtcc taactctttt tataatgata attaaccttt gaacaactaa 2040
ttaatacata caatatgttt ttttttcta aaaattggtc gattaaatat tcatatataa 2100
tcctcatcat catttattag ccttttgtag cttacttaaa aaatcacttc ccaccaaatt 2160
gattattttt tcacttcata cgttgatcaa tttaaaaaaa aaataataat aatatatgca 2220
cgtccggcgt cccatgactt cagacgcttt tctgtttcct tgattttata ggttagaaat 2280
ttccaaaatg ctcatatttt tcactgatat gtattatacg cacaaaatag taaagtcata 2340
aaaatttatg atggttcttt tatatgtata gagtagtgaa aatttatata tattgtagtt 2400
ccgcttaaaa taaattaata tttttctttt atcgcccata tttaagttac taaacgtata 2460
taattaaaaa ctgaaatgca atatgtagaa atccgggcat tgattgttga ttaacattga 2520
tatacccatg cgactggctt atgatgaacc atacctgcta atactcattg ttacaaactc 2580
gcagcaacat cataaatcca tcactcgcca caataatttt cttcagtgta tgttcaattg 2640
atcacatttt gacccttcac tttcttgaat gagaaattat acaagaaagt gatttgagtg 2700
tgttaaaaaa tgatttgtca ttctgaccaa ttatctggca gagagtataa taaaatactt 2760
ctaattacct taaatcatta ggcgttgttt cttgccgaat atagctaggg tttccactcc 2820
ctcacgctaa cacacatcac cgcagccatt tccatctctc aaccaacttc aaacaatggc 2880
tgaacgaggc ggagaacgag gtgccgagcg aggaggagac cgcggcggtt tcggacgcgg 2940
attcggagga ggtcgcggcg acagaggagg ccggggaggt ccgagaggcc gaggcggcag 3000
acgcggagga cgtccgacag aggaggagaa gtggacccca gtgaccaagc tcggccgtct 3060
cgtgcaagcc ggaaagatcc agaagctcga gcagatctac ctccactccc tccccgtcaa 3120
ggagtaccag atcatcgacc tcctcgtcgg ccccaccttg aaagacgagg tgatgaagat 3180
catgccggtt cagaaacaga ccagggccgg tcagaggacg aggttcaagg cctttgtcgt 3240
cgtcggagac acgaacgggc acgttggttt gggtgtgaag tgctccaagg aggtggcgac 3300
ggcgatcaga ggtgggatta tattggcgaa gctgtcggtt attcccgtga ggagagggta 3360
ctgggggaac aagattggga agccgcatac ggttccttgt aaggttacgg ggaagtgtgg 3420
gtctgttacg gtgaggatgg tgcctgctcc gaggggtgcg gggattgtgg cggctagggt 3480
tcctaagaag gtgcttcagt tcgctgggat tgatgatgtg tttacttcgt cgagggggtc 3540
tactaagact cttggaaact tcgtaaaggt ttgaactttc ttcatttatt tagagtttgg 3600
agttgtgtat ggattgaaag ttgattcctt tttgatggtt gcgtgtggag ttgttttggg 3660
taatttagct tgttgtagtt gatgtaaagt gagaattgct aagcttgatt agtttgaata 3720
agctgtctgt gttaaatgat gatttgtttg tgttgtattg agctgtctga atttcattat 3780
ttgtttgtgt tattgctaaa ttacaagctt aaatttgata acttttgatt ctttcgtgag 3840 agttttttt gggtaatata gcttgatgta gttgatggaa gtaaattgtt aacctttaga 3900
gctgtctgtt aatggtgatt tgtttgtgtt gtattgagct gtctgaatta taatttgttt 3960
gtgtttattg ctaaatcaca aagctttgaa gtcgtttgta catattcatc atttttgtgt 4020
ttattgactt gtttgtgttt attgctaaat cacaagtttc tatgattaat cttcatgatt 4080
tggttgtgtt tattactaaa tcacaagttt ctatgattaa tcttaatgat ttggttgtgt 4140
ttattgctaa atttgagatt acattataat cttagtttat acatgtataa catcatttca 4200
cttgaatttt cacagacgag ctggtgatat gtttttttag tattttccat gtattgcttt 4260
gtaagaactt ttaaatgttt gttttcttcc tttgaagaac aattaaatgt ttgttcagta 4320
tttttgaatc attcattggt taatcatgtg taattttatt tttgtaggct acattcgact 4380
gtctccagaa gacttatgga ttcctgacac cagagttctg gaaagagacg agctttaaaa 4440
agtcaccgta ccaggagtac actgatctgc tggccgagaa gggaattgca accaaagcca 4500
tcaccgaggt tgaagaccaa gccgcctcct aaataaacaa acaaacaatg tccccttgt 4560
tttgtttttg gatgatcctt tcttgagttt tattttgttc gaacctttag tatatgttgt 4620
ttgctggatt gctgctttct tatgttttca tcatctcccc caaacaaagt tatttttgct 4680
ctagtttttt tttataatcg atggttatgc cctctagtat ttttttact tgaatttttc 4740
actaattttc tatcaacttc cctatgttac actttctaag gttgattaca taggtggatt 4800
gttgtgaaac aaatactaat aataaactaa tacttttaga ataatataat tagtgggatt 4860
aaattataaa ttataaatta aaaagacaag tctgaaatgg attgtttaac tgtaaaaggt 4920
aaagagactt tgaatagaag agaataaatc aaaagttgac gtatcttctc cgaaatttca 4980
gctatttcta aatacgcgga ttctgattac tctgttctct ctcgcctgat aaaccttaga 5040
attgagtttt ttttttttt atctttttgg ttcttttta gttcttgtcg gaatcgtgag 5100
aagctctgtc tctctgtcgg aaccaatggg gactccggag tttccagatc tggggaaaca 5160
ctgctccgtc gatatctgca agcaaatcga tttcttgcct ttcacctgcg accgttgtct 5220
ccaggttcct ctctctctat ctctgttttg aatcacatgc aaaaaagaat cgtctttgtt 5280
gcgaatagtt gtgtcgtatg actgtctgaa tcgcctgtct tcgatcctgg gaactactat 5340
atcatcatcc ttgttctttt gtcgttcgtg ttctgggaga accaagtgaa aagtctccgt 5400
ctttctctta attaccgcga ggaaaattca tcttttctac atgcgaccag tttgatttga 5460
tttgttccga cattaagttt atcacttaag ttcttgtaat tacgaaccaa cgtgttgagc 5520
catctgtcat ttcgagctta atcatcgaca tttcgcaatt ctccgcactt aaattcacca 5580
gagttgttca aaattcactt aattcatcat gattgccatt aaagattcga tctttttgtt 5640
ggtttacatt aacatatttg agtttatg 5668

<210> SEQ ID NO 17
<211> LENGTH: 5717
<212> TYPE: DNA
<213> ORGANISM: Brassica napus

<400> SEQUENCE: 17
catatatgga tggacatagt tggacatatt taggtcctta tccaaatgat gttttaagat 60
ttgatttatg gatgcacata gttggataca ttttatgttt aaaatgtgtt tttaatatta 120
ttattgctgt ggtgtgaaat tttgtgtatt cactttagtt ataatatcta tgtataccaa 180
agagaagaag ataacatata ttatagtatt ggtacatact ataatataac atacttaatt 240
agtaaatttc acaccacagc aaaaaataata taaaaggtca ctttttaata tacaacgtgc 300

```
caaacttcgt ccatttataa tcttatatat ttttgtcttc gcatatgata gatcataaga    360
tttggagaaa catataaaat taacctatga aattaagggg atctatatat tatagtatgt    420
atccaaagaa catatatatg aaatatttga atacatcata agatttgggg aatataaatt    480
aatataaaat aaaatcgtcc aattttaaac gtaaacgtct ccgctgtatt tatataaact    540
tttcaaaatc acggtgtcgc tcgtgttaag atttggattt ctaatccaac tttcagaaag    600
tttatgtgaa agataatact caaacacaat agttcgttta gaacgctctt aagattaatg    660
tcacacacac aaaattgatg tcactagatt tatatgtttt gtcgtttaag ggatccatc     720
aactacacat ggaagaatag aaaacactgg tcacacacaa aaaataatat aagcatgttg    780
agtcctattc atcagaaaat tttctccaaa ggatgaacaa taacctacaa ttaaggaaac    840
ttattataac aacgaccaag aagttttccc ataagtcatg ctttcgtcca taccttcggg    900
tctttcaagc aagcttcaca catgccttat cgtatatttg tatacgtttt cattttgtgt    960
acgtctatta attagtatat gcctagatta tatatttata tagtcgacaa ttacctatcc   1020
taaaggttta ttttaatttt tattcagaaa gatatgcacg tagggccact agtgtttccc   1080
gttgttattg gaaattccat gtgttgaact gtttgattaa gtttttgaac ccgtaagtca   1140
aatttattta ggtttaacag ggtttcatta ctgttataag cttgtcaaga aagaatttgt   1200
cacaaatttc gagactcatg catgcatgca tgtttcttaa ctttcgagaa acatgaagtg   1260
tggttttacc agctgaagtt tgtgttaaaa cacattttta atttgaccac gtgtgatatt   1320
caaatatcaa caattctgtt caacgggaga ttcatacata tgttcagatg ttctttaatc   1380
ttgagcacct aactttgctt cccatacgca aatgtgtgtg ccgcgaacta tggtgaatgt   1440
acggcatcgt ttttcttttt ggagcatttt taaaagaaaa tataatttag ttatttccgt   1500
tttgattgat atagatgcat taataaaccg acttacgtgg gtgatgggat gagcaaaatt   1560
aaaatatgca ttttagtaac caattacggt ccatcttgac aaactaacaa acaaaaagtc   1620
tattatgacg ttgatttgtg accttgccat ataaatgcca aaatttcatt ctttcaataa   1680
gcaacgagat caataagatg tggcagtcac gtgaacgtta gttatcgcca tttcaactga   1740
accttcacga acatataaag ttcatttgtt ctttgctaaa attacgcaaa tctctgttgt   1800
gcacgaaatt acgactattt tttaatgaca actcctgttc ttgtatcgtg tatctagcac   1860
gtaaatttga attatggcgg cattatcgat aaaatatgta aagaatatat tttcatcata   1920
caccacaaac aaatgttctg gaaatatcac cttttatcac atatacaaag ctgaccctga   1980
atttttggaa actacaagcc aaaaaaaaat ggacaaaaga aaaattatgc acaaaagtgg   2040
actcgtccta actcttttta taatgataat taacctttga acaactaatt aatacataca   2100
atatgttttt tttttctaaa aattggtcga ttaaatattc atatataatc ctcatcatca   2160
tttattagcc ttttgtagct tacttaaaaa atcacttccc accaaattga ttattttttc   2220
acttcatacg ttgatcaatt taaaaaaaaa ataataataa tatatgcacg tccggcgtcc   2280
catgacttca gacgcttttc tgtttccttg attttatagg ttagaaattt ccaaaatgct   2340
catatttttc actgatatgt attatacgca caaaatagta aagtcataaa aatttatgat   2400
ggttctttta tatgtataga gtagtgaaaa tttatatata ttgtagttcc gcttaaaata   2460
aattaatatt tttcttttat cgcccatatt taagttacta aacgtatata attaaaaact   2520
gaaatgcaat atgtagaaat ccgggcattg attgttgatt aacattgata tacccatgcg   2580
actggcttat gatgaaccat acctgctaat actcattgtt acaaactcgc agcaacatca   2640
```

taaatccatc actcgccaca ataattttct tcagtgtatg ttcaattgat cacattttga 2700
cccttcactt tcttgaatga gaaattatac aagaaagtga tttgagtgtg ttaaaaaatg 2760
atttgtcatt ctgaccaatt atctggcaga gagtataata aaatacttct aattacctta 2820
aatcattagg cgttgtttct tgccgaatat aagctagggt ttccactccc tcacgctaac 2880
acacatcacc gcagccattt ccatctctca accaacttca aacaatggct gaacgaggcg 2940
gagaacgagg tgccgagcga ggaggagacc gcggcggttt cggacgcgga ttcggaggag 3000
gtcgcggcga cagaggaggc cggggaggtc cgagaggccg aggcggcaga cgcggaggac 3060
gtccgacaga ggaggagaag tggaccccag tgaccaagct cggccgtctc gtgcaagccg 3120
gaaagatcca gaagctcgag cagatctacc tccactccct ccccgtcaag gagtaccaga 3180
tcatcgacct cctcgtcggc cccaccttga aagacgaggt gatgaagatc atgccggttc 3240
agaaacagac cagggccggt cagaggacga ggttcaaggc ctttgtcgtc gtcggagaca 3300
cgaacgggca cgttggtttg ggtgtgaagt gctccaagga ggtggcgacg gcgatcagag 3360
gtgggattat attggcgaag ctgtcggtta ttcccgtgag gagagggtac tgggggaaca 3420
agattgggaa gccgcatacg gttccttgta aggttacggg gaagtgtggg tctgttacgg 3480
tgaggatggt gcctgctccg aggggtgcgg ggattgtggc ggctagggtt cctaagaagg 3540
tgcttcagtt cgctgggatt gatgatgtgt ttacttcgtc gagggggtct actaagactc 3600
ttggaaactt cgtaaaggtt tgaactttct tcatttattt agagtttgga gttgtgtatg 3660
gattgaaagt tgattccttt ttgatggttg cgtgtggagt tgttttgggt aatttagctt 3720
gttgtagttg atgtaaagtg agaattgcta agcttgatta gtttgaataa gctgtctgtg 3780
ttaaatgatg atttgtttgt gttgtattga gctgtctgaa tttcattatt tgtttgtgtt 3840
attgctaaat tacaagctta aatttgataa cttttgattc tttcgtgaga gtttttttg 3900 ggtaatatag cttgatgtag ttgatggaag taaattgtta acctttagag ctgtctgtta 3960
atggtgattt gtttgtgttg tattgagctg tctgaattat aatttgtttg tgtttattgc 4020
taaatcacaa agctttgaag tcgtttgtac atattcatca tttttgtgtt tattgacttg 4080
tttgtgttta ttgctaaatc acaagtttct atgattaatc ttcatgattt ggttgtgttt 4140
attactaaat cacaagtttc tatgattaat cttaatgatt tggttgtgtt tattgctaaa 4200
tttgagatta cattataatc ttagtttata catgtataac atcatttcac ttgaattttc 4260
acagacgagc tggtgatatg tttttttagt attttccatg tattgctttg taagaacttt 4320
taaatgtttg ttttcttcct ttgaagaaca attaaatgtt tgttcagtat ttttgaatca 4380
ttcattggtt aatcatgtgt aattttattt ttgtaggcta cattcgactg tctccagaag 4440
acttatggat tcctgacacc agagttctgg aaagagacga gctttaaaaa gtcaccgtac 4500
caggagtaca ctgatctgct ggccgagaag ggaattgcaa ccaaagccat caccgaggtt 4560
gaagaccaag ccgcctccta aataaacaaa caaacaatgt cccccttgtt ttgtttttgg 4620
atgatccttt cttgagtttt attttgttcg aacctttagt atatgttgtt tgctggattg 4680
ctgctttctt atgttttcat catctccccc aaacaaagtt atttttgctc tagttttttt 4740
ttataatcga tggttatgcc ctctagtatt ttttttactt gaatttttca ctaattttct 4800
atcaacttcc ctatgttaca ctttctaagg ttgattacat aggtggattg ttgtgaaaca 4860
aatactaata ataaactaat acttttagaa taatataatt agtgggatta aattataaat 4920
tataaattaa aaagacaagt ctgaaatgga ttgtttaact gtaaaaggta aagagacttt 4980
gaatagaaga gaataaatca aaagttgacg tatcttctcc gaaatttcag ctatttctaa 5040
atacgcggat tctgattact ctgttctctc tcgcctgata aaccttagaa ttgagttttt 5100
ttttttttta tctttttggt tctttttttag ttcttgtcgg aatcgtgaga agctctgtct 5160
ctctgtcgga accaatgggg actccggagt ttccagatct ggggaaacac tgctccgtcg 5220
atatctgcaa gcaaatcgat ttcttgcctt tcacctgcga ccgttgtctc caggttcctc 5280
tctctctatc tctgttttga atcacatgca aaaaagaatc gtctttgttg cgaatagttg 5340
tgtcgtatga ctgtctgaat cgcctgtctt cgatcctggg aactactata tcatcatcct 5400
tgttcttttg tcgttcgtgt tctgggagaa ccaagtgaaa agtctccgtc tttctcttaa 5460
ttaccgcgag gaaaattcat cttttctaca tgcgaccagt ttgatttgat ttgttccgac 5520
attaagttta tcacttaagt tcttgtaatt acgaaccaac gtgttgagcc atctgtcatt 5580
tcgagcttaa tcatcgacat ttcgcaattc tccgcactta aattcaccag agttgttcaa 5640
aattcactta attcatcatg attgccatta aagattcgat ctttttgttg gtttacatta 5700
acatatttga gtttatg 5717

<210> SEQ ID NO 18
<211> LENGTH: 8882
<212> TYPE: DNA
<213> ORGANISM: Brassica napus

<400> SEQUENCE: 18
gtgaaatttt gtgttattca cttaaattat aatatctatg tataccaaag agaagaagat 60
aacatatatt atagtatttg gtacatacta tactataaca tacttagtaa atttcacacc 120
acaacaaaaa taatataaaa ggtcacattt taatatacaa cgtgccaaac ttcgtccatt 180
tgtaatctta tacattttcg tcttcgcata tgatagatca taagatttgg agaaacatat 240
aaaattaacc tatgaaatta agggggtcta tatcttatag tatgtatcca aagaacatat 300
ataggaaata tttgaataca tcataagatt tggggaatat aaattaatat aaaataaaat 360
cttccaattt taaacgtaaa cgtctcctct gtatttatat aaacttttca aaatcacggt 420
gtcgctcgtg ttaagatttg gatttctaat ccaactttca gaaagtatat gtgaaagata 480
aaactcaaac acaatagttc gtttagaacg ctcttaagat taatgtcaca cacacaaaat 540
tgatgtcact agatttattt gttttgtcgt ttaaggggat ccatcaacta cacatggaag 600
aatagaaaac actggtcaca cacaaaaaat aatataagca tgttgaattc tattcatcaa 660
agaattttct tcaaaggatg aacaataacc tataattagg aaacattata acaacgagca 720
ggaagttttc ccagaagtca tgccttcgtc catacccttcg ggtctttcaa gcaagcttca 780
cacatgcctt atcatatgtt tgtatacgtt ttcattttgt gtacgtctat taactagcta 840
gtatatgcca agattatata ttttatatag tcgacaatta cctatcctaa aagttcattt 900
taatttttat tcagaaagat atgcacgtag ggccactagt gtttcccgtt gttattggaa 960
attcatttcc atgtgttgaa ttgtttgttt aagtttttga acccgtaagt caaatttatt 1020
ttggtttaac agggtttcat tactgttata agcttgtcaa gaaagaattt gttacaaatt 1080
tcgaggctca tgcatgcatg attcttaact ttctagaaac atgaaatgtg gttttaccag 1140
ctcaagcttg tgttaaaaca catttttaat ttgaccacgt gtgatattca aatatcaaca 1200
attctgttca acgggagatt catacatatg ttcagatgtt ctttaatctt aagcacctaa 1260
ctttgcttcc catacgcaaa tgtgtgtgcc gcgaactatg gtgaaatgtt ttctttttgg 1320
agcattttta aaagaaaata taatttactt atttccgttt tgattgatat acatgcatta 1380

-continued ataaaccgac ttacgtgggt gatgggatga gcaaaattaa aatatgcatt ttagtaacca 1440
attacggtct atcttgacaa actaacaaac aaaaagtcta ttatgacgtt gatttgtgac 1500
ctggccatat aaatgccaaa atttcattct ttcaataagc aacgagatca ataagatgtg 1560
gcagtcacgt gaacgttagt tatcgccatt tcaactgaac cttcacgaac atataaagtt 1620
catttgttct ttgctaaaat tacgcaaatc tctgttgtgc acgaaattac gactattttt 1680
taaatacaac tcctgttctt gtatcgtgta tctctcgcac gtaaatttga attatggggg 1740
cattatcgat aaaatatgta aagaatatat tttcatcata caccacaaac aaatgttctg 1800
gaaatgtcac cttttatcac atatacaaag ctgaccctga aattttggaa actacaagcc 1860
aaaaaaaatg gtcaaaagaa atattatgca caaaggttgg actcgtccta actcttttta 1920
caatgataat taacctttga acaactaatt aaagatacat acaatatgtt ttttttctaa 1980
aaattggtcg attaaatatt catatataat ccttatcatc atttattagc cttttgtagc 2040
ttacttaaaa aaccccttcc caccaaattg attagtgtag attgattatt tttcacttca 2100
tacgttgatc aattttaaaa tatatatata tatatatata tatatatata tgcacgtccg 2160
gcgtcccatg acttcagacg cttttctgtt tccttgattt tataggttaa aattttccaa 2220
aatgctcata tttttcactc atatgtataa tgtattatta tacgcacaaa atagtaaagt 2280
cataaacatt tatgatggct cttttatatg tatagagtag tgaaatttat atatatcgga 2340
gttccgctta aaataaatta atattgttct tttatcgccc attttttagt tactaaacgt 2400
atataattaa aaactgaaat gcaatatgta gaaatccggc ttatgatgaa ccatactaat 2460
actcattgtt acaaactcac agcaacatca taattccatc actcgccaca ataattttct 2520
ttagtgtatg ttctatttca cattttgacc cttcactttc ttgaatgaaa attatacaag 2580
aaaatgattt gagtgtgtta aaaaaaaaat gttttgagtc attctgacca attatctggc 2640
agagactata ataaaatact tccaattacc ttaaatcatt aggcgttgtt tcttgccgaa 2700
tatatgatgg agcatggtct cgctaagaga caacaaaatc tttaaataaa ttaaacaagt 2760
tgtttagcaa aaaataaaaa ataaattaaa caagagagag tacaaatata aaactctaaa 2820
ggaagataaa tgtataaaat acaaaatata gaatagaggc cttaagtagt gtttacgtga 2880
caatctcaat ttcactccat acctcgaact cattcaagct tagaaaccta acttttactg 2940
ttccttttga tttgcctata aatacacgtt catccatact tctgtaattt caaataacaa 3000
agcaaaacac aaagataaga atcacaaaca acaaacattc tcaacctaat cccaaaaaga 3060
cgacacgcat tcctttttcc aaaaatccac ttcctacgta ccaaccacaa tggctcattg 3120
ttggacagtt cttaccggtt tactagtatg gtctcttttg atgctctcat ggtgcgaagc 3180
ttcaagaaac aacattaata gatatgatca ttcttatgga acgttcaaat ccaatagctt 3240
aatcaagcga agagacgata tcactcgtct gaaaagtgtt gcaagagctt ctttgcggct 3300
tccaaccacc gttagtgttt ctgattttgg agctaaagga gatggaaaaa ccgacgacac 3360
gcaggtatat acgcatacac acatatctac atgacttata agttataaat attgtgagac 3420
ggtcacgtat ataaatttac gttgtttgta ctaatgatcc atgcatgcgc atgcatatga 3480
tcaggcgttc gtgaatgcat ggaagaaagc ttgttcttca agtggacctg taaatctctt 3540
agttcctgaa ggaaaaactt attttctcaa gtctcttcga ttaaatggcc catgcaaatc 3600
agttcttacc gttcaggtaa attacaaagt ttcttttgtt ttgcttaaat ttgggtaaat 3660
tacaaagttg acaaaaaaat tacaaagttg actatttgtt aattatatac gtatactaca 3720
tgtgatcacg tatatggttt tgaatatatt aaagagcggt tggtgaatgg aacgacagat 3780

```
tttaggaacg ttatcggcat ctcaacaacg atcggattat aaagatctca gcaaatggat   3840
tacgtttgac ggcgttaaca gtctaacggt tgatggcggg gccaccggaa ctgtcaacgg   3900
aaacggcgaa acgtggtggg aaaactcatg caaacggaac gaagctaagg tgtgtgtctg   3960
tacatgtttc atttacttaa tatatatcta ctatctacat gtcatcttga tatattgaca   4020
ctttttttatt gttattgttt tgaagaaatg cacaaaagcc ccaacggtac gtagaaacat   4080
atttgacatt ttcatgtaat actgacgatg gctgtgatca tgattggaca aatgttttac   4140
atgcatgaat atatgtattt tatatgcagg ctcttacttt ctacaactcg aagaatttga   4200
gagttaataa tctgagggtg aaagatgcgc aacagatcca gatttcgatt gagaaatgct   4260
ccaacgttca ggtctcaaat gttgaggtca ctgcgcctgc tgatagtcct aacactgatg   4320
gtatccacat cactaacact caaaacattc aagtctccaa atccatcatt ggaacaggtt   4380
agtaattaca tcctcgttat ttaaaagagt tgcgtgcata tccagaaaac taatatttaa   4440
gggtttatcg ttataattta tagagattgg tcttaaaaga gttttttaat gtttgctttt   4500
ctatgcaggt gatgattgta tatctattga aagtggatca caaaacgtta aaatcaacga   4560
tttaacttgc ggccccggtc acggtatcag gtatcaatga attgttttca gtaaatatac   4620
ctaagaaata caaccgtaat cttttacata taaatttgaa atttccttat aaaacatgag   4680
cagcattggg agcttaggag atgacaattc aaaggcattt gtatcaggcg tgactgtgga   4740
tggtgctaaa ctttccggta cagacaatgg agttaggatc aaaacttacc aggtgaaaat   4800
cacaaactaa accttcaatt ttaactagcc tatcaagttc atcccaattt aacttttaaa   4860
cccaattcaa tatagggagg gtctggaact gctagcaaca taatatttca gaacattcag   4920
atggagaatg tgaagaatcc aatcataatc gaccaagatt attgcgacaa gagcaaatgc   4980
accgaacaag ttcgtttgaa cctaatcaaa tcttccatta ctaatcctca tgataataaa   5040
cacttttatc tctaatcatt tactacatat attttcagaa atcagcggtc caaatcaaga   5100
acgtggtgta ccggaacata agcggcacaa gcgcatcaga catagcaata actttcaact   5160
gtagcaagaa ctatccatgc caaggaattg tactcgacaa agtgaacatt aagggaggga   5220
aagcgagttg cagcaacgct aatgtgatgg ataaagacgg tgttttgcct cagtgcaaat   5280
ccacttgatt aactagacct atcaaaaact cacacagatg tataaataca tatagaccga   5340
tacaaagtat acaaaattat gatatatact tgtggatata tacatggaca atgaatttaa   5400
acatattatt tatatgtcaa aatagtttat gaatagacat ataaacaaca tgttcaagag   5460
atttattgtc ttaatgtata tactccatac taaattgttt gtctaaaact tcatataata   5520
aaaaactgtt aatcttcatg atggtgtgat ttgttgtgat aacagtatga tgtctattgt   5580
agatttttat ttaaatacat aaaaattgaa agaaaaaaaa tgacatggct acttgaccaa   5640
ttgattcaag ttaattgtta ctaaccaggc cgataaacta attgggcctt taaagcccat   5700
taatatttgt cagtggaagc gaagtctgtt acttgggtta caaaacaaag gcctttagaa   5760
aaccctaact cttatcgcag cacctgagct atatattgcc gcagctaggg ttttccctag   5820
ctcacgctaa cacacaaagc cgcagccatt tccatctctc tcgcaactca acttcgaaca   5880
atggctgaac gaggcggaga acgaggcgcc gagcgaggag gagaccgcgg cggtttcgga   5940
cggggattcg gaggaggtcg cggcgaccga ggaggccgcg gaggtccgag aggccgaggc   6000
ggcagacgcg gaggacgtcc cacagaggag gagaagtgga ccccagtgac caagctcggc   6060
cgtctcgtgc aagccggaaa gatccagaag ctcgagcaga tctacctcca ctcgctcccc   6120
```

gtcaaggagt accagatcat cgacctcctc gtcggtccaa ctttaaaaga cgaggtgatg 6180
aagatcatgc cggttcagaa acagaccagg gccggtcaga ggacgaggtt caaggctttt 6240
gtcgttgtcg gagacacgaa tggtcatgtt ggtttgggtg tgaagtgctc caaggaggtg 6300
gcgacggcga tcagaggtgg gattatattg gcgaagctgt cggtgattcc cgtgaggaga 6360
gggtactggg ggaacaagat tgggaagccg catacggttc cttgtaaggt tacggggaag 6420
tgtgggtctg ttacggtgag gatggtgcct gctccgaggg ggcggggat tgtggcggct 6480
agggttccta agaaggtgct tcagttcgct gggattgatg atgtgtttac ttcttccagg 6540
ggatctacta agactcttgg aaacttcgta aaggtttgaa ctttattcat ttacttggtg 6600
tttggagctg tgtatagatt gaaagttgat tcctttttga tcgttgcgtg tggaggtgtt 6660
ttgggtaata ttgctaaatg taaaaattgc taagcttgat tagtttgaat aagctgtctg 6720
tgttaaatga tgatttgttt gtgttgtaat gagctgtctg aatttcatta tttgtttgtg 6780
ttattgctaa tttacaagct taaatttgat tccttttgat cgtttcgtgt gagttgtttt 6840
gtgtaattta gcttgatgta gttgatggaa gtaagaattg ttaagcttta gagctgtctg 6900
ttaatgttga attgtttgtg ttgtattgag ctgtctgaat tattatttgt ttgcgattta 6960
tttctaaatc acaaagctct aaagtcgttt gaacatatgc atcatttggt tagtgtttat 7020
tgctgaattt tcatgatttg gttgtgttta ttgctaaatt tgagattaca ttataatctt 7080
aatttgtaca tatattcatc atttttgtgt ttattgattt gtttgtgttt attgatgaat 7140
cacaagtttc tatgattaat cttcatgatt tggttgtgat tattgctaaa tttgagatta 7200
cattataagc ttagtttgta catgtataca tcatttcact tgaattttca cagacgagct 7260
ggtgatatat ttttttttt agtattttcc atgtattgct ttgtaagaac gtttaaatgt 7320
tagttttctt gaatgttttt ttctttgtaa gaacaattaa atgtttgttc agtatttttg 7380
aatcattcat tggttaatca tgttcaacat gtatttttg taggctacat ttgactgtct 7440
ccagaagact tatggattcc tgacaccaga gttctggaaa gagacgagct ttaaaaagtc 7500
accgtaccag gagtacactg atttgctggc cgagaaggga actgcaacca aagccatcac 7560
cgaggttgaa gaccaagccg cctcctaaat aaacaaacaa gcaatgtcca ccttgttttg 7620
tttttggatg atcctttcat gagttttatt ttgttcgaac cttttagtat atgttgtttg 7680
ctggattgct gctatcttaa gttttcatca tcttcccaaa caaagttatt tttgctctag 7740
ttttttttt tttaataatc gatggttata ctctagtatt tttttacttg aatttctcta 7800
attttctatc agttgcgcta tgttacacat tctaaggttg attacatagt tgatccgaaa 7860
tgattaaaaa ggctggatgt tgtaataaat tgttggatat acttttagaa taatataatt 7920
agggggatta aattataaat taaaattaaa aaagacaagt cttaaatgga ttgttgaact 7980
gtgagaaggt gaaaaggtgg agactttgaa tagaagagaa taaatcaaaa gttgacgtat 8040
cttctccgaa atttcagctg tttctaaata cgcggattct gattactctg ttctctcttg 8100
cctgataaac cttcgaattg agtttttttt tttttttca tttctttttt tggttcttgt 8160
cggaatcgtg agaagctctg tctctttgtc ggaaccaatg gggactccgg aatttccaga 8220
tctggggaaa cactgctccg tcgatatctg caagcagatc gatttcttgc ctttcacctg 8280
cgaccgttgt ctccaggttc ctctttcctt ctctctctgt tttgaatcac atgcaaaatg 8340
aatcgtcttt gttgcgaata attgtgttgt atcactgtct gaatcgcatg tcttcgatcc 8400
tgggaactac tatatcatct tccttgttct tttgtcgttc gtgttcttgg agaaccaaga 8460
gaaaagtccc cgtctttctc ttattaccca agaggaaaat catcttttct acatgcgacc 8520
agtttgatat aggatcgagt ttgatttgat ttgttccgac attaagtttg tcacttaagt 8580
tctttgtaat tacgaccttg ttctttggca tttcgcaatt ctccgcactt aattcaccag 8640
agttcttcaa aattcactta actcatcatg attgccatta aagattcgat ctttttgttg 8700
gtttacatta acatatttga gtttatggct ggttcttatg ttttcgctag aaatttgcat 8760
ttaaagattt gttcttttta tgttaatgac ttgtgtgttc gctcttgttt acattgattt 8820
gatctttttc aggtcttttg tttggatcat cggagctata tgaaacacac ttgccccaaa 8880
gg 8882

<210> SEQ ID NO 19
<211> LENGTH: 4463
<212> TYPE: DNA
<213> ORGANISM: Brassica napus

<400> SEQUENCE: 19
catatatgga tggacatagt tggacatatt taggtcctta tccaaatgct ggtgttaaga 60
attgatttat ggatgtacat agttggatac attttatgtt taaaatgtga tttttatatt 120
attattgctg tggtgtgaaa ttttgtgtta ttcacttaaa ttataatatc tatgtatacc 180
aaagagaaga agataacata tattatagta tttggtacat actatactat aacatactta 240
gtaaatttca caccacaaca aaaataatat aaaaggtcac attttaatat acaacgtgcc 300
aaacttcgtc catttgtaat cttatacatt ttcgtcttcg catatgatag atcataagat 360
ttggagaaac atataaaatt aacctatgaa attaaggggg tctatatctt atagtatgta 420
tccaaagaac atatatagga aatatttgaa tacatcataa gatttgggga atataaatta 480
atataaaata aaatcttcca attttaaacg taaacgtctc ctctgtattt atataaactt 540
ttcaaaatca cggtgtcgct cgtgttaaga tttggatttc taatccaact ttcagaaagt 600
atatgtgaaa gataaaactc aaacacaata gttcgtttag aacgctctta agattaatgt 660
cacacacaca aaattgatgt cactagattt atttgttttg tcgtttaagg ggatccatca 720
actacacatg gaagaataga aaacactggt cacacacaaa aaataatata agcatgttga 780
attctattca tcaaagaatt ttcttcaaag gatgaacaat aacctataat taggaaacat 840
tataacaacg agcaggaagt tttcccagaa gtcatgcctt cgtccatacc ttcgggtctt 900
tcaagcaagc ttcacacatg ccttatcata tgtttgtata cgttttcatt ttgtgtacgt 960
ctattaacta gctagtatat gccaagatta tatattttat atagtcgaca attacctatc 1020
ctaaaagttc attttaattt ttattcagaa agatatgcac gtagggccac tagtgtttcc 1080
cgttgttatt ggaaattcat ttccatgtgt tgaattgttt gtttaagttt ttgaacccgt 1140
aagtcaaatt tattttggtt taacagggtt tcattactgt tataagcttg tcaagaaaga 1200
atttgttaca aatttcgagg ctcatgcatg catgattctt aactttctag aaacatgaaa 1260
tgtggtttta ccagctcaag cttgtgttaa aacacatttt taatttgacc acgtgtgata 1320
ttcaaatatc aacaattctg ttcaacggga gattcataca tatgttcaga tgttctttaa 1380
tcttaagcac ctaactttgc ttcccatacg caaatgtgtg tgccgcgaac tatggtgaaa 1440
tgttttcttt ttggagcatt tttaaaagaa aatataattt acttatttcc gttttgattg 1500
atatacatgc attaataaac cgacttacgt gggtgatggg atgagcaaaa ttaaaatatg 1560
cattttagta accaattacg gtctatcttg acaaactaac aaacaaaaag tctattatga 1620
cgttgatttg tgacctggcc atataaatgc caaaatttca ttctttcaat aagcaacgag 1680

-continued

```
atcaataaga tgtggcagtc acgtgaacgt tagttatcgc catttcaact gaaccttcac   1740
gaacatataa agttcatttg ttctttgcta aaattacgca aatctctgtt gtgcacgaaa   1800
ttacgactat tttttaaata caactcctgt tcttgtatcg tgtatctctc gcacgtaaat   1860
ttgaattatg gggcattat cgataaaata tgtaaagaat atattttcat catacaccac   1920
aaacaaatgt tctggaaatg tcacctttta tcacatatac aaagctgacc ctgaaatttt   1980
ggaaactaca agccaaaaaa aatggtcaaa agaaatatta tgcacaaagg ttggactcgt   2040
cctaactctt tttacaatga taattaacct ttgaacaact aattaaagat acatacaata   2100
tgtttttttt ctaaaaattg gtcgattaaa tattcatata taatccttat catcatttat   2160
tagccttttg tagcttactt aaaaaacccc ttcccaccaa attgattagt gtagattgat   2220
tatttttcac ttcatacgtt gatcaatttt aaaatatata tatatatata tatatatata   2280
tatatgcacg tccggcgtcc catgacttca gacgcttttc tgtttccttg attttatagg   2340
ttaaaatttt ccaaaatgct catatttttc actcatatgt ataatgtatt attatacgca   2400
caaaatagta aagtcataaa catttatgat ggctctttta tatgtataga gtagtgaaat   2460
ttatatatat cggagttccg cttaaaataa attaatattg ttcttttatc gcccattttt   2520
tagttactaa acgtatataa ttaaaaactg aaatgcaata tgtagaaatc cggcttatga   2580
tgaaccatac taatactcat tgttacaaac tcacagcaac atcataattc catcactcgc   2640
cacaataatt ttctttagtg tatgttctat ttcacatttt gacccttcac tttcttgaat   2700
gaaaattata caagaaaatg atttgagtgt gttaaaaaaa aaatgttttg agtcattctg   2760
accaattatc tggcagagac tataataaaa tacttccaat taccttaaat cattaggcgt   2820
tgtttcttgc cgaatatact agggttttcc ctagctcacg ctaacacaca aagccgcagc   2880
catttccatc tctctcgcaa ctcaacttcg aacaatggct gaacgaggcg gagaacgagg   2940
cgccgagcga ggaggagacc gcggcggttt cggacgggga ttcggaggag gtcgcggcga   3000
ccgaggaggc cgcggaggtc cgagaggccg aggcggcaga cgcggaggac gtcccacaga   3060
ggaggagaag tggaccccag tgaccaagct cggccgtctc gtgcaagccg gaaagatcca   3120
gaagctcgag cagatctacc tccactcgct ccccgtcaag gagtaccaga tcatcgacct   3180
cctcgtcggt ccaactttaa aagacgaggt gatgaagatc atgccggttc agaaacagac   3240
cagggccggt cagaggacga ggttcaaggc ttttgtcgtt gtcggagaca cgaatggtca   3300
tgttggtttg ggtgtgaagt gctccaagga ggtggcgacg gcgatcagag gtgggattat   3360
attggcgaag ctgtcggtga ttcccgtgag gagagggtac tgggggaaca agattgggaa   3420
gccgcatacg gttccttgta aggttacggg gaagtgtggg tctgttacgg tgaggatggt   3480
gcctgctccg aggggggcgg ggattgtggc ggctagggtt cctaagaagg tgcttcagtt   3540
cgctgggatt gatgatgtgt ttacttcttc caggggatct actaagactc ttggaaactt   3600
cgtaaaggtt tgaactttat tcatttactt ggtgtttgga gctgtgtata gattgaaagt   3660
tgattccttt ttgatcgttg cgtgtggagg tgttttgggt aatattgcta aatgtaaaaa   3720
ttgctaagct tgattagttt gaataagctg tctgtgttaa atgatgattt gtttgtgttg   3780
taatgagctg tctgaatttc attatttgtt tgtgttattg ctaatttaca agcttaaatt   3840
tgattccttt tgatcgtttc gtgtgagttg ttttgtgtaa tttagcttga tgtagttgat   3900
ggaagtaaga attgttaagc tttagagctg tctgttaatg ttgaattgtt tgtgttgtat   3960
tgagctgtct gaattattat ttgtttgcga tttatttcta aatcacaaag ctctaaagtc   4020
gtttgaacat atgcatcatt tggttagtgt ttattgctga attttcatga tttggttgtg   4080
```

tttattgcta aatttgagat tacattataa tcttaatttg tacatatatt catcattttt 4140
gtgtttattg atttgtttgt gtttattgat gaatcacaag tttctatgat taatcttcat 4200
gatttggttg tgattattgc taaatttgag attacattat aagcttagtt tgtacatgta 4260
tacatcattt cacttgaatt ttcacagacg agctggtgat atattttttt ttttagtatt 4320
ttccatgtat tgctttgtaa gaacgtttaa atgttagttt tcttgaatgt ttttttcttt 4380
gtaagaacaa ttaaatgttt gttcagtatt tttgaatcat tcaatggtta atcatgttca 4440
acatgtattt tttgtaggct aca 4463

<210> SEQ ID NO 20
<211> LENGTH: 4789
<212> TYPE: DNA
<213> ORGANISM: Brassica napus

<400> SEQUENCE: 20
tgccttatga agatctacgt ctaactgcat catctgagcc atcctatgaa aatttatttt 60
tgaccagatt tacttgcacc atgttgaaac ttctttataa acctttcttt tctagtttgc 120
attaataaat cgctcttttc tctttctctg atacatatta ttcatgttgg ttatacctgt 180
acacgcacgg acaatatttt ccaactttaa aacgaatcaa atcagttaat ttaataactt 240
tggactagta actgtatttg aatttaaatt tctcttttca gaatattcta caaaacagtt 300
ttaattccgt ttgtcagtag aatcacatat atggatggac atagttggac atatttaggt 360
ccttatccaa atgctggtgt taagaattga tttatggatg tacatagttg gatacatttt 420
atgtttaaaa tgtgattttt atattattat tgctgtggtg tgaaattttg tgttattcac 480
ttaaattata atatctatgt ataccaaaga gaagaagata acatatatta tagtatttgg 540
tacatactat actataacat acttagtaaa tttcacacca caacaaaaat aatataaaag 600
gtcacatttt aatatacaac gtgccaaact tcgtccattt gtaatcttat acattttcgt 660
cttcgcatat gatagatcat aagatttgga gaaacatata aaattaacct atgaaattaa 720
gggggtctat atcttatagt atgtatccaa agaacatata taggaaatat ttgaatacat 780
cataagattt ggggaatata aattaatata aaataaaatc ttccaatttt aaacgtaaac 840
gtctcctctg tatttatata aacttttcaa aatcacggtg tcgctcgtgt taagatttgg 900
atttctaatc caactttcag aaagtatatg tgaaagataa aactcaaaca caatagttcg 960
tttagaacgc tcttaagatt aatgtcacac acacaaaatt gatgtcacta gatttatttg 1020
ttttgtcgtt taaggggatc catcaactac acatggaaga atagaaaaca ctggtcacac 1080
acaaaaaata atataagcat gttgaattct attcatcaaa gaattttctt caaaggatga 1140
acaataacct ataattagga aacattataa caacgagcag gaagttttcc cagaagtcat 1200
gccttcgtcc ataccttcgg gtctttcaag caagcttcac acatgcctta tcatatgttt 1260
gtatacgttt tcattttgtg tacgtctatt aactagctag tatatgccaa gattatatat 1320
tttatatagt cgacaattac ctatcctaaa agttcatttt aatttttatt cagaaagata 1380
tgcacgtagg gccactagtg tttcccgttg ttattggaaa ttcatttcca tgtgttgaat 1440
tgtttgttta agtttttgaa cccgtaagtc aaatttattt tggtttaaca gggtttcatt 1500
actgttataa gcttgtcaag aaagaatttg ttacaaattt cgaggctcat gcatgcatga 1560
ttcttaactt tctagaaaca tgaaatgtgg ttttaccagc tcaagcttgt gttaaaacac 1620
atttttaatt tgaccacgtg tgatattcaa atatcaacaa ttctgttcaa cgggagattc 1680

-continued atacatatgt tcagatgttc tttaatctta agcacctaac tttgcttccc atacgcaaat 1740
gtgtgtgccg cgaactatgg tgaaatgttt tctttttgga gcatttttaa aagaaaatat 1800
aatttactta tttccgtttt gattgatata catgcattaa taaaccgact tacgtgggtg 1860
atgggatgag caaaattaaa atatgcattt tagtaaccaa ttacggtcta tcttgacaaa 1920
ctaacaaaca aaaagtctat tatgacgttg atttgtgacc tggccatata aatgccaaaa 1980
tttcattctt tcaataagca acgagatcaa taagatgtgg cagtcacgtg aacgttagtt 2040
atcgccattt caactgaacc ttcacgaaca tataaagttc atttgttctt tgctaaaatt 2100
acgcaaatct ctgttgtgca cgaaattacg actatttttt aaatacaact cctgttcttg 2160
tatcgtgtat ctctcgcacg taaatttgaa ttatgggggc attatcgata aaatatgtaa 2220
agaatatatt ttcatcatac accacaaaca aatgttctgg aaatgtcacc ttttatcaca 2280
tatacaaagc tgaccctgaa attttggaaa ctacaagcca aaaaaaatgg tcaaaagaaa 2340
tattatgcac aaaggttgga ctcgtcctaa ctctttttac aatgataatt aacctttgaa 2400
caactaatta aagatacata caatatgttt tttttctaaa aattggtcga ttaaatattc 2460
atatataatc cttatcatca tttattagcc ttttgtagct tacttaaaaa accccttccc 2520
accaaattga ttagtgtaga ttgattattt ttcacttcat acgttgatca attttaaaat 2580
atatatatat atatatatat atatatatat gcacgtccgg cgtcccatga cttcagacgc 2640
ttttctgttt ccttgatttt ataggttaaa attttccaaa atgctcatat ttttcactca 2700
tatgtataat gtattattat acgcacaaaa tagtaaagtc ataaacattt atgatggctc 2760
ttttatatgt atagagtagt gaaatttata tatatcggag ttccgcttaa aataaattaa 2820
tattgttctt ttatcgccca ttttttagtt actaaacgta tataattaaa aactgaaatg 2880
caatatgtag aaatccggct tatgatgaac catactaata ctcattgtta caaactcaca 2940
gcaacatcat aattccatca ctcgccacaa taattttctt tagtgtatgt tctatttcac 3000
attttgaccc ttcactttct tgaatgaaaa ttatacaaga aaatgatttg agtgtgttaa 3060
aaaaaaaatg ttttgagtca ttctgaccaa ttatctggca gagactataa taaaatactt 3120
ccaattacct taaatcatta ggcgttgttt cttgccgaat atagctaggg ttttccctag 3180
ctcacgctaa cacacaaagc cgcagccatt tccatctctc tcgcaactca acttcgaaca 3240
atggctgaac gaggcggaga acgaggcgcc gagcgaggag gagaccgcgg cggtttcgga 3300
cggggattcg gaggaggtcg cggcgaccga ggaggccgcg gaggtccgag aggccgaggc 3360
ggcagacgcg gaggacgtcc cacagaggag gagaagtgga ccccagtgac caagctcggc 3420
cgtctcgtgc aagccggaaa gatccagaag ctcgagcaga tctacctcca ctcgctcccc 3480
gtcaaggagt accagatcat cgacctcctc gtcggtccaa ctttaaaaga cgaggtgatg 3540
aagatcatgc cggttcagaa acagaccagg gccggtcaga ggacgaggtt caaggctttt 3600
gtcgttgtcg gagacacgaa tggtcatgtt ggtttgggtg tgaagtgctc caaggaggtg 3660
gcgacggcga tcagaggtgg gattatattg gcgaagctgt cggtgattcc cgtgaggaga 3720
gggtactggg ggaacaagat tgggaagccg catacggttc cttgtaaggt tacggggaag 3780
tgtgggtctg ttacggtgag gatggtgcct gctccgaggg gggcggggat tgtggcggct 3840
agggttccta agaaggtgct tcagttcgct gggattgatg atgtgtttac ttcttccagg 3900
ggatctacta agactcttgg aaacttcgta aaggtttgaa ctttattcat ttacttggtg 3960
tttggagctg tgtatagatt gaaagttgat tcctttttga tcgttgcgtg tggaggtgtt 4020
ttgggtaata ttgctaaatg taaaaattgc taagcttgat tagtttgaat aagctgtctg 4080
tgttaaatga tgatttgttt gtgttgtaat gagctgtctg aatttcatta tttgtttgtg 4140
ttattgctaa tttacaagct taaatttgat tccttttgat cgtttcgtgt gagttgtttt 4200
gtgtaattta gcttgatgta gttgatggaa gtaagaattg ttaagcttta gagctgtctg 4260
ttaatgttga attgtttgtg ttgtattgag ctgtctgaat tattatttgt ttgcgattta 4320
tttctaaatc acaaagctct aaagtcgttt gaacatatgc atcatttggt tagtgtttat 4380
tgctgaattt tcatgatttg gttgtgttta ttgctaaatt tgagattaca ttataatctt 4440
aatttgtaca tatattcatc atttttgtgt ttattgattt gtttgtgttt attgatgaat 4500
cacaagtttc tatgattaat cttcatgatt tggttgtgat tattgctaaa tttgagatta 4560
cattataagc ttagtttgta catgtataca tcatttcact tgaattttca cagacgagct 4620
ggtgatatat tttttttttt agtattttcc atgtattgct ttgtaagaac gtttaaatgt 4680
tagttttctt gaatgttttt ttctttgtaa gaacaattaa atgtttgttc agtatttttg 4740
aatcattcaa tggttaatca tgttcaacat gtattttttg taggctaca 4789

<210> SEQ ID NO 21
<211> LENGTH: 4465
<212> TYPE: DNA
<213> ORGANISM: Brassica napus

<400> SEQUENCE: 21
catatatgga tggacatagt tggacatatt taggtcctta tccaaatgct ggtgttaaga 60
attgatttat ggatgtacat agttggatac attttatgtt taaaatgtga tttttatatt 120
attattgctg tggtgtgaaa ttttgtgtta ttcacttaaa ttataatatc tatgtatacc 180
aaagagaaga agataacata tattatagta tttggtacat actatactat aacatactta 240
gtaaatttca caccacaaca aaaataatat aaaaggtcac attttaatat acaacgtgcc 300
aaacttcgtc catttgtaat cttatacatt ttcgtcttcg catatgatag atcataagat 360
ttggagaaac atataaaatt aacctatgaa attaaggggg tctatatctt atagtatgta 420
tccaaagaac atatatagga aatatttgaa tacatcataa gatttgggga atataaatta 480
atataaaata aaatcttcca attttaaacg taaacgtctc ctctgtattt atataaactt 540
ttcaaaatca cggtgtcgct cgtgttaaga tttggatttc taatccaact ttcagaaagt 600
atatgtgaaa gataaaactc aaacacaata gttcgtttag aacgctctta agattaatgt 660
cacacacaca aaattgatgt cactagattt atttgttttg tcgtttaagg ggatccatca 720
actacacatg gaagaataga aaacactggt cacacacaaa aaataatata agcatgttga 780
attctattca tcaaagaatt ttcttcaaag gatgaacaat aacctataat taggaaacat 840
tataacaacg agcaggaagt tttcccagaa gtcatgcctt cgtccatacc ttcgggtctt 900
tcaagcaagc ttcacacatg ccttatcata tgtttgtata cgttttcatt ttgtgtacgt 960
ctattaacta gctagtatat gccaagatta tatattttat atagtcgaca attacctatc 1020
ctaaaagttc attttaattt ttattcagaa agatatgcac gtagggccac tagtgtttcc 1080
cgttgttatt ggaaattcat ttccatgtgt tgaattgttt gtttaagttt ttgaacccgt 1140
aagtcaaatt tattttggtt taacagggtt tcattactgt tataagcttg tcaagaaaga 1200
atttgttaca aatttcgagg ctcatgcatg catgattctt aactttctag aaacatgaaa 1260
tgtggtttta ccagctcaag cttgtgttaa aacacatttt taatttgacc acgtgtgata 1320
ttcaaatatc aacaattctg ttcaacggga gattcataca tatgttcaga tgttctttaa 1380

```
tcttaagcac ctaactttgc ttcccatacg caaatgtgtg tgccgcgaac tatggtgaaa   1440
tgttttcttt ttggagcatt tttaaaagaa aatataattt acttatttcc gttttgattg   1500
atatacatgc attaataaac cgacttacgt gggtgatggg atgagcaaaa ttaaaatatg   1560
cattttagta accaattacg gtctatcttg acaaactaac aaacaaaaag tctattatga   1620
cgttgatttg tgacctggcc atataaatgc caaaatttca ttctttcaat aagcaacgag   1680
atcaataaga tgtggcagtc acgtgaacgt tagttatcgc catttcaact gaaccttcac   1740
gaacatataa agttcatttg ttctttgcta aaattacgca aatctctgtt gtgcacgaaa   1800
ttacgactat tttttaaata caactcctgt tcttgtatcg tgtatctctc gcacgtaaat   1860
ttgaattatg ggggcattat cgataaaata tgtaaagaat atattttcat catacaccac   1920
aaacaaatgt tctggaaatg tcacctttta tcacatatac aaagctgacc ctgaaatttt   1980
ggaaactaca agccaaaaaa aatggtcaaa agaaatatta tgcacaaagg ttggactcgt   2040
cctaactctt tttacaatga taattaacct ttgaacaact aattaaagat acatacaata   2100
tgtttttttt ctaaaaattg gtcgattaaa tattcatata taatccttat catcatttat   2160
tagccttttg tagcttactt aaaaaacccc ttcccaccaa attgattagt gtagattgat   2220
tatttttcac ttcatacgtt gatcaatttt aaaatatata tatatatata tatatatata   2280
tatatgcacg tccggcgtcc catgacttca gacgcttttc tgtttccttg attttatagg   2340
ttaaaatttt ccaaaatgct catatttttc actcatatgt ataatgtatt attatacgca   2400
caaaatagta aagtcataaa catttatgat ggctctttta tatgtataga gtagtgaaat   2460
ttatatatat cggagttccg cttaaaataa attaatattg ttcttttatc gcccattttt   2520
tagttactaa acgtatataa ttaaaaactg aaatgcaata tgtagaaatc cggcttatga   2580
tgaaccatac taatactcat tgttacaaac tcacagcaac atcataattc catcactcgc   2640
cacaataatt ttctttagtg tatgttctat ttcacatttt gacccttcac tttcttgaat   2700
gaaaattata caagaaaatg atttgagtgt gttaaaaaaa aaatgttttg agtcattctg   2760
accaattatc tggcagagac tataataaaa tacttccaat taccttaaat cattaggcgt   2820
tgtttcttgc cgaatataag ctagggtttt ccctagctca cgctaacaca caaagccgca   2880
gccatttcca tctctctcgc aactcaactt cgaacaatgg ctgaacgagg cggagaacga   2940
ggcgccgagc gaggaggaga ccgcggcggt ttcggacggg gattcggagg aggtcgcggc   3000
gaccgaggag gccgcggagg tccgagaggc cgaggcggca gacgcggagg acgtcccaca   3060
gaggaggaga agtggacccc agtgaccaag ctcggccgtc tcgtgcaagc cggaaagatc   3120
cagaagctcg agcagatcta cctccactcg ctccccgtca aggagtacca gatcatcgac   3180
ctcctcgtcg gtccaacttt aaaagacgag gtgatgaaga tcatgccggt tcagaaacag   3240
accagggccg gtcagaggac gaggttcaag gcttttgtcg ttgtcggaga cacgaatggt   3300
catgttggtt tgggtgtgaa gtgctccaag gaggtggcga cggcgatcag aggtgggatt   3360
atattggcga agctgtcggt gattcccgtg aggagagggt actgggggaa caagattggg   3420
aagccgcata cggttccttg taaggttacg gggaagtgtg ggtctgttac ggtgaggatg   3480
gtgcctgctc cgaggggggc ggggattgtg gcggctaggg ttcctaagaa ggtgcttcag   3540
ttcgctggga ttgatgatgt gtttacttct tccaggggat ctactaagac tcttggaaac   3600
ttcgtaaagg tttgaacttt attcatttac ttggtgtttg gagctgtgta tagattgaaa   3660
gttgattcct ttttgatcgt tgcgtgtgga ggtgttttgg gtaatattgc taaatgtaaa   3720
aattgctaag cttgattagt ttgaataagc tgtctgtgtt aaatgatgat ttgtttgtgt   3780
```

tgtaatgagc tgtctgaatt tcattatttg tttgtgttat tgctaattta caagcttaaa 3840
tttgattcct tttgatcgtt tcgtgtgagt tgttttgtgt aatttagctt gatgtagttg 3900
atggaagtaa gaattgttaa gctttagagc tgtctgttaa tgttgaattg tttgtgttgt 3960
attgagctgt ctgaattatt atttgtttgc gatttatttc taaatcacaa agctctaaag 4020
tcgtttgaac atatgcatca tttggttagt gtttattgct gaattttcat gatttggttg 4080
tgtttattgc taaatttgag attacattat aatcttaatt tgtacatata ttcatcattt 4140
ttgtgtttat tgatttgttt gtgtttattg atgaatcaca agtttctatg attaatcttc 4200
atgatttggt tgtgattatt gctaaatttg agattacatt ataagcttag tttgtacatg 4260
tatacatcat ttcacttgaa ttttcacaga cgagctggtg atatattttt ttttttagta 4320
ttttccatgt attgctttgt aagaacgttt aaatgttagt tttcttgaat gtttttttct 4380
ttgtaagaac aattaaatgt ttgttcagta tttttgaatc attcaatggt taatcatgtt 4440
caacatgtat tttttgtagg ctaca 4465

<210> SEQ ID NO 22
<211> LENGTH: 6656
<212> TYPE: DNA
<213> ORGANISM: Brassica napus

<400> SEQUENCE: 22
aaaaatattt gatttatata ttcttattaa aaatattaat ttactgttta ttattttata 60
taattttata aatcatttta tttagagttt aatttattta cgatttattg ttttaatttg 120
ttaggcaaat tagtctaaca aattaaacaa aaaaaaatat aaataaatta aattttaaac 180
aaaatgtttt ataaaaatat ttatatcctt ataaggatat aaactataat tttgtgttat 240
ttttatattt aaactattat tatatttaat tatttttaaa taaatttatt tatatttttg 300
tatattttta ttaaaactaa tattttattt aattatgaaa attgaaaacg tttttttggt 360
tatttttgaa aattttgaca aggttgaaaa atcgctggaa atatttttga ggaattttag 420
acaaaaaaat atcgatgata aacaattggt tggaatccgt caagaatttt tgacaaaata 480
aactcgaaat ttgttttcac tgggaattag ttattttctt gtatttgcat tatctaataa 540
acaatgcaac cataaacaac aaatgaaata aagttttaat tgacaaatct tttagaagag 600
tgaaacgtta atggtggacg aagcccccac ctcaattgac aataaaaaga gtggaaaaga 660
gggaagatgg cagagagaaa agtccaaaga gaggaaatca tgaagagaag aagacaatgt 720
aacctactta tttgcctcga tgaagataga ggagaagata gaggtggaat atatatagaa 780
gagagaaaga tttgggagga aacccgattg agcatatatc agatctagaa tggattggat 840
tagataactc gaacttattt ggttaatctt tttagtttag ggaaggttat gaaaaattac 900
ctctgatcta atttttaaat tttttatctt atatacattg tgccccccga ctaacaatat 960
atctagatcc atccctgatt aggtccatga gatatatcat atttttttatt tttcttattt 1020 aattaattat ctataatatt tgttgatata tttaaaattt tacatatcgt tgaaagccag 1080
aaaaatatgt ggaagtgtaa taaaacaatt ttctccagga agaagatatt tcagccattc 1140
gcccatctat gtgtatgaga tcccattcaa ggccatattc taagattgac tttatctaat 1200
ttactgtatt ttccgtgggc tactgaatga atacgatgct tttgttgtaa aacgcaacct 1260
attgttctcc attttgaatt tgaagtgtta cattgttgat aaaaaggaag aaagtacaaa 1320
gcttttcatt tagtggttgt tgcatatata tacttatttg atgggtttat gataagtatg 1380

-continued aacatttcac gtaacgggtt tattttgtcg tcaacacatt atcggcaatg tgaaaagaag 1440
gggtgaggta tctccatttc aattcttctc tttatatatt aatcgaatta tttacgtatg 1500
aaatgaacgt ttatatagaa atttcgtgtg gaaaacgaca tgtacacggc atctcaagac 1560
caattagtaa tatactttag tggtgattac atgtttactt atccaattga gaatttaaag 1620
catcgacaat accttaatgt cgattaagcc gtccccactt catgtaatga gttatggggg 1680
gagagagaga tcccgaaatt cgtcaaataa aacaacttag aactaaaaac cgacaccaag 1740
tatcataaag gaaatgttga agaagtcatt tatcgtatcc agctcacaat tcctaagatt 1800
aaatcatgac cgttggaaga gcttataaga ttaaactgaa gaaattgtgg gttttagaag 1860
aaagacaaga aagagaagaa catgatctta cattgcctat tttggtgtat aggagttgtc 1920
aaaaagagga gagagaggag acaattaggt caaataaatg agcactaaaa atggagacat 1980
gtgttgagta actattacaa gagcgactta tgcttctata tggcaatgat atcatcacca 2040
aagtgcaatg cccctttttg ccctagtttc gtaaagtctc tctccttctt cgtccttagg 2100
aaaaacccta aattaaatcc tgtgttcttg atctttcttt ttgagtaacc atgattttga 2160
ccacacacta gttcttctat attttgtggt ctataggatt ttgctttata tgtgtttctt 2220
gtattgctcc gtacgtgcgt atataaattt aaatggttac aacaaggttt attataaata 2280
ggcacaaatt agtccatgaa gttatttagc ttgcacaagt ataatttgtt aagtatttaa 2340
atatataaat ttgttacaaa acttaattaa atttatctga ttatattttc tttagtgttc 2400
ttcctttgcc aacgttgagg tagctattat tattattatt ttgaacatta tgtacgtagt 2460
tatcttggct agttatgatt cgaattctta atttggatca cacttaacag tatttaaaat 2520
attcttagaa ctaaaataat taagagttac ctttaaattg aagtattcgt gctaaacaga 2580
aactagaata aacaaatgat tgcatgttaa tttttttttt cgattttcct atcagaataa 2640
acacatgatt gcatgcaaat attgtttttg attacgttat cttttgttta ttttagtttt 2700
gatgctaatt aatatttttt attaacaact cacatacatt ctacctgatt ctaggtcaga 2760
taatgacaca gcgcaacaaa attaatacaa aaccttcgga aagtagaata ccgcagaagt 2820
aactttttttg ggtacatacg aaatacagtg aaatctctat aaattaataa tgttgagact 2880
ataccaaaac tataaaattt ttattaattt atagagatta atttatcgat atactaattg 2940
aatcaaaaac ttaatttgag attaaaaaat tatattattt tatagagatt tttagtgtat 3000
attaatttat agaatattat tttataaaaa attttagtgt gtattaattt atagagtatt 3060
aatttaaaga agttatactg taatgtgaat cttcgaaaaa catgccatac ataaccacgg 3120
atcatagtcg acacctcaac gtgaagcaaa tttgacaatc tacatacata accaacaaaa 3180
agtagaatac cttgaaaatc taaaacccaa aatatgatgt aaaactcaag cttggtccag 3240
agcataaaaa aattaaagcc atcgctttgg tatcacatat ttaaacgtca gttttttttt 3300
tttttttggg gggggggggg gggggtaata taaaaatata attaacaaaa acaatttatg 3360
aaacaattag catgtaaaac actaatcttt tggttgtgac aaaacgtttt cacaaatgtt 3420
ctataaataa attcaagtgc attttatctg caaaatatat actttcactc ataaaataag 3480
agcgtttaaa acattcatac acgcactaca ttgacatgac aaaagaaatc cgcaaataca 3540
catgatgtat gtcgaaaaaa acaaaaaaat acacatgatg tatatataga gaggatagta 3600
tctaggaaat aagactatat tatatatata aagaaaatag agaaaagata aaaatataaa 3660
ttggtatgta taaaataaag gtctatgcgt ctctagtcca aaaactctat atatgtctgg 3720
ctcaaaagca gatgcagcca tagccccaat agtcatgatg gagcatcatc atctccttat 3780
gaattggaac aaacctattg atctcattac agaagaaaac tcttttaacc acaatcctca 3840
tttcatagta gatccacctt ccgaaaccct aagccacttc cagccccccgc cgacaatctt 3900
ctccgatcac ggaggaggag aggaagcaga agaagaagaa ggagaggaag agatggatcc 3960
gatgaagaag atgcaatacg cgattgctgc catgcagccc gtagacctcg atccagccac 4020
cgttcctaag ccgaaccgcc gtaacgtaag ggtaagcgac gaccctcaga cggtggtggc 4080
tcgtcggcgt agagaaagga taagcgagaa gatccggata ttgaagagga tggtgccagg 4140
cggtgcaaag atggacactg cctccatgct cgacgaagcc atccgctaca ccaagttctt 4200
gaaacggcag gtgaggctag cttcttcagc ctcacactca gcttggagct cctatgtctg 4260
acccttcttg cctttgttat taattaccac aactcggata actaattata attctatcac 4320
gcgtttcatg ttgatatata tagataaatg gtcgaataag gatttcgatc gaagattgta 4380
tggctattga ttacattata tattgtacaa taaatgatgt gtgtatttca attaatgtat 4440
gatatatata tatatgtatg cagtatgcat ttatattcta ttctctataa ggaggcaaca 4500
ttgccggatt agggctttga tcttatgcaa gttttccgac caaaaatatg aaatacttgt 4560
ttggatataa catatgaatc ggataagtgt tactagttat ataactggaa aacaaatgtc 4620
tggaataaga attcccggga gaaccaagcc tttctctaat ccctaagatt atagctactg 4680
aaacaatgaa acaatgaaga atcagttggg cattagtaaa aaaaaaagaa tcagttgggt 4740
tgcttataaa attttgttat aaaatttatg tcgtatgtgt gttagccgta gctgtaaatt 4800
tatttccttt gtatgttaat tgtaaaagta aatttattat tcccgatgtt tttaatgatg 4860
taaatttaaa tcaagaaaac atattaagtt ctgttaataa atgtattatt tttgtttact 4920
aatttccaat aattttttca agaagtacaa ttttttgttt gaaatttcta atttatcatt 4980
attgaataat agaacatacc taaaaaccat aaaacatgta ttccttgaaa cattttttt 5040
aatataaaaa ttatctttta ggagcaggta aagtactttt ttttataaaa ttgttagtgt 5100
atttatgttc gttatagatg tagatatttt gcataataat taataatata tgagatgtgt 5160
aatgtatata tgtgagagaa ttgccatatt tattaagcgg tttttgtaaa attgactcaa 5220
aatttaaagt caaccacaaa actaacatat gtttttttgg acatttcatt tgccatattc 5280
actccacaag ttcagattat ttacgaaaat gtcattaatt tttttctttt ctgaaatggt 5340
atttttactc tctcaacctc atcatcttca agtatttaca agattgtcat tgccatcaat 5400
acaccaacca ccatgaacaa ccaatttgaa taatgcacct taaatcgatt tacacttctt 5460
ccttctcaat tcttatgaac taaaaacaac atctctttca ctttctctcc atattcatcc 5520
aaaaaatcta agatttttat tcaaaaaaat ttatggttca tagaaccatt gaagcttacg 5580
attcttggtg tgtcactttt gtttgagatt ataggtgctt ggagaagact tttgtgtgct 5640
aaacaagtta tctcaatggt tgaactatga aaatcagtgt ttttttccag atttgttcgc 5700
ccaaccgact ttcgggtaag ttttctggct gtagacgact aacatggaag tcttctggtc 5760
aatgcacttc tctttgattg tcttcttctg atttacatta tgtagaatga acaagagatg 5820
ggaggaacta ggggtaggta aaaaaaccgg aatcgaatta tcaaaccgaa caaacccgaa 5880
aaaaccgaac caaatttatg aattatccaa ttggatactg aaattgtata cccgaagaat 5940
tagaaccgaa ctcgtaccga accgaaaacc gaataatacc catatagaac cagatgaaaa 6000
acctttatac actacttata cgtatatctt tatagtttat attttataca cttgtttttt 6060
ttattgatca acgcttgttt tataggagaa ccttgtattg tttggatatt ttatcctcat 6120
aatttaagtt ttggtttctg aatgggaaaa tcatttgaat gttattttgg tgttggtttt 6180
aattcattta tttgcaagta catcagatta atttggataa tatggttaca aagtaaaaag 6240
aaaaaactga acttcaggaa cctaaaaaac cgagaaccga tctgatctga tccgaaattt 6300
ttatggttct ttaatggtta ccaatttcaa gaaccgaaat aaacgagaac cgaaagaacc 6360
aataaccgaa gaaccgagcg cccactccta ggaggaacca aacaatactt tgatttgaag 6420
cccaagataa ttggaaccat gttatattac gcagcttatc tgatgtgggc tttatgtaga 6480
actgataatg ggctttaagg cagcctattt cggtccgtca agaagattcc tcctaacgta 6540
aggtaggggc aatgagctgc tactctgacc aattaattac gtttcaatag tgatctctca 6600
tctgttgtcg gtgtgaaagg aatcgtcttt tgaatttatc ttcatgcgat tcattg 6656

<210> SEQ ID NO 23
<211> LENGTH: 7512
<212> TYPE: DNA
<213> ORGANISM: Brassica napus

<400> SEQUENCE: 23
aacaaaaatg atagatggtg cactaataat taatttatag tcagtttaat aaaaagctta 60
ttatatattt agatgaacca acatattttt ctaatgatta taagaatcat catggtgatg 120
acctaaaaag ttgtaatgct cttcttttaa catatagggg atttcacatc tgattcttta 180
ttataagctc tattcttgtt tggaaaatat aatatacata ttaaggaaat tcgaggggtt 240
taattttgtt gtgatttatt agaattaatt tttatggaac tttttaacta atttattatg 300
tgagaataca tatggtgttg atacgtcaac tttttttttt gtgagaaata ttattgtatt 360
gacacttcaa cttttttttgt gagaaacatt ttggtgacga cacatcaaca aggctctctc 420
aatgattctc aaataatata tagaagattt taaggagaaa ataggaatat aaatagtaat 480
ttcataaatt tgagagcata ctattcacaa tcttatttta tttttgaaca ttgttattta 540
taaactgatc cttaaatttt atgtgttttg ttattaatac aattataagt tcatataaat 600
cattgtatat tccgatggaa ttaaagttta gggtttaaaa acacgtgcaa aataggttac 660
acacgattcg ttaaagatcc acgagcacta caataagaca taaaaacttt atatggtata 720
acatatgcta actaatcgaa tattacaata tttgtatacg gtaaataaaa aatcaactta 780
caaagacgat ttcgggaatt ctcatagtat tttcaaatct attttaccag tgattttgaa 840
gcagttcaaa catcataaac ctcgttaaat cattgtataa tgcatttatc gttgatatgc 900
ttttctttgg atttggtaac cttaactcca aatcgttaga aatccgtcaa gaatttgtca 960
agaacctgtt gagaatttat atctgattct gacaaatcgg ggtttagggt cttgtttaac 1020
gaaaacaaat tcttgatggc ttcttgatgg atgtgtattt catcagaaaa ctaaattttt 1080
acccataaaa caaagcacca atattttggc aacctcctaa agtgaatatt tctttacaga 1140
ttcccgacaa catatcattt gctcgataat ccgttacgaa tctgaaaatt tacccataaa 1200
aagaaaacta aatttttcta tacataattt agccgatttt tttcttcaat atttccattt 1260
gatttattct ctcaaaatac attaaactcc tctttatcct caaaatcata atcgaaatca 1320
catgttaagt tggttgcttt aggaattaga atattttgtt agattttttc aatgttaagt 1380
taaataagtt gttggtttta agattgttaa ttttagaaat ttagatgttt gttttaccga 1440
tttagatgtt agttttattt ttgaatgtta atttagggtt tgcatgttag ttttacgatg 1500
tagttgttaa ttttaggatt tgtagtttaa aatttttttt ttacgttcgc gtaacattaa 1560
aaatattttt catactgaaa acatattttt taattttaaa gttattatat tatttaaaag 1620

```
taattctaaa catttattat atatatttac taatttatga atgtttttac aaaaaaaaat   1680
taatttacaa ttgatttttt attattttat attttatatg tatttttatt ataaataatc   1740
tttacaattt gtttttgtat tttacatatc ttcaaacact ttattattta aagatgattt   1800
tatttaattt tattaaaaat atttgattta tatattctta ttaaaaatat taatttactg   1860
tttattattt tatataattt tataaatcat tttatttaga gtttaattta tttacgattt   1920
attgttttaa tttgttaggc aaattagtct aacaaattaa acaaaaaaaa atataaataa   1980
attaaatttt aaacaaaatg ttttataaaa atatttatat ccttataagg atataaacta   2040
taattttgtg ttatttttat atttaaacta ttattatatt taattatttt taaataaatt   2100
tatttatatt tttgtatatt tttattaaaa ctaatatttt atttaattat gaaaattgaa   2160
aacgtttttt tggttatttt tgaaaatttt gacaaggttg aaaaatcgct ggaaatattt   2220
ttgaggaatt ttagacaaaa aaatatcgat gataaacaat tggttggaat ccgtcaagaa   2280
tttttgacaa aataaactcg aaatttgttt tcactgggaa ttagttattt tcttgtattt   2340
gcattatcta ataaacaatg caaccataaa caacaaatga aataaagttt taattgacaa   2400
atcttttaga agagtgaaac gttaatggtg gacgaagccc ccacctcaat tgacaataaa   2460
aagagtggaa aagagggaag atggcagaga gaaaagtcca aagagaggaa atcatgaaga   2520
gaagaagaca atgtaaccta cttatttgcc tcgatgaaga tagaggagaa gatagaggtg   2580
gaatatatat agaagagaga aagatttggg aggaaacccg attgagcata tatcagatct   2640
agaatggatt ggattagata actcgaactt atttggttaa tctttttagt ttagggaagg   2700
ttatgaaaaa ttacctctga tctaattttt aaatttttta tcttatatac attgtgcccc   2760
ccgactaaca atatatctag atccatccct gattaggtcc atgagatata tcatattttt   2820
tatttttctt atttaattaa ttatctataa tatttgttga tatatttaaa attttacata   2880
tcgttgaaag ccagaaaaat atgtggaagt gtaataaaac aattttctcc aggaagaaga   2940
tatttcagcc attcgcccat ctatgtgtat gagatcccat tcaaggccat attctaagat   3000
tgactttatc taatttactg tattttccgt gggctactga atgaatacga tgcttttgtt   3060
gtaaaacgca acctattgtt ctccattttg aatttgaagt gttacattgt tgataaaaag   3120
gaagaaagta caaagctttt catttagtgg ttgttgcata tatatactta tttgatgggt   3180
ttatgataag tatgaacatt tcacgtaacg ggtttatttt gtcgtcaaca cattatcggc   3240
aatgtgaaaa gaaggggtga ggtatctcca tttcaattct tctctttata tattaatcga   3300
attatttacg tatgaaatga acgtttatat agaaatttcg tgtggaaaac gacatgtaca   3360
cggcatctca agaccaatta gtaatatact ttagtggtga ttacatgttt acttatccaa   3420
ttgagaattt aaagcatcga caatacctta atgtcgatta agccgtcccc acttcatgta   3480
atgagttatg gggggagaga gagatcccga aattcgtcaa ataaaacaac ttagaactaa   3540
aaaccgacac caagtatcat aaaggaaatg ttgaagaagt catttatcgt atccagctca   3600
caattcctaa gattaaatca tgaccgttgg aagagcttat aagattaaac tgaagaaatt   3660
gtgggtttta gaagaaagac aagaaagaga agaacatgat cttacattgc ctattttggt   3720
gtataggagt tgtcaaaaag aggagagaga ggagacaatt aggtcaaata aatgagcact   3780
aaaaatggag acatgtgttg agtaactatt acaagagcga cttatgcttc tagaaccaag   3840
cctttctcta atccctaaga ttatagctac tgaaacaatg aaacaatgaa gaatcagttg   3900
ggcattagta aaaaaaaaag aatcagttgg gttgcttata aaattttgtt ataaaattta   3960
```

-continued

```
tgtcgtatgt gtgttagccg tagctgtaaa tttatttcct ttgtatgtta attgtaaaag   4020
taaatttatt attcccgatg tttttaatga tgtaaattta aatcaagaaa acatattaag   4080
ttctgttaat aaatgtatta tttttgttta ctaatttcca ataatttttt caagaagtac   4140
aattttttgt ttgaaatttc taatttatca ttattgaata atagaacata cctaaaaacc   4200
ataaaacatg tattccttga aacatttttt ttaatataaa aattatcttt taggagcagg   4260
taaagtactt tttttataa aattgttagt gtatttatgt tcgttataga tgtagatatt   4320
ttgcataata attaataata tatgagatgt gtaatgtata tatgtgagag aattgccata   4380
tttattaagc ggtttttgta aaattgactc aaaatttaaa gtcaaccaca aaactaacat   4440
atgttttttt ggacatttca tttgccatat tcactccaca agttcagatt atttacgaaa   4500
atgtcattaa ttttttttct ttctgaaatg gtatttttac tctctcaacc tcatcatctt   4560
caagtattta caagattgtc attgccatca atacaccaac caccatgaac aaccaatttg   4620
aataatgcac cttaaatcga tttacacttc ttccttctca attcttatga actaaaaaca   4680
acatctcttt cactttctct ccatattcat ccaaaaaatc taagattttt attcaaaaaa   4740
atttatggtt catagaacca ttgaagctta cgattcttgg tgtgtcactt ttgtttgaga   4800
ttataggtgc ttggagaaga cttttgtgtg ctaaacaagt tatctcaatg gttgaactat   4860
gaaaatcagt gtttttttcc agatttgttc gcccaaccga ctttcgggta agttttctgg   4920
ctgtagacga ctaacatgga agtcttctgg tcaatgcact tctctttgat tgtcttcttc   4980
tgatttacat tatgtagaat gaacaagaga tgggaggaac taggggtagg taaaaaaacc   5040
ggaatcgaat tatcaaaccg aacaaacccg aaaaaaccga accaaattta tgaattatcc   5100
aattggatac tgaaattgta tacccgaaga attagaaccg aactcgtacc gaaccgaaaa   5160
ccgaataata cccatataga accagatgaa aaacctttat acactactta tacgtatatc   5220
tttatagttt atattttata cacttgtttt ttttattgat caacgcttgt tttataggag   5280
aaccttgtat tgtttggata ttttatcctc ataatttaag ttttggtttc tgaatgggaa   5340
aatcatttga atgttatttt ggtgttggtt ttaattcatt tatttgcaag tacatcagat   5400
taatttggat aatatggtta caaagtaaaa agaaaaaact gaacttcagg aacctaaaaa   5460
accgagaacc gatctgatct gatccgaaat ttttatggtt ctttaatggt taccaatttc   5520
aagaaccgaa ataaacgaga accgaaagaa ccaataaccg aagaaccgag cgcccactcc   5580
taggaggaac caaacaatac tttgatttga agcccaagat aattggaacc atgttatatt   5640
acgcagctta tctgatgtgg gctttatgta gaactgataa tgggctttaa ggcagcctat   5700
ttcggtccgt caagaagatt cctcctaacg taaggtaggg gcaatgagct gctactctga   5760
ccaattaatt acgtttcaat agtgatctct catctgttgt cggtgtgaaa ggaatcgtct   5820
tttgaattta tcttcatgcg attcattgtt ttataactac cacacatgtg acataactaa   5880
tagtctcgaa tcaggacatc aaaatttatt tttttgtttg tggcaatgat tcaaatcgac   5940
ggcatagcat actgattaaa aatatataca atacactggt tattaaaacg ttatagttgt   6000
ctagatttta ataacaggtg ataatagatc aagtatatag taaatgtttt atctcaccca   6060
ttacatattt catattaaac atttcagatt tatttgtaaa tggattcaac tgcctgttac   6120
ccttcactcc ttttgattaa catcgcgtcg caagtcacaa ccaccattta gttggggcga   6180
ttcgtatatt ttgggagtat ataataacat acataactat caaaccaact ggtgtcgacc   6240
tttggtgtta actaatttga tttaactctt ttttggaata aataaaataa aatttcagag   6300
cagctgttca atagtaaaat gacaggtggg atctagggtt tgtggtcctt acgatcgatt   6360
```

```
gattactact acttaacttg gcattatttg gagtcacttt tgcttattaa taattagatt   6420

ttgtttacaa acgtgtggtg atagtctggg acaagttgac ctgttgacac ccaatcattt   6480

agaacacctt ttacaaatat aaatattcgc acactgttac aaacattatc atcaaattat   6540

tgtggaattt tgcagacaaa gcatatgcca ttgtgtttcc ttcgatttgg cttttatgct   6600

tattcgtggt gtcataatta attcgtgaaa acgaatgatt ttacatactg taagtagggc   6660

tgaaagcgga tcgaatagta ccatattttc tactatttgt gatttattcc atatttcagt   6720

tttcttcgta aaaatacgaa tatccagttt ttcgaatatc cggaattttt ttgacatttg   6780

cgaatattca cagatattta cagatgattc atccactttg ttcaatacaa atctaaaaaa   6840

atatcaaatt attttttaga aatatctttt acatgataaa aatattaagt aaaaaattaat   6900

gaaactaaat gttttattaa attttaaaat tagtaatttt tcttataaaa atgtttttag   6960

aaaaatatgc agttttgtat aaagaattat atatttttaa tttaatattt tataagtagt   7020

ttttaaaata aaatttaata aattatatgt taaataatta tataagatta tacatttaaa   7080

actctatatt taatcgtaga tatacatcta tttgtacaac tccgatccgt ctctaatttt   7140

ttttagtatt tgtggtttgg ttcgttttta acggatattg atttttaata tttgcttttt   7200

tttagagact tacgaatatt catatttttt tggatcgagt cgaaacaaat aataaattga   7260

atcaatttaa cggataaaat gttcagccct aactatggtt aactatggat actgaaacca   7320

ccacttatca acaaaaaaaa gtagttgttc gcttctggtt tagagtgagg ttacaaattc   7380

aaaacataat aattattttc tcggacgata accagatcct ttttagaggc tttaaaatgt   7440

aaatcatagt catgtgtagc ctatacatac aaattaaatt acaatggaat tttgaccaaa   7500

aaaaaaaaaa aa                                                       7512
```

<210> SEQ ID NO 24
<211> LENGTH: 6463
<212> TYPE: DNA
<213> ORGANISM: Brassica napus

<400> SEQUENCE: 24

```
aagccagaaa aaaatgtgga agtgtaataa aacaattttc tccaggaaga agatatttca     60

gccattcgcc tatttatgtg tatgagatcc cattcaagga catactgttt tccgtgagct    120

actgaatgaa tacgatgctt ttgttgtaaa cgcaacctat tggttttttt tttccgccaa    180

gttttgtttt tattaatcaa acgggccaag cccaaacggt cgaagcccaa atacactaag    240

taccaaacaa aaggcccaca gacacaacgg gctacaacat taatggctga agcccaagta    300

aactaaacgg cccaaaggcc caaacattga aaccggacag cttgacctag gcgcgcgata    360

aggagactgg ggtttgaaca cgtgtaagaa tctgggccat tagtatgaca cgcgtcgccc    420

gcctcgactt gatcgaaacc tcttcgcaca gccgcatgaa cttgccaccg acgacctcgt    480

ttcgccggag ctcagagact gaagagcctc caacgaaacc atagctattc tacgccgctc    540

tgtcttcacg ccggagagtt ccatcgatct aacgagatct cctccgacta tgtatcacca    600

caaaccctag acaggcgagc cgagaaccac tgatatcctc ctcttgtacg tcctcgccgt    660

tgtcggagag tttcatcatc atccgagatc tcatccgcga tggcccacga ccccatacct    720

gaccacaaga accacaccgc acttatctca cctcgatcta atcaccacaa cccaaaggac    780

atcgggttcc aagacggcag cgcggagctt tgcaagcctc cactctccgt gaccaaaagc    840

cggcgaagac ggagctgaat gagcctcccc ttcccggaag ctaaagcggc gacggtggat    900
```

```
ctgagaaagc ctccacctcc cgcataaaga ccggcgacga tggatctagg gtagcctcca    960
tctcccggaa aaaacaccac ctgaacatgc aagccgctcc atctccaccg ggagcctcca   1020
attgatcgcg tcgttactcc aaaggccgag ccaccgttga tggatggttg cggtcccaga   1080
gctccgacaa ggcgatcgat gacgggactg cgaagaagga gcggagagtg acaactacaa   1140
aggaagggaa agagctctgg cgacagcacg gacgctcacg cgccagccgt acgccgaacc   1200
caaaagtaga tctggtttct ctcttttctc tctctcgcaa aagaaaacac gcaacctatt   1260
gttctccatt ttgaatttga agtgttacat tattaataaa aaggaagaaa gtacaaagct   1320
tttcatttag tggttgttgc atatatagta tacttatttg atgggcttat gataagtatg   1380
aacatttcac gtaacgggtt tattttgtcg tcaacacatt accggcaatg tgaaaagaag   1440
gggcgaggta tctccatttc aattcttctc tttatagatt aatcgaatta tttacatatg   1500
aaatgagcgt ttatatagaa ttttcgtgtg gaaaacgaca tgtacacggc atcgaaagac   1560
caattagtaa tatactttag tggtgattac atgtttactt atccaattga gaatttaaag   1620
catcgacaat accttaatgt cgattaagcc gtccccactt catgtaatga gttatggggg   1680
gagagagagg tcccgaaatt cgtcaaataa aacaacttag aactaaaaac cgacaccaag   1740
tatcataaag gaaacgttga agaagtcatt tatcgtatcc agctcacaat tcctaagatt   1800
aaatcatgac cgttggaaga gcttataaga ttaaattgaa gaaattgtgg gttttagaag   1860
aaagacaaga aagagaagaa catgatctta cattgcctat tttggtgtat aggagttgtc   1920
aaaaagagga gagagaggag acaattaggt caaataaatg agcactaaaa atggagacat   1980
gtgttgagta actattacaa gagcgactta tgcttctata tggcaatgat atcatcacca   2040
aagtgcaatg cccctttttg ccctagtttc gtaaagtctc tttccttctt catccttagg   2100
aaaaacccta aattaaatcc tgtgttcttg atcttgcttt ttgagtaacc atgattttga   2160
ccacacacta gttcttctat attttgtggt ctataggatt ttgctttata tgtgtttctt   2220
gtattgcacc gtacgtgcgt atataaattt aaatggttac aacaaggttt attataaaca   2280
ggcacaaatt agtccatgag gttatttagc ttgcacaaga ggtatataaa tgtgtgtgtg   2340
tgtgttaagt atttaaatat ataaatttgc tacaaaactt aattaacttt atctgattat   2400
attttcttta gtgttcttca tttgccaacg ttgaggtagc tattattatt attattatta   2460
ttattattat tattattatt attattatta ttattattat tattattatt attattatta   2520
ttattatttt gaacattatg tactatgtac gtagttattt tggctagtta tgattcaaat   2580
tcttaatttg gataacactt aacagtattt aaaaaaaaaa tactatttaa aatattctta   2640
gtactaaaat aattaagatt taacttgaaa ttgaagtatt cgtgttaaac agaaactaca   2700
ataaacaaat gattgcatgt taattttttt ttcgattatc ctatatatca gaataaacac   2760
atgattgcat gcaaattttg tttttgatta tgtcatcttt tgtttatttt agttttgatg   2820
ctaattaata tttttttat taacaacttc catacattct acctgattct aggtcagata   2880
atgacacagc gcaacaaaat tatacaaaac tttcggaaag tagattaccg cggaagtaac   2940
atttttgggt agacatacga agtagtttga atcttcaaaa atcatgccat acataaccac   3000
ggatcatagt cgacacctca acgtgaagca aatttgacaa tctacataca taaccaacaa   3060
aaagtagaat accgtgaaaa cctaaaccca aaatatgatg taaaactcaa gcttggtcca   3120
gagcataaaa aaattaaagc catcgctttg gtatcacata tttaaacgtc agtttttttt   3180
tggggaagta atataaaaat ataattaaca agaaaattta tgaaataatt agcatgtaaa   3240
acactagtct tttggttgtg acaaaacgtt ttcacaaatg ttctataaat aaattcaagc   3300
```

```
acattttatc tgcaaaatat atactttcac tcataaaata agagcgttta aaacattcat   3360
atacgcacta cattgacatg acaaaagaaa tccgcaaata caaacatatt tagttcggat   3420
atatctagga aataagacta tattatatat ataaagaaat tagaaaaaaa gaaaattggt   3480
atgtataaaa gaaaggtcta tgcgtctcta gtccaaaaac tctatatgtc tggttcaaaa   3540
gcagatgcag cagccatagc cccaatagtc atgatggagc ctcatcatct ccttatgaac   3600
tggaacaaac ctattgatct cattacacaa gaaaactctt ttaaccacaa tcctcatttc   3660
atggtagatc caccttccga aaccctaagc cacttccagc ccccgccgac agtcttctcc   3720
gatcccggag gaggagagga agcagaagac gaagaaggag aggaagagat agatgagatg   3780
aaggagatgc aatacgcgat tgctgccatg cagcccgtag acatcgatcc agccaccgtt   3840
cctaagccga accgccgtaa cgtaagggta agcgaggacc cccagacggt ggtggctcgt   3900
cggcgtagag aaaggataag cgagaagatc cggatattga agaggatggt gccaggcggt   3960
gcaaagatgg acactgcctc catgcttgac gaagccatcc gctacaccaa gttcttgaaa   4020
cggcaggtga ggcttcttca gcctcacact cagcttgggg ctcctatgtc tgacccttct   4080
cgcctttgtt attaccacaa ctcggatacc taattataat tctatcacgc gtttcatgtt   4140
gatatatata gataaatggt tgaataagga tttcgatcga agattgtatg gctattgatt   4200
acattatata ttgtacaata aatgatgtgt gtatttctat taatgtatat atgatatata   4260
tctgtttgca gtatgcattt atattctatt ctttataggg aggcaacatg ccggattagg   4320
gctttgatcg tatgcaagtt ttccgaccaa aaatatgaaa tacttgtttg gatataacat   4380
atgaatcgga taagtgttac tagttatata actggaaaaa aattgtttgg tataagaatt   4440
cccgggagaa ccaagccttt ctctaatccc taagatcata gctactgaaa taatgaaaaa   4500
aaacaaaaaa aaaacaatga agaatcagtt gggcattagt ccaaaaaaaa aaaagaatca   4560
gttggattgc ttataaaatt ttgttataaa atttatgtcg tatgtgtgtt agccgtagct   4620
gtaaatttat ttcctttgta tgttaattgt aaaatttaat ttattattcc cgatgttttt   4680
aatgatgtaa gtttacatca agaaaacata ttaagttctg ttaataaatg tattattttt   4740
gtttactaat ttccaataat tttttcaaga agtacaattt tttgtttgaa atttctaatt   4800
tatcaacata cctaaaaacc ataaacatgt attttttgaa acattttttt aatataaaaa   4860
ttatttttta ggagcaggtg aagtatttct tttaataaaa ttgttagtgt atttacgttg   4920
gttatagttg tagatatttt gcataataat taataatata taagatgtgt aatgtatata   4980
tgtgagagaa ataccatatt tactaagagt ttttcgcaat attgactcaa aattcaaagt   5040
caatcacaaa actaacatat gtttcttttt agacatttcc tttgccttat tcactccacg   5100
ggttcagatt attcacgaaa atgtcattaa attttttttc ttttcgaaaa tggcattttt   5160
actctctcaa tttcatcctc ttcaagtatt tacaagattt ccattgccat caatacacca   5220
accacaatga acaaccaatt tgaagctctt aatgcacctc aaatcgattt acacttcttc   5280
tttttcaatt cttatgaact aaaaacaaca tctctttcaa tttctcccca tattcatcca   5340
aaaaacccaa gatttttatt ctaaaatttt aatggttcat agagccattg aagcttacga   5400
ttcttggtgg gtcacttttg ttcgagattt taggtacttg gagaagactt ttgtatgcta   5460
aacaagttat ctcattggct gaaactatga aatcagtttt ttttccagat ctgttcgccc   5520
ggacgacttc cggataagtc ttctggctgt agacgactta catcgaagta ttctggttaa   5580
tgcagatgtt agttttgcaa ttgactttta agatgcttac tcgaagatta gtactcttct   5640
```

gttcttgtac cttatgagca ttccaatagt attatatttt tcattctaaa atatatttca 5700
atgatatttt acttttcact ctataataga gtgaaaatga gtttacttta taatccccta 5760
tatattattt gtgaaacact acaacttctt tttgtagcca catgtcatca ctaggatgat 5820
ttttagaatt attagagaaa taggttggtc catctaatta tataataagt tttttattaa 5880
attaaccata aattcattat taatgtcatt tattatttcc ttaaataaag attacggaat 5940
tgcctaatgt gggtaaagta tatatgacaa ttaatgatct tgaataataa agatatgata 6000
aaaaaaatgt atcttctatc aaatttgttt aatttaaaac tattaaaata atttttaaaa 6060
aaacacaata accatattat aaaaatttag atttttctgt atatttttat attttgaact 6120
ttaaaaaatg acgataaatt actaaaactg ttaaaagtct cacattcaaa ttttgctatc 6180
catgttttaa aatttttgtt atgacaaaat acaaatgatt acaaaatcat ataagtaaaa 6240
gtctaattta attaatcatt aagatttaaa atatatatgt atatatatca ttctaaatta 6300
aactataaac catattgaat aaataaatat tttagtttca aaattttact ttgaataatt 6360
ttttttgata aaagttttga actaacattg ataaatgttt ttaaactatc aattaccaaa 6420
attattgatc ccacaatgaa aattttgtta tcagtaattt aaa 6463

<210> SEQ ID NO 25
<211> LENGTH: 4034
<212> TYPE: DNA
<213> ORGANISM: Brassica napus

<400> SEQUENCE: 25
aagccagaaa aaaatgtgga agtgtaataa aacaattttc tccaggaaga agatatttca 60
gccattcgcc tatttatgtg tatgagatcc cattcaagga catactgttt tccgtgagct 120
actgaatgaa tacgatgctt ttgttgtaaa cgcaacctat tggttttttt tttccgccaa 180
gttttgtttt tattaatcaa acgggccaag cccaaacggt cgaagcccaa atacactaag 240
taccaaacaa aaggcccaca gacacaacgg gctacaacat taatggctga agcccaagta 300
aactaaacgg cccaaaggcc caaacattga aaccggacag cttgacctag gcgcgcgata 360
aggagactgg ggtttgaaca cgtgtaagaa tctgggccat tagtatgaca cgcgtcgccc 420
gcctcgactt gatcgaaacc tcttcgcaca gccgcatgaa cttgccaccg acgacctcgt 480
ttcgccggag ctcagagact gaagagcctc caacgaaacc atagctattc tacgccgctc 540
tgtcttcacg ccggagagtt ccatcgatct aacgagatct cctccgacta tgtatcacca 600
caaaccctag acaggcgagc cgagaaccac tgatatcctc ctcttgtacg tcctcgccgt 660
tgtcggagag tttcatcatc atccgagatc tcatccgcga tggcccacga ccccatacct 720
gaccacaaga accacaccgc acttatctca cctcgatcta atcaccacaa cccaaaggac 780
atcgggttcc aagacggcag cgcggagctt tgcaagcctc cactctccgt gaccaaaagc 840
cggcgaagac ggagctgaat gagcctcccc ttcccggaag ctaaagcggc gacggtggat 900
ctgagaaagc ctccacctcc cgcataaaga ccggcgacga tggatctagg gtagcctcca 960
tctcccggaa aaaacaccac ctgaacatgc aagccgctcc atctccaccg ggagcctcca 1020
attgatcgcg tcgttactcc aaaggccgag ccaccgttga tggatggttg cggtcccaga 1080
gctccgacaa ggcgatcgat gacgggactg cgaagaagga gcggagagtg acaactacaa 1140
aggaagggaa agagctctgg cgacagcacg gacgctcacg cgccagccgt acgccgaacc 1200
caaaagtaga tctggtttct ctcttttctc tctctcgcaa aagaaaacac gcaacctatt 1260
gttctccatt ttgaatttga agtgttacat tattaataaa aaggaagaaa gtacaaagct 1320

```
tttcatttag tggttgttgc atatatagta tacttatttg atgggcttat gataagtatg   1380
aacatttcac gtaacgggtt tattttgtcg tcaacacatt accggcaatg tgaaaagaag   1440
gggcgaggta tctccatttc aattcttctc tttatagatt aatcgaatta tttacatatg   1500
aaatgagcgt ttatatagaa ttttcgtgtg gaaaacgaca tgtacacggc atcgaaagac   1560
caattagtaa tatactttag tggtgattac atgtttactt atccaattga gaatttaaag   1620
catcgacaat accttaatgt cgattaagcc gtccccactt catgtaatga gttatggggg   1680
gagagagagg tcccgaaatt cgtcaaataa aacaacttag aactaaaaac cgacaccaag   1740
tatcataaag gaaacgttga agaagtcatt tatcgtatcc agctcacaat tcctaagatt   1800
aaatcatgac cgttggaaga gcttataaga ttaaattgaa gaaattgtgg gttttagaag   1860
aaagacaaga aagagaagaa catgatctta cattgcctat tttggtgtat aggagttgtc   1920
aaaaagagga gagagaggag acaattaggt caaataaatg agcactaaaa atggagacat   1980
gtgttgagta actattacaa gagcgactta tgcttctaga accaagcctt tctctaatcc   2040
ctaagatcat agctactgaa ataatgaaaa aaaacaaaaa aaaaacaatg aagaatcagt   2100
tgggcattag tccaaaaaaa aaaaagaatc agttggattg cttataaaat tttgttataa   2160
aatttatgtc gtatgtgtgt tagccgtagc tgtaaattta tttcctttgt atgttaattg   2220
taaaatttaa tttattattc ccgatgtttt taatgatgta agtttacatc aagaaaacat   2280
attaagttct gttaataaat gtattatttt tgtttactaa tttccaataa ttttttcaag   2340
aagtacaatt ttttgtttga aatttctaat ttatcaacat acctaaaaac cataaacatg   2400
tatttttttga aacatttttt taatataaaa attatttttt aggagcaggt gaagtatttc   2460
ttttaataaa attgttagtg tatttacgtt ggttatagtt gtagatattt tgcataataa   2520
ttaataatat ataagatgtg taatgtatat atgtgagaga aataccatat ttactaagag   2580
tttttcgcaa tattgactca aaattcaaag tcaatcacaa aactaacata tgtttctttt   2640
tagacatttc ctttgcctta ttcactccac gggttcagat tattcacgaa aatgtcatta   2700
aattttttttt cttttcgaaa atggcatttt tactctctca atttcatcct cttcaagtat   2760
ttacaagatt tccattgcca tcaatacacc aaccacaatg aacaaccaat ttgaagctct   2820
taatgcacct caaatcgatt tacacttctt ctttttcaat tcttatgaac taaaaacaac   2880
atctctttca atttctcccc atattcatcc aaaaaaccca agatttttat tctaaaattt   2940
taatggttca tagagccatt gaagcttacg attcttggtg ggtcactttt gttcgagatt   3000
ttaggtactt ggagaagact tttgtatgct aaacaagtta tctcattggc tgaaactatg   3060
aaatcagttt tttttccaga tctgttcgcc cggacgactt ccggataagt cttctggctg   3120
tagacgactt acatcgaagt attctggtta atgcagatgt tagttttgca attgactttt   3180
aagatgctta ctcgaagatt agtactcttc tgttcttgta ccttatgagc attccaatag   3240
tattatattt ttcattctaa aatatatttc aatgatattt tacttttcac tctataatag   3300
agtgaaaatg agtttacttt ataatcccct atatattatt tgtgaaacac tacaacttct   3360
ttttgtagcc acatgtcatc actaggatga tttttagaat tattagagaa ataggttggt   3420
ccatctaatt atataataag ttttttatta aattaaccat aaattcatta ttaatgtcat   3480
ttattatttc cttaaataaa gattacggaa ttgcctaatg tgggtaaagt atatatgaca   3540
attaatgatc ttgaataata aagatatgat aaaaaaaatg tatcttctat caaatttgtt   3600
taatttaaaa ctattaaaat aatttttaaa aaaacacaat aaccatatta taaaaattta   3660
```

gatttttctg tatattttta tattttgaac tttaaaaaat gacgataaat tactaaaact 3720
gttaaaagtc tcacattcaa attttgctat ccatgtttta aaatttttgt tatgacaaaa 3780
tacaaatgat tacaaaatca tataagtaaa agtctaattt aattaatcat taagatttaa 3840
aatatatatg tatatatatc attctaaatt aaactataaa ccatattgaa taaataaata 3900
ttttagtttc aaaattttac tttgaataat ttttttgat aaaagttttg aactaacatt 3960
gataaatgtt tttaaactat caattaccaa aattattgat cccacaatga aaattttgtt 4020
atcagtaatt taaa 4034

<210> SEQ ID NO 26
<211> LENGTH: 3168
<212> TYPE: DNA
<213> ORGANISM: Brassica napus

<400> SEQUENCE: 26
atatggacca aaacatgaat gatttttcgg aatcagatac tccattcagc ttcgaacagt 60
tattatatgg agatgattgg cagaggtggg acacttatcc gagcgttgat gttaatgcca 120
actcaataga gcctaatcat tcgatggtcg agatgaacca tgatggtatg acaatagatg 180
ctactccaat ttcaatgata tatccaatgg taataatcta ctttctgcat gtttttttta 240
gagatattaa agtatggata aataatataa gacttattga aaatgtatag gaagaaacat 300
tcgagcagtg gttacagaca ctggccaatg gatcatttga aataccatca tatgaagaac 360
tcaacttcac gtatgaggta tggtgaaaga taatatatat aaaggtatat tttatgtaac 420
atataatcaa tttattggta acttatttgg ttatattgca tttgtacatt tttttctcag 480
tggatatgca tttgaatcat agttgaagaa aactaaaagg aatatatatg ctgcaattgg 540
attgttgatt tttaaaatga tatgacgtcc aatgacttat ttcattattt ccataaattt 600
ttacagtatt taacatgaat agaatgaaat actcattcca tcaattccac aaacattcca 660
aaaaatatac aaaaaataca ttcatatgca attttaatta tgagtgaata gaatgaaaat 720
atttcttttt taactaattc cattcatctt attccatcta ttttgattcc actaatttca 780
tttcattgtt accattgaca accataatgt gcatggttgt aaatttagaa ctctgtaacc 840
atatatatat atattcaaaa gtttattagt gtattttttt ctaggaatta ttgctcatta 900
gtgagcagat aggagatgtc tgcattggtg tagacgttga tatcattgag gggaatctga 960
aacgaagaaa gtatgaagat cgttctggtc aagcggagaa gtgtgtgata tgtctcgatg 1020
aacttaagtg caatgatgag gcttctacac tggcatgtgg gcatgatttt cactacgagt 1080
gtatcaaaaa ctggctaatg gtcaagaaca agtgtcctct ttgcaagcaa caagctcttt 1140
aattgtttca tgatgctgaa tatttgaatg tgttagtatt gctaacattg gtttcttttg 1200
ttcaagtatc ggtattcggt agtttaataa aaacaaatat ggaagtttca taacaaaaaa 1260
aaaagtctac caaaatttat gcaagttaat tatcattcaa gacaacaccc actgcaattt 1320
gtcaaaaatg gtgaaactct tgcaagacct tacctgtgaa gtgattgtcc tttttcatgt 1380
ttaataataa taattaatta cagtattatt tatgactttc agaaaactct atctatcaac 1440
cgttctttac tgatttttcc acccatcact gctctatttt ttatttatgg catcgggaaa 1500
aaaagagaag aaaaagaaat attatatgca atcttttttt tttttttttt atgcaatctt 1560
accgggtgtt aatacttata actacattta gtgataaatc tgctttgtta aatccagtac 1620
aaaatcaatt attgaattta tagactataa agttgtgaac aaaatacaaa ttatcactaa 1680
tgggaatatt catatacagt ataataacgt aagccaccag attatggcta gagtgatttg 1740
ccacgcgcct gcctatttat tatgaaaagc ctcagtaact ctgtgacgag aagaattcac 1800
agagagagag aggagagaga tgggtaattc cgacgaaggt ggtcgtcttc ctgctccatc 1860
ttcttcagac gaactctcga gcattctgcg gcaggtactg tcccgtactc ccacagctca 1920
accttctttc tcaccgaaga aaatcgtttc ctccgctgag atgttcaacc gaacattccc 1980
cctcgttccc ggcggagcgg tttcttacgc cgcttgtgca gccgctgaaa ctggggaagg 2040
caaatgtggt ttcgaaaaca aggtaaactt aacgatgtta gttgccgtga aactaccctc 2100
cttttgatta aagaaaaaaa ataacttagt tgttgttttt gcttggtaat ggttaacaca 2160
acactaaaga gaaatggagc taaacagcga aattcattga agagaaacat tgatgcacag 2220
tttcacaact tgtctgaaaa ggtttttgtc tttatccttt ttaagattct tgatttggta 2280
aaaaaaaaac tagagataat aatagaaact ggatatattg cagaggagga ggagcaagat 2340
caatgagaaa atgaaagctt tgcagaaact gatacccaat tccaacaagg tggtaaatac 2400
caagttcgcc tttttatcct tcagaactca gttgtgagaa ccatttgttt tgttttttat 2460
gttttgtaga cagataaggc ctcaatgctt gatgaagcta tagaatatct gaaacagctt 2520
caacttcagt ttcaggttct ttttctatat gttccttacg ctatgatcat gaacaactaa 2580
atttgtaaaa ccaaacatct gattaactta atgaatgcag acgttagccg ctatgaatgg 2640
tttaggccta aatcctctgc gattaccacc aattctaccg cctacgcaga caaggatcac 2700
tggaacctca gaacaagggc tgaaccttga gactctgctt ggtggttctc actcgatggc 2760
taaccgtgaa ccacccgaaa ctcaggaaat gtgctttccc acaaccactc tgctttgaag 2820
acaacgttca gacagtgaag aggatccgaa gtcagatttc ctctccacag aaacatgagt 2880
cgaaaatgat ttgtagagtc tagtatttgg ttatataagt gttatgctaa taagctttag 2940
gactgaacaa aactgagtag cttcattata atgatgtcag aataaattta actacatgat 3000
taagatcaaa tggctatgtc tgtgagttgc agccatccgt acgcacaccg gtctcggata 3060
cttcgagcca tggatgctgc tgactgaacc gcaggtctta tcttcgtcaa tgctttctct 3120
acttgaattc tgacaccaac atccatctgc actgattccg gcgccata 3168

<210> SEQ ID NO 27
<211> LENGTH: 7697
<212> TYPE: DNA
<213> ORGANISM: Brassica napus

<400> SEQUENCE: 27
acatgaatga tttttcggaa tcagatactc cattcagctt ccaacagtta ttatatggag 60
ataattggca gaggtgggac acttatccga gcgttgatgt taatgccaac tcaatagagc 120
ctaatcattc gatggttgag atgaaccatg atggtctgac aatagagcct aatccaattt 180
caatgatata tccaatggta ataatctact ttctgcatgt ttttttgaga gatattaaag 240
tatggatgaa caatataaga cttattgaaa atgtatagga agaaacattc gagcagtggt 300
tacagacact ggccaatgga tcatttgaaa taccatcata tgaagaactc aacttcatat 360
atgaggtatg gtgaaagata atatatatac atagaaaaca atatatatat atatatatat 420
aaaaaaataa aagggtatat tttatgtaac atataatcaa tttattggta acttaattgg 480
ttatattgca tttgtacatt ttttcgagtg gatatgcatt tgaatcatag ttgaagaaaa 540
ctaaaaggaa tatatatgct gcaattggat tgttgatttt tggaatgata tgacgtggaa 600
tgacttattt cattatttcc ataaaaaatt ttcagtattt aacatgaata taataaaata 660

```
ttcattccat caattccaca aacattccaa aaaaaaacat tcatatgcaa ttttagttat    720

gaatgaataa aatgaaaata tttctttttt aactaattcc attcatctta ttccatctat    780

ttttattcca ttaatttcat ttcattgtta ccattgacaa ccataatgtg catggttgta    840

aatttagaac tctgtaacta tatatattca aaaatttatt agtgcatttt tttctaggaa    900

ttattgctca ttagtgagca gataggagat gtctgcattg gtttagacgt tgatatcatt    960

gaggggaatc tgaaaggaag aaagtatgaa gatcgttctg gtgaagcgga gaagtgtgtg   1020

atatgtctcg atgaacttaa gtgcaatgat gaggcttcta cactggcatg tggacatgat   1080

tttcactacg agtgtatcaa gaaatggcta atggtcaaga acaaatgtcc tctttgcaag   1140

caacaagctc tttaagtgtt tcattatgct gaatatttga atgtgttagt attgccaaca   1200

ttggtttctt ttgttcaagt atcggtattc ggtagtttaa tgaatacaaa tatggaagtt   1260

tcataacaaa aaaaaaagtc taccgaaatt tatgcaagtt aattatcatt caagacaaca   1320

cccactgcaa tttgtcaaaa atggtgaaac tcttgcaaga ccttacctgt gaagtgattg   1380

tcctttttca tgtttaataa taataattaa ttacagtatt atttgaaact ctttgtaaac   1440

ttaaagtact tttcttattg aatgaaggca acataagagt tgcttaaata acaaagcgta   1500

cagatactcc cgacagtttt ggtaaagtct taaccacttc ctatagtaga ggaagactta   1560

ttcaaataac ttaaagcaga aaataattca aaactaccaa ctaaagactc taccaactaa   1620

agactcgatc ttttttattc attaatccct cccttaaact tgaactcctt tataaagttt   1680

aaacttcctt taagctgact cccatgtgtg ctctcagctt ctcaaacgct tcaagtttca   1740

ccggctttgt catgatatcc gacaattgct tatgagttga acaatactcc attgagatga   1800

tgccttcatt cacaagctct cttaagaaat gaaacctcac atgaatatgc ttgcttcttc   1860

catgtagaac aggattcctt gacaacttga tagctgaact attatcacag aaaagaacag   1920

ttccatcacc ttgatcaaac ccaatttcag ccaacacgtt cctcatccat acagcttgac   1980

aagctccaat tgctgcagca acatactctg cttccgtggt agagagtgtg acaattggtt   2040

gtttctttga gctccaggac acagctcctc ctccaaacat gaaagtgtag cctgatgtac   2100

tctttctgtc atcctcatcg cctgcataat cactgtccac ataccctaca agcttttctt   2160

ctccaccacg caagtactga ataccatagc ttgcagttcc ttgcacatac ctcaaaatac   2220

gcttaacagc catcatgtgc ccttcatttg gattctccat gtatctacta accacattca   2280

cagagtatat cagatcaggt cgagtagctg ttaagtacct caagcttccc acgagttgct   2340

tgtaagcggt tggatcaact tcttctccag ctcctgtctt ggtcagtttg ttccctggaa   2400

ccattggatt cttcacagag ttgcagtctt tcattccata cttctttaaa gtctccagtg   2460

catacttctt ttggccaata aagatcccaa cctcgtcttg cacaacctcc acgcctagaa   2520

agtacttcat ctttcctaga tcagtcattg agaactcttc ttgcattgaa gttttgaagc   2580

tctccagcat gctttccgag ttactagtgt aaatgaggtc gtctacgtac aagctcagga   2640

tcaacgagtt cccttcttct gtttttacga acaatgtgtg ttcgcaataa catttctcaa   2700

agccttcctt tataaagtaa ctctcgatcc tgctatacca ggccctagga gcttgtctta   2760

atccatacaa agccttttc aacttgtaga ccttctcact gtcaacctga gactcgaacc   2820

ccttaggctg ctcaacgtaa acgtcctcct taagctcacc atgtaggaac gcgctcttca   2880

catctagttg atatacactc catcttcttt gagccgctaa gccgagaatc agcctgatcg   2940

tgtcccatct ggccacaggt gcaaaaactt catggaagtc tactccatag gtttggtgaa   3000

agccctttgc caccagtctc gctttgtact tatccacctc tcctttttca ttcaacttgg   3060
```

tcttgaagac ccatttcact cctatcacct tcacattggc aggtagacta accagctccc 3120
aagtgttgtt atcctctatt gattcaatct cagtttccat tgcctttctc catttgtcat 3180
gttggatagc atcttcaaac ttctctggat cctcatctga caagaacagc gcaactagtt 3240
cttctccatc atcttccatg ataagacccc tcccatcaac cacgtaatct ttcatccaga 3300
ctggtcttag tttgcttctt cctgctctgc ttgtgtctga tctttcttct ggtgtagaga 3360
cagttctttc tccatcagac tcagtgttat ctcctccttc tgtctcttcg ttagttgctg 3420
gtgctgtcac caggttctca ccctgattcc tctcttcctc ttcttcagct tctccacatt 3480
cgacaaattt gtcttcatca atgttatctt cccagttcca ccgcgtttct tcgtcaaacc 3540
tcacgtcttt gcttattatg atcctcttcc caataggatc ataaagtctg taagccttcg 3600
actccttgct tacaccaaac atgacacatc tcacactttt ctcatccagc ttcacacgct 3660
tctcataagg tataagtgca taagccacac agccaaacac acggagatgc tctacagacg 3720
gcttgtgctt actccacttc tcacttggcg tcacttctcc caatatcttt gttggacttc 3780
tgttaagtat atggacagca tactgtgttg cttctgtcca atacttgatc ggcaccttca 3840
taccaaacag catgcacctg accatattca gaatgcttct attcttcctc tctgccacgc 3900
cgttctgctg aggcgtgtat gcggctgtca gctgtcgttt gatgccgtgc tccacacaat 3960
agtcctgaaa cgcctttgaa ttgtattctc cacctctgtc ggttcttaga cagacgagca 4020
gctcaccact ctccctctca gcggcatttt tgaactcctt gaaagttcta agtgcctctg 4080
atttctctgc tagaaagaag ctccaacact ttcggctaaa ctcatcaatg aaattgatta 4140
tgtacctctt gccgctttca gatgtgggtg atattggccc gcagatgtca ctgtgaacta 4200
gctccagtcg ttgtgttgct ctccatagac tcttctttgg tatcttttct ctgatctgct 4260
tccccttcat acacacctca catactgtcc cgttggtgtt gatctttggt agaccttcca 4320
ccatcgcctt ttctgctagt gttagcaaac tgttgtggtt caaatgtccg aagcgtttgt 4380
gccaagtttc ctccattgtc tccatcgtat tctgaacttg gtttgcctcc aacgcttcct 4440
taggctccct gacaatagca gttactacaa acatcctgtt tgtggtcatc agagaatgca 4500
tgatcagtct ccgttgttgt ttgtgccaga tctcacacgt atctccttca attataatcc 4560
tcaacccctt ctgttgcaac tgaccgacag acagtagatt gttcttcaag ccaggcacaa 4620
agtatactgc agtgatcact tgagtagtac cattgatctc caatcttagg ttacctcttc 4680
cctcaacttg cattcgccta tcatctccaa gctttacttg ttgtctgaac tggctatcaa 4740
actctgaaaa ccactccttg gttccacaca tgtggttgct acaccctgag tcaaggtacc 4800
acacgtgtct ttcttcagtc tcaacttgag tcatcagcaa aatatcctcc tctaactctg 4860
catagttagc tgccttctcc cagctaggac attcgttttt gaaatgcccc atcttgtggc 4920
acttaaagca ctcaatgttg ctcttgtcaa agcttgtatt tcctctgtct tgtcctccac 4980
gacctcctct gtaactgcct cttcctctgg tttgatatcc tcctcgtcca ttggagtaac 5040
ctgagtagcc acctcgtccc cttcctcctt ccatcttcag gacttgttcc tctcctgtgt 5100
gtttactcag gttctgctca tgtacgagta atgagctttg taactcatcc accgacagct 5160
ccttgatatc ctttgattcc tctatcgcac ataccacata tgtgaacttc tccacaaggg 5220
ttcttaggat cttctcaacc accttttcat ctggcatgtc ttctccacgg ttccgcatgt 5280
cattagcaac caccatgact ctagagaaat agtctgcgat tgagtcacct tccttcatct 5340
ccaggacttc aaagtttctt ctcagcctct gtaattgcgc actttgaacc ctcttgttgc 5400

-continued

```
cttggtactt tgccttcagc gactcccata tgtcttttgc ggtgtccttc ttcacaatcg   5460
tcttcagaac agtcttgtcg atggaggcaa agagatagtt cttcaccttg aagtctttga   5520
gcttttgctc cgcaagctcg gttctctgag cttcagacag tgtcacacta ctttcatgtt   5580
gaatgattcc ggtattgatc agttcccacc actccttgga tctcaacaaa ttctccataa   5640
gcattgccca atgctcatag tctccatcaa gctttggtat gctcaacgag gactcctttt   5700
cactcatctc tcttactttc ggattaccta gaactcacaa cagtttttgt tagagctctg   5760
ataccacttg aaactctttg taaacttaaa gtatttttct tattgaatga aggcaacata   5820
agagttgctt aaataacaaa gcgtacagat actcccgaca gttttggtaa agtcttaacc   5880
acttcctata gtagaggaag acttattcaa ataacttaaa gcagaaaata attcaaaact   5940
accaactaaa gactctacca actaaagact cgatcttttt tattcattat tatttatgac   6000
tttcagaaaa ctctatctat caaccgttct ttactgattt ttccacccat cactgctcta   6060
tttttattt atttatggca tcgggaaaaa aagagaagaa aaagaaaaat tatatgcaat   6120
tttaccgggt gttaaaactt ataattacat ttggtgataa atctgctttg ttaaatccag   6180
tacaaaatca attattgaat tcatagacta taaagttgtg aaccaaatac aaattatcac   6240
taatgggaat attcatatac agtatagtaa cgtaagccac cagattatgt ctagagtgat   6300
ttgccacgcg cctgcctatt tattatgaaa agcctcagta acttgtgatg agaagaattc   6360
acagagagag aggagagaga tgggtaattc cgatgaaggt gatcgtcttc ctgctccatc   6420
ttcttcggac gaactctcga gcattctccg gcaggtactg tcccgtactc ccacagctca   6480
accttctttc tcaccgaaga aaatcgtttc ctccgctgag atgttcaacc gaaccttccc   6540
cctcgttccc ggcggagcgg tttcttacgc cgcttgtgca gtcgctgaaa ctggggaagg   6600
caaatgtggt ttcgaaaaca aggtaaactt aacgatgtta gttgccgtga aactaccctc   6660
gcttgttgat taaagaaaaa aataacttta ttgtgttttt ggttggtaat ggttaaaaaa   6720
cactaaagag aaatggagct agacagcgaa attcattgaa gagaaacatt gatgcacagt   6780
tccacacctt gtctgaaaag gttttgtctt tatcctttta agattcttga tttggtttaa   6840
aaaaaaaact agagataata atagaaactg gatatattgc agaggaggag gagcaagatc   6900
aacgagaaaa tgaaagcttt gcagaaactg atacccaatt ccaacaaggt ggtaaatacc   6960
aagttcgact ttttatcttt cagaactcag ttgtgagata catttgtttt ggttttttt    7020
tatgttttgt agacagataa ggcctcaatg cttgatgaag ctatagaata tctgaaacag   7080
cttcaacttc agtttcaggt tctttttcta tatgttcctt acgctatgat cataaacaac   7140
taaatttgta aacccaaaca tctgattaac ttgatgaatg cagacgttag ccgctatgaa   7200
tggtttaggc ctaaatcctc tgcgattacc accaattcta ccgcctacgc agacagggat   7260
cactggaacc tcagaacaag ggctgaacct tgagactctg cttggtggtt ctcactcgat   7320
ggctaacctt gaaccacccg aaccaactca ggaaatgtgc tttcccacaa ccactctgct   7380
ttgaagacaa cgttcagaca gtgaagagga ttcgaagtca gatttcctct ccacagaaac   7440
atgagccgaa aatgatttgg ttatatttca aagtgttatg ctaataagct ttaggactga   7500
acaaaactgc tactggttat atttcaaagt gttatgctaa taagctttag gactgaacaa   7560
aactgagtag cttcattata atgatgtaag aaaaaaaatg tataaattta actacatgat   7620
tacgatcaaa tggctatgtc tgtgagttgc agccatccgt acgcacaccg gtctcggata   7680
cttcgagcca tggatgc                                                  7697
```

<210> SEQ ID NO 28
<211> LENGTH: 7239
<212> TYPE: DNA
<213> ORGANISM: Brassica napus

<400> SEQUENCE: 28
ataatataag catgttgagt cctattcatc agaaaatttt ctccaaagga tgaacaataa 60
cctacaatta aggaaactta ttataacaac gaccaagaag ttttcccata agtcatgctt 120
tcgtccatac cttcgggtct ttcaagcaag cttcacacat gccttatcgt atatttgtat 180
acgttttcat tttgtgtacg tctattaatt agtatatgcc tagattatat atttatatag 240
tcgacaatta cctatcctaa aggtttattt taatttttat tcagaaagat atgcacgtag 300
ggccactagt gtttcccgtt gttattggaa attccatgtg ttgaactgtt tgattaagtt 360
tttgaacccg taagtcaaat ttatttaggt ttaacagggt ttcattactg ttataagctt 420
gtcaagaaag aatttgtcac aaatttcgag actcatgcat gcatgcatgt ttcttaactt 480
tcgagaaaca tgaagtgtgg ttttaccagc tgaagtttgt gttaaaacac atttttaatt 540
tgaccacgtg tgatattcaa atatcaacaa ttctgttcaa cgggagattc atacatatgt 600
tcagatgttc tttaatcttg agcacctaac tttgcttccc atacgcaaat gtgtgtgccg 660
cgaactatgg tgaatgtacg gcatcgtttt tctttttgga gcatttttaa aagaaaatat 720
aatttagtta tttccgtttt gattgatata gatgcattaa taaaccgact tacgtgggtg 780
atgggatgag caaaattaaa atatgcattt tagtaaccaa ttacggtcca tcttgacaaa 840
ctaacaaaca aaaagtctat tatgacgttg atttgtgacc ttgccatata aatgccaaaa 900
tttcattctt tcaataagca acgagatcaa taagatgtgg cagtcacgtg aacgttagtt 960
atcgccattt caactgaacc ttcacgaaca tataaagttc atttgttctt tgctaaaatt 1020
acgcaaatct ctgttgtgca cgaaattacg actatttttt aatgacaact cctgttcttg 1080
tatcgtgtat ctagcacgta aatttgaatt atggcggcat tatcgataaa atatgtaaag 1140
aatatatttt catcatacac cacaaacaaa tgttctggaa atatcacctt ttatcacata 1200
tacaaagctg accctgaatt tttggaaact acaagccaaa aaaaaatgga caaaagaaaa 1260
attatgcaca aaagtggact cgtcctaact ctttttataa tgataattaa cctttgaaca 1320
actaattaat acatacaata tgtttttttt ttctaaaaat tggtcgatta aatattcata 1380
tataatcctc atcatcattt attagccttt tgtagcttac ttaaaaaatc acttcccacc 1440
aaattgatta tttttcact tcatacgttg atcaatttaa aaaaaaaata ataataatat 1500
atgcacgtcc ggcgtcccat gacttcagac gcttttctgt ttccttgatt ttataggtta 1560
gaaatttcca aaatgctcat atttttcact gatatgtatt atacgcacaa aatagtaaag 1620
tcataaaaat ttatgatggt tcttttatat gtatagagta gtgaaaattt atatatattg 1680
tagttccgct taaaataaat taatattttt cttttatcgc ccatatttaa gttactaaac 1740
gtatataatt aaaaactgaa atgcaatatg tagaaatccg ggcattgatt gttgattaac 1800
attgatatac ccatgcgact ggcttatgat gaaccatacc tgctaatact cattgttaca 1860
aactcgcagc aacatcataa atccatcact cgccacaata attttcttca gtgtatgttc 1920
aattgatcac attttgaccc ttcactttct tgaatgagaa attatacaag aaagtgattt 1980
gagtgtgtta aaaaatgatt tgtcattctg accaattatc tggcagagag tataataaaa 2040
tacttctaat taccttaaat cattaggcgt tgtttcttgc cgaatatatg atggagcatg 2100
gtctcgctaa gagacaacaa aatctttaaa taaattaaag aaattgttta gcaaaaaaat 2160

```
taaataaatt aaacaagaga gagtacaaat ataaaacact ctaacggaag ataaatatat   2220
aaaatacaaa atatagaata gaggcctcaa gtagtgttta cgtgacaatc tcaatttcac   2280
tccatacctc gaactcattc aagcttagaa acctaacttc tactgttcct tttgatttgc   2340
ctataaatac acgttggtcc atacttctct aatttcaaat atacaaagca aaacacagag   2400
acaagaatca taaataacaa acattttcaa cataatccca aaaaacgaca cgcgttcctt   2460
ttccaaaaat tcacttctct acgtaccaac cacaatggct cattgttgca cagttcttac   2520
cggtttacta gtatggtctc tttttatgct ctcatggtgt gaagcttcaa gaaacaacat   2580
taatagatat gatcattctt atggaacgtt caaatccaat agcttaatca agcgaagaga   2640
cgatataact cgtctgaaaa gtgttgcaag agcctctttg cggcttccaa ccaccgttag   2700
tgtttctgat tttggagcta aaggagatgg aaaaaaccgac gacacgcagg tatatacgca   2760
tatacacata tctacatgac ttataaatat tttgagacgg tcacgcatat aaatttacgt   2820
tgtttgtact aatgatccat gcatgcgcat gcatatgatc aggcgttcgt gaatgcatgg   2880
aagaaagctt gttcttcaag tggagctgta aatctcttag ttcctgaagg aaaaacttat   2940
tttctcaagt ctcttcgatt aaatggccca tgcaaatcag ttcttaccgt tcaggtaaat   3000
tacaaagttt ttttttctta aatttgggta aattacaaag ttgactattt gttaattaaa   3060
tacgtatact acatgtgatc acgtatatgg ttttgaatat ttaaatgagc ggttgatgaa   3120
tggaacgaca gattttagga acgttatcgg cttctcaaca acgatcggat tatgaagatc   3180
tcagcaaatg gattacgttt gacggcgtta acagtctaac ggttgatggc ggagccaccg   3240
gaactgtcaa cggaaacggc gaaacgtggt gggaaaactc atgcaaacgg aacgaagcta   3300
aggtgtgtgt ttgtacatgt ttcatttact taatatatat ctactgtcta catgtcatct   3360
tgatatatta acactctttt attgttattg ttttgaagaa atgcacaaaa gcccctacgg   3420
tacgtagaaa catatttgac attttcatgt aatactgacg atggcggtga tcatgattgg   3480
acaaatgttt tacatgcatg aatatatgta ttttatatgc aggctcttac tttctacaac   3540
tcgaagaatt taagagtgaa taatctgagg gtgaaagatg cgcaacagat tcagatttcg   3600
attgagaaat gctccaacgt tcaggtctca aatgttgagg tcactgcacc tgctgatagt   3660
cctaacactg atggtatcca catcactaac actcaaaaca ttcaagtctc caattccatc   3720
attggaacag gttagtagtt atatcctcgt tatttaaaag agttgcgtgc atatccagaa   3780
aactaaaatt taagagtatc gttataattt ataattttat agagattggt cttaaaagag   3840
tttttaatgg ttgcttttct ttgcaggtga tgattgtata tctattgaaa gtggatcaca   3900
aaacgttaaa atcaacgatt taacttgcgg cccaggccac ggtatcaggt atcaatgaat   3960
tgttttcagt atatgtacct aagaaattca accgtaatct tttaaattaa catagaaatt   4020
tgatatttcc atataaaaca tgagcagcat tgggagctta ggagatgaca attcaaaggc   4080
atttgtatca ggcgtgactg tggatggtgc taaactttcc ggtacagaca atggagttag   4140
gatcaaaact taccaggtga aaatcacaaa ctagaccttc aattttaact agcctattga   4200
caagttcatc tcaatttaac ttttaaaccc aattcaatat agggagggtc tggaactgct   4260
agcaacatta tatttcagaa cattcagatg gagaatgtga agaatccaat cataattgac   4320
caagattatt gcgacaagag caaatgcact gaacaagttc gtttgaatct gatcaaatct   4380
cccattacta atcatcatga taataaacac tattgtctct aatcatttac tacatatatt   4440
ttcagaaatc agcggtccaa ataaagaacg tggtgtaccg gaacataagc ggcacaagcg   4500
catcggacat agcaataact ttcaactgca gcaagaacta tccatgccaa ggaattgtac   4560
```

```
tcgacaaagt gaacattaag ggagggaaag ccagttgcag caatgctaat gtgatggata   4620
aagacggtgt tttacctcag tgcaaatcca cttgattaat aagacctata aaaaaaactc   4680
acatagatgt ataaaaatac atatataccg atacaaagta tacaaaatta tgatatacac   4740
ttgtggatat atacatggac aatgaattta aacatattgt ctatatgtca aaaatagttt   4800
atgaatatac atatagacaa catggtcaag agatttattg ttttaatgta tatatatact   4860
actaaactac ttgtctaaaa tttcatgaat aaaggattac gtttttaagt ggttatgtat   4920
catgatgtgg ttacagtatg atgtgtattg tagattttca attaaataca taaaaatgaa   4980
aaagatgaca tggctggtca atgatgttac ttgaccaact aattcaagct aattgataca   5040
cgatgaacat ctaacgaaac agaagcgact ttcatattgt ttagttgtgc tcaaaccagg   5100
ccgataaact cattgggcct ataagcccat taatatttat ccgtgagagc gaagtctgtt   5160
acttgggtta ctaaacaaag aggcctttag aaaaccctaa ctcttaccgt agcacctgag   5220
ctatatattg ccgcagctag ggtttccact ccctcacgct aacacacatc accgcagcca   5280
tttccatctc tcaaccaact tcaaacaatg gctgaacgag gcggagaacg aggtgccgag   5340
cgaggaggag accgcggcgg tttcggacgc ggattcggag gaggtcgcgg cgacagagga   5400
ggccggggag gtccgagagg ccgaggcggc agacgcggag gacgtccgac agaggaggag   5460
aagtggaccc cagtgaccaa gctcggccgt ctcgtgcaag ccggaaagat ccagaagctc   5520
gagcagatct acctccactc cctccccgtc aaggagtacc agatcatcga cctcctcgtc   5580
ggccccacct tgaaagacga ggtgatgaag atcatgccgg ttcagaaaca gaccagggcc   5640
ggtcagagga cgaggttcaa ggcctttgtc gtcgtcggag acacgaacgg gcacgttggt   5700
ttgggtgtga agtgctccaa ggaggtggcg acggcgatca gaggtgggat tatattggcg   5760
aagctgtcgg ttattcccgt gaggagaggg tactggggga acaagattgg gaagccgcat   5820
acggttcctt gtaaggttac ggggaagtgt gggtctgtta cggtgaggat ggtgcctgct   5880
ccgaggggtg cggggattgt ggcggctagg gttcctaaga aggtgcttca gttcgctggg   5940
attgatgatg tgtttacttc gtcgaggggg tctactaaga ctcttggaaa cttcgtaaag   6000
gtttgaactt tcttcattta tttagagttt ggagttgtgt atggattgaa agttgattcc   6060
tttttgatgg ttgcgtgtgg agttgttttg ggtaatttag cttgttgtag ttgatgtaaa   6120
gtgagaattg ctaagcttga ttagtttgaa taagctgtct gtgttaaatg atgatttgtt   6180
tgtgttgtat tgagctgtct gaatttcatt atttgtttgt gttattgcta aattacaagc   6240
ttaaatttga taacttttga ttctttcgtg agagtttttt ttgggtaata tagcttgatg   6300
tagttgatgg aagtaaattg ttaaccttta gagctgtctg ttaatggtga tttgtttgtg   6360
ttgtattgag ctgtctgaat tataatttgt ttgtgtttat tgctaaatca caaagctttg   6420
aagtcgtttg tacatattca tcatttttgt gtttattgac ttgtttgtgt ttattgctaa   6480
atcacaagtt tctatgatta atcttcatga tttggttgtg tttattacta aatcacaagt   6540
ttctatgatt aatcttaatg atttggttgt gtttattgct aaatttgaga ttacattata   6600
atcttagttt atacatgtat aacatcattt cacttgaatt ttcacagacg agctggtgat   6660
atgttttttt agtattttcc atgtattgct ttgtaagaac ttttaaatgt ttgttttctt   6720
cctttgaaga acaattaaat gtttgttcag tatttttgaa tcattcattg gttaatcatg   6780
tgtaatttta tttttgtagg ctacattcga ctgtctccag aagacttatg gattcctgac   6840
accagagttc tggaaagaga cgagctttaa aaagtcaccg taccaggagt acactgatct   6900
```

gctggccgag aagggaattg caaccaaagc catcaccgag gttgaagacc aagccgcctc 6960
ctaaataaac aaacaaacaa tgtcccccctt gttttgtttt tggatgatcc tttcttgagt 7020
tttattttgt tcgaaccttt agtatatgtt gtttgctgga ttgctgcttt cttatgtttt 7080
catcatctcc cccaaacaaa gttatttttg ctctagtttt tttttataat cgatggttat 7140
gccctctagt attttttta cttgaatttt tcactaattt tctatcaact tccctatgtt 7200
acactttcta aggttgatta cataggtgga ttgttgtga 7239

<210> SEQ ID NO 29
<211> LENGTH: 4666
<212> TYPE: DNA
<213> ORGANISM: Brassica napus

<400> SEQUENCE: 29
gtcttcgcat atgatagatc ataagatttg gagaaacata taaaattaac ctatgaaatt 60
aaggggatct atatattata gtatgtatcc aaagaacata tatatgaaat atttgaatac 120
atcataagat ttggggaata taaattaata taaaataaaa tcgtccaatt ttaaacgtaa 180
acgtctccgc tgtatttata taaacttttc aaaatcacgg tgtcgctcgt gttaagattt 240
ggatttctaa tccaactttc agaaagttta tgtgaaagat aatactcaaa cacaatagtt 300
cgtttagaac gctcttaaga ttaatgtcac acacacaaaa ttgatgtcac tagatttata 360
tgttttgtcg tttaagggga tccatcaact acacatggaa gaatagaaaa cactggtcac 420
acacaaaaaa taatataagc atgttgagtc ctattcatca gaaaattttc tccaaaggat 480
gaacaataac ctacaattaa ggaaacttat tataacaacg accaagaagt tttcccataa 540
gtcatgcttt cgtccatacc ttcgggtctt tcaagcaagc ttcacacatg ccttatcgta 600
tatttgtata cgttttcatt ttgtgtacgt ctattaatta gtatatgcct agattatata 660
tttatatagt cgacaattac ctatcctaaa ggtttatttt aatttttatt cagaaagata 720
tgcacgtagg gccactagtg tttcccgttg ttattggaaa ttccatgtgt tgaactgttt 780
gattaagttt ttgaacccgt aagtcaaatt tatttaggtt taacagggtt tcattactgt 840
tataagcttg tcaagaaaga atttgtcaca aatttcgaga ctcatgcatg catgcatgtt 900
tcttaacttt cgagaaacat gaagtgtggt tttaccagct gaagtttgtg ttaaaacaca 960
tttttaattt gaccacgtgt gatattcaaa tatcaacaat tctgttcaac gggagattca 1020
tacatatgtt cagatgttct ttaatcttga gcacctaact ttgcttccca tacgcaaatg 1080
tgtgtgccgc gaactatggt gaatgtacgg catcgttttt ctttttggag catttttaaa 1140
agaaaatata atttagttat ttccgttttg attgatatag atgcattaat aaaccgactt 1200
acgtgggtga tgggatgagc aaaattaaaa tatgcatttt agtaaccaat tacggtccat 1260
cttgacaaac taacaaacaa aaagtctatt atgacgttga tttgtgacct tgccatataa 1320
atgccaaaat ttcattcttt caataagcaa cgagatcaat aagatgtggc agtcacgtga 1380
acgttagtta tcgccatttc aactgaacct tcacgaacat ataaagttca tttgttcttt 1440
gctaaaatta cgcaaatctc tgttgtgcac gaaattacga ctatttttta atgacaactc 1500
ctgttcttgt atcgtgtatc tagcacgtaa atttgaatta tggcggcatt atcgataaaa 1560
tatgtaaaga atatattttc atcatacacc acaaacaaat gttctggaaa tatcaccttt 1620
tatcacatat acaaagctga ccctgaattt ttggaaacta caagccaaaa aaaaatggac 1680
aaaagaaaaa ttatgcacaa aagtggactc gtcctaactc tttttataat gataattaac 1740
ctttgaacaa ctaattaata catacaatat gtttttttt tctaaaaatt ggtcgattaa 1800

```
atattcatat ataatcctca tcatcattta ttagcctttt gtagcttact taaaaaatca   1860
cttcccacca aattgattat tttttcactt catacgttga tcaatttaaa aaaaaaataa   1920
taataatata tgcacgtccg gcgtcccatg acttcagacg cttttctgtt tccttgattt   1980
tataggttag aaatttccaa aatgctcata tttttcactg atatgtatta tacgcacaaa   2040
atagtaaagt cataaaaatt tatgatggtt cttttatatg tatagagtag tgaaaattta   2100
tatatattgt agttccgctt aaaataaatt aatatttttc ttttatcgcc catatttaag   2160
ttactaaacg tatataatta aaaactgaaa tgcaatatgt agaaatccgg gcattgattg   2220
ttgattaaca ttgatatacc catgcgactg gcttatgatg aaccatacct gctaatactc   2280
attgttacaa actcgcagca acatcataaa tccatcactc gccacaataa ttttcttcag   2340
tgtatgttca attgatcaca ttttgaccct tcactttctt gaatgagaaa ttatacaaga   2400
aagtgatttg agtgtgttaa aaaatgattt gtcattctga ccaattagct agggtttcca   2460
ctccctcacg ctaacacaca tcaccgcagc catttccatc tctcaaccaa cttcaaacaa   2520
tggctgaacg aggcggagaa cgaggtgccg agcgaggagg agaccgcggc ggtttcggac   2580
gcggattcgg aggaggtcgc ggcgacagag gaggccgggg aggtccgaga ggccgaggcg   2640
gcagacgcgg aggacgtccg acagaggagg agaagtggac cccagtgacc aagctcggcc   2700
gtctcgtgca agccggaaag atccagaagc tcgagcagat ctacctccac tccctccccg   2760
tcaaggagta ccagatcatc gacctcctcg tcggccccac cttgaaagac gaggtgatga   2820
agatcatgcc ggttcagaaa cagaccaggg ccggtcagag gacgaggttc aaggcctttg   2880
tcgtcgtcgg agacacgaac gggcacgttg gtttgggtgt gaagtgctcc aaggaggtgg   2940
cgacggcgat cagaggtggg attatattgg cgaagctgtc ggttattccc gtgaggagag   3000
ggtactgggg gaacaagatt gggaagccgc atacggttcc ttgtaaggtt acggggaagt   3060
gtgggtctgt tacggtgagg atggtgcctg ctccgagggg tgcggggatt gtggcggcta   3120
gggttcctaa gaaggtgctt cagttcgctg ggattgatga tgtgtttact tcgtcgaggg   3180
ggtctactaa gactcttgga aacttcgtaa aggtttgaac tttcttcatt tatttagagt   3240
ttggagttgt gtatggattg aaagttgatt cctttttgat ggttgcgtgt ggagttgttt   3300
tgggtaattt agcttgttgt agttgatgta aagtgagaat tgctaagctt gattagtttg   3360
aataagctgt ctgtgttaaa tgatgatttg tttgtgttgt attgagctgt ctgaatttca   3420
ttatttgttt gtgttattgc taaattacaa gcttaaattt gataactttt gattctttcg   3480
tgagagtttt ttttgggtaa tatagcttga tgtagttgat ggaagtaaat tgttaacctt   3540
tagagctgtc tgttaatggt gatttgtttg tgttgtattg agctgtctga attataattt   3600
gtttgtgttt attgctaaat cacaaagctt tgaagtcgtt tgtacatatt catcattttt   3660
gtgtttattg acttgtttgt gtttattgct aaatcacaag tttctatgat taatcttcat   3720
gatttggttg tgtttattac taaatcacaa gtttctatga ttaatcttaa tgatttggtt   3780
gtgtttattg ctaaatttga gattacatta taatcttagt ttatacatgt ataacatcat   3840
ttcacttgaa ttttcacaga cgagctggtg atatgttttt ttagtatttt ccatgtattg   3900
ctttgtaaga acttttaaat gtttgttttc ttcctttgaa gaacaattaa atgtttgttc   3960
agtatttttg aatcattcat tggttaatca tgtgtaattt tatttttgta ggctacattc   4020
gactgtctcc agaagactta tggattcctg acaccagagt tctggaaaga gacgagcttt   4080
aaaaagtcac cgtaccagga gtacactgat ctgctggccg agaagggaat tgcaaccaaa   4140
```

gccatcaccg aggttgaaga ccaagccgcc tcctaaataa acaaacaaac aatgtccccc 4200
ttgttttgtt tttggatgat cctttcttga gttttatttt gttcgaacct ttagtatatg 4260
ttgtttgctg gattgctgct ttcttatgtt ttcatcatct cccccaaaca aagttatttt 4320
tgctctagtt ttttttata atcgatggtt atgccctcta gtattttttt tacttgaatt 4380
tttcactaat tttctatcaa cttccctatg ttacactttc taaggttgat tacataggtg 4440
gattgttgtg aaacaaatac taataataaa ctaatacttt tagaataata taattagtgg 4500
gattaaatta taaattataa attaaaaaga caagtctgaa atggattgtt taactgtaaa 4560
aggtaaagag actttgaata gaagagaata aatcaaaagt tgacgtatct tctccgaaat 4620
ttcagctatt tctaaatacg cggattctga ttactctgtt ctctct 4666

<210> SEQ ID NO 30
<211> LENGTH: 7200
<212> TYPE: DNA
<213> ORGANISM: Brassica napus

<400> SEQUENCE: 30
ctggtcacac acaaaaaata atataagcat gttgaattct attcatcaaa gaattttctt 60
caaaggatga acaataacct ataattagga aacattataa caacgagcag gaagttttcc 120
cagaagtcat gccttcgtcc ataccttcgg gtctttcaag caagcttcac acatgcctta 180
tcatatgttt gtatacgttt tcattttgtg tacgtctatt aactagctag tatatgccaa 240
gattatatat tttatatagt cgacaattac ctatcctaaa agttcatttt aatttttatt 300
cagaaagata tgcacgtagg gccactagtg tttcccgttg ttattggaaa ttcatttcca 360
tgtgttgaat tgtttgttta agtttttgaa cccgtaagtc aaatttattt tggtttaaca 420
gggtttcatt actgttataa gcttgtcaag aaagaatttg ttacaaattt cgaggctcat 480
gcatgcatga ttcttaactt tctagaaaca tgaaatgtgg ttttaccagc tcaagcttgt 540
gttaaaacac atttttaatt tgaccacgtg tgatattcaa atatcaacaa ttctgttcaa 600
cgggagattc atacatatgt tcagatgttc tttaatctta agcacctaac tttgcttccc 660
atacgcaaat gtgtgtgccg cgaactatgg tgaaatgttt tctttttgga gcatttttaa 720
aagaaaatat aatttactta tttccgtttt gattgatata catgcattaa taaaccgact 780
tacgtgggtg atgggatgag caaaattaaa atatgcattt tagtaaccaa ttacggtcta 840
tcttgacaaa ctaacaaaca aaaagtctat tatgacgttg atttgtgacc tggccatata 900
aatgccaaaa tttcattctt tcaataagca acgagatcaa taagatgtgg cagtcacgtg 960
aacgttagtt atcgccattt caactgaacc ttcacgaaca tataaagttc atttgttctt 1020
tgctaaaatt acgcaaatct ctgttgtgca cgaaattacg actatttttt aaatacaact 1080
cctgttcttg tatcgtgtat ctctcgcacg taaatttgaa ttatgggggc attatcgata 1140
aaatatgtaa agaatatatt ttcatcatac accacaaaca aatgttctgg aaatgtcacc 1200
ttttatcaca tatacaaagc tgaccctgaa attttggaaa ctacaagcca aaaaaaatgg 1260
tcaaaagaaa tattatgcac aaaggttgga ctcgtcctaa ctctttttac aatgataatt 1320
aacctttgaa caactaatta aagatacata caatatgttt tttttctaaa aattggtcga 1380
ttaaatattc atatataatc cttatcatca tttattagcc ttttgtagct tacttaaaaa 1440 acccccttccc accaaattga ttagtgtaga ttgattattt ttcacttcat acgttgatca 1500
attttaaaat atatatatat atatatatat atatatatat gcacgtccgg cgtcccatga 1560
cttcagacgc ttttctgttt ccttgatttt ataggttaaa attttccaaa atgctcatat 1620

```
ttttcactca tatgtataat gtattattat acgcacaaaa tagtaaagtc ataaacattt   1680
atgatggctc ttttatatgt atagagtagt gaaatttata tatatcggag ttccgcttaa   1740
aataaattaa tattgttctt ttatcgccca ttttttagtt actaaacgta tataattaaa   1800
aactgaaatg caatatgtag aaatccggct tatgatgaac catactaata ctcattgtta   1860
caaactcaca gcaacatcat aattccatca ctcgccacaa taattttctt tagtgtatgt   1920
tctatttcac attttgaccc ttcactttct tgaatgaaaa ttatacaaga aaatgatttg   1980
agtgtgttaa aaaaaaaaat gttttgagtc attctgacca attatctggc agagactata   2040
ataaaatact tccaattacc ttaaatcatt aggcgttgtt tcttgccgaa tatatgatgg   2100
agcatggtct cgctaagaga caacaaaatc tttaaataaa ttaaacaagt tgtttagcaa   2160
aaaataaaaa ataaattaaa caagagagag tacaaatata aaactctaaa ggaagataaa   2220
tgtataaaat acaaaatata gaatagaggc cttaagtagt gtttacgtga caatctcaat   2280
ttcactccat acctcgaact cattcaagct tagaaaccta acttttactg ttccttttga   2340
tttgcctata aatacacgtt catccatact tctgtaattt caaataacaa agcaaaacac   2400
aaagataaga atcacaaaca acaaacattc tcaacctaat cccaaaaaga cgacacgcat   2460
tccttttttcc aaaaatccac ttcctacgta ccaaccacaa tggctcattg ttggacagtt   2520
cttaccggtt tactagtatg gtctcttttg atgctctcat ggtgcgaagc ttcaagaaac   2580
aacattaata gatatgatca ttcttatgga acgttcaaat ccaatagctt aatcaagcga   2640
agagacgata tcactcgtct gaaaagtgtt gcaagagctt ctttgcggct tccaaccacc   2700
gttagtgttt ctgattttgg agctaaagga gatggaaaaa ccgacgacac gcaggtatat   2760
acgcatacac acatatctac atgacttata agttataaat attgtgagac ggtcacgtat   2820
ataaatttac gttgtttgta ctaatgatcc atgcatgcgc atgcatatga tcaggcgttc   2880
gtgaatgcat ggaagaaagc ttgttcttca agtggacctg taaatctctt agttcctgaa   2940
ggaaaaactt attttctcaa gtctcttcga ttaaatggcc catgcaaatc agttcttacc   3000
gttcaggtaa attacaaagt ttcttttgtt ttgcttaaat ttgggtaaat tacaaagttg   3060
acaaaaaaat tacaaagttg actatttgtt aattatatac gtatactaca tgtgatcacg   3120
tatatggttt tgaatatatt aaagagcggt tggtgaatgg aacgacagat tttaggaacg   3180
ttatcggcat ctcaacaacg atcggattat aaagatctca gcaaatggat tacgtttgac   3240
ggcgttaaca gtctaacggt tgatggcggg gccaccggaa ctgtcaacgg aaacggcgaa   3300
acgtggtggg aaaactcatg caaacggaac gaagctaagg tgtgtgtctg tacatgtttc   3360
atttacttaa tatatatcta ctatctacat gtcatcttga tatattgaca ctttttttatt   3420
gttattgttt tgaagaaatg cacaaaagcc ccaacggtac gtagaaacat atttgacatt   3480
ttcatgtaat actgacgatg gctgtgatca tgattggaca aatgttttac atgcatgaat   3540
atatgtattt tatatgcagg ctcttacttt ctacaactcg aagaatttga gagttaataa   3600
tctgagggtg aaagatgcgc aacagatcca gatttcgatt gagaaatgct ccaacgttca   3660
ggtctcaaat gttgaggtca ctgcgcctgc tgatagtcct aacactgatg gtatccacat   3720
cactaacact caaaacattc aagtctccaa atccatcatt ggaacaggtt agtaattaca   3780
tcctcgttat ttaaaagagt tgcgtgcata tccagaaaac taatatttaa gggtttatcg   3840
ttataattta tagagattgg tcttaaaaga gttttttaat gtttgctttt ctatgcaggt   3900
gatgattgta tatctattga aagtggatca caaaacgtta aaatcaacga tttaacttgc   3960
```

```
ggccccggtc acggtatcag gtatcaatga attgttttca gtaaatatac ctaagaaata   4020
caaccgtaat cttttacata taaatttgaa atttccttat aaaacatgag cagcattggg   4080
agcttaggag atgacaattc aaaggcattt gtatcaggcg tgactgtgga tggtgctaaa   4140
ctttccggta cagacaatgg agttaggatc aaaacttacc aggtgaaaat cacaaactaa   4200
accttcaatt ttaactagcc tatcaagttc atcccaattt aacttttaaa cccaattcaa   4260
tatagggagg gtctggaact gctagcaaca taatatttca gaacattcag atggagaatg   4320
tgaagaatcc aatcataatc gaccaagatt attgcgacaa gagcaaatgc accgaacaag   4380
ttcgtttgaa cctaatcaaa tcttccatta ctaatcctca tgataataaa cacttttatc   4440
tctaatcatt tactacatat attttcagaa atcagcggtc caaatcaaga acgtggtgta   4500
ccggaacata agcggcacaa gcgcatcaga catagcaata actttcaact gtagcaagaa   4560
ctatccatgc caaggaattg tactcgacaa agtgaacatt aagggaggga aagcgagttg   4620
cagcaacgct aatgtgatgg ataaagacgg tgttttgcct cagtgcaaat ccacttgatt   4680
aactagacct atcaaaaact cacacagatg tataaataca tatagaccga tacaaagtat   4740
acaaaattat gatatatact tgtggatata tacatggaca atgaatttaa acatattatt   4800
tatatgtcaa aatagtttat gaatagacat ataaacaaca tgttcaagag atttattgtc   4860
ttaatgtata tactccatac taaattgttt gtctaaaact tcatataata aaaaactgtt   4920
aatcttcatg atggtgtgat ttgttgtgat aacagtatga tgtctattgt agatttttat   4980
ttaaatacat aaaaattgaa agaaaaaaaa tgacatggct acttgaccaa ttgattcaag   5040
ttaattgtta ctaaccaggc cgataaacta attgggcctt taaagcccat taatatttgt   5100
cagtggaagc gaagtctgtt acttgggtta caaaacaaag gcctttagaa aaccctaact   5160
cttatcgcag cacctgagct atatattgcc gcagctaggg ttttccctag ctcacgctaa   5220
cacacaaagc cgcagccatt tccatctctc tcgcaactca acttcgaaca atggctgaac   5280
gaggcggaga acgaggcgcc gagcgaggag gagaccgcgg cggtttcgga cggggattcg   5340
gaggaggtcg cggcgaccga ggaggccgcg gaggtccgag aggccgaggc ggcagacgcg   5400
gaggacgtcc cacagaggag gagaagtgga ccccagtgac caagctcggc cgtctcgtgc   5460
aagccggaaa gatccagaag ctcgagcaga tctacctcca ctcgctcccc gtcaaggagt   5520
accagatcat cgacctcctc gtcggtccaa ctttaaaaga cgaggtgatg aagatcatgc   5580
cggttcagaa acagaccagg gccggtcaga ggacgaggtt caaggctttt gtcgttgtcg   5640
gagacacgaa tggtcatgtt ggtttgggtg tgaagtgctc caaggaggtg gcgacggcga   5700
tcagaggtgg gattatattg gcgaagctgt cggtgattcc cgtgaggaga gggtactggg   5760
ggaacaagat tgggaagccg catacggttc cttgtaaggt tacggggaag tgtgggtctg   5820
ttacggtgag gatggtgcct gctccgaggg gggcggggat tgtggcggct agggttccta   5880
agaaggtgct tcagttcgct gggattgatg atgtgtttac ttcttccagg ggatctacta   5940
agactcttgg aaacttcgta aaggtttgaa ctttattcat ttacttggtg tttggagctg   6000
tgtatagatt gaaagttgat tcctttttga tcgttgcgtg tggaggtgtt ttgggtaata   6060
ttgctaaatg taaaaattgc taagcttgat tagtttgaat aagctgtctg tgttaaatga   6120
tgatttgttt gtgttgtaat gagctgtctg aatttcatta tttgtttgtg ttattgctaa   6180
tttacaagct taaatttgat tccttttgat cgtttcgtgt gagttgtttt gtgtaattta   6240
gcttgatgta gttgatggaa gtaagaattg ttaagcttta gagctgtctg ttaatgttga   6300
attgtttgtg ttgtattgag ctgtctgaat tattatttgt ttgcgattta tttctaaatc   6360
```

acaaagctct aaagtcgttt gaacatatgc atcatttggt tagtgtttat tgctgaattt 6420
tcatgatttg gttgtgttta ttgctaaatt tgagattaca ttataatctt aatttgtaca 6480
tatattcatc atttttgtgt ttattgattt gtttgtgttt attgatgaat cacaagtttc 6540
tatgattaat cttcatgatt tggttgtgat tattgctaaa tttgagatta cattataagc 6600
ttagtttgta catgtataca tcatttcact tgaattttca cagacgagct ggtgatatat 6660 ttttttttt agtattttcc atgtattgct ttgtaagaac gtttaaatgt tagttttctt 6720
gaatgttttt ttctttgtaa gaacaattaa atgtttgttc agtatttttg aatcattcat 6780
tggttaatca tgttcaacat gtattttttg taggctacat ttgactgtct ccagaagact 6840
tatggattcc tgacaccaga gttctggaaa gagacgagct ttaaaaagtc accgtaccag 6900
gagtacactg atctgctggc cgagaaggga actgcaacca aagccatcac cgaggttgaa 6960
gaccaagccg cctcctaaat aaacaaacaa gcaatgccca ccttgttttg tttttggatg 7020
atcctttcat gagttttatt ttgttcgaac cttttagtat atgttgtttg ctggattgct 7080
gctatcttaa gttttcatca tcttcccaaa caaagttatt tttgctctag ttttttttt 7140 ttataatcga tggttatact ctagtatttt tttacttgaa tttctctaat tttccatcag 7200

<210> SEQ ID NO 31
<211> LENGTH: 185
<212> TYPE: DNA
<213> ORGANISM: Brassica napus

<400> SEQUENCE: 31
cattttgacc cttcactttc ttgaatgaaa attatacaag aaaatgattt gagtgtgtta 60
aaaaaaaaat gttttgagtc attctgacca atagctaggg ttttccctag ctcacgctaa 120
cacacaaagc cgcagccatt tccatctctc tcgcaactca acttcgaaca atggctgaac 180
gaggc 185

<210> SEQ ID NO 32
<211> LENGTH: 41
<212> TYPE: DNA
<213> ORGANISM: Artificial Sequence
<220> FEATURE:
<223> OTHER INFORMATION: synthesized oligonucleotide

<400> SEQUENCE: 32
gaaggtcgga gtcaacggat ttgaaacggc aggtgaggct a 41

<210> SEQ ID NO 33
<211> LENGTH: 23
<212> TYPE: DNA
<213> ORGANISM: Artificial Sequence
<220> FEATURE:
<223> OTHER INFORMATION: synthesized oligonucleotide

<400> SEQUENCE: 33
yccaagctga gtgtgaggct gaa 23

<210> SEQ ID NO 34
<211> LENGTH: 43
<212> TYPE: DNA
<213> ORGANISM: Artificial Sequence
<220> FEATURE:
<223> OTHER INFORMATION: synthesized oligonucleotide

<400> SEQUENCE: 34
gaaggtgacc aagttcatgc tgggaggtct ttaacatctg ctc 43

<210> SEQ ID NO 35
<211> LENGTH: 24
<212> TYPE: DNA
<213> ORGANISM: Artificial Sequence
<220> FEATURE:
<223> OTHER INFORMATION: synthesized oligonucleotide

<400> SEQUENCE: 35
atgtattgat tgttgttgcg cttt 24

<210> SEQ ID NO 36
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 36
tctctcgctc attcatccaa 20

<210> SEQ ID NO 37
<211> LENGTH: 23
<212> TYPE: DNA
<213> ORGANISM: Artificial Sequence
<220> FEATURE:
<223> OTHER INFORMATION: synthesized oligonucleotide

<400> SEQUENCE: 37
tgattcgtat tgaaagcaac aaa 23

<210> SEQ ID NO 38
<211> LENGTH: 17
<212> TYPE: DNA
<213> ORGANISM: Artificial Sequence
<220> FEATURE:
<223> OTHER INFORMATION: synthesized oligonucleotide

<400> SEQUENCE: 38
ctctaaccca aagtaaa 17

<210> SEQ ID NO 39
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 39
tctctcgctc attcatccaa 20

<210> SEQ ID NO 40
<211> LENGTH: 21
<212> TYPE: DNA
<213> ORGANISM: Artificial Sequence
<220> FEATURE:
<223> OTHER INFORMATION: synthesized oligonucleotide

<400> SEQUENCE: 40
tcgataaggg tagggaggtc t 21

<210> SEQ ID NO 41
<211> LENGTH: 19
<212> TYPE: DNA
<213> ORGANISM: Artificial Sequence
<220> FEATURE:
<223> OTHER INFORMATION: synthesized oligonucleotide

<400> SEQUENCE: 41
ggcatatacc tattagtac 19

<210> SEQ ID NO 42
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 42
tcgagtatag ggagcgcaat 20

<210> SEQ ID NO 43
<211> LENGTH: 22
<212> TYPE: DNA
<213> ORGANISM: Artificial Sequence
<220> FEATURE:
<223> OTHER INFORMATION: synthesized oligonucleotide

<400> SEQUENCE: 43
gggaggtctt taacatctgc tc 22

<210> SEQ ID NO 44
<211> LENGTH: 14
<212> TYPE: DNA
<213> ORGANISM: Artificial Sequence
<220> FEATURE:
<223> OTHER INFORMATION: synthesized oligonucleotide

<400> SEQUENCE: 44
gctccctata ctcg 14

<210> SEQ ID NO 45
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 45
aaaaatagag mcagacgtct ttagcgtcca accatcttgg acaactaggc ctctcckgtc 60
mcattagaga tctcttggac cctagatata accattctct ccttggtttg tacgtaacag 120
g 121

<210> SEQ ID NO 46
<211> LENGTH: 21
<212> TYPE: DNA
<213> ORGANISM: Artificial Sequence
<220> FEATURE:
<223> OTHER INFORMATION: synthesized oligonucleotide

<400> SEQUENCE: 46
agagaaaagg cccaatcatt t 21

<210> SEQ ID NO 47
<211> LENGTH: 16
<212> TYPE: DNA
<213> ORGANISM: Artificial Sequence
<220> FEATURE:
<223> OTHER INFORMATION: synthesized oligonucleotide

<400> SEQUENCE: 47
gcaacaacaa tcaata 16

<210> SEQ ID NO 48
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 48
aaacgtggat ggttacttta ctttg 25

<210> SEQ ID NO 49
<211> LENGTH: 18
<212> TYPE: DNA
<213> ORGANISM: Artificial Sequence
<220> FEATURE:
<223> OTHER INFORMATION: synthesized oligonucleotide

<400> SEQUENCE: 49
ctaacccaaa gtaaagta 18

<210> SEQ ID NO 50
<211> LENGTH: 17
<212> TYPE: DNA
<213> ORGANISM: Artificial Sequence
<220> FEATURE:
<223> OTHER INFORMATION: synthesized oligonucleotide

<400> SEQUENCE: 50
atattcctga cactctc 17

<210> SEQ ID NO 51
<211> LENGTH: 42
<212> TYPE: DNA
<213> ORGANISM: Artificial Sequence
<220> FEATURE:
<223> OTHER INFORMATION: synthesized oligonucleotide

<400> SEQUENCE: 51
gaaggtgacc aagttcatgc ttcgataagg gtagggaggt ct 42

<210> SEQ ID NO 52
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 52
ttgattgttg ttgcgctttc 20

<210> SEQ ID NO 53
<211> LENGTH: 43
<212> TYPE: DNA
<213> ORGANISM: Artificial Sequence
<220> FEATURE:
<223> OTHER INFORMATION: synthesized oligonucleotide

<400> SEQUENCE: 53
gaaggtgacc aagttcatgc tgggaggtct ttaacatctg ctc 43

<210> SEQ ID NO 54
<211> LENGTH: 24

<212> TYPE: DNA
<213> ORGANISM: Artificial Sequence
<220> FEATURE:
<223> OTHER INFORMATION: synthesized oligonucleotide

<400> SEQUENCE: 54
atgtattgat tgttgttgcg cttt 24

<210> SEQ ID NO 55
<211> LENGTH: 21
<212> TYPE: DNA
<213> ORGANISM: Artificial Sequence
<220> FEATURE:
<223> OTHER INFORMATION: synthesized oligonucleotide

<400> SEQUENCE: 55
agagaaaagg cccaatcatt t 21

<210> SEQ ID NO 56
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 56
tctctcgctc attcatccaa 20

<210> SEQ ID NO 57
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 57
tgttgcgctt tctgtctctc 20

<210> SEQ ID NO 58
<211> LENGTH: 24
<212> TYPE: DNA
<213> ORGANISM: Artificial Sequence
<220> FEATURE:
<223> OTHER INFORMATION: synthesized oligonucleotide

<400> SEQUENCE: 58
acataggagc yccaagctga gtgt 24

<210> SEQ ID NO 59
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 59
ataaaacgct agatggaacc tgcatcaata ccaaaamaaa aaaaaaaggt tagaaaaata 60
tgcgaggctc atttaattca ggatccggtg aaagctataa tactatacat tgtgacgagt 120
cccctcttca aaatccttct ttgaagcctc ratggcagct ctgatcattt cttcttccgc 180
atcgttccca tagacaggtg attcagcatc cctatgtgtt gttccaccat agacttggga 240
tccgtagcta ggtgaatgtc tagcataacc gtctcctccg acatctccaa gtccaggagg 300
a 301

<210> SEQ ID NO 60
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 60
acattccaag tttctttttg gtgtaatgtg ttgaaactct ttaagctaac taaagacttt 60
gtactttgaa gcccgggagc tctacattac aagaaaagcg cgaagatatt aaacaaaagc 120
agccaattga tgtaagctct cagcacggac rtgaagcttc ttatcctgaa gaggtaatta 180
ttcaaaaaca gtttgatttc tcttatcagt gatagtagca aaagcatctt tttagtgact 240
agcttctagt tgatcatgtg ttcttcttac cctgttttca cctcctgttg ctggacttct 300
a 301

<210> SEQ ID NO 61
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 61
ttataaatgt tttacttatt ctcagtactg atccggaytg atatggcacc taaaacagac 60
maaaaaatac tgccatgtaa ctataacttt ttgcttattc taatcatctt aagagccaaa 120
a 121

<210> SEQ ID NO 62
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 62
ataagcaaaa agttatagtt acatggcagt83 attttttkgt ctgttttagg tgccatatca 60
rtccggatca gtactgagaa taagtaaaac atttataatg ctttagcata tatcgaacaa 120
a 121

<210> SEQ ID NO 63
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 63
gtactgagaa taagtaaaac atttataatg ctttagcata tatcgaacaa actagcataa 60
raagtttcta aaaatccacm gaaattagag cataagttca atgcaattag catgkgaaaa 120
t 121

<210> SEQ ID NO 64
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 64
atgttaattt tgtaattggt craaawwttg caaaatttaa tttyttcata taaaatttay 60
rgagaagttt gatattagta aacttatgaa aaatacttta ctatcatatg aagttttcgg 120
g 121

<210> SEQ ID NO 65
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 65
cttgtagaag actttatgag agaaaattca tagaatagat attttataaa gtgaaacatg 60
rtcaattata aaattaattt gcctatattt tttkgcaata tttmgaagwr tgtgattggt 120
a 121

<210> SEQ ID NO 66
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 66
gccawattaa tcaaatattc gmatatttcg caagctgttt cctatcgaat aaatttcaat 60
raaacaaatg aaaagacaat tagcgacaac aatacaataa tgattgaaag gcaccaatcc 120
a 121

<210> SEQ ID NO 67
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 67
aacaacaaca caaagatcct tgagattttt caatcgcagt ttctatgcga ctgctgtgac 60
actcgtctaa tttgcaggac tgagaagaag ctcctagaga tttcagcatg ggaaaaaaag 120
caaacaacca agatcgaatc tcaactcgct ratacccagg tgattccaac aaaaagacct 180
ctccactttt aatgcattaa tactgttcta ttgctaatgg acaaaagggt tgttttgttt 240
tgcgcagcgg aagatggaca gtaagaaaaa ggagaaagcg gagaaactga ggcgcaagaa 300
a 301

<210> SEQ ID NO 68
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 68
cgattaaaac cgcaaacatc cgcgttcgca aacatccaca accgcacctg caaccgttgc 60
rgttacatca ctcggaccct aagtctacaa ggttgaaagt ttattataaa tctacaaatt 120
a 121

<210> SEQ ID NO 69

<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 69
cgattaaaac cgcaaacatc cgcgttcgca aacatccaca accgcacctg caaccgttgc 60
rgttacatca ctcggaccct aagtctacaa ggttgaaagt ttattataaa tctacaaatt 120
a 121

<210> SEQ ID NO 70
<211> LENGTH: 401
<212> TYPE: DNA
<213> ORGANISM: Artificial Sequence
<220> FEATURE:
<223> OTHER INFORMATION: synthesized oligonucleotide

<400> SEQUENCE: 70
atattttata attatataaa atgtaaatat tgttaattta ttatttaacc actgatgcgt 60
tyggtagtta gctagtcata agtatcctgc aaatgtatca atttctaacc gctataccag 120
tcatacaaat cttttagtaa cgattaaaac cgcaaacatc cgcgttcgca aacatccaca 180
accgcacctg caaccgttgc rgttacatca ctcggaccct aagtctacaa ggttgaaagt 240
ttattataaa tctacaaatt atttyaacct ggttctgctc aactaagaga ttttagataa 300
acagttcaat caaaaggatt agataatcat cacttaagac ctgcaattca actaagaaat 360
tttaggaaaa ctcgcttggg ttagtgatat taatcaaaty a 401

<210> SEQ ID NO 71
<211> LENGTH: 201
<212> TYPE: DNA
<213> ORGANISM: Artificial Sequence
<220> FEATURE:
<223> OTHER INFORMATION: synthesized oligonucleotide

<400> SEQUENCE: 71
gtgggccaaa tagaagtttc tttctcaaaa gcccattgat aaacactatt tttaaagtaa 60
aaccctaaag tgggttaatg ttgatggttg acttctggtg rggaatgtgg aggcccatgt 120
atagctagag tacaggaaac tctttcagtg tttgcgagct tctacttaat tcatcatatt 180
cgttatctta acaaacaaaa c 201

<210> SEQ ID NO 72
<211> LENGTH: 201
<212> TYPE: DNA
<213> ORGANISM: Artificial Sequence
<220> FEATURE:
<223> OTHER INFORMATION: synthesized oligonucleotide

<400> SEQUENCE: 72
aaacggaraa ctaaccaacc aataggagga ggaggagrtt gctccaaatg aaccaaagtt 60
kgggttttga cagcgaagat tgaagctggg mgctgtgaag maattgattg agcaaggggg 120
gagaggaaga cgaaaccaat ttagaagaag aagcaaagag tctctctctc tctttctctc 180
tcttttgggg ytktctactt t 201

<210> SEQ ID NO 73
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 73
ctactttact atttagcccc tgtaaagtaa atgattccag ggatgaaact agagggcaaa 60
rtagkgaata tattayagag cagwaaaggt taagattttc ttcaaaccag gagaagwgtg 120
t 121

<210> SEQ ID NO 74
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 74
acaataggac agtaataata tttacctgca gtgttagcag ttccatcctc aawgtcaaca 60
mttttatcag taggttcagt ttctgttggt tggatagaat tgtcaggttc cttgcttata 120
t 121

<210> SEQ ID NO 75
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 75
aacttcaaaa ggtkatatta ttgacaattg ccctttacat atcacatgtt tatttattaa 60
ytggttgaat atttatattc ttaacttacc actgctaatt attgatgaac aattgagaaa 120
g 121

<210> SEQ ID NO 76
<211> LENGTH: 401
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (8)..(8)
<223> OTHER INFORMATION: n is a, t, c, or g
<220> FEATURE:
<221> NAME/KEY: misc_feature
<222> LOCATION: (14)..(14)
<223> OTHER INFORMATION: n is a, t, c, or g

<400> SEQUENCE: 76
aaawttcntt tttnttttwt tttwttttat ttawttttat ttatttattt aattttaaac 60
caagagtatt agggatattt taccctttaa tgaatgtcat ttttgtgact ttctccttct 120
artrttattt ttgagacata aacttcaaaa ggtkatatta ttgacaattg ccctttacat 180
atcacatgtt tatttattaa ytggttgaat atttatattc ttaacttacc actgctaatt 240
attgatgaac aattgagaaa gtatcaatat ggagctggaa caagaaaaat caagatatgc 300
gatacttgyt gcattatatt ctacaatact tgcacttaca aaaatttaat atattctcca 360
aattttctca gcatgtagca ttttgttttt ycagcatgta g 401

<210> SEQ ID NO 77
<211> LENGTH: 121
<212> TYPE: DNA

<213> ORGANISM: Artificial Sequence
<220> FEATURE:
<223> OTHER INFORMATION: synthesized oligonucleotide

<400> SEQUENCE: 77
ctttctcaat tgttcatcaa taattagcag tggtaagtta agaatataaa tattcaacca 60
rttaataaat aaacatgtga tatgtaaagg gcaattgtca ataatatmac cttttgaagt 120
t 121

<210> SEQ ID NO 78
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 78
ggtttagttt tatcttctgc caaaaatatg ttggctggac ggtagctgac tgtgcattgt 60
rgttgcgtta caaaaaagaa tacgtctcat taactttcca caatggtgtc tttttcacaa 120
c 121

<210> SEQ ID NO 79
<211> LENGTH: 201
<212> TYPE: DNA
<213> ORGANISM: Artificial Sequence
<220> FEATURE:
<223> OTHER INFORMATION: synthesized oligonucleotide

<400> SEQUENCE: 79
aaagttgtca agagaacatt caaaagctat taagcagcgc tttaactgaa gggactgtat 60
gtataagttt tcttggtttt accctctatg tgaatctgta rgtttaccga caaataatat 120
tttgttattt cgtattccat atctttaaaa aaataagaaa agttatatta tattttaaaa 180
ataaaaaata aaaataaata a 201

<210> SEQ ID NO 80
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 80
aaataattat aagatagtta gtgctaatga tgattagatg ataagttaaa tagagaaaag 60
tgagtctgca gttaatttgc atgggcttag ggatattttt tcaatataag taaaagataa 120
ttcaagggaa ttcgtgagca ctcccacatt mcactcacca ccttttcgca gcgacaccga 180
catatgccac attttcattt taccttttt ttcttgcaaa agatcgttaa ttaaagaact 240
ggatttaaga ttaatctcta catatataca tatttacgga tatgtacgtt ttttttgaac 300
a 301

<210> SEQ ID NO 81
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 81
cattttcatt ttaccttttt tttcttgcaa aagatcgtta attaaagaac tggatttaag 60
attaatctct acatatatac atatttacgg atatgtacgt ttttttgaa caacaagtgc 120 ttatgctaaa attaaacgca catgagttaa rtcagttaaa tccaaagaga cactaaattg 180
ataaactaac ataactaaaa cataaatata catattcatt ctcgtaaaat atactcaata 240
ttacagagat atatgtgcca gctgtttaga tacatacata tgcatgaata ataaaaccca 300
c 301

<210> SEQ ID NO 82
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 82
tggttgtwca gacagacgga caggtcttta attactacct agtcttttwc tttccaaata 60
magaagagtc tctccctgag agggtattct gaatctaatg gcgaagaagg tgttgatgay 120
c 121

<210> SEQ ID NO 83
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 83
gcaaaacact tggttaccaa atagccctas tagtacaaaa araagataac araaaagttc 60
raaggctttt tcatttgatg attgcattct actctcttag cctttgttaa agctggaaaa 120
c 121

<210> SEQ ID NO 84
<211> LENGTH: 201
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (137)..(140)
<223> OTHER INFORMATION: n is a, t, c, or g

<400> SEQUENCE: 84
acattgatgt gtttttctgt ttcagttctc acttacggtg ttatatgtct ttgccagttc 60
gttgttggtg ttggtatgta tagaatgtag cacaattatc rcaagtaaca gtatcaaaga 120
catgtttgtg cgagtgnnnn agagacgtgc acaaggttgt ataacaagta aagcaaatct 180
atgctaacac taataaatat c 201

<210> SEQ ID NO 85
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 85
twatatttta taatgggatt agaattaaca aaagaaatka tatattggca tttgtagttg 60
ragagaactt tccaaacttg aaattcaagg taaaggaggt tggagatgag tcaattttgt 120
a 121

<210> SEQ ID NO 86
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 86
tttgcagcgt aacaaagctg taatgacaac aagttgaagg tttctcagac ctccaaggct 60
ktaaggagga acaakaaggt ttaaaagaaa actgtggcac tgaaatactc acctggaatc 120
c 121

<210> SEQ ID NO 87
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 87
ggattccagg tgagtatttc agtgccacag ttttctttta aaccttmttg ttcctcctta 60
magccttgga ggtctgagaa accttcaact tgttgtcatt acagctttgt tacgctgcaa 120
a 121

<210> SEQ ID NO 88
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 88
ggattccagg tgagtatttc agtgccacag ttttctttta aaccttmttg ttcctcctta 60
magccttgga ggtctgagaa accttcaact tgttgtcatt acagctttgt tacgctgcaa 120
a 121

<210> SEQ ID NO 89
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 89
tctgtccttc aagtgagaag cgaccacact tgtgatgctt tgatcacgac agctgaacat 60
ccctccggct gaaaccamcc gtctgaacag gagatcagac gttggagact gcggcttatg 120
cctgatgaga tcaagcggag tcataccaga rgcatccttg atgttgatat caatcgattt 180
cacagacatg agmatctcaa cgaackcgag aggaacgttt ccggagattg ccaagtgaag 240
agccgtacgt ccctcgttgt tcctgcagtt gacgacatcg cmgggggagt tggaggcagc 300
g 301

<210> SEQ ID NO 90
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 90
cagcaagagt tggtatccac ccacctagag aagagtgatg atgcaatatc aataatacta 60
mmggtcccat ctaatgctaa gacagtaaac agtacgtytg atagctaaaa ctgaacaggt 120
a 121

<210> SEQ ID NO 91
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 91
ctgcccttag tgagctcagg aggaagaacg tcgagactct tccctacgat gacctsaaac 60
gttttgtcaa gctygacmcc cgtgccaaaa tcaaggagaa caactccatc aaggccaaga 120
actgatctgt ctccggttta gagagatcta rattgatttt gcttcttact gcttaatgtt 180
ttttkgrgtg tggttaagat tatctatcat ttaagttatg ttacattttc agagtttata 240
aktttcctag taaacccaat aagaattgct gcttcatcta ttgctttttt tttagaccaa 300
a 301

<210> SEQ ID NO 92
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 92
tagtctgtgg cgtactgttg cmaaagcagc aaacattcag atcgagatgg tttatgttgg 60
aaaaaggaac cctaagaacg ggatccagcs gataatcaac acaatcagag atgaaaacct 120
cagccataca ttgccggact tgtttcagat mtggttcttc tgggcgaggg ttgagagcat 180
gtgggagtcg aaacaaagga tgctaaaagc ccaaagaaca aaaggagggc ggcaagggtt 240
taaagaagaa gaggaaaagg accttgtgct gcaagaaatc gttgctttgt taggttttgg 300
a 301

<210> SEQ ID NO 93
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 93
ctccacacgg cgtcaaggct cgcttccata ccaatcttcg aacggatwcg ccgcgagctc 60
ttctcgagct tcttcacctc tatgagaacc ccatcgtcgc ctaccaccac caattcctca 120
ctcttctcat ctgtcaagca atcaaccaaa yaatcatctt catcggtttc actttcatcc 180
tcgttacaat aatcatcgtc gccgattcgg catgtgaaac atctacgtgm gggaggggaa 240
ggtagatgta gtgtcgagga aggtggaaag tagggtgaca atacgtttgt agagtggaat 300
t 301

<210> SEQ ID NO 94
<211> LENGTH: 121
<212> TYPE: DNA

<213> ORGANISM: Artificial Sequence
<220> FEATURE:
<223> OTHER INFORMATION: synthesized oligonucleotide

<400> SEQUENCE: 94
tagggcttta ggcaacatcc taactcctcc aatgtaatcc taaactccta acgctgaatc 60
rtacttgcaa agatcttgga cagagaagac aatacaaagt ttcggaaatg gtgactttta 120
c 121

<210> SEQ ID NO 95
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 95
caggcaacgg atgaagatga cggagagaga aaatcwtagg gtgtgagaat cttmtttcag 60
ractattaat gggtctaaac atgggtccat taatagaata atctgtttat caaacgtgca 120
t 121

<210> SEQ ID NO 96
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 96
gtatagtgta taacatgaaa aagataaggg aaaagaagat racacagtga tcggggagct 60
rgcagcccac attatcatca cctttaaaga aataaataag caaagcatgc acatgattat 120
c 121

<210> SEQ ID NO 97
<211> LENGTH: 201
<212> TYPE: DNA
<213> ORGANISM: Artificial Sequence
<220> FEATURE:
<223> OTHER INFORMATION: synthesized oligonucleotide

<400> SEQUENCE: 97
atgtygtaka tmacayagca agttccaaat tcctcttgct cttttacttg attaataatt 60
gtacacagct cctgattatc tccttcaaac cacactcttc rccagccaca aatccaaact 120
tgttgaagag ctataaggaa acttaaagct tccccttcta awgatgtctg catctttttt 180
macttggmca cttcccgctc c 201

<210> SEQ ID NO 98
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 98
atagggagtg gttgcacaag gaatgtgyac ggtgggaata tcatggtgta ttaaacaacg 60
aggacctgtc tttacctcag catttactcc tgtcatgctt atgtctgcaa ccttgttcga 120
tttcttgata tttcatcgta tgatttattt rggaaggtaa ggatgtattc tctaaaagaa 180
aacaatgcat atttgatata tagaactttc atattgraaa gaatatactt agtttatcaa 240
atacgaaaca ttgatcattg cattaacttt caactgatat taatatggaa ctcttctaga 300
a 301

<210> SEQ ID NO 99
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 99
gaagggatgt aatctatatg ggcatattaa aagaaaaaaa taataagcat attgcgtatg 60
mttgaaaaag ttagtaatat aaactcgttt ggatgccaga gttaaacaaa gtttaagatg 120
t 121

<210> SEQ ID NO 100
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 100
ctcaccygat ttggtcccat aggacattat tttgggttgt acggtcaagg aatgttcgag 60
raaggcaaaa agccgcwgty cggaaacgcg ttaggtrtta agcgctagtc rgayggtygg 120 r 121

<210> SEQ ID NO 101
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 101
tgccttyctc gaacattcct tgaccgtaca acccaaaata atgtcctatg ggaccaaatc 60
rggtgagcaa ccrtaagttt tctattatat tttaaattta caagttccta gaaatttatg 120
t 121

<210> SEQ ID NO 102
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 102
tcakcstcaa cacmacaatg atgcagwgac taagtcaggc tttgaagttt cctcataaaa 60
rcacaaagtt tcagtaatat cactagcttg gacagaagct tataacccct aagrttwaca 120
t 121

<210> SEQ ID NO 103
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 103
tcakcstcaa cacmacaatg atgcagwgac taagtcaggc tttgaagttt cctcataaaa 60
rcacaaagtt tcagtaatat cactagcttg gacagaagct tataacccct aagrttwaca 120
t 121

<210> SEQ ID NO 104
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 104
tcakcstcaa cacmacaatg atgcagwgac taagtcaggc tttgaagttt cctcataaaa 60
rcacaaagtt tcagtaatat cactagcttg gacagaagct tataacccct aagrttwaca 120
t 121

<210> SEQ ID NO 105
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 105
tgatacaata aacaagagct ttaaatctca agaaaagcag cagcaaaggt aagtcggagg 60
atgaagaaat acctcagaat gcgattagaa gtggcgccgc ttaaacacac agattagggt 120
tttgcaatgc agccaaggag tggatcgtca rttataaata gagcaaatct accgaaactt 180
tgttgggcct atggatgaag gcccattttg gaaacctgac gtttcggcct tatttttcgc 240
gtggcttttc tacaatatat ctctctatgc gaacatgcat cggccattgt ttcactttca 300
g 301

<210> SEQ ID NO 106
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 106
ttagcctttt gtctcaactt ctccatcttc tatgtcattc actccgcagc tgcagtcaca 60
rtcaatttag ctggaaacct tacggttgaa ggttgcagtg gctgtactgg tgttgtgktt 120
g 121

<210> SEQ ID NO 107
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 107
atgaagagga agaagacgat gatgacaatc aagatgtgga tagggaagaa ggtcaggagg 60
agttagctga agatgaagac aacaatattg atattgatat tgagacagca gaagatgaag 120
agaaatcacc ctctcctatt gacgaagaaa rggaagagta ttcctttctt ctctcacttc 180
ctcctcatgg ttctgaagtt ttcattggcg gcctccctag ggatgttgga gaagaggacc 240
tgagggatct atgtgaacca atcggcgmca tmtttgaggt tggaacatca ataatatttt 300
g 301

<210> SEQ ID NO 108
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 108
gtcttcttct gtccaatatg ggcaggract cagcttcatc gccttgttca acgyaatttt 60
rtaaaacttg ctgactcatt agacggtaag ggtgataaca aaataggaaa cttgtcacgc 120
a 121

<210> SEQ ID NO 109
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 109
tttatttcaa cctacaagag aaaggsatgt gttaatgagt atacttctca aatattgtag 60
aagagagaga atggagttga ctgacctcac accagtcaaa acagtctaaa actctcacgc 120
ttttcccatc tcctttgcat ttaacttttg rattcatttc cctgcaascc ctccacataa 180
ccattggatc ccaacttagt ccagatgtct tatcgagaac atttctgaca atcacaggtt 240
ctgccttcat ccaatgcgac tgaaaatgaa caatatcatc ttcagccaga tcaacagcat 300
t 301

<210> SEQ ID NO 110
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 110
aatagtttac catctcttga tgcagtcata gcaatagcgc ttcttaatgc atttagaaca 60
gaagacraga tcaaccttat acgttaagtt cttrcactga tgacaagtca aacccgcata 120 ctttttgtt ccatcagagt tatcatcctg maaaaggaaa acagtgttca catttatcca 180
aaaaaaaaaa catttccaca aatagaagta aacaaagatg attcaagctt gttgacaaac 240
tgaacaattc aattacaaaa agaaaatamc cttgtkgggc gtagacatgc ctctctctct 300
c 301

<210> SEQ ID NO 111
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 111
tgagaagcaa ttagattttc tgaaagacat cattatgaat tgaattttgc atatgagaag 60
aatgaatcta ttacatacct ccatatcttt tgctgaactg aagtcakcaa agttaagtgg 120
ttcaacacgt ttgcaacaca ytgcatcaac mgtctctgtt tctccagcaa ctccttcttg 180
cttaacttca gaatcattgc cttgattctt aacatctaca accgtttcac aagctacttc 240
caccagattc ttttctgcgt ctttatataa attatcttcc ttttcagtct gaaccattgc 300
a 301

<210> SEQ ID NO 112
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 112
ctccgcagat cagccgctgg agatgcgtcg ggatgtgagt gtggtcgaag atccgctgct 60
tgatctggtc gccataggct aagggagagg agaaagctac ggttatcgat tttccgttga 120
gtagcctaac gaataactgc aacggyttag rgctctgatc cgccattgtt agcaaagttc 180
agtgatcgaa gaagaagaaa atcgattttg tggaaatcac aacgaaatgt aaaaatcttg 240
ggatgggcaa taaaccgagc cgaacttatg gtatttccgg ttaacgaaac tcgaacctta 300
a 301

<210> SEQ ID NO 113
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 113
caacaatatt gatctgaaca gtctataacg ccgtgagaaa caaccgcaca actgggaatt 60
cataaaatta atctacaaca aatactagat aacctcacag gagaagaacg cgagaaagaa 120
caaaaacaca tagatggtga cggttcaaga rgaaaatatg grgagatgac aaaaacatct 180
tacaaataat gtttaaaatt ttaaaaataa tatcccgcgt gaagcgcggc tacaccctta 240
gttcttaata aaaaaacgtt gcttctagct gctgtatcaa cagtttgatc attcaccctt 300
a 301

<210> SEQ ID NO 114
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 114
gccatttaaa ttaaatcaaa gtggtgatca gatgattttc ctaggagttt attactctgg 60
rtctgattta tatgagaaaa catgtagcat ttagttcttg cttctcttaa cgtctgacca 120
t 121

<210> SEQ ID NO 115
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 115
gcgtaaatca acgttaggca taacgggaag tgaaaatagt gaggaaggac atctgagagt 60
acaggtttgt tttgggaatt gtggtgaggg ctgcaggtgt tgttgtaagc cacagattta 120
tagtagtcgt tcgattgata cgtgaaacgc maggagaggg aacctgttga gtagtagtta 180
agagtaataa taagaattca tgtagatgtg gaaggaataa atttattaac aacgattgtg 240
tatgtaacgg aggctgattg aactccttaa gaactaaatt agggttcacc ttaagcgtca 300
c 301

<210> SEQ ID NO 116
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 116
tcgaacgttt gtagatgcct tctacattat tcacattgtg tttcagttta ggacagckta 60
tgtctctcct ttgtcccgrg ttttcggkag aggcgagttg gttgaagatc ctaaagccat 120
tgctttaaag tacatctcct cttacttcat matcgatgtt ctctctatcc ttccactccc 180
acaggtaata ttaagtgact gaacctttta attaagttga aatggtttct tgataacttc 240
rttcagtgat gttctgtttg tttcttctcc agcttgtagt cttggctgtt atcccgaatg 300
t 301

<210> SEQ ID NO 117
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 117
tcaaattttt ttcttgtttt gtcagatcaa atatggagta atttatggat aaaagttata 60
rgttattcga ataatttggt tatttgagta atttggatca ttttcaatat aaaaactgct 120
t 121

<210> SEQ ID NO 118
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 118
atcctttaga gttcctacac atcatttgca tcaaatataa taagaccaat tctcatgtga 60
aactgtttcc aagaaactat gagaaaccaa ccacggcgta atgtaagcca acactggata 120
atcataatgc ctagctgatg aattctctga mgcctttgaa tgttcctgaa ccaaaactca 180
aatcccctaa acctttcagc tttttttttc aaaggattct caaacattga aacgaaaaaa 240
agtaaggcaa cactcacagt gaggatctct tggaaatgaa tatcggtttt gattattccc 300
t 301

<210> SEQ ID NO 119
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 119
ttcataggtc tataaagtca gtctttagaa attacagtat gatttaaata ataacaattc 60
rtattaaaar tggtttgaat ctgtggcacg aaggaaccaa tccatcgcat aaccactaga 120
c 121

<210> SEQ ID NO 120
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 120
tggtgagttt ccatgtgcaa tatattgttt ttgcaattgt ccaaaagagg aaagtttttc 60
rgaactgata tgaatgcacc ttaytgcagt caggtaaagg aaggagacct agrakggatg 120
a 121

<210> SEQ ID NO 121
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 121
attycagmtr aaaaacatta ttatcaggac aagaagstta tattcagaca gcttcactac 60
rttttccaca aaagaaacca atcccaaata aaaagcacaa ataatgtgaa attaatamaa 120
a 121

<210> SEQ ID NO 122
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 122
tcggcgtcgc cttttgtaat ttctgttgat aaggatttct cgtttaaccc ttgtaaaagt 60
mraccttycc gttaaagccc caaaattaat ttttgaagtt caaattaacc caaaagaggg 120
a 121

<210> SEQ ID NO 123
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 123
gacaacaatc acaggatcat ccacgggcag cgacacatcc tccagcagct ggtgcgactc 60
rgattttacg tcagagtttt taccgtcagc atggggaggt aacgttgaaa aagaggaagg 120
t 121

<210> SEQ ID NO 124
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 124
wtttgttcac attctgtgtt acttaattat aggctccact csgccgatgc attcgactta 60 mactttcgg gtaaggtttg aagtaccttg tttatcacat gatatcatga ataacacata 120
g 121

<210> SEQ ID NO 125
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 125
aacatgatcg taaattcatc tcmcgtcttt cttatataat attgtagcaa gtcyaagtcc 60
rgggtgtgta gagatagttt ccctttcaaa gtattttttt ttcataattt taacccccctt 120 a 121

<210> SEQ ID NO 126
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 126
ttwtttgmta ataaggacaa actaaaaacc ttattgctaa gctcacatta attacatata 60
mttttcaatw cgctwmtata taatcaaaaa gaattgtgcg ttaatgacaa aaggcacaac 120
a 121

<210> SEQ ID NO 127
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 127
atgctctaga tatggccttg ttacttaccg taagtccttg ccttttccct gattgagaat 60
raccctctcc gagcattgat ytcaaygttg ttttcaggga gctacgatcg ttgatcaaac 120
c 121

<210> SEQ ID NO 128
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 128
kacgragagg aaggagaaga aatgataacg agtccaaggt ttttggaatg acctggatat 60
rgaatwtata ttcaatyycg rrttagaaaa tgcgartarr aaaatctcka aaagaaagac 120
a 121

<210> SEQ ID NO 129
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 129
tctcgcsttt cacttttagt tgtgtctccc ataacgtttc tgacttcttg tctttctttt 60
mgagatttty ytaytcgcat tttctaayyc grrattgaat atawattcya tatccaggtc 120
a 121

<210> SEQ ID NO 130
<211> LENGTH: 201
<212> TYPE: DNA
<213> ORGANISM: Artificial Sequence
<220> FEATURE:
<223> OTHER INFORMATION: synthesized oligonucleotide

<400> SEQUENCE: 130
ttagtgcttt cttcattgga tggaggatat aacttaaacg aatgatttta caggcttttc 60
aaatatataa agatatttat catttttaaa aatagaaact rtgtggtcca tttgctatca 120
attcaactag aggtgtaagc ccttgtatag gagataaagg attgaaatta ttagtttaca 180
aaaatcaaat gtttacacta t 201

<210> SEQ ID NO 131
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 131
caccaatgat caaacatgaa tcattgtctc taaatataaa ttgctracat ctcaaaaccg 60
rattctgttt ttattacctg agctgggaca gcagcagcaa gcacacgggg aatattctta 120
g 121

<210> SEQ ID NO 132
<211> LENGTH: 201
<212> TYPE: DNA
<213> ORGANISM: Artificial Sequence
<220> FEATURE:
<223> OTHER INFORMATION: synthesized oligonucleotide

<400> SEQUENCE: 132
gaaccaytgt ttcctcgtca aacatggtag atgttttaat atttatttat gtgyataata 60
attaataagc atatacatgc aaatcagcta actttttaaa stccctacca agctaccaac 120
cctaaacttg tgaccttaat ttcaacatat taaaattcac attagaactt gaacgttttc 180
akaccgtcct ggtttgtttg t 201

<210> SEQ ID NO 133
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 133
gccctatgat cagcttgcga aacttcaaaa tattgacgac catgcacggc cgtggatgtt 60
ratggtggca tctggttagg aaatgagtct ggtcgttgck gttggacaag gctggtctga 120
c 121

<210> SEQ ID NO 134
<211> LENGTH: 121

<212> TYPE: DNA
<213> ORGANISM: Artificial Sequence
<220> FEATURE:
<223> OTHER INFORMATION: synthesized oligonucleotide

<400> SEQUENCE: 134
gccctatgat cagcttgcga aacttcaaaa tattgacgac catgcacggc cgtggatgtt 60
ratggtggca tctggttagg aaatgagtct ggtcgttgck gttggacaag gctggtctga 120
c 121

<210> SEQ ID NO 135
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 135
gccctatgat cagcttgcga aacttcaaaa tattgacgac catgcacggc cgtggatgtt 60
ratggtggca tctggttagg aaatgagtct ggtcgttgck gttggacaag gctggtctga 120
c 121

<210> SEQ ID NO 136
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 136
ggacttggag gaagacaaac atcagagaaa cttatcattc ktggctmaaa gcggtaaagc 60
rtcagagaaa tttgtaatgt ttttgagttt atgatggcaa atccttgagt ttgmtttgtg 120
g 121

<210> SEQ ID NO 137
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 137
tggttaatga gagattaatt aatcttgaag cacactagta gagttgaaat attgttatac 60
rttttattga ctcttaacat gttytacgtg attgattcaa ataaacaata taaatgctcc 120
c 121

<210> SEQ ID NO 138
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 138
tggttaatga gagattaatt aatcttgaag cacactagta gagttgaaat attgttatac 60
rttttattga ctcttaacat gttytacgtg attgattcaa ataaacaata taaatgctcc 120
c 121

<210> SEQ ID NO 139

<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 139
tggttaatga gagattaatt aatcttgaag cacactagta gagttgaaat attgttatac 60
rttttattga ctcttaacat gttytacgtg attgattcaa ataaacaata taaatgctcc 120
c 121

<210> SEQ ID NO 140
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 140
taaataaact aaaccacgta tcatatatga gtatttagtg ttgctaaatc ctatgaagaa 60
gctatgcata cacagatgac aaaattcaaa acacatgaat gctaatatgc taattcataa 120
attcacgagt taacgtttaa cttgtataga ratatwtcag gaaaacatag tgcaaaattt 180
aactacctta ttatttttgt tttgtgtccc ctctgttgcg aacacatcga acatttcatt 240
gtttcaataa tctaatyaca tgggattatc acttcctcta ctagtctggt tgagttggac 300
t 301

<210> SEQ ID NO 141
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 141
ttactagcta aaagaatttg gcaagaatat gcaccatttg gtgaggttgc ggttgatcac 60
mcactgaatt ctgatcttat ggcaccaacg gctctggttt tacttgtyga gttttcacct 120
t 121

<210> SEQ ID NO 142
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 142
ttttttggca attcatcata atagggtctg atgttttgtc atctgttagg tgccaaagta 60
ragaactttg tgtgaattga gctgcttttt ccctcgagaa atggttctac atgttatgtt 120
g 121

<210> SEQ ID NO 143
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 143
ttttttggca attcatcata atagggtctg atgttttgtc atctgttagg tgccaaagta 60
ragaactttg tgtgaattga gctgcttttt ccctcgagaa atggttctac atgttatgtt 120
g 121

<210> SEQ ID NO 144
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 144 tttttggca attcatcata atagggtctg atgttttgtc atctgttagg tgccaaagta 60
ragaactttg tgtgaattga gctgcttttt ccctcgagaa atggttctac atgttatgtt 120
g 121

<210> SEQ ID NO 145
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 145
tctgctccaa cctcagagaa actaggagca cctcttttct ctttattaat tgggaaacgg 60
ggaagagcat aaacaaacgg cacctcctcc rcttctcctg tataacgaat aacatccttg 120
actataccag aatcaccaag acaacactca mcgtctgaaa caccagaacc agatcccaaa 180
tcctctaatg cctgaacaat atccagagaa ttaccctcta ctctaccggc cacgttagca 240
taaamctgag cagamttycc aatgctctgg atatactgaa ccgctacgca ggtwagcgta 300
t 301

<210> SEQ ID NO 146
<211> LENGTH: 201
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (124)..(124)
<223> OTHER INFORMATION: n is a, t, c, or g

<400> SEQUENCE: 146
gaaccttagt agacggcctc tcctgctctc atcatcatcc aaaccaamcc aatcaaacaa 60
cacacatttt catcagtttc taaatcaaaa gtttcaatct raaaatgtaa caaagtctaw 120
tccntttacc gtgaggaagt tgccacagtt ttgrccttct gatctgaagt agttattagg 180
acttcctcta acacctgcag g 201

<210> SEQ ID NO 147
<211> LENGTH: 201
<212> TYPE: DNA
<213> ORGANISM: Artificial Sequence
<220> FEATURE:
<223> OTHER INFORMATION: synthesized oligonucleotide

<400> SEQUENCE: 147
taytctagyc tatcakycaw cggttaacga tcagatctta aattgarawg gctaagaatg 60
gtacctcggg accagcatca gcccaggcga gctgggaagt raatcggacg acggcgagaa 120
acggatcttc ttcggargtg ggaacaatcg tcgtcatagc ttagctcgaa gctcttctct 180
cggcggcgct gatgaacaaa a 201

<210> SEQ ID NO 148
<211> LENGTH: 201
<212> TYPE: DNA
<213> ORGANISM: Artificial Sequence
<220> FEATURE:
<223> OTHER INFORMATION: synthesized oligonucleotide

<400> SEQUENCE: 148
cctcagcctc yctacatagc ctgrtgatct ctggctctgc agcctakaag agtagctcaa 60
ttagagtaat ttgaatttgt catatgcatc agaatcatga rcgattacar actaytctag 120
yctatcakyc awcggttaac gatcagatct taaattgara wggctaagaa tggtacctcg 180
ggaccagcat cagcccaggc g 201

<210> SEQ ID NO 149
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 149
atgcttacat ggaattccaa gctgcaaatk cagagtgtct gcaaaccyat ggtactaaat 60
ygtaaatcag tttactgctt tttcgtaaat acaatgtcct gaagaatcct tcatttctat 120
a 121

<210> SEQ ID NO 150
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 150
tatagaaatg aaggattctt caggacattg tatttacgaa aaagcagtaa actgatttac 60
ratttagtac catrggtttg cagacactct gmatttgcag cttggaattc catgtaagca 120
t 121

<210> SEQ ID NO 151
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 151
tatagaaatg aaggattctt caggacattg tatttacgaa aaagcagtaa actgatttac 60
ratttagtac catrggtttg cagacactct gmatttgcag cttggaattc catgtaagca 120
t 121

<210> SEQ ID NO 152
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 152
attcattacg aagaggaaaa gcccatgggc ctgcaaagtt tattgcattt caggttcagc 60
rtcgtttctt cgttcgttcg attttgccaa atccgaaacg attcaaattc cctccgactc 120
t 121

<210> SEQ ID NO 153
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 153
tgycgagtgt taattaaacc ttgtaatttg caaagtaagt gactcttggt tccggatttg 60
rtgagatcay watctactta atcatgcttt tgttcagtgc aagttttggc ctgaagttat 120
a 121

<210> SEQ ID NO 154
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 154
cattctgggt tytccgaaag tcatgatttt tatgtaaatg gtgctgagat cgctacaatt 60
gaagcttctg aagrwggatc cgttgcagaa gccgaggaag ctcaatctga ggaagtgact 120
caatttgacg aggaaaagtt tgmatctttg mtatctctgt tacgaagtga agaggagtct 180
ttggagttta gtctgaagac gctcgacgtc gatctaaact cagaccttgt cgtcaaagtg 240
tttgagtcct ctccaggaat ctcaggtaag aacttgatta agtttctgaa gtgggcaatt 300
a 301

<210> SEQ ID NO 155
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 155
aagcatgtct atagccttga gccggcatga ttcaaatctt gtgtctccta ctcctgaggt 60
rgctactgaa gatgacaagt ctagtacatc atcagatgaa rawtcatctr yggacaatga 120
a 121

<210> SEQ ID NO 156
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 156
attaaacttc aaaatacact actaatcaaa ttcagccgac gtcctgaaaa gtacaattac 60
mtcttcattt acacgkccaa ttgttttstr tsttttcttt taaawatcgt ttcgttatat 120
c 121

<210> SEQ ID NO 157

```
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 157

ttgaattagr tggggsaata ctcctttrga tgaagcccta ggttgtggta acargatgtt     60

rataaagtta ctagaagacg ctaagagttc acagatgtct tcgcttccaa gtagctccaa    120

a                                                                    121


<210> SEQ ID NO 158
<211> LENGTH: 121
<212> TYPE: DNA
<213> ORGANISM: Artificial Sequence
<220> FEATURE:
<223> OTHER INFORMATION: synthesized oligonucleotide

<400> SEQUENCE: 158

aaaaaamata ttagatatgt ttcaagaaac caagaaggtt ttaaaaaagc ataccaaagg     60

mgatcttcca tcataatctg ttttattsgg gtcacctccr gctcgaatca agctcttaag    120

c                                                                    121


<210> SEQ ID NO 159
<211> LENGTH: 301
<212> TYPE: DNA
<213> ORGANISM: Artificial Sequence
<220> FEATURE:
<223> OTHER INFORMATION: synthesized oligonucleotide

<400> SEQUENCE: 159

tgagaagcaa ataaatttat tatttaagct attttttgac atcaaaaggt ggtttcttgt     60

tcttctggat ctaatcgtca atgatgcaaa aagagctatt ttcaacgagg ttgactattt    120

taagatgggt ggtgaaactt ccaacactct rttaacacgt aatgatgatg actgatgacc    180

atatctaacc gaaccaaaca aaacgctaat agagttcasa agacacaaga atagcaaaaa    240

tgaatgtcaa atgttttaaa gcattttttt tttttgtcaa actttttttt ttaccttgtg    300

a                                                                    301
```